US011617766B2

(12) United States Patent
Roybal et al.

(10) Patent No.: US 11,617,766 B2
(45) Date of Patent: *Apr. 4, 2023

(54) NOTCH RECEPTORS WITH HINGE DOMAIN

(71) Applicant: The Regents of the University of California, Oakland, CA (US)

(72) Inventors: Kole T. Roybal, San Francisco, CA (US); Raymond Liu, San Francisco, CA (US); Iowis Zhu, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/529,091

(22) Filed: Nov. 17, 2021

(65) Prior Publication Data

US 2022/0133797 A1    May 5, 2022

Related U.S. Application Data

(63) Continuation of application No. 17/217,618, filed on Mar. 30, 2021, now Pat. No. 11,202,801, which is a continuation of application No. PCT/US2020/052327, filed on Sep. 23, 2020.

(60) Provisional application No. 62/905,263, filed on Sep. 24, 2019, provisional application No. 62/905,251, filed on Sep. 24, 2019.

(51) Int. Cl.
| | |
|---|---|
| *A61K 35/17* | (2015.01) |
| *A61P 35/00* | (2006.01) |
| *C07K 14/705* | (2006.01) |
| *C07K 16/28* | (2006.01) |
| *C07K 16/32* | (2006.01) |
| *A61K 38/00* | (2006.01) |
| *A61K 39/00* | (2006.01) |

(52) U.S. Cl.
CPC .............. *A61K 35/17* (2013.01); *A61P 35/00* (2018.01); *C07K 14/705* (2013.01); *C07K 14/70517* (2013.01); *C07K 14/70521* (2013.01); *C07K 16/2803* (2013.01); *C07K 16/2878* (2013.01); *C07K 16/32* (2013.01); *A61K 38/00* (2013.01); *A61K 2039/505* (2013.01); *A61K 2039/5156* (2013.01); *A61K 2039/5158* (2013.01); *C07K 2317/53* (2013.01); *C07K 2317/622* (2013.01); *C07K 2317/76* (2013.01); *C07K 2317/92* (2013.01); *C07K 2319/03* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| 9,834,608 B2 | 12/2017 | Lim et al. |
| 11,202,801 B2 | 12/2021 | Roybal et al. |
| 2019/0111080 A1 | 4/2019 | Shah |

FOREIGN PATENT DOCUMENTS

WO    WO-96/03883 A1    2/1996

OTHER PUBLICATIONS

Altschul, S.F et al. (Oct. 5, 1990). "Basic local alignment search tool," *J Mol Biol* 215(3):403-410.
Devereux, J. et al. (Jan. 11, 1984). "A comprehensive set of sequence analysis programs for the VAX," *Nucleic Acids Res*. 12(Pt 1):387-395.
Dudani, U.S et al. (2018). "Harnessing Protease Activity to Improve Cancer Care," *Annu. Rev. Cancer Biol.* 2:353-376.
Frankel, M.E et al. (1979). "The rapid determination of binding constants for antiviral antibodies by a radioimmunoassay. An analysis of the interaction between hybridoma proteins and influenza virus," *Mol Immunol* 16(2):101-106.
Gordon, W.R. et al. (Jun. 22, 2015, e-published Jun. 4, 2015). "Mechanical Allostery: Evidence for a Force Requirement in the Proteolytic Activation of Notch," *Dev Cell* 33(6):729-736.
Gordon, W.R. et al. (Oct. 1, 2008). "The molecular logic of Notch signaling—a structural and biochemical perspective," *J Cell Sci* 121 (Pt 19):3109-3119.
International Search Report dated Jan. 6, 2021 for PCT Application No. PCT/US2020/052327, filed Sep. 23, 2020, 4 pages.
McCaffrey, A.P. et al. (Jul. 4, 2002). "RNA interference in adult mice," *Nature* 418(6893):38-39.
Morsut, L. et al. (Feb. 11, 2016, e-published Jan. 28, 2016). "Engineering Customized Cell Sensing and Response Behaviors Using Synthetic Notch Receptors," *Cell* 164(4):780-791.
Naso, M.F. et al. (Aug. 2017). "Adeno-Associated Virus (AAV) as a Vector for Gene Therapy," *BioDrugs* 31 (4):317-334.
Nasri, M. et al. (Dec. 2014, e-published Mar. 6, 2014). "Production, purification and titration of a lentivirus-based vector for gene delivery purposes," *Cytotechnology* 66(6):1031-1038.

(Continued)

*Primary Examiner* — Michael D Burkhart
(74) *Attorney, Agent, or Firm* — Mintz, Levin, Cohn, Ferris, Glovsky and Popeo, P.C.

(57) ABSTRACT

The present disclosure generally relates to, inter alia, a new class of receptors engineered to modulate transcriptional regulation in a ligand-dependent manner. Particularly, the new receptors, even though derived from Notch, do not require the Notch negative regulatory regions previously believed to be essential for the functioning of the receptors. In addition, the new receptors described herein incorporate an extracellular oligomerization domain to promote oligomer formation of the chimeric receptors. The disclosure also provides compositions and methods useful for producing such receptors, nucleic acids encoding same, host cells genetically modified with the nucleic acids, as well as methods for modulating an activity of a cell and/or for the treatment of various health conditions such as cancers.

29 Claims, 48 Drawing Sheets

Specification includes a Sequence Listing.

(56) References Cited

OTHER PUBLICATIONS

Porter, D.L. et al. (Aug. 25, 2011, e-published Aug. 10, 2011). "Chimeric antigen receptor-modified T cells in chronic lymphoid leukemia," *N. Engl J Med.* 365(8): 725-733.

Putnam, D.A. (Jan. 15, 1996). "Antisense strategies and therapeutic applications," *Am. J. Health Syst. Pharm.* 53(2):151-160, erratum at *Am. J. Health Syst. Pharm.* 53:325.

Roybal, K.T. et al. (Oct. 6, 2016, e-published Sep. 29, 2016). "Engineering T Cells with Customized Therapeutic Response Programs Using Synthetic Notch Receptors," *Cell* 167(2):419-432.

Roybal, K.T. et al. (Feb. 11, 2016, e-published Jan. 28, 2016). "Precision Tumor Recognition by T Cells With Combinatorial Antigen-Sensing Circuits," *Cell* 164(4):770-779.

Sakuma, T. et al. (May 1, 2012). "Lentiviral vectors: basic to translational," *Biochem J.* 443(3):603-618.

Samulski, R.J. et al. (Nov. 2014). "AAV-Mediated Gene Therapy for Research and Therapeutic Purposes," *Annu Rev Virol* 1(1):427-451.

Vidarsson G. et al. (Oct. 20, 2014). "IgG subclasses and allotypes: from structure to effector functions," *Frontiers Immunol.* 5:520.

Watson, D.J. et al. (2003). Lentiviral Vectors for Gene Transfer to the Central Nervous System. *Viral vectors for Gene Therapy: Methods and Protocols*. Totowa, NJ, USA: Humana Press, pp. 383-404.

Written Opinion dated Jan. 6, 2021 for PCT Application No. PCT/US2020/052327, filed Sep. 23, 2020, 5 pages.

Xia, H. et al. (Oct. 2002, e-published Sep. 16, 2002). "siRNA-mediated gene silencing in vitro and in vivo," *Nat Biotechnol* 20(10):1006-1010.

Yang, Z. et al. (2020). "Engineering of an enhanced synthetic Notch receptor by reducing ligand-independent activation," *Comm Biology* 3:1-7.

Zhang, X. et al. (Dec. 11, 2014). "The γ-secretase complex: from structure to function," *Frontiers Cell Neurosci* 8:427.

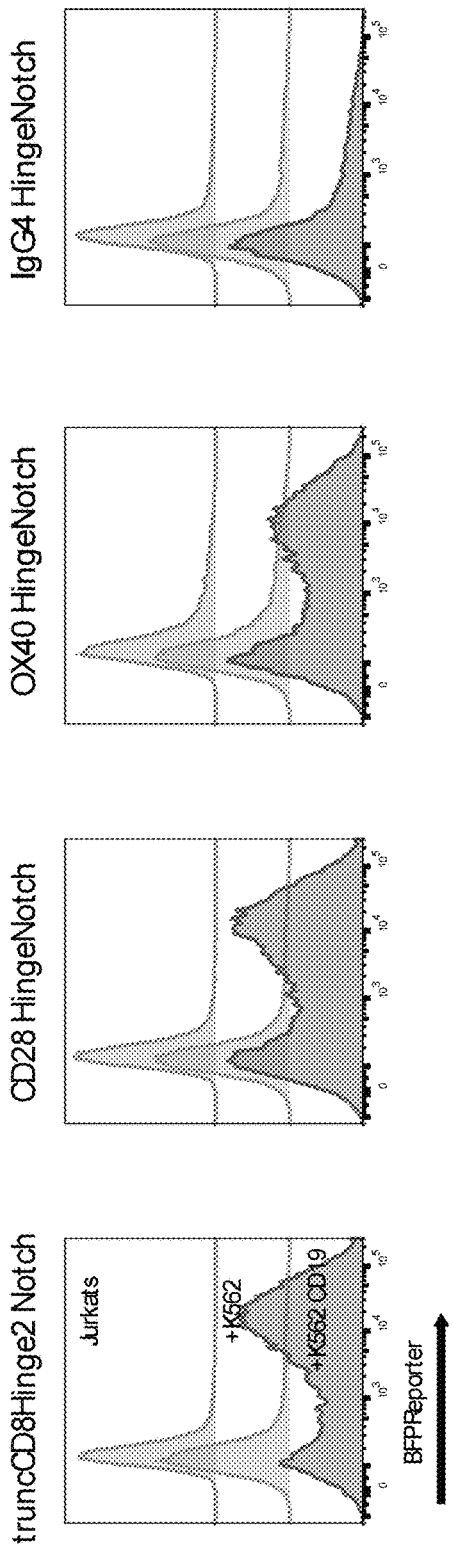
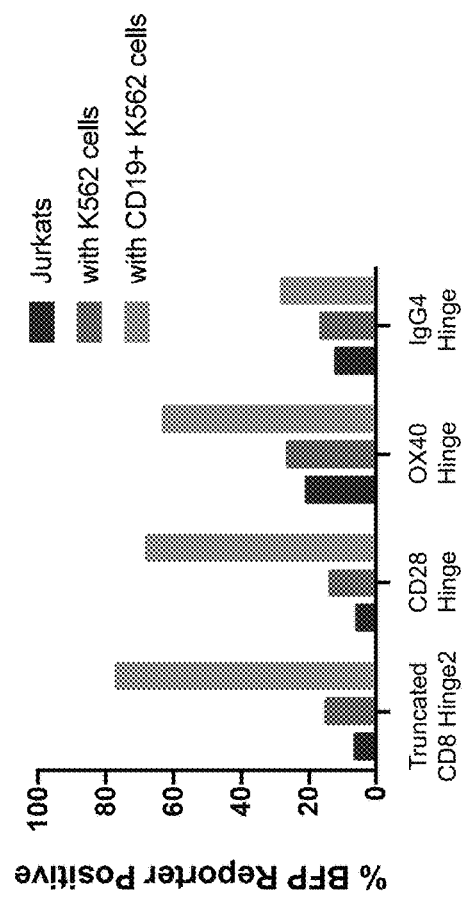
FIG. 6A
FIG. 6B

Tunable, ligand-dependent expansion of T cells using HingeNotch-controlled expression of an engineered cytokine Tunable, ligand-dependent expansion of T cells using HingeNotch-controlled expression of an engineered cytokine Tunable, ligand-dependent expansion of T cells using HingeNotch-controlled expression of an engineered cytokine

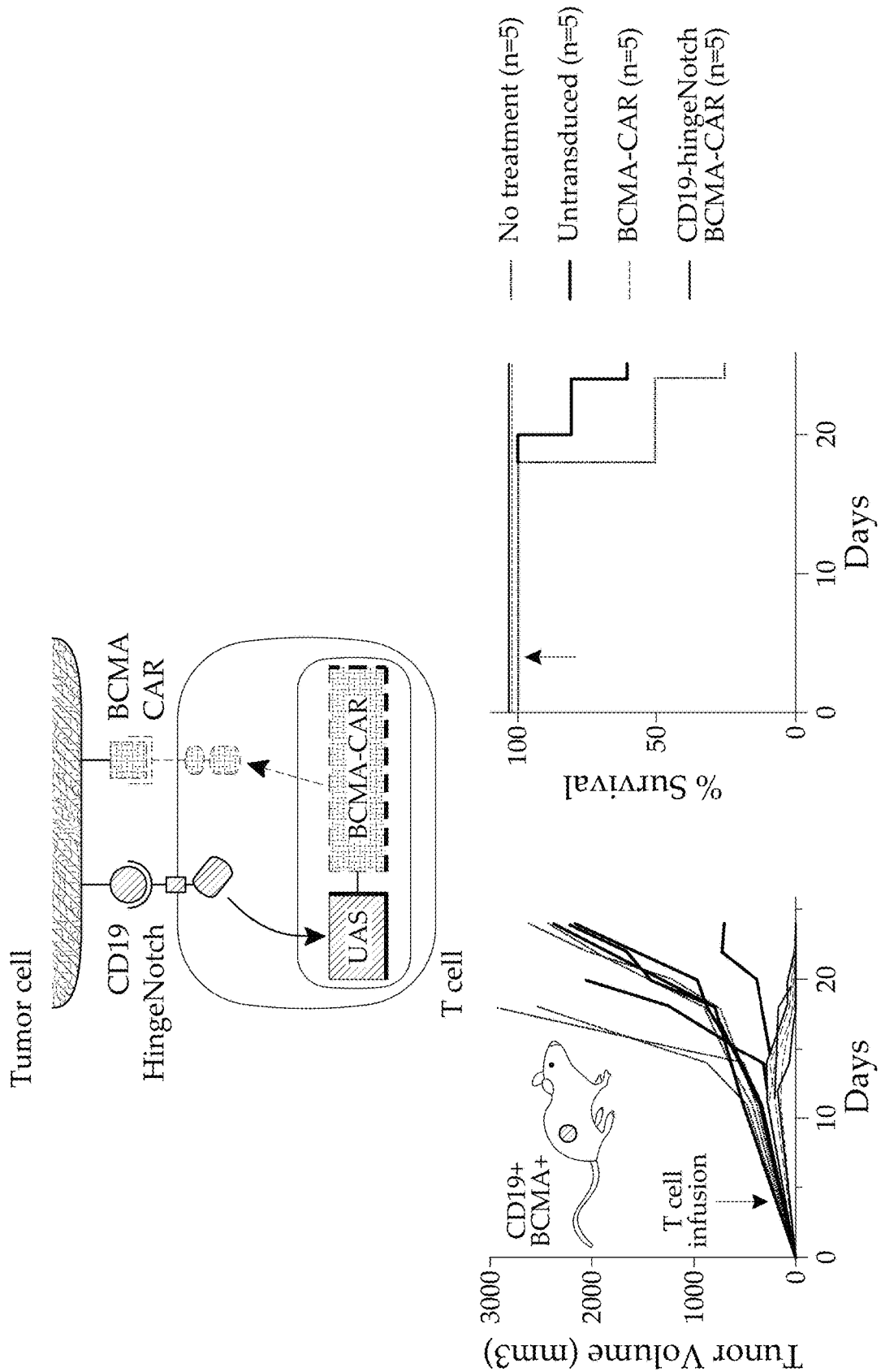
FIG. 23 Selective Dual Antigen Tumor Clearance with a HingeNotch CAR Circuit

SEQUENCE LISTING

```
<160> NUMBER OF SEQ ID NOS: 80

<210> SEQ ID NO 1
<211> LENGTH: 556
<212> TYPE: PRT
<213> ORGANISM: Artificial Sequence
<220> FEATURE:
<223> OTHER INFORMATION: Synthetic construct

<400> SEQUENCE: 1

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
    130                 135                 140

Gly Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220
```

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                    245                 250                 255

Ser Tyr Ala Met Asp Tyr Trp Gly Gln Gly Thr Ser Val Thr Val Ser
                260                 265                 270

Ser Thr Thr Thr Pro Ala Pro Arg Pro Pro Thr Pro Ala Pro Thr Ile
            275                 280                 285

Ala Ser Gln Pro Leu Ser Leu Arg Pro Glu Ala Cys Arg Pro Ala Ala
        290                 295                 300

Gly Gly Ala Val His Thr Arg Gly Leu Asp Phe Ala Cys Asp Phe Met
305                 310                 315                 320

Tyr Val Ala Ala Ala Phe Val Leu Leu Phe Phe Val Gly Cys Gly
                325                 330                 335

Val Leu Leu Ser Arg Lys Arg Arg Met Lys Leu Leu Ser Ser Ile
                340                 345                 350

Glu Gln Ala Cys Asp Ile Cys Arg Leu Lys Lys Leu Lys Cys Ser Lys
                355                 360                 365

Glu Lys Pro Lys Cys Ala Lys Cys Leu Lys Asn Asn Trp Glu Cys Arg
370                 375                 380

Tyr Ser Pro Lys Thr Lys Arg Ser Pro Leu Thr Arg Ala His Leu Thr
385                 390                 395                 400

Glu Val Glu Ser Arg Leu Glu Arg Leu Glu Gln Leu Phe Leu Leu Ile
                405                 410                 415

Phe Pro Arg Glu Asp Leu Asp Met Ile Leu Lys Met Asp Ser Leu Gln
                420                 425                 430

Asp Ile Lys Ala Leu Leu Thr Gly Leu Phe Val Gln Asp Asn Val Asn
                435                 440                 445

Lys Asp Ala Val Thr Asp Arg Leu Ala Ser Val Glu Thr Asp Met Pro
450                 455                 460

Leu Thr Leu Arg Gln His Arg Ile Ser Ala Thr Ser Ser Ser Glu Glu
465                 470                 475                 480

Ser Ser Asn Lys Gly Gln Arg Gln Leu Thr Val Ser Ala Ala Ala Gly
                485                 490                 495

Gly Ser Gly Gly Ser Gly Gly Ser Asp Ala Leu Asp Asp Phe Asp Leu
                500                 505                 510

Asp Met Leu Gly Ser Asp Ala Leu Asp Asp Phe Asp Leu Asp Met Leu
                515                 520                 525

Gly Ser Asp Ala Leu Asp Asp Phe Asp Leu Asp Met Leu Gly Ser Asp
                530                 535                 540

Ala Leu Asp Asp Phe Asp Leu Asp Met Leu Gly Ser
545                 550                 555

<210> SEQ ID NO 2
<211> LENGTH: 538
<212> TYPE: PRT
<213> ORGANISM: Artificial Sequence
<220> FEATURE:
<223> OTHER INFORMATION: Synthetic construct

<400> SEQUENCE: 2

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
                20                  25                  30

-continued

Ile Gln Met Thr Gln Thr Thr Ser Ser Leu Ser Ala Ser Leu Gly Asp
         35                  40                  45

Arg Val Thr Ile Ser Cys Arg Ala Ser Gln Asp Ile Ser Lys Tyr Leu
 50                  55                  60

Asn Trp Tyr Gln Gln Lys Pro Asp Gly Thr Val Lys Leu Leu Ile Tyr
 65                  70                  75                  80

His Thr Ser Arg Leu His Ser Gly Val Pro Ser Arg Phe Ser Gly Ser
                 85                  90                  95

Gly Ser Gly Thr Asp Tyr Ser Leu Thr Ile Ser Asn Leu Glu Gln Glu
                100                 105                 110

Asp Ile Ala Thr Tyr Phe Cys Gln Gln Gly Asn Thr Leu Pro Tyr Thr
                115                 120                 125

Phe Gly Gly Gly Thr Lys Leu Glu Ile Thr Gly Gly Gly Gly Ser Gly
        130                 135                 140

Gly Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
                180                 185                 190

Pro Pro Arg Lys Gly Leu Glu Trp Leu Gly Val Ile Trp Gly Ser Glu
                195                 200                 205

Thr Thr Tyr Tyr Asn Ser Ala Leu Lys Ser Arg Leu Thr Ile Ile Lys
        210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Gly Gly
                245                 250                 255

Ser Tyr Ala Met Asp Tyr Trp Gly Gln Gly Thr Ser Val Thr Val Ser
                260                 265                 270

Ser Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Phe Met Tyr Val
        290                 295                 300

Ala Ala Ala Ala Phe Val Leu Leu Phe Phe Val Gly Cys Gly Val Leu
305                 310                 315                 320

Leu Ser Arg Lys Arg Arg Arg Met Lys Leu Leu Ser Ser Ile Glu Gln
                325                 330                 335

Ala Cys Asp Ile Cys Arg Leu Lys Lys Leu Lys Cys Ser Lys Glu Lys
                340                 345                 350

Pro Lys Cys Ala Lys Cys Leu Lys Asn Asn Trp Glu Cys Arg Tyr Ser
                355                 360                 365

Pro Lys Thr Lys Arg Ser Pro Leu Thr Arg Ala His Leu Thr Glu Val
        370                 375                 380

Glu Ser Arg Leu Glu Arg Leu Glu Gln Leu Phe Leu Leu Ile Phe Pro
385                 390                 395                 400

Arg Glu Asp Leu Asp Met Ile Leu Lys Met Asp Ser Leu Gln Asp Ile
                405                 410                 415

Lys Ala Leu Leu Thr Gly Leu Phe Val Gln Asp Asn Val Asn Lys Asp
                420                 425                 430

Ala Val Thr Asp Arg Leu Ala Ser Val Glu Thr Asp Met Pro Leu Thr
                435                 440                 445

```
Leu Arg Gln His Arg Ile Ser Ala Thr Ser Ser Glu Glu Ser Ser
    450                 455                 460

Asn Lys Gly Gln Arg Gln Leu Thr Val Ser Ala Ala Gly Gly Ser
465                 470                 475                 480

Gly Gly Ser Gly Gly Ser Asp Ala Leu Asp Asp Phe Asp Leu Asp Met
                485                 490                 495

Leu Gly Ser Asp Ala Leu Asp Asp Phe Asp Leu Asp Met Leu Gly Ser
            500                 505                 510

Asp Ala Leu Asp Asp Phe Asp Leu Asp Met Leu Gly Ser Asp Ala Leu
        515                 520                 525

Asp Asp Phe Asp Leu Asp Met Leu Gly Ser
    530                 535
```

<210> SEQ ID NO 3
<211> LENGTH: 550
<212> TYPE: PRT
<213> ORGANISM: Artificial Sequence
<220> FEATURE:
<223> OTHER INFORMATION: Synthetic construct

<400> SEQUENCE: 3

```
Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
                20                  25                  30

Ile Gln Met Thr Gln Thr Thr Ser Ser Leu Ser Ala Ser Leu Gly Asp
            35                  40                  45

Arg Val Thr Ile Ser Cys Arg Ala Ser Gln Asp Ile Ser Lys Tyr Leu
50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
    130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270
```

```
Ser Ile Glu Val Met Tyr Pro Pro Tyr Leu Asp Asn Glu Lys Ser
        275                 280                 285

Asn Gly Thr Ile Ile His Val Lys Gly Lys His Leu Cys Pro Ser Pro
    290                 295                 300

Leu Phe Pro Gly Pro Ser Lys Pro Phe Met Tyr Val Ala Ala Ala Ala
305                 310                 315                 320

Phe Val Leu Leu Phe Phe Val Gly Cys Gly Val Leu Leu Ser Arg Lys
                325                 330                 335

Arg Arg Arg Met Lys Leu Leu Ser Ser Ile Glu Gln Ala Cys Asp Ile
            340                 345                 350

Cys Arg Leu Lys Lys Leu Lys Cys Ser Lys Glu Lys Pro Lys Cys Ala
        355                 360                 365

Lys Cys Leu Lys Asn Asn Trp Glu Cys Arg Tyr Ser Pro Lys Thr Lys
        370                 375                 380

Arg Ser Pro Leu Thr Arg Ala His Leu Thr Glu Val Glu Ser Arg Leu
385                 390                 395                 400

Glu Arg Leu Glu Gln Leu Phe Leu Leu Ile Phe Pro Arg Glu Asp Leu
                405                 410                 415

Asp Met Ile Leu Lys Met Asp Ser Leu Gln Asp Ile Lys Ala Leu Leu
            420                 425                 430

Thr Gly Leu Phe Val Gln Asp Asn Val Asn Lys Asp Ala Val Thr Asp
        435                 440                 445

Arg Leu Ala Ser Val Glu Thr Asp Met Pro Leu Thr Leu Arg Gln His
    450                 455                 460

Arg Ile Ser Ala Thr Ser Ser Glu Glu Ser Ser Asn Lys Gly Gln
465                 470                 475                 480

Arg Gln Leu Thr Val Ser Ala Ala Ala Gly Gly Ser Gly Ser Gly
                485                 490                 495

Gly Ser Asp Ala Leu Asp Asp Phe Asp Leu Asp Met Leu Gly Ser Asp
            500                 505                 510

Ala Leu Asp Asp Phe Asp Leu Asp Met Leu Gly Ser Asp Ala Leu Asp
        515                 520                 525

Asp Phe Asp Leu Asp Met Leu Gly Ser Asp Ala Leu Asp Asp Phe Asp
    530                 535                 540

Leu Asp Met Leu Gly Ser
545                 550

<210> SEQ ID NO 4
<211> LENGTH: 538
<212> TYPE: PRT
<213> ORGANISM: Artificial Sequence
<220> FEATURE:
<223> OTHER INFORMATION: Synthetic construct

<400> SEQUENCE: 4

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
                20                  25                  30

Ile Gln Met Thr Gln Thr Thr Ser Ser Leu Ser Ala Ser Leu Gly Asp
            35                  40                  45

Arg Val Thr Ile Ser Cys Arg Ala Ser Gln Asp Ile Ser Lys Tyr Leu
        50                  55                  60

Asn Trp Tyr Gln Gln Lys Pro Asp Gly Thr Val Lys Leu Leu Ile Tyr
65                  70                  75                  80
```

-continued

```
His Thr Ser Arg Leu His Ser Gly Val Pro Ser Arg Phe Ser Gly Ser
                 85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
            115                 120                 125

Phe Gly Gly Gly Thr Lys Leu Glu Ile Thr Gly Gly Gly Gly Ser Gly
130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
            195                 200                 205

Thr Thr Tyr Tyr Asn Ser Ala Leu Lys Ser Arg Leu Thr Ile Ile Lys
210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser Gly Gly Gly Gly Ser Gly Gly Gly Gly Ser Gly Gly Gly Gly Ser
            275                 280                 285

Glu Ser Lys Tyr Gly Pro Pro Cys Pro Pro Cys Pro Phe Met Tyr Val
290                 295                 300

Ala Ala Ala Ala Phe Val Leu Leu Phe Phe Val Gly Cys Gly Val Leu
305                 310                 315                 320

Leu Ser Arg Lys Arg Arg Arg Met Lys Leu Leu Ser Ser Ile Glu Gln
                325                 330                 335

Ala Cys Asp Ile Cys Arg Leu Lys Lys Leu Lys Cys Ser Lys Glu Lys
            340                 345                 350

Pro Lys Cys Ala Lys Cys Leu Lys Asn Asn Trp Glu Cys Arg Tyr Ser
            355                 360                 365

Pro Lys Thr Lys Arg Ser Pro Leu Thr Arg Ala His Leu Thr Glu Val
370                 375                 380

Glu Ser Arg Leu Glu Arg Leu Glu Gln Leu Phe Leu Leu Ile Phe Pro
385                 390                 395                 400

Arg Glu Asp Leu Asp Met Ile Leu Lys Met Asp Ser Leu Gln Asp Ile
                405                 410                 415

Lys Ala Leu Leu Thr Gly Leu Phe Val Gln Asp Asn Val Asn Lys Asp
            420                 425                 430

Ala Val Thr Asp Arg Leu Ala Ser Val Glu Thr Asp Met Pro Leu Thr
            435                 440                 445

Leu Arg Gln His Arg Ile Ser Ala Thr Ser Ser Ser Glu Glu Ser Ser
450                 455                 460

Asn Lys Gly Gln Arg Gln Leu Thr Val Ser Ala Ala Ala Gly Gly Ser
465                 470                 475                 480

Gly Gly Ser Gly Gly Ser Asp Ala Leu Asp Asp Phe Asp Leu Asp Met
            485                 490                 495
```

```
Leu Gly Ser Asp Ala Leu Asp Asp Phe Asp Leu Asp Met Leu Gly Ser
                500                 505                 510

Asp Ala Leu Asp Asp Phe Asp Leu Asp Met Leu Gly Ser Asp Ala Leu
            515                 520                 525

Asp Asp Phe Asp Leu Asp Met Leu Gly Ser
        530                 535

<210> SEQ ID NO 5
<211> LENGTH: 697
<212> TYPE: PRT
<213> ORGANISM: Artificial Sequence
<220> FEATURE:
<223> OTHER INFORMATION: Synthetic construct

<400> SEQUENCE: 5

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
    130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser Leu His Cys Val Gly Asp Thr Tyr Pro Ser Asn Asp Arg Cys Cys
        275                 280                 285

His Glu Cys Arg Pro Gly Asn Gly Met Val Ser Arg Cys Ser Arg Ser
    290                 295                 300

Gln Asn Thr Val Cys Arg Pro Cys Gly Pro Gly Phe Tyr Asn Asp Val
305                 310                 315                 320
```

```
Val Ser Ser Lys Pro Cys Lys Pro Cys Thr Trp Cys Asn Leu Arg Ser
            325                 330                 335

Gly Ser Glu Arg Lys Gln Leu Cys Thr Ala Thr Gln Asp Thr Val Cys
            340                 345                 350

Arg Cys Arg Ala Gly Thr Gln Pro Leu Asp Ser Tyr Lys Pro Gly Val
            355                 360                 365

Asp Cys Ala Pro Cys Pro Pro Gly His Phe Ser Pro Gly Asp Asn Gln
370                 375                 380

Ala Cys Lys Pro Trp Thr Asn Cys Thr Leu Ala Gly Lys His Thr Leu
385                 390                 395                 400

Gln Pro Ala Ser Asn Ser Ser Asp Ala Ile Cys Glu Asp Arg Asp Pro
            405                 410                 415

Pro Ala Thr Gln Pro Gln Glu Thr Gln Gly Pro Pro Ala Arg Pro Ile
            420                 425                 430

Thr Val Gln Pro Thr Glu Ala Trp Pro Arg Thr Ser Gln Gly Pro Ser
            435                 440                 445

Thr Arg Pro Val Glu Val Pro Gly Gly Arg Ala Phe Met Tyr Val Ala
            450                 455                 460

Ala Ala Ala Phe Val Leu Leu Phe Phe Val Gly Cys Gly Val Leu Leu
465                 470                 475                 480

Ser Arg Lys Arg Arg Arg Met Lys Leu Leu Ser Ser Ile Glu Gln Ala
            485                 490                 495

Cys Asp Ile Cys Arg Leu Lys Lys Leu Lys Cys Ser Lys Glu Lys Pro
            500                 505                 510

Lys Cys Ala Lys Cys Leu Lys Asn Asn Trp Glu Cys Arg Tyr Ser Pro
            515                 520                 525

Lys Thr Lys Arg Ser Pro Leu Thr Arg Ala His Leu Thr Glu Val Glu
530                 535                 540

Ser Arg Leu Glu Arg Leu Glu Gln Leu Phe Leu Leu Ile Phe Pro Arg
545                 550                 555                 560

Glu Asp Leu Asp Met Ile Leu Lys Met Asp Ser Leu Gln Asp Ile Lys
            565                 570                 575

Ala Leu Leu Thr Gly Leu Phe Val Gln Asp Asn Val Asn Lys Asp Ala
            580                 585                 590

Val Thr Asp Arg Leu Ala Ser Val Glu Thr Asp Met Pro Leu Thr Leu
            595                 600                 605

Arg Gln His Arg Ile Ser Ala Thr Ser Ser Glu Glu Ser Ser Asn
            610                 615                 620

Lys Gly Gln Arg Gln Leu Thr Val Ser Ala Ala Gly Gly Ser Gly
625                 630                 635                 640

Gly Ser Gly Gly Ser Asp Ala Leu Asp Asp Phe Asp Leu Asp Met Leu
            645                 650                 655

Gly Ser Asp Ala Leu Asp Asp Phe Asp Leu Asp Met Leu Gly Ser Asp
            660                 665                 670

Ala Leu Asp Asp Phe Asp Leu Asp Met Leu Gly Ser Asp Ala Leu Asp
            675                 680                 685

Asp Phe Asp Leu Asp Met Leu Gly Ser
690                 695

<210> SEQ ID NO 6
<211> LENGTH: 539
<212> TYPE: PRT
<213> ORGANISM: Artificial Sequence
<220> FEATURE:
```

<223> OTHER INFORMATION: Synthetic construct

<400> SEQUENCE: 6

```
Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
    130                 135                 140

Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Phe Met Tyr Val
    290                 295                 300

Ala Ala Ala Ala Phe Val Leu Leu Phe Phe Val Gly Cys Gly Val Leu
305                 310                 315                 320

Leu Ser Lys Arg Lys Arg Lys His Met Lys Leu Leu Ser Ser Ile Glu
                325                 330                 335

Gln Ala Cys Asp Ile Cys Arg Leu Lys Lys Leu Lys Cys Ser Lys Glu
            340                 345                 350

Lys Pro Lys Cys Ala Lys Cys Leu Lys Asn Asn Trp Glu Cys Arg Tyr
        355                 360                 365

Ser Pro Lys Thr Lys Arg Ser Pro Leu Thr Arg Ala His Leu Thr Glu
    370                 375                 380

Val Glu Ser Arg Leu Glu Arg Leu Glu Gln Leu Phe Leu Leu Ile Phe
385                 390                 395                 400
```

```
Pro Arg Glu Asp Leu Asp Met Ile Leu Lys Met Asp Ser Leu Gln Asp
            405                 410                 415

Ile Lys Ala Leu Leu Thr Gly Leu Phe Val Gln Asp Asn Val Asn Lys
            420                 425                 430

Asp Ala Val Thr Asp Arg Leu Ala Ser Val Glu Thr Asp Met Pro Leu
            435                 440                 445

Thr Leu Arg Gln His Arg Ile Ser Ala Thr Ser Ser Glu Glu Ser
    450                 455                 460

Ser Asn Lys Gly Gln Arg Gln Leu Thr Val Ser Ala Ala Ala Gly Gly
465                 470                 475                 480

Ser Gly Gly Ser Gly Gly Ser Asp Ala Leu Asp Asp Phe Asp Leu Asp
            485                 490                 495

Met Leu Gly Ser Asp Ala Leu Asp Asp Phe Asp Leu Asp Met Leu Gly
            500                 505                 510

Ser Asp Ala Leu Asp Asp Phe Asp Leu Asp Met Leu Gly Ser Asp Ala
            515                 520                 525

Leu Asp Asp Phe Asp Leu Asp Met Leu Gly Ser
            530                 535
```

<210> SEQ ID NO 7
<211> LENGTH: 542
<212> TYPE: PRT
<213> ORGANISM: Artificial Sequence
<220> FEATURE:
<223> OTHER INFORMATION: Synthetic construct

<400> SEQUENCE: 7

```
Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Gln
            20                  25                  30

Val Gln Leu Gln Gln Ser Gly Gly Gly Leu Val Lys Pro Gly Gly Ser
        35                  40                  45

Leu Arg Leu Ser Cys Ala Ala Ser Gly Phe Thr Phe Ser Ser Tyr Ala
    50                  55                  60

Met His Trp Val Arg Gln Ala Pro Gly Lys Gly Leu Glu Trp Val Ala
65                  70                  75                  80

Val Ile Ser Tyr Asp Gly Ser Asn Lys Tyr Tyr Ala Asp Ser Val Lys
                85                  90                  95

Gly Arg Phe Thr Ile Ser Arg Asp Asn Ser Lys Asn Thr Leu Tyr Leu
            100                 105                 110

Gln Met Asp Ser Leu Arg Ala Glu Asp Thr Ala Val Tyr Tyr Cys Ala
        115                 120                 125

Lys Glu Gly Asp Ser Ser Arg Trp Ser Tyr Asp Leu Trp Gly Arg Gly
    130                 135                 140

Thr Leu Val Thr Val Ser Ser Gly Gly Gly Ser Gly Gly Gly Gly
145                 150                 155                 160

Ser Gly Gly Gly Gly Ser Gln Ser Ala Leu Thr Gln Pro Ala Ser Val
            165                 170                 175

Ser Gly Ser Pro Gly Gln Ser Ile Thr Ile Ser Cys Thr Gly Thr Ser
        180                 185                 190

Ser Asp Val Gly Gly Tyr Asn Tyr Val Ser Trp Tyr Gln Gln His Pro
    195                 200                 205

Gly Lys Ala Pro Lys Val Met Ile Tyr Asp Val Thr Asn Arg Pro Ser
    210                 215                 220
```

Gly Val Ser Asn Arg Phe Gly Ser Lys Ser Gly Asn Thr Ala Ser
225                 230                 235                 240

Leu Thr Ile Ser Gly Leu Gln Ala Glu Asp Glu Ala Asp Tyr Tyr Cys
            245                 250                 255

Ser Ser Tyr Thr Ile Ala Ser Thr Leu Val Val Phe Gly Gly Gly Thr
                260                 265                 270

Lys Leu Thr Val Leu Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
    290                 295                 300

Phe Met Tyr Val Ala Ala Ala Phe Val Leu Leu Phe Phe Val Gly
305                 310                 315                 320

Cys Gly Val Leu Leu Ser Arg Lys Arg Arg Met Lys Leu Leu Ser
            325                 330                 335

Ser Ile Glu Gln Ala Cys Asp Ile Cys Arg Leu Lys Lys Leu Lys Cys
                340                 345                 350

Ser Lys Glu Lys Pro Lys Cys Ala Lys Cys Leu Lys Asn Asn Trp Glu
        355                 360                 365

Cys Arg Tyr Ser Pro Lys Thr Lys Arg Ser Pro Leu Thr Arg Ala His
    370                 375                 380

Leu Thr Glu Val Glu Ser Arg Leu Glu Arg Leu Glu Gln Leu Phe Leu
385                 390                 395                 400

Leu Ile Phe Pro Arg Glu Asp Leu Asp Met Ile Leu Lys Met Asp Ser
            405                 410                 415

Leu Gln Asp Ile Lys Ala Leu Leu Thr Gly Leu Phe Val Gln Asp Asn
                420                 425                 430

Val Asn Lys Asp Ala Val Thr Asp Arg Leu Ala Ser Val Glu Thr Asp
        435                 440                 445

Met Pro Leu Thr Leu Arg Gln His Arg Ile Ser Ala Thr Ser Ser Ser
    450                 455                 460

Glu Glu Ser Ser Asn Lys Gly Gln Arg Gln Leu Thr Val Ser Ala Ala
465                 470                 475                 480

Ala Gly Ser Gly Gly Ser Gly Gly Ser Asp Ala Leu Asp Asp Phe
            485                 490                 495

Asp Leu Asp Met Leu Gly Ser Asp Ala Leu Asp Asp Phe Asp Leu Asp
                500                 505                 510

Met Leu Gly Ser Asp Ala Leu Asp Asp Phe Asp Leu Asp Met Leu Gly
        515                 520                 525

Ser Asp Ala Leu Asp Asp Phe Asp Leu Asp Met Leu Gly Ser
    530                 535                 540

<210> SEQ ID NO 8
<211> LENGTH: 525
<212> TYPE: PRT
<213> ORGANISM: Artificial Sequence
<220> FEATURE:
<223> OTHER INFORMATION: Synthetic construct

<400> SEQUENCE: 8

Met Glu Thr Asp Thr Leu Leu Leu Trp Val Leu Leu Leu Trp Val Pro
1               5                   10                  15

Gly Ser Thr Gly Asp Met Val Ser Lys Gly Glu Glu Leu Phe Thr Gly
            20                  25                  30

Val Val Pro Ile Leu Val Glu Leu Asp Gly Asp Val Asn Gly His Lys
        35                  40                  45

```
Phe Ser Val Ser Gly Glu Gly Glu Gly Asp Ala Thr Tyr Gly Lys Leu
 50                  55                  60

Thr Leu Lys Phe Ile Cys Thr Thr Gly Lys Leu Pro Val Pro Trp Pro
 65                  70                  75                  80

Thr Leu Val Thr Thr Leu Thr Tyr Gly Val Gln Cys Phe Ser Arg Tyr
                 85                  90                  95

Pro Asp His Met Lys Gln His Asp Phe Phe Lys Ser Ala Met Pro Glu
                100                 105                 110

Gly Tyr Val Gln Glu Arg Thr Ile Phe Phe Lys Asp Asp Gly Asn Tyr
                115                 120                 125

Lys Thr Arg Ala Glu Val Lys Phe Glu Gly Asp Thr Leu Val Asn Arg
130                 135                 140

Ile Glu Leu Lys Gly Ile Asp Phe Lys Glu Asp Gly Asn Ile Leu Gly
145                 150                 155                 160

His Lys Leu Glu Tyr Asn Tyr Asn Ser His Asn Val Tyr Ile Met Ala
                165                 170                 175

Asp Lys Gln Lys Asn Gly Ile Lys Val Asn Phe Lys Ile Arg His Asn
                180                 185                 190

Ile Glu Asp Gly Ser Val Gln Leu Ala Asp His Tyr Gln Gln Asn Thr
                195                 200                 205

Pro Ile Gly Asp Gly Pro Val Leu Leu Pro Asp Asn His Tyr Leu Ser
210                 215                 220

Thr Gln Ser Ala Leu Ser Lys Asp Pro Asn Glu Lys Arg Asp His Met
225                 230                 235                 240

Val Leu Leu Glu Phe Val Thr Ala Ala Gly Ile Thr Leu Gly Met Asp
                245                 250                 255

Glu Leu Tyr Lys Thr Thr Thr Pro Ala Pro Arg Pro Pro Thr Pro Ala
                260                 265                 270

Pro Thr Ile Ala Ser Gln Pro Leu Ser Leu Arg Pro Glu Ala Cys Phe
                275                 280                 285

Met Tyr Val Ala Ala Ala Phe Val Leu Leu Phe Phe Val Gly Cys
                290                 295                 300

Gly Val Leu Leu Ser Arg Lys Arg Arg Met Lys Leu Leu Ser Ser
305                 310                 315                 320

Ile Glu Gln Ala Cys Asp Ile Cys Arg Leu Lys Lys Leu Lys Cys Ser
                325                 330                 335

Lys Glu Lys Pro Lys Cys Ala Lys Cys Leu Lys Asn Asn Trp Glu Cys
                340                 345                 350

Arg Tyr Ser Pro Lys Thr Lys Arg Ser Pro Leu Thr Arg Ala His Leu
                355                 360                 365

Thr Glu Val Glu Ser Arg Leu Glu Arg Leu Glu Gln Leu Phe Leu Leu
                370                 375                 380

Ile Phe Pro Arg Glu Asp Leu Asp Met Ile Leu Lys Met Asp Ser Leu
385                 390                 395                 400

Gln Asp Ile Lys Ala Leu Leu Thr Gly Leu Phe Val Gln Asp Asn Val
                405                 410                 415

Asn Lys Asp Ala Val Thr Asp Arg Leu Ala Ser Val Glu Thr Asp Met
                420                 425                 430

Pro Leu Thr Leu Arg Gln His Arg Ile Ser Ala Thr Ser Ser Ser Glu
                435                 440                 445

Glu Ser Ser Asn Lys Gly Gln Arg Gln Leu Thr Val Ser Ala Ala Ala
450                 455                 460
```

Gly Gly Ser Gly Gly Ser Gly Ser Asp Ala Leu Asp Asp Phe Asp
465                 470                 475                 480

Leu Asp Met Leu Gly Ser Asp Ala Leu Asp Asp Phe Asp Leu Asp Met
                485                 490                 495

Leu Gly Ser Asp Ala Leu Asp Asp Phe Asp Leu Asp Met Leu Gly Ser
            500                 505                 510

Asp Ala Leu Asp Asp Phe Asp Leu Asp Met Leu Gly Ser
        515                 520                 525

<210> SEQ ID NO 9
<211> LENGTH: 273
<212> TYPE: PRT
<213> ORGANISM: Artificial Sequence
<220> FEATURE:
<223> OTHER INFORMATION: Synthetic construct

<400> SEQUENCE: 9

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Ser Gly
130                 135                 140

Gly Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser

<210> SEQ ID NO 10
<211> LENGTH: 277

```
<212> TYPE: PRT
<213> ORGANISM: Artificial Sequence
<220> FEATURE:
<223> OTHER INFORMATION: Synthetic construct

<400> SEQUENCE: 10

Met Ala Leu Pro Val Thr Ala Leu Leu Pro Leu Ala Leu Leu Leu
1               5                   10                  15

His Ala Ala Arg Pro Glu Gln Lys Leu Ile Ser Glu Glu Asp Leu Gln
            20                  25                  30

Val Gln Leu Gln Gln Ser Gly Gly Leu Val Lys Pro Gly Gly Ser
        35                  40                  45

Leu Arg Leu Ser Cys Ala Ala Ser Gly Phe Thr Phe Ser Ser Tyr Ala
    50                  55                  60

Met His Trp Val Arg Gln Ala Pro Gly Lys Gly Leu Glu Trp Val Ala
65                  70                  75                  80

Val Ile Ser Tyr Asp Gly Ser Asn Lys Tyr Tyr Ala Asp Ser Val Lys
                85                  90                  95

Gly Arg Phe Thr Ile Ser Arg Asp Asn Ser Lys Asn Thr Leu Tyr Leu
            100                 105                 110

Gln Met Asp Ser Leu Arg Ala Glu Asp Thr Ala Val Tyr Tyr Cys Ala
        115                 120                 125

Lys Glu Gly Asp Ser Ser Arg Trp Ser Tyr Asp Leu Trp Gly Arg Gly
    130                 135                 140

Thr Leu Val Thr Val Ser Ser Gly Gly Gly Ser Gly Gly Gly Gly
145                 150                 155                 160

Ser Gly Gly Gly Gly Ser Gln Ser Ala Leu Thr Gln Pro Ala Ser Val
                165                 170                 175

Ser Gly Ser Pro Gly Gln Ser Ile Thr Ile Ser Cys Thr Gly Thr Ser
            180                 185                 190

Ser Asp Val Gly Gly Tyr Asn Tyr Val Ser Trp Tyr Gln Gln His Pro
        195                 200                 205

Gly Lys Ala Pro Lys Val Met Ile Tyr Asp Val Thr Asn Arg Pro Ser
    210                 215                 220

Gly Val Ser Asn Arg Phe Ser Gly Ser Lys Ser Gly Asn Thr Ala Ser
225                 230                 235                 240

Leu Thr Ile Ser Gly Leu Gln Ala Glu Asp Glu Ala Asp Tyr Tyr Cys
                245                 250                 255

Ser Ser Tyr Thr Ile Ala Ser Thr Leu Val Val Phe Gly Gly Gly Thr
            260                 265                 270

Lys Leu Thr Val Leu
        275

<210> SEQ ID NO 11
<211> LENGTH: 260
<212> TYPE: PRT
<213> ORGANISM: Artificial Sequence
<220> FEATURE:
<223> OTHER INFORMATION: Synthetic construct

<400> SEQUENCE: 11

Met Glu Thr Asp Thr Leu Leu Leu Trp Val Leu Leu Leu Trp Val Pro
1               5                   10                  15

Gly Ser Thr Gly Asp Met Val Ser Lys Gly Glu Glu Leu Phe Thr Gly
            20                  25                  30

Val Val Pro Ile Leu Val Glu Leu Asp Gly Asp Val Asn Gly His Lys
        35                  40                  45
```

```
Phe Ser Val Ser Gly Glu Gly Asp Ala Thr Tyr Gly Lys Leu
    50                  55                  60

Thr Leu Lys Phe Ile Cys Thr Thr Gly Lys Leu Pro Val Pro Trp Pro
65                  70                  75                  80

Thr Leu Val Thr Thr Leu Thr Tyr Gly Val Gln Cys Phe Ser Arg Tyr
                85                  90                  95

Pro Asp His Met Lys Gln His Asp Phe Phe Lys Ser Ala Met Pro Glu
                100                 105                 110

Gly Tyr Val Gln Glu Arg Thr Ile Phe Phe Lys Asp Asp Gly Asn Tyr
            115                 120                 125

Lys Thr Arg Ala Glu Val Lys Phe Glu Gly Asp Thr Leu Val Asn Arg
            130                 135                 140

Ile Glu Leu Lys Gly Ile Asp Phe Lys Glu Asp Gly Asn Ile Leu Gly
145                 150                 155                 160

His Lys Leu Glu Tyr Asn Tyr Asn Ser His Asn Val Tyr Ile Met Ala
                165                 170                 175

Asp Lys Gln Lys Asn Gly Ile Lys Val Asn Phe Lys Ile Arg His Asn
                180                 185                 190

Ile Glu Asp Gly Ser Val Gln Leu Ala Asp His Tyr Gln Gln Asn Thr
            195                 200                 205

Pro Ile Gly Asp Gly Pro Val Leu Leu Pro Asp Asn His Tyr Leu Ser
    210                 215                 220

Thr Gln Ser Ala Leu Ser Lys Asp Pro Asn Glu Lys Arg Asp His Met
225                 230                 235                 240

Val Leu Leu Glu Phe Val Thr Ala Ala Gly Ile Thr Leu Gly Met Asp
                245                 250                 255

Glu Leu Tyr Lys
            260

<210> SEQ ID NO 12
<211> LENGTH: 45
<212> TYPE: PRT
<213> ORGANISM: Artificial Sequence
<220> FEATURE:
<223> OTHER INFORMATION: Synthetic construct

<400> SEQUENCE: 12

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
            35                  40                  45

<210> SEQ ID NO 13
<211> LENGTH: 27
<212> TYPE: PRT
<213> ORGANISM: Artificial Sequence
<220> FEATURE:
<223> OTHER INFORMATION: Synthetic construct

<400> SEQUENCE: 13

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys
            20                  25
```

<210> SEQ ID NO 14
<211> LENGTH: 39
<212> TYPE: PRT
<213> ORGANISM: Artificial Sequence
<220> FEATURE:
<223> OTHER INFORMATION: Synthetic construct

<400> SEQUENCE: 14

```
Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
            35
```

<210> SEQ ID NO 15
<211> LENGTH: 27
<212> TYPE: PRT
<213> ORGANISM: Artificial Sequence
<220> FEATURE:
<223> OTHER INFORMATION: Synthetic construct

<400> SEQUENCE: 15

```
Gly Gly Gly Gly Ser Gly Gly Gly Ser Gly Gly Gly Ser Glu
1               5                   10                  15

Ser Lys Tyr Gly Pro Pro Cys Pro Pro Cys Pro
            20                  25
```

<210> SEQ ID NO 16
<211> LENGTH: 186
<212> TYPE: PRT
<213> ORGANISM: Artificial Sequence
<220> FEATURE:
<223> OTHER INFORMATION: Synthetic construct

<400> SEQUENCE: 16

```
Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
            35                  40                  45

Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
            115                 120                 125

Pro Ala Ser Asn Ser Ser Asp Ala Ile Cys Glu Asp Arg Asp Pro Pro
        130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala
            180                 185
```

```
<210> SEQ ID NO 17
<211> LENGTH: 22
<212> TYPE: PRT
<213> ORGANISM: Artificial Sequence
<220> FEATURE:
<223> OTHER INFORMATION: Synthetic construct

<400> SEQUENCE: 17

Phe Met Tyr Val Ala Ala Ala Phe Val Leu Leu Phe Phe Val Gly
1               5                   10                  15

Cys Gly Val Leu Leu Ser
            20

<210> SEQ ID NO 18
<211> LENGTH: 5
<212> TYPE: PRT
<213> ORGANISM: Artificial Sequence
<220> FEATURE:
<223> OTHER INFORMATION: Synthetic construct

<400> SEQUENCE: 18

Arg Lys Arg Arg Arg
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic construct

<400> SEQUENCE: 19

Lys Arg Lys Arg Lys His
1               5

<210> SEQ ID NO 20
<211> LENGTH: 211
<212> TYPE: PRT
<213> ORGANISM: Artificial Sequence
<220> FEATURE:
<223> OTHER INFORMATION: Synthetic construct

<400> SEQUENCE: 20

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
                20                  25                  30

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
        50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
                100                 105                 110

Ser Val Glu Thr Asp Met Pro Leu Thr Leu Arg Gln His Arg Ile Ser
            115                 120                 125

Ala Thr Ser Ser Ser Glu Glu Ser Ser Asn Lys Gly Gln Arg Gln Leu
        130                 135                 140
```

```
Thr Val Ser Ala Ala Gly Gly Ser Gly Gly Ser Asp
145                 150                 155                 160

Ala Leu Asp Asp Phe Asp Leu Asp Met Leu Gly Ser Asp Ala Leu Asp
                165                 170                 175

Asp Phe Asp Leu Asp Met Leu Gly Ser Asp Ala Leu Asp Asp Phe Asp
                180                 185                 190

Leu Asp Met Leu Gly Ser Asp Ala Leu Asp Asp Phe Asp Leu Asp Met
        195                 200                 205

Leu Gly Ser
    210

<210> SEQ ID NO 21
<211> LENGTH: 21
<212> TYPE: PRT
<213> ORGANISM: Artificial Sequence
<220> FEATURE:
<223> OTHER INFORMATION: Synthetic construct

<400> SEQUENCE: 21

Met Ala Leu Pro Val Thr Ala Leu Leu Leu Pro Leu Ala Leu Leu Leu
1               5                   10                  15

His Ala Ala Arg Pro
            20

<210> SEQ ID NO 22
<211> LENGTH: 10
<212> TYPE: PRT
<213> ORGANISM: Artificial Sequence
<220> FEATURE:
<223> OTHER INFORMATION: Synthetic construct

<400> SEQUENCE: 22

Glu Gln Lys Leu Ile Ser Glu Glu Asp Leu
1               5                   10

<210> SEQ ID NO 23
<211> LENGTH: 20
<212> TYPE: DNA
<213> ORGANISM: Artificial Sequence
<220> FEATURE:
<223> OTHER INFORMATION: Synthetic construct

<400> SEQUENCE: 23
ggagcactgt cctccgaacg                                                    20

<210> SEQ ID NO 24
<211> LENGTH: 537
<212> TYPE: PRT
<213> ORGANISM: Artificial Sequence
<220> FEATURE:
<223> OTHER INFORMATION: Synthetic construct

<400> SEQUENCE: 24

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60
```

-continued

```
Asn Trp Tyr Gln Gln Lys Pro Asp Gly Thr Val Lys Leu Leu Ile Tyr
 65                  70                  75                  80

His Thr Ser Arg Leu His Ser Gly Val Pro Ser Arg Phe Ser Gly Ser
                 85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
            115                 120                 125

Phe Gly Gly Gly Thr Lys Leu Glu Ile Thr Gly Gly Gly Gly Ser Gly
        130                 135                 140

Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser Thr Thr Thr Pro Ala Pro Arg Pro Pro Thr Pro Ala Pro Thr Ile
        275                 280                 285

Ala Ser Gln Pro Leu Ser Leu Arg Pro Glu Ala Phe Met Tyr Val Ala
    290                 295                 300

Ala Ala Ala Phe Val Leu Leu Phe Phe Val Gly Cys Gly Val Leu Leu
305                 310                 315                 320

Ser Arg Lys Arg Arg Met Lys Leu Leu Ser Ser Ile Glu Gln Ala
                325                 330                 335

Cys Asp Ile Cys Arg Leu Lys Lys Leu Lys Cys Ser Lys Glu Lys Pro
            340                 345                 350

Lys Cys Ala Lys Cys Leu Lys Asn Asn Trp Glu Cys Arg Tyr Ser Pro
        355                 360                 365

Lys Thr Lys Arg Ser Pro Leu Thr Arg Ala His Leu Thr Glu Val Glu
    370                 375                 380

Ser Arg Leu Glu Arg Leu Glu Gln Leu Phe Leu Leu Ile Phe Pro Arg
385                 390                 395                 400

Glu Asp Leu Asp Met Ile Leu Lys Met Asp Ser Leu Gln Asp Ile Lys
                405                 410                 415

Ala Leu Leu Thr Gly Leu Phe Val Gln Asp Asn Val Asn Lys Asp Ala
            420                 425                 430

Val Thr Asp Arg Leu Ala Ser Val Glu Thr Asp Met Pro Leu Thr Leu
        435                 440                 445

Arg Gln His Arg Ile Ser Ala Thr Ser Ser Ser Glu Glu Ser Ser Asn
    450                 455                 460

Lys Gly Gln Arg Gln Leu Thr Val Ser Ala Ala Ala Gly Gly Ser Gly
465                 470                 475                 480
```

```
Gly Ser Gly Gly Ser Asp Ala Leu Asp Asp Phe Asp Leu Asp Met Leu
                485                 490                 495

Gly Ser Asp Ala Leu Asp Asp Phe Asp Leu Asp Met Leu Gly Ser Asp
            500                 505                 510

Ala Leu Asp Asp Phe Asp Leu Asp Met Leu Gly Ser Asp Ala Leu Asp
        515                 520                 525

Asp Phe Asp Leu Asp Met Leu Gly Ser
    530                 535

<210> SEQ ID NO 25
<211> LENGTH: 529
<212> TYPE: PRT
<213> ORGANISM: Artificial Sequence
<220> FEATURE:
<223> OTHER INFORMATION: Synthetic construct

<400> SEQUENCE: 25

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
    130                 135                 140

Gly Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser Arg Pro Ala Ala Gly Gly Ala Val His Thr Arg Gly Leu Asp Phe
        275                 280                 285

Ala Cys Asp Phe Met Tyr Val Ala Ala Ala Phe Val Leu Leu Phe
    290                 295                 300
```

```
Phe Val Gly Cys Gly Val Leu Leu Ser Arg Lys Arg Arg Met Lys
305                 310                 315                 320

Leu Leu Ser Ser Ile Glu Gln Ala Cys Asp Ile Cys Arg Leu Lys Lys
            325                 330                 335

Leu Lys Cys Ser Lys Glu Lys Pro Lys Cys Ala Lys Cys Leu Lys Asn
            340                 345                 350

Asn Trp Glu Cys Arg Tyr Ser Pro Lys Thr Lys Arg Ser Pro Leu Thr
            355                 360                 365

Arg Ala His Leu Thr Glu Val Glu Ser Arg Leu Glu Arg Leu Glu Gln
            370                 375                 380

Leu Phe Leu Leu Ile Phe Pro Arg Glu Asp Leu Asp Met Ile Leu Lys
385                 390                 395                 400

Met Asp Ser Leu Gln Asp Ile Lys Ala Leu Leu Thr Gly Leu Phe Val
            405                 410                 415

Gln Asp Asn Val Asn Lys Asp Ala Val Thr Asp Arg Leu Ala Ser Val
            420                 425                 430

Glu Thr Asp Met Pro Leu Thr Leu Arg Gln His Arg Ile Ser Ala Thr
            435                 440                 445

Ser Ser Ser Glu Glu Ser Ser Asn Lys Gly Gln Arg Gln Leu Thr Val
450                 455                 460

Ser Ala Ala Gly Gly Ser Gly Ser Gly Ser Asp Ala Leu
465                 470                 475                 480

Asp Asp Phe Asp Leu Asp Met Leu Gly Ser Asp Ala Leu Asp Asp Phe
            485                 490                 495

Asp Leu Asp Met Leu Gly Ser Asp Ala Leu Asp Asp Phe Asp Leu Asp
            500                 505                 510

Met Leu Gly Ser Asp Ala Leu Asp Asp Phe Asp Leu Asp Met Leu Gly
            515                 520                 525

Ser

<210> SEQ ID NO 26
<211> LENGTH: 530
<212> TYPE: PRT
<213> ORGANISM: Artificial Sequence
<220> FEATURE:
<223> OTHER INFORMATION: Synthetic construct

<400> SEQUENCE: 26

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
            35                  40                  45

Arg Val Thr Ile Ser Cys Arg Ala Ser Gln Asp Ile Ser Lys Tyr Leu
50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
            85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
            115                 120                 125
```

```
Phe Gly Gly Gly Thr Lys Leu Glu Ile Thr Gly Gly Ser Gly
    130                 135                 140
Gly Gly Gly Ser Gly Gly Gly Ser Glu Val Lys Leu Gln Glu Ser
145             150                 155                 160
Gly Pro Gly Leu Val Ala Pro Ser Gln Ser Leu Ser Val Thr Cys Thr
                165                 170                 175
Val Ser Gly Val Ser Leu Pro Asp Tyr Gly Val Ser Trp Ile Arg Gln
            180                 185                 190
Pro Pro Arg Lys Gly Leu Glu Trp Leu Gly Val Ile Trp Gly Ser Glu
        195                 200                 205
Thr Thr Tyr Tyr Asn Ser Ala Leu Lys Ser Arg Leu Thr Ile Ile Lys
    210                 215                 220
Asp Asn Ser Lys Ser Gln Val Phe Leu Lys Met Asn Ser Leu Gln Thr
225             230                 235                 240
Asp Asp Thr Ala Ile Tyr Tyr Cys Ala Lys His Tyr Tyr Tyr Gly Gly
                245                 250                 255
Ser Tyr Ala Met Asp Tyr Trp Gly Gln Gly Thr Ser Val Thr Val Ser
            260                 265                 270
Ser Cys Arg Pro Ala Ala Gly Gly Ala Val His Thr Arg Gly Leu Asp
        275                 280                 285
Phe Ala Cys Asp Phe Met Tyr Val Ala Ala Ala Phe Val Leu Leu
    290                 295                 300
Phe Phe Val Gly Cys Gly Val Leu Leu Ser Arg Lys Arg Arg Arg Met
305             310                 315                 320
Lys Leu Leu Ser Ser Ile Glu Gln Ala Cys Asp Ile Cys Arg Leu Lys
                325                 330                 335
Lys Leu Lys Cys Ser Lys Glu Lys Pro Lys Cys Ala Lys Cys Leu Lys
            340                 345                 350
Asn Asn Trp Glu Cys Arg Tyr Ser Pro Lys Thr Lys Arg Ser Pro Leu
        355                 360                 365
Thr Arg Ala His Leu Thr Glu Val Glu Ser Arg Leu Glu Arg Leu Glu
    370                 375                 380
Gln Leu Phe Leu Leu Ile Phe Pro Arg Glu Asp Leu Asp Met Ile Leu
385             390                 395                 400
Lys Met Asp Ser Leu Gln Asp Ile Lys Ala Leu Leu Thr Gly Leu Phe
                405                 410                 415
Val Gln Asp Asn Val Asn Lys Asp Ala Val Thr Asp Arg Leu Ala Ser
            420                 425                 430
Val Glu Thr Asp Met Pro Leu Thr Leu Arg Gln His Arg Ile Ser Ala
        435                 440                 445
Thr Ser Ser Ser Glu Glu Ser Ser Asn Lys Gly Gln Arg Gln Leu Thr
    450                 455                 460
Val Ser Ala Ala Ala Gly Gly Ser Gly Gly Ser Gly Ser Asp Ala
465             470                 475                 480
Leu Asp Asp Phe Asp Leu Asp Met Leu Gly Ser Asp Ala Leu Asp Asp
                485                 490                 495
Phe Asp Leu Asp Met Leu Gly Ser Asp Ala Leu Asp Asp Phe Asp Leu
            500                 505                 510
Asp Met Leu Gly Ser Asp Ala Leu Asp Asp Phe Asp Leu Asp Met Leu
        515                 520                 525
Gly Ser
    530
```

-continued

```
<210> SEQ ID NO 27
<211> LENGTH: 543
<212> TYPE: PRT
<213> ORGANISM: Artificial Sequence
<220> FEATURE:
<223> OTHER INFORMATION: Synthetic construct

<400> SEQUENCE: 27

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Gln
            20                  25                  30

Val Gln Leu Gln Gln Ser Gly Gly Gly Leu Val Lys Pro Gly Gly Ser
        35                  40                  45

Leu Arg Leu Ser Cys Ala Ala Ser Gly Phe Thr Phe Ser Ser Tyr Ala
    50                  55                  60

Met His Trp Val Arg Gln Ala Pro Gly Lys Gly Leu Glu Trp Val Ala
65                  70                  75                  80

Val Ile Ser Tyr Asp Gly Ser Asn Lys Tyr Tyr Ala Asp Ser Val Lys
                85                  90                  95

Gly Arg Phe Thr Ile Ser Arg Asp Asn Ser Lys Asn Thr Leu Tyr Leu
            100                 105                 110

Gln Met Asp Ser Leu Arg Ala Glu Asp Thr Ala Val Tyr Tyr Cys Ala
        115                 120                 125

Lys Glu Gly Asp Ser Ser Arg Trp Ser Tyr Asp Leu Trp Gly Arg Gly
    130                 135                 140

Thr Leu Val Thr Val Ser Ser Gly Gly Gly Ser Gly Gly Gly Gly
145                 150                 155                 160

Ser Gly Gly Gly Gly Ser Gln Ser Ala Leu Thr Gln Pro Ala Ser Val
                165                 170                 175

Ser Gly Ser Pro Gly Gln Ser Ile Thr Ile Ser Cys Thr Gly Thr Ser
            180                 185                 190

Ser Asp Val Gly Gly Tyr Asn Tyr Val Ser Trp Tyr Gln Gln His Pro
        195                 200                 205

Gly Lys Ala Pro Lys Val Met Ile Tyr Asp Val Thr Asn Arg Pro Ser
    210                 215                 220

Gly Val Ser Asn Arg Phe Ser Gly Ser Lys Ser Gly Asn Thr Ala Ser
225                 230                 235                 240

Leu Thr Ile Ser Gly Leu Gln Ala Glu Asp Glu Ala Asp Tyr Tyr Cys
                245                 250                 255

Ser Ser Tyr Thr Ile Ala Ser Thr Leu Val Val Phe Gly Gly Gly Thr
            260                 265                 270

Lys Leu Thr Val Leu Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
    290                 295                 300

Phe Met Tyr Val Ala Ala Ala Ala Phe Val Leu Leu Phe Phe Val Gly
305                 310                 315                 320

Cys Gly Val Leu Leu Ser Arg Lys Arg Lys His Met Lys Leu Leu
                325                 330                 335

Ser Ser Ile Glu Gln Ala Cys Asp Ile Cys Arg Leu Lys Lys Leu Lys
            340                 345                 350

Cys Ser Lys Glu Lys Pro Lys Cys Ala Lys Cys Leu Lys Asn Asn Trp
        355                 360                 365
```

```
Glu Cys Arg Tyr Ser Pro Lys Thr Lys Arg Ser Pro Leu Thr Arg Ala
        370                 375                 380

His Leu Thr Glu Val Glu Ser Arg Leu Glu Arg Leu Glu Gln Leu Phe
385                 390                 395                 400

Leu Leu Ile Phe Pro Arg Glu Asp Leu Asp Met Ile Leu Lys Met Asp
            405                 410                 415

Ser Leu Gln Asp Ile Lys Ala Leu Leu Thr Gly Leu Phe Val Gln Asp
        420                 425                 430

Asn Val Asn Lys Asp Ala Val Thr Asp Arg Leu Ala Ser Val Glu Thr
            435                 440                 445

Asp Met Pro Leu Thr Leu Arg Gln His Arg Ile Ser Ala Thr Ser Ser
        450                 455                 460

Ser Glu Glu Ser Ser Asn Lys Gly Gln Arg Gln Leu Thr Val Ser Ala
465                 470                 475                 480

Ala Ala Gly Gly Ser Gly Gly Ser Gly Gly Ser Asp Ala Leu Asp Asp
            485                 490                 495

Phe Asp Leu Asp Met Leu Gly Ser Asp Ala Leu Asp Asp Phe Asp Leu
            500                 505                 510

Asp Met Leu Gly Ser Asp Ala Leu Asp Asp Phe Asp Leu Asp Met Leu
        515                 520                 525

Gly Ser Asp Ala Leu Asp Asp Phe Asp Leu Asp Met Leu Gly Ser
        530                 535                 540

<210> SEQ ID NO 28
<211> LENGTH: 542
<212> TYPE: PRT
<213> ORGANISM: Artificial Sequence
<220> FEATURE:
<223> OTHER INFORMATION: Synthetic construct

<400> SEQUENCE: 28

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Gln
            20                  25                  30

Val Gln Leu Val Gln Ser Gly Ala Glu Val Lys Lys Pro Gly Ala Ser
        35                  40                  45

Val Lys Val Ser Cys Lys Ala Ser Gly Tyr Ser Phe Pro Asp Tyr Tyr
    50                  55                  60

Ile Asn Trp Val Arg Gln Ala Pro Gly Gln Gly Leu Glu Trp Met Gly
65                  70                  75                  80

Trp Ile Tyr Phe Ala Ser Gly Asn Ser Glu Tyr Asn Gln Lys Phe Thr
                85                  90                  95

Gly Arg Val Thr Met Thr Arg Asp Thr Ser Ile Asn Thr Ala Tyr Met
            100                 105                 110

Glu Leu Ser Ser Leu Thr Ser Glu Asp Thr Ala Val Tyr Phe Cys Ala
        115                 120                 125

Ser Leu Tyr Asp Tyr Asp Trp Tyr Phe Asp Val Trp Gly Gln Gly Thr
    130                 135                 140

Met Val Thr Val Ser Ser Gly Gly Gly Ser Gly Gly Gly Gly Gly Ser
145                 150                 155                 160

Gly Gly Gly Gly Ser Asp Ile Val Met Thr Gln Thr Pro Leu Ser Leu
                165                 170                 175

Ser Val Thr Pro Gly Gln Pro Ala Ser Ile Ser Cys Lys Ser Ser Gln
            180                 185                 190
```

```
Ser Leu Val His Ser Asn Gly Asn Thr Tyr Leu His Trp Tyr Leu Gln
            195                 200                 205

Lys Pro Gly Gln Ser Pro Gln Leu Leu Ile Tyr Lys Val Ser Asn Arg
        210                 215                 220

Phe Ser Gly Val Pro Asp Arg Phe Ser Gly Ser Gly Ser Gly Thr Asp
225                 230                 235                 240

Phe Thr Leu Lys Ile Ser Arg Val Glu Ala Glu Asp Val Gly Ile Tyr
                245                 250                 255

Tyr Cys Ser Gln Ser Ser Ile Tyr Pro Trp Thr Phe Gly Gln Gly Thr
            260                 265                 270

Lys Leu Glu Ile Lys Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
290                 295                 300

Phe Met Tyr Val Ala Ala Ala Phe Val Leu Leu Phe Phe Val Gly
305                 310                 315                 320

Cys Gly Val Leu Leu Ser Arg Lys Arg Arg Met Lys Leu Leu Ser
                325                 330                 335

Ser Ile Glu Gln Ala Cys Asp Ile Cys Arg Leu Lys Lys Leu Lys Cys
            340                 345                 350

Ser Lys Glu Lys Pro Lys Cys Ala Lys Cys Leu Lys Asn Asn Trp Glu
        355                 360                 365

Cys Arg Tyr Ser Pro Lys Thr Lys Arg Ser Pro Leu Thr Arg Ala His
370                 375                 380

Leu Thr Glu Val Glu Ser Arg Leu Glu Arg Leu Glu Gln Leu Phe Leu
385                 390                 395                 400

Leu Ile Phe Pro Arg Glu Asp Leu Asp Met Ile Leu Lys Met Asp Ser
                405                 410                 415

Leu Gln Asp Ile Lys Ala Leu Leu Thr Gly Leu Phe Val Gln Asp Asn
            420                 425                 430

Val Asn Lys Asp Ala Val Thr Asp Arg Leu Ala Ser Val Glu Thr Asp
        435                 440                 445

Met Pro Leu Thr Leu Arg Gln His Arg Ile Ser Ala Thr Ser Ser Ser
450                 455                 460

Glu Glu Ser Ser Asn Lys Gly Gln Arg Gln Leu Thr Val Ser Ala Ala
465                 470                 475                 480

Ala Gly Gly Ser Gly Gly Ser Gly Ser Asp Ala Leu Asp Asp Phe
                485                 490                 495

Asp Leu Asp Met Leu Gly Ser Asp Ala Leu Asp Asp Phe Asp Leu Asp
            500                 505                 510

Met Leu Gly Ser Asp Ala Leu Asp Asp Phe Asp Leu Asp Met Leu Gly
        515                 520                 525

Ser Asp Ala Leu Asp Asp Phe Asp Leu Asp Met Leu Gly Ser
530                 535                 540

<210> SEQ ID NO 29
<211> LENGTH: 543
<212> TYPE: PRT
<213> ORGANISM: Artificial Sequence
<220> FEATURE:
<223> OTHER INFORMATION: Synthetic construct

<400> SEQUENCE: 29

Met Ala Leu Pro Val Thr Ala Leu Leu Leu Pro Leu Ala Leu Leu Leu
1               5                   10                  15
```

His Ala Ala Arg Pro Glu Gln Lys Leu Ile Ser Glu Asp Leu Gln
          20                  25                  30

Val Gln Leu Val Gln Ser Gly Ala Glu Val Lys Lys Pro Gly Ala Ser
            35                  40                  45

Val Lys Val Ser Cys Lys Ala Ser Gly Tyr Ser Phe Pro Asp Tyr Tyr
    50                  55                  60

Ile Asn Trp Val Arg Gln Ala Pro Gly Gln Gly Leu Glu Trp Met Gly
65                  70                  75                  80

Trp Ile Tyr Phe Ala Ser Gly Asn Ser Glu Tyr Asn Gln Lys Phe Thr
                85                  90                  95

Gly Arg Val Thr Met Thr Arg Asp Thr Ser Ile Asn Thr Ala Tyr Met
            100                 105                 110

Glu Leu Ser Ser Leu Thr Ser Glu Asp Thr Ala Val Tyr Phe Cys Ala
        115                 120                 125

Ser Leu Tyr Asp Tyr Asp Trp Tyr Phe Asp Val Trp Gly Gln Gly Thr
    130                 135                 140

Met Val Thr Val Ser Ser Gly Gly Gly Ser Gly Gly Gly Gly Ser
145                 150                 155                 160

Gly Gly Gly Gly Ser Asp Ile Val Met Thr Gln Thr Pro Leu Ser Leu
                165                 170                 175

Ser Val Thr Pro Gly Gln Pro Ala Ser Ile Ser Cys Lys Ser Ser Gln
            180                 185                 190

Ser Leu Val His Ser Asn Gly Asn Thr Tyr Leu His Trp Tyr Leu Gln
        195                 200                 205

Lys Pro Gly Gln Ser Pro Gln Leu Leu Ile Tyr Lys Val Ser Asn Arg
    210                 215                 220

Phe Ser Gly Val Pro Asp Arg Phe Ser Gly Ser Gly Ser Gly Thr Asp
225                 230                 235                 240

Phe Thr Leu Lys Ile Ser Arg Val Glu Ala Glu Asp Val Gly Ile Tyr
                245                 250                 255

Tyr Cys Ser Gln Ser Ser Ile Tyr Pro Trp Thr Phe Gly Gln Gly Thr
            260                 265                 270

Lys Leu Glu Ile Lys Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
    290                 295                 300

Phe Met Tyr Val Ala Ala Ala Phe Val Leu Leu Phe Phe Val Gly
305                 310                 315                 320

Cys Gly Val Leu Leu Ser Lys Arg Lys Arg Lys His Met Lys Leu Leu
                325                 330                 335

Ser Ser Ile Glu Gln Ala Cys Asp Ile Cys Arg Leu Lys Lys Leu Lys
            340                 345                 350

Cys Ser Lys Glu Lys Pro Lys Cys Ala Lys Cys Leu Lys Asn Asn Trp
        355                 360                 365

Glu Cys Arg Tyr Ser Pro Lys Thr Lys Arg Ser Pro Leu Thr Arg Ala
    370                 375                 380

His Leu Thr Glu Val Glu Ser Arg Leu Glu Arg Leu Glu Gln Leu Phe
385                 390                 395                 400

Leu Leu Ile Phe Pro Arg Glu Asp Leu Asp Met Ile Leu Lys Met Asp
                405                 410                 415

Ser Leu Gln Asp Ile Lys Ala Leu Leu Thr Gly Leu Phe Val Gln Asp
            420                 425                 430

```
Asn Val Asn Lys Asp Ala Val Thr Asp Arg Leu Ala Ser Val Glu Thr
            435                 440                 445
Asp Met Pro Leu Thr Leu Arg Gln His Arg Ile Ser Ala Thr Ser Ser
    450                 455                 460
Ser Glu Glu Ser Ser Asn Lys Gly Gln Arg Gln Leu Thr Val Ser Ala
465                 470                 475                 480
Ala Ala Gly Gly Ser Gly Gly Ser Gly Gly Ser Asp Ala Leu Asp Asp
                485                 490                 495
Phe Asp Leu Asp Met Leu Gly Ser Asp Ala Leu Asp Asp Phe Asp Leu
                500                 505                 510
Asp Met Leu Gly Ser Asp Ala Leu Asp Asp Phe Asp Leu Asp Met Leu
            515                 520                 525
Gly Ser Asp Ala Leu Asp Asp Phe Asp Leu Asp Met Leu Gly Ser
            530                 535                 540
```

<210> SEQ ID NO 30
<211> LENGTH: 542
<212> TYPE: PRT
<213> ORGANISM: Artificial Sequence
<220> FEATURE:
<223> OTHER INFORMATION: Synthetic construct

<400> SEQUENCE: 30

```
Met Ala Leu Pro Val Thr Ala Leu Leu Leu Pro Leu Ala Leu Leu Leu
1               5                   10                  15
His Ala Ala Arg Pro Glu Gln Lys Leu Ile Ser Glu Glu Asp Leu Asp
                20                  25                  30
Ile Gln Met Thr Gln Ser Pro Ser Ser Leu Ser Ala Ser Val Gly Asp
            35                  40                  45
Arg Val Thr Ile Thr Cys Arg Ala Ser Gln Asp Val Asn Thr Ala Val
    50                  55                  60
Ala Trp Tyr Gln Gln Lys Pro Gly Lys Ala Pro Lys Leu Leu Ile Tyr
65                  70                  75                  80
Ser Ala Ser Phe Leu Tyr Ser Gly Val Pro Ser Arg Phe Ser Gly Ser
                85                  90                  95
Arg Ser Gly Thr Asp Phe Thr Leu Thr Ile Ser Ser Leu Gln Pro Glu
                100                 105                 110
Asp Phe Ala Thr Tyr Tyr Cys Gln Gln His Tyr Thr Thr Pro Pro Thr
            115                 120                 125
Phe Gly Gln Gly Thr Lys Val Glu Ile Lys Arg Thr Gly Ser Thr Ser
    130                 135                 140
Gly Ser Gly Lys Pro Gly Ser Gly Glu Gly Ser Glu Val Gln Leu Val
145                 150                 155                 160
Glu Ser Gly Gly Gly Leu Val Gln Pro Gly Gly Ser Leu Arg Leu Ser
                165                 170                 175
Cys Ala Ala Ser Gly Phe Asn Ile Lys Asp Thr Tyr Ile His Trp Val
                180                 185                 190
Arg Gln Ala Pro Gly Lys Gly Leu Glu Trp Val Ala Arg Ile Tyr Pro
            195                 200                 205
Thr Asn Gly Tyr Thr Arg Tyr Ala Asp Ser Val Lys Gly Arg Phe Thr
    210                 215                 220
Ile Ser Ala Asp Thr Ser Lys Asn Thr Ala Tyr Leu Gln Met Asn Ser
225                 230                 235                 240
Leu Arg Ala Glu Asp Thr Ala Val Tyr Tyr Cys Ser Arg Trp Gly Gly
                245                 250                 255
```

```
Asp Gly Phe Tyr Ala Met Asp Val Trp Gly Gln Gly Thr Leu Val Thr
            260                 265                 270

Val Ser Ser Gly Ser Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
    290                 295                 300

Phe Met Tyr Val Ala Ala Ala Phe Val Leu Leu Phe Phe Val Gly
305                 310                 315                 320

Cys Gly Val Leu Leu Ser Arg Lys Arg Arg Met Lys Leu Leu Ser
                325                 330                 335

Ser Ile Glu Gln Ala Cys Asp Ile Cys Arg Leu Lys Lys Leu Lys Cys
        340                 345                 350

Ser Lys Glu Lys Pro Lys Cys Ala Lys Cys Leu Lys Asn Asn Trp Glu
        355                 360                 365

Cys Arg Tyr Ser Pro Lys Thr Lys Arg Ser Pro Leu Thr Arg Ala His
    370                 375                 380

Leu Thr Glu Val Glu Ser Arg Leu Glu Arg Leu Glu Gln Leu Phe Leu
385                 390                 395                 400

Leu Ile Phe Pro Arg Glu Asp Leu Asp Met Ile Leu Lys Met Asp Ser
                405                 410                 415

Leu Gln Asp Ile Lys Ala Leu Leu Thr Gly Leu Phe Val Gln Asp Asn
        420                 425                 430

Val Asn Lys Asp Ala Val Thr Asp Arg Leu Ala Ser Val Glu Thr Asp
        435                 440                 445

Met Pro Leu Thr Leu Arg Gln His Arg Ile Ser Ala Thr Ser Ser Ser
450                 455                 460

Glu Glu Ser Ser Asn Lys Gly Gln Arg Gln Leu Thr Val Ser Ala Ala
465                 470                 475                 480

Ala Gly Gly Ser Gly Ser Gly Gly Ser Asp Ala Leu Asp Asp Phe
                485                 490                 495

Asp Leu Asp Met Leu Gly Ser Asp Ala Leu Asp Asp Phe Asp Leu Asp
                500                 505                 510

Met Leu Gly Ser Asp Ala Leu Asp Phe Asp Leu Asp Met Leu Gly
            515                 520                 525

Ser Asp Ala Leu Asp Asp Phe Asp Leu Asp Met Leu Gly Ser
    530                 535                 540
```

```
<210> SEQ ID NO 31
<211> LENGTH: 543
<212> TYPE: PRT
<213> ORGANISM: Artificial Sequence
<220> FEATURE:
<223> OTHER INFORMATION: Synthetic construct

<400> SEQUENCE: 31

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
                20                  25                  30

Ile Gln Met Thr Gln Ser Pro Ser Ser Leu Ser Ala Ser Val Gly Asp
            35                  40                  45

Arg Val Thr Ile Thr Cys Arg Ala Ser Gln Asp Val Asn Thr Ala Val
        50                  55                  60

Ala Trp Tyr Gln Gln Lys Pro Gly Lys Ala Pro Lys Leu Leu Ile Tyr
65                  70                  75                  80
```

```
Ser Ala Ser Phe Leu Tyr Ser Gly Val Pro Ser Arg Phe Ser Gly Ser
             85                  90                  95
Arg Ser Gly Thr Asp Phe Thr Leu Thr Ile Ser Ser Leu Gln Pro Glu
        100                 105                 110
Asp Phe Ala Thr Tyr Tyr Cys Gln Gln His Tyr Thr Thr Pro Pro Thr
        115                 120                 125
Phe Gly Gln Gly Thr Lys Val Glu Ile Lys Arg Thr Gly Ser Thr Ser
    130                 135                 140
Gly Ser Gly Lys Pro Gly Ser Gly Glu Gly Ser Glu Val Gln Leu Val
145                 150                 155                 160
Glu Ser Gly Gly Gly Leu Val Gln Pro Gly Gly Ser Leu Arg Leu Ser
                165                 170                 175
Cys Ala Ala Ser Gly Phe Asn Ile Lys Asp Thr Tyr Ile His Trp Val
            180                 185                 190
Arg Gln Ala Pro Gly Lys Gly Leu Glu Trp Val Ala Arg Ile Tyr Pro
        195                 200                 205
Thr Asn Gly Tyr Thr Arg Tyr Ala Asp Ser Val Lys Gly Arg Phe Thr
    210                 215                 220
Ile Ser Ala Asp Thr Ser Lys Asn Thr Ala Tyr Leu Gln Met Asn Ser
225                 230                 235                 240
Leu Arg Ala Glu Asp Thr Ala Val Tyr Tyr Cys Ser Arg Trp Gly Gly
                245                 250                 255
Asp Gly Phe Tyr Ala Met Asp Val Trp Gly Gln Gly Thr Leu Val Thr
            260                 265                 270
Val Ser Ser Gly Ser Thr Thr Thr Pro Ala Pro Arg Pro Pro Thr Pro
        275                 280                 285
Ala Pro Thr Ile Ala Ser Gln Pro Leu Ser Leu Arg Pro Glu Ala Cys
    290                 295                 300
Phe Met Tyr Val Ala Ala Ala Phe Val Leu Leu Phe Phe Val Gly
305                 310                 315                 320
Cys Gly Val Leu Leu Ser Lys Arg Lys Arg Lys His Met Lys Leu Leu
                325                 330                 335
Ser Ser Ile Glu Gln Ala Cys Asp Ile Cys Arg Leu Lys Lys Leu Lys
            340                 345                 350
Cys Ser Lys Glu Lys Pro Lys Cys Ala Lys Cys Leu Lys Asn Asn Trp
        355                 360                 365
Glu Cys Arg Tyr Ser Pro Lys Thr Lys Arg Ser Pro Leu Thr Arg Ala
    370                 375                 380
His Leu Thr Glu Val Glu Ser Arg Leu Glu Arg Leu Glu Gln Leu Phe
385                 390                 395                 400
Leu Leu Ile Phe Pro Arg Glu Asp Leu Asp Met Ile Leu Lys Met Asp
                405                 410                 415
Ser Leu Gln Asp Ile Lys Ala Leu Leu Thr Gly Leu Phe Val Gln Asp
            420                 425                 430
Asn Val Asn Lys Asp Ala Val Thr Asp Arg Leu Ala Ser Val Glu Thr
        435                 440                 445
Asp Met Pro Leu Thr Leu Arg Gln His Arg Ile Ser Ala Thr Ser Ser
    450                 455                 460
Ser Glu Glu Ser Ser Asn Lys Gly Gln Arg Gln Leu Thr Val Ser Ala
465                 470                 475                 480
Ala Ala Gly Gly Ser Gly Gly Ser Gly Gly Ser Asp Ala Leu Asp Asp
                485                 490                 495
```

```
Phe Asp Leu Asp Met Leu Gly Ser Asp Ala Leu Asp Phe Asp Leu
                500                 505                 510

Asp Met Leu Gly Ser Asp Ala Leu Asp Asp Phe Asp Leu Asp Met Leu
            515                 520                 525

Gly Ser Asp Ala Leu Asp Asp Phe Asp Leu Asp Met Leu Gly Ser
        530                 535                 540

<210> SEQ ID NO 32
<211> LENGTH: 542
<212> TYPE: PRT
<213> ORGANISM: Artificial Sequence
<220> FEATURE:
<223> OTHER INFORMATION: Synthetic construct

<400> SEQUENCE: 32

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Ser Pro Ser Ser Leu Ser Ala Ser Val Gly Asp
        35                  40                  45

Arg Val Thr Ile Thr Cys Arg Ala Ser Gln Asp Val Asn Thr Ala Val
    50                  55                  60

Ala Trp Tyr Gln Gln Lys Pro Gly Lys Ala Pro Lys Leu Leu Ile Tyr
65                  70                  75                  80

Ser Ala Ser Phe Leu Glu Ser Gly Val Pro Ser Arg Phe Ser Gly Ser
                85                  90                  95

Arg Ser Gly Thr Asp Phe Thr Leu Thr Ile Ser Ser Leu Gln Pro Glu
            100                 105                 110

Asp Phe Ala Thr Tyr Tyr Cys Gln Gln His Tyr Thr Thr Pro Pro Thr
        115                 120                 125

Phe Gly Gln Gly Thr Lys Val Glu Ile Lys Arg Thr Gly Ser Thr Ser
    130                 135                 140

Gly Ser Gly Lys Pro Gly Ser Gly Glu Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Phe Asn Ile Lys Asp Thr Tyr Ile His Trp Val
            180                 185                 190

Arg Gln Ala Pro Gly Lys Gly Leu Glu Trp Val Ala Arg Ile Tyr Pro
        195                 200                 205

Thr Asn Gly Tyr Thr Arg Tyr Ala Asp Ser Val Lys Gly Arg Phe Thr
    210                 215                 220

Ile Ser Ala Asp Thr Ser Lys Asn Thr Ala Tyr Leu Gln Met Asn Ser
225                 230                 235                 240

Leu Arg Ala Glu Asp Thr Ala Val Tyr Tyr Cys Ser Arg Trp Gly Gly
                245                 250                 255

Asp Gly Phe Tyr Ala Met Asp Val Trp Gly Gln Gly Thr Leu Val Thr
            260                 265                 270

Val Ser Ser Gly Ser Thr Thr Pro Ala Pro Arg Pro Pro Thr Pro
        275                 280                 285

Ala Pro Thr Ile Ala Ser Gln Pro Leu Ser Leu Arg Pro Glu Ala Cys
    290                 295                 300

Phe Met Tyr Val Ala Ala Ala Phe Val Leu Leu Phe Phe Val Gly
305                 310                 315                 320
```

```
Cys Gly Val Leu Leu Ser Arg Lys Arg Arg Met Lys Leu Leu Ser
            325                 330                 335

Ser Ile Glu Gln Ala Cys Asp Ile Cys Arg Leu Lys Lys Leu Lys Cys
            340                 345                 350

Ser Lys Glu Lys Pro Lys Cys Ala Lys Cys Leu Lys Asn Asn Trp Glu
            355                 360                 365

Cys Arg Tyr Ser Pro Lys Thr Lys Arg Ser Pro Leu Thr Arg Ala His
            370                 375                 380

Leu Thr Glu Val Glu Ser Arg Leu Glu Arg Leu Glu Gln Leu Phe Leu
385                 390                 395                 400

Leu Ile Phe Pro Arg Glu Asp Leu Asp Met Ile Leu Lys Met Asp Ser
            405                 410                 415

Leu Gln Asp Ile Lys Ala Leu Leu Thr Gly Leu Phe Val Gln Asp Asn
            420                 425                 430

Val Asn Lys Asp Ala Val Thr Asp Arg Leu Ala Ser Val Glu Thr Asp
            435                 440                 445

Met Pro Leu Thr Leu Arg Gln His Arg Ile Ser Ala Thr Ser Ser Ser
            450                 455                 460

Glu Glu Ser Ser Asn Lys Gly Gln Arg Gln Leu Thr Val Ser Ala Ala
465                 470                 475                 480

Ala Gly Gly Ser Gly Gly Ser Gly Gly Ser Asp Ala Leu Asp Asp Phe
            485                 490                 495

Asp Leu Asp Met Leu Gly Ser Asp Ala Leu Asp Asp Phe Asp Leu Asp
            500                 505                 510

Met Leu Gly Ser Asp Ala Leu Asp Phe Asp Leu Asp Met Leu Gly
            515                 520                 525

Ser Asp Ala Leu Asp Asp Phe Asp Leu Asp Met Leu Gly Ser
            530                 535                 540

<210> SEQ ID NO 33
<211> LENGTH: 543
<212> TYPE: PRT
<213> ORGANISM: Artificial Sequence
<220> FEATURE:
<223> OTHER INFORMATION: Synthetic construct

<400> SEQUENCE: 33

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Ser Pro Ser Ser Leu Ser Ala Ser Val Gly Asp
            35                  40                  45

Arg Val Thr Ile Thr Cys Arg Ala Ser Gln Asp Val Asn Thr Ala Val
            50                  55                  60

Ala Trp Tyr Gln Gln Lys Pro Gly Lys Ala Pro Lys Leu Leu Ile Tyr
65                  70                  75                  80

Ser Ala Ser Phe Leu Glu Ser Gly Val Pro Ser Arg Phe Ser Gly Ser
            85                  90                  95

Arg Ser Gly Thr Asp Phe Thr Leu Thr Ile Ser Ser Leu Gln Pro Glu
            100                 105                 110

Asp Phe Ala Thr Tyr Tyr Cys Gln Gln His Tyr Thr Thr Pro Pro Thr
            115                 120                 125

Phe Gly Gln Gly Thr Lys Val Glu Ile Lys Arg Thr Gly Ser Thr Ser
            130                 135                 140
```

Gly Ser Gly Lys Pro Gly Ser Gly Glu Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Phe Asn Ile Lys Asp Thr Tyr Ile His Trp Val
            180                 185                 190

Arg Gln Ala Pro Gly Lys Gly Leu Glu Trp Val Ala Arg Ile Tyr Pro
        195                 200                 205

Thr Asn Gly Tyr Thr Arg Tyr Ala Asp Ser Val Lys Gly Arg Phe Thr
    210                 215                 220

Ile Ser Ala Asp Thr Ser Lys Asn Thr Ala Tyr Leu Gln Met Asn Ser
225                 230                 235                 240

Leu Arg Ala Glu Asp Thr Ala Val Tyr Tyr Cys Ser Arg Trp Gly Gly
                245                 250                 255

Asp Gly Phe Tyr Ala Met Asp Val Trp Gly Gln Gly Thr Leu Val Thr
            260                 265                 270

Val Ser Ser Gly Ser Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
    290                 295                 300

Phe Met Tyr Val Ala Ala Ala Phe Val Leu Leu Phe Phe Val Gly
305                 310                 315                 320

Cys Gly Val Leu Leu Ser Lys Arg Lys Arg Lys His Met Lys Leu Leu
                325                 330                 335

Ser Ser Ile Glu Gln Ala Cys Asp Ile Cys Arg Leu Lys Lys Leu Lys
            340                 345                 350

Cys Ser Lys Glu Lys Pro Lys Cys Ala Lys Cys Leu Lys Asn Asn Trp
        355                 360                 365

Glu Cys Arg Tyr Ser Pro Lys Thr Lys Arg Ser Pro Leu Thr Arg Ala
370                 375                 380

His Leu Thr Glu Val Glu Ser Arg Leu Glu Arg Leu Glu Gln Leu Phe
385                 390                 395                 400

Leu Leu Ile Phe Pro Arg Glu Asp Leu Asp Met Ile Leu Lys Met Asp
                405                 410                 415

Ser Leu Gln Asp Ile Lys Ala Leu Leu Thr Gly Leu Phe Val Gln Asp
            420                 425                 430

Asn Val Asn Lys Asp Ala Val Thr Asp Arg Leu Ala Ser Val Glu Thr
        435                 440                 445

Asp Met Pro Leu Thr Leu Arg Gln His Arg Ile Ser Ala Thr Ser Ser
    450                 455                 460

Ser Glu Glu Ser Ser Asn Lys Gly Gln Arg Gln Leu Thr Val Ser Ala
465                 470                 475                 480

Ala Ala Gly Gly Ser Gly Gly Ser Gly Gly Ser Asp Ala Leu Asp Asp
                485                 490                 495

Phe Asp Leu Asp Met Leu Gly Ser Asp Ala Leu Asp Asp Phe Asp Leu
            500                 505                 510

Asp Met Leu Gly Ser Asp Ala Leu Asp Asp Phe Asp Leu Asp Met Leu
        515                 520                 525

Gly Ser Asp Ala Leu Asp Asp Phe Asp Leu Asp Met Leu Gly Ser
    530                 535                 540

<210> SEQ ID NO 34
<211> LENGTH: 416

<212> TYPE: PRT
<213> ORGANISM: Artificial Sequence
<220> FEATURE:
<223> OTHER INFORMATION: Synthetic construct

<400> SEQUENCE: 34

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Glu Val Gln
            20                  25                  30

Leu Leu Glu Ser Gly Gly Gly Leu Val Gln Pro Gly Gly Ser Leu Arg
            35                  40                  45

Leu Ser Cys Ala Ala Ser Gly Phe Thr Phe Ser Ser Tyr Ala Met Ser
    50                  55                  60

Trp Val Arg Gln Ala Pro Gly Lys Gly Leu Glu Trp Val Ser Ser Ile
65                  70                  75                  80

Ser Gly Ser Gly Asp Tyr Ile Tyr Tyr Ala Asp Ser Val Lys Gly Arg
                85                  90                  95

Phe Thr Ile Ser Arg Asp Ile Ser Lys Asn Thr Leu Tyr Leu Gln Met
            100                 105                 110

Asn Ser Leu Arg Ala Glu Asp Thr Ala Val Tyr Tyr Cys Ala Lys Glu
            115                 120                 125

Gly Thr Gly Ala Asn Ser Ser Leu Ala Asp Tyr Arg Gly Gln Gly Thr
    130                 135                 140

Leu Val Thr Val Ser Ser Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Phe Met Tyr Val Ala Ala Ala Phe Val Leu Leu Phe Phe Val
            180                 185                 190

Gly Cys Gly Val Leu Leu Ser Lys Arg Lys Arg Lys His Met Lys Leu
    195                 200                 205

Leu Ser Ser Ile Glu Gln Ala Cys Asp Ile Cys Arg Leu Lys Lys Leu
    210                 215                 220

Lys Cys Ser Lys Glu Lys Pro Lys Cys Ala Lys Cys Leu Lys Asn Asn
225                 230                 235                 240

Trp Glu Cys Arg Tyr Ser Pro Lys Thr Lys Arg Ser Pro Leu Thr Arg
                245                 250                 255

Ala His Leu Thr Glu Val Glu Ser Arg Leu Glu Arg Leu Glu Gln Leu
            260                 265                 270

Phe Leu Leu Ile Phe Pro Arg Glu Asp Leu Asp Met Ile Leu Lys Met
        275                 280                 285

Asp Ser Leu Gln Asp Ile Lys Ala Leu Leu Thr Gly Leu Phe Val Gln
    290                 295                 300

Asp Asn Val Asn Lys Asp Ala Val Thr Asp Arg Leu Ala Ser Val Glu
305                 310                 315                 320

Thr Asp Met Pro Leu Thr Leu Arg Gln His Arg Ile Ser Ala Thr Ser
                325                 330                 335

Ser Ser Glu Glu Ser Ser Asn Lys Gly Gln Arg Gln Leu Thr Val Ser
            340                 345                 350

Ala Ala Ala Gly Gly Ser Gly Gly Ser Gly Gly Ser Asp Ala Leu Asp
        355                 360                 365

Asp Phe Asp Leu Asp Met Leu Gly Ser Asp Ala Leu Asp Asp Phe Asp
    370                 375                 380
```

Leu Asp Met Leu Gly Ser Asp Ala Leu Asp Asp Phe Asp Leu Asp Met
385                 390                 395                 400

Leu Gly Ser Asp Ala Leu Asp Asp Phe Asp Leu Asp Met Leu Gly Ser
                405                 410                 415

<210> SEQ ID NO 35
<211> LENGTH: 426
<212> TYPE: PRT
<213> ORGANISM: Artificial Sequence
<220> FEATURE:
<223> OTHER INFORMATION: Synthetic construct

<400> SEQUENCE: 35

Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Glu Val Gln
                20                  25                  30

Leu Leu Glu Ser Gly Gly Gly Leu Val Gln Pro Gly Gly Ser Leu Arg
            35                  40                  45

Leu Ser Cys Ala Ala Ser Gly Phe Thr Phe Ser Ser Tyr Ala Met Ser
        50                  55                  60

Trp Val Arg Gln Ala Pro Gly Lys Gly Leu Glu Trp Val Ser Ser Ile
65                  70                  75                  80

Ser Gly Ser Gly Asp Tyr Ile Tyr Tyr Ala Asp Ser Val Lys Gly Arg
                85                  90                  95

Phe Thr Ile Ser Arg Asp Ile Ser Lys Asn Thr Leu Tyr Leu Gln Met
                100                 105                 110

Asn Ser Leu Arg Ala Glu Asp Thr Ala Val Tyr Tyr Cys Ala Lys Glu
            115                 120                 125

Gly Thr Gly Ala Asn Ser Ser Leu Ala Asp Tyr Arg Gly Gln Gly Thr
        130                 135                 140

Leu Val Thr Val Ser Ser Phe Val Pro Val Phe Leu Pro Ala Lys Pro
145                 150                 155                 160

Thr Thr Thr Pro Ala Pro Arg Pro Pro Thr Pro Ala Pro Thr Ile Ala
                165                 170                 175

Ser Gln Pro Leu Ser Leu Arg Pro Glu Ala Cys Phe Met Tyr Val Ala
                180                 185                 190

Ala Ala Ala Phe Val Leu Leu Phe Phe Val Gly Cys Gly Val Leu Leu
            195                 200                 205

Ser Lys Arg Lys Arg Lys His Met Lys Leu Leu Ser Ser Ile Glu Gln
        210                 215                 220

Ala Cys Asp Ile Cys Arg Leu Lys Lys Leu Lys Cys Ser Lys Glu Lys
225                 230                 235                 240

Pro Lys Cys Ala Lys Cys Leu Lys Asn Asn Trp Glu Cys Arg Tyr Ser
                245                 250                 255

Pro Lys Thr Lys Arg Ser Pro Leu Thr Arg Ala His Leu Thr Glu Val
                260                 265                 270

Glu Ser Arg Leu Glu Arg Leu Glu Gln Leu Phe Leu Leu Ile Phe Pro
            275                 280                 285

Arg Glu Asp Leu Asp Met Ile Leu Lys Met Asp Ser Leu Gln Asp Ile
        290                 295                 300

Lys Ala Leu Leu Thr Gly Leu Phe Val Gln Asp Asn Val Asn Lys Asp
305                 310                 315                 320

Ala Val Thr Asp Arg Leu Ala Ser Val Glu Thr Asp Met Pro Leu Thr
                325                 330                 335

```
Leu Arg Gln His Arg Ile Ser Ala Thr Ser Ser Glu Glu Ser Ser
                340                 345                 350

Asn Lys Gly Gln Arg Gln Leu Thr Val Ser Ala Ala Gly Gly Ser
                355                 360                 365

Gly Gly Ser Gly Gly Ser Asp Ala Leu Asp Phe Asp Leu Asp Met
            370                 375                 380

Leu Gly Ser Asp Ala Leu Asp Phe Asp Leu Asp Met Leu Gly Ser
385                 390                 395                 400

Asp Ala Leu Asp Asp Phe Asp Leu Asp Met Leu Gly Ser Asp Ala Leu
                405                 410                 415

Asp Asp Phe Asp Leu Asp Met Leu Gly Ser
                420                 425

<210> SEQ ID NO 36
<211> LENGTH: 277
<212> TYPE: PRT
<213> ORGANISM: Artificial Sequence
<220> FEATURE:
<223> OTHER INFORMATION: Synthetic construct

<400> SEQUENCE: 36

Met Ala Leu Pro Val Thr Ala Leu Leu Leu Pro Leu Ala Leu Leu
1               5                   10                  15

His Ala Ala Arg Pro Glu Gln Lys Leu Ile Ser Glu Glu Asp Leu Gln
                20                  25                  30

Val Gln Leu Val Gln Ser Gly Ala Glu Val Lys Lys Pro Gly Ala Ser
            35                  40                  45

Val Lys Val Ser Cys Lys Ala Ser Gly Tyr Ser Phe Pro Asp Tyr Tyr
        50                  55                  60

Ile Asn Trp Val Arg Gln Ala Pro Gly Gln Gly Leu Glu Trp Met Gly
65                  70                  75                  80

Trp Ile Tyr Phe Ala Ser Gly Asn Ser Glu Tyr Asn Gln Lys Phe Thr
                85                  90                  95

Gly Arg Val Thr Met Thr Arg Asp Thr Ser Ile Asn Thr Ala Tyr Met
                100                 105                 110

Glu Leu Ser Ser Leu Thr Ser Glu Asp Thr Ala Val Tyr Phe Cys Ala
            115                 120                 125

Ser Leu Tyr Asp Tyr Asp Trp Tyr Phe Asp Val Trp Gly Gln Gly Thr
        130                 135                 140

Met Val Thr Val Ser Ser Gly Gly Gly Ser Gly Gly Gly Gly Ser
145                 150                 155                 160

Gly Gly Gly Gly Ser Asp Ile Val Met Thr Gln Thr Pro Leu Ser Leu
                165                 170                 175

Ser Val Thr Pro Gly Gln Pro Ala Ser Ile Ser Cys Lys Ser Ser Gln
                180                 185                 190

Ser Leu Val His Ser Asn Gly Asn Thr Tyr Leu His Trp Tyr Leu Gln
            195                 200                 205

Lys Pro Gly Gln Ser Pro Gln Leu Leu Ile Tyr Lys Val Ser Asn Arg
        210                 215                 220

Phe Ser Gly Val Pro Asp Arg Phe Ser Gly Ser Gly Ser Gly Thr Asp
225                 230                 235                 240

Phe Thr Leu Lys Ile Ser Arg Val Glu Ala Glu Asp Val Gly Ile Tyr
                245                 250                 255

Tyr Cys Ser Gln Ser Ser Ile Tyr Pro Trp Thr Phe Gly Gln Gly Thr
                260                 265                 270
```

Lys Leu Glu Ile Lys
        275

<210> SEQ ID NO 37
<211> LENGTH: 277
<212> TYPE: PRT
<213> ORGANISM: Artificial Sequence
<220> FEATURE:
<223> OTHER INFORMATION: Synthetic construct

<400> SEQUENCE: 37

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Ser Pro Ser Ser Leu Ser Ala Ser Val Gly Asp
        35                  40                  45

Arg Val Thr Ile Thr Cys Arg Ala Ser Gln Asp Val Asn Thr Ala Val
    50                  55                  60

Ala Trp Tyr Gln Gln Lys Pro Gly Lys Ala Pro Lys Leu Leu Ile Tyr
65                  70                  75                  80

Ser Ala Ser Phe Leu Tyr Ser Gly Val Pro Ser Arg Phe Ser Gly Ser
                85                  90                  95

Arg Ser Gly Thr Asp Phe Thr Leu Thr Ile Ser Ser Leu Gln Pro Glu
            100                 105                 110

Asp Phe Ala Thr Tyr Tyr Cys Gln Gln His Tyr Thr Thr Pro Pro Thr
        115                 120                 125

Phe Gly Gln Gly Thr Lys Val Glu Ile Lys Arg Thr Gly Ser Thr Ser
    130                 135                 140

Gly Ser Gly Lys Pro Gly Ser Gly Glu Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Phe Asn Ile Lys Asp Thr Tyr Ile His Trp Val
            180                 185                 190

Arg Gln Ala Pro Gly Lys Gly Leu Glu Trp Val Ala Arg Ile Tyr Pro
        195                 200                 205

Thr Asn Gly Tyr Thr Arg Tyr Ala Asp Ser Val Lys Gly Arg Phe Thr
    210                 215                 220

Ile Ser Ala Asp Thr Ser Lys Asn Thr Ala Tyr Leu Gln Met Asn Ser
225                 230                 235                 240

Leu Arg Ala Glu Asp Thr Ala Val Tyr Tyr Cys Ser Arg Trp Gly Gly
                245                 250                 255

Asp Gly Phe Tyr Ala Met Asp Val Trp Gly Gln Gly Thr Leu Val Thr
            260                 265                 270

Val Ser Ser Gly Ser
        275

<210> SEQ ID NO 38
<211> LENGTH: 150
<212> TYPE: PRT
<213> ORGANISM: Artificial Sequence
<220> FEATURE:
<223> OTHER INFORMATION: Synthetic construct

<400> SEQUENCE: 38

Met Ala Leu Pro Val Thr Ala Leu Leu Leu Pro Leu Ala Leu Leu Leu
1               5                   10                  15

```
His Ala Ala Arg Pro Asp Tyr Lys Asp Asp Asp Lys Glu Val Gln
            20                  25                  30

Leu Leu Glu Ser Gly Gly Gly Leu Val Gln Pro Gly Gly Ser Leu Arg
        35                  40                  45

Leu Ser Cys Ala Ala Ser Gly Phe Thr Phe Ser Ser Tyr Ala Met Ser
 50                  55                  60

Trp Val Arg Gln Ala Pro Gly Lys Gly Leu Glu Trp Val Ser Ser Ile
 65                  70                  75                  80

Ser Gly Ser Gly Asp Tyr Ile Tyr Tyr Ala Asp Ser Val Lys Gly Arg
                85                  90                  95

Phe Thr Ile Ser Arg Asp Ile Ser Lys Asn Thr Leu Tyr Leu Gln Met
            100                 105                 110

Asn Ser Leu Arg Ala Glu Asp Thr Ala Val Tyr Tyr Cys Ala Lys Glu
        115                 120                 125

Gly Thr Gly Ala Asn Ser Ser Leu Ala Asp Tyr Arg Gly Gln Gly Thr
    130                 135                 140

Leu Val Thr Val Ser Ser
145                 150

<210> SEQ ID NO 39
<211> LENGTH: 26
<212> TYPE: PRT
<213> ORGANISM: Artificial Sequence
<220> FEATURE:
<223> OTHER INFORMATION: Synthetic construct

<400> SEQUENCE: 39

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala
            20                  25

<210> SEQ ID NO 40
<211> LENGTH: 18
<212> TYPE: PRT
<213> ORGANISM: Artificial Sequence
<220> FEATURE:
<223> OTHER INFORMATION: Synthetic construct

<400> SEQUENCE: 40

Arg Pro Ala Ala Gly Gly Ala Val His Thr Arg Gly Leu Asp Phe Ala
1               5                   10                  15

Cys Asp

<210> SEQ ID NO 41
<211> LENGTH: 19
<212> TYPE: PRT
<213> ORGANISM: Artificial Sequence
<220> FEATURE:
<223> OTHER INFORMATION: Synthetic construct

<400> SEQUENCE: 41

Cys Arg Pro Ala Ala Gly Gly Ala Val His Thr Arg Gly Leu Asp Phe
1               5                   10                  15

Ala Cys Asp

<210> SEQ ID NO 42
<211> LENGTH: 37
<212> TYPE: PRT
<213> ORGANISM: Artificial Sequence
```

```
<220> FEATURE:
<223> OTHER INFORMATION: Synthetic construct

<400> SEQUENCE: 42

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys
        35

<210> SEQ ID NO 43
<211> LENGTH: 6
<212> TYPE: PRT
<213> ORGANISM: Artificial Sequence
<220> FEATURE:
<223> OTHER INFORMATION: Synthetic construct

<400> SEQUENCE: 43

Arg Arg Arg Arg Glu His
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic construct

<400> SEQUENCE: 44

Lys Tyr Lys Gln Lys Pro Lys
1               5

<210> SEQ ID NO 45
<211> LENGTH: 4
<212> TYPE: PRT
<213> ORGANISM: Artificial Sequence
<220> FEATURE:
<223> OTHER INFORMATION: Synthetic construct

<400> SEQUENCE: 45

Lys Arg Arg Arg
1

<210> SEQ ID NO 46
<211> LENGTH: 7
<212> TYPE: PRT
<213> ORGANISM: Artificial Sequence
<220> FEATURE:
<223> OTHER INFORMATION: Synthetic construct

<400> SEQUENCE: 46

Arg Lys Lys Arg Lys Gly Lys
1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic construct

<400> SEQUENCE: 47

Lys Gln Gln Arg Ile Lys
1               5
```

```
<210> SEQ ID NO 48
<211> LENGTH: 6
<212> TYPE: PRT
<213> ORGANISM: Artificial Sequence
<220> FEATURE:
<223> OTHER INFORMATION: Synthetic construct

<400> SEQUENCE: 48

Lys Arg Lys Arg Thr His
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic construct

<400> SEQUENCE: 49

Arg Arg Gln Arg Arg
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic construct

<400> SEQUENCE: 50

Lys Lys Gly Arg Arg Ser Tyr Lys
1               5

<210> SEQ ID NO 51
<211> LENGTH: 14
<212> TYPE: PRT
<213> ORGANISM: Artificial Sequence
<220> FEATURE:
<223> OTHER INFORMATION: Synthetic construct

<400> SEQUENCE: 51

Lys Thr Lys Lys Gln Arg Lys Lys Leu His Asp Arg Leu Arg
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic construct

<400> SEQUENCE: 52

Lys Arg Lys Arg Arg Thr Lys Thr Ile Arg Arg
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Synthetic construct

<400> SEQUENCE: 53

Arg Lys Arg Arg Lys Glu Arg Glu Arg Ser Arg Leu Pro Arg
1               5                   10
```

```
<210> SEQ ID NO 54
<211> LENGTH: 10
<212> TYPE: PRT
<213> ORGANISM: Artificial Sequence
<220> FEATURE:
<223> OTHER INFORMATION: Synthetic construct

<400> SEQUENCE: 54

Arg Lys Lys Arg Met Ala Lys Tyr Glu Lys
1               5                   10

<210> SEQ ID NO 55
<211> LENGTH: 8
<212> TYPE: PRT
<213> ORGANISM: Artificial Sequence
<220> FEATURE:
<223> OTHER INFORMATION: Synthetic construct

<400> SEQUENCE: 55

Arg Ser Arg Lys Val Asp Lys Arg
1               5

<210> SEQ ID NO 56
<211> LENGTH: 10
<212> TYPE: PRT
<213> ORGANISM: Artificial Sequence
<220> FEATURE:
<223> OTHER INFORMATION: Synthetic construct

<400> SEQUENCE: 56

Lys Arg Arg Asp Lys Glu Arg Gln Ala Lys
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Synthetic construct

<400> SEQUENCE: 57

Lys Thr Lys Lys Gln Arg Lys Gln Met His Asn His Leu Arg
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Synthetic construct

<400> SEQUENCE: 58

Lys Lys Ser Lys Leu Ala Lys Lys Arg Lys
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic construct

<400> SEQUENCE: 59

His Pro Leu Arg Lys Arg Arg Lys Arg Lys Lys Lys
1               5                   10

<210> SEQ ID NO 60
```

```
<211> LENGTH: 10
<212> TYPE: PRT
<213> ORGANISM: Artificial Sequence
<220> FEATURE:
<223> OTHER INFORMATION: Synthetic construct

<400> SEQUENCE: 60

Arg Arg Arg Ser Lys Tyr Ser Lys Ala Lys
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic construct

<400> SEQUENCE: 61

His Arg Arg Cys Lys His Arg Thr Gly Lys
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Synthetic construct

<400> SEQUENCE: 62

Lys Lys Arg Lys Leu Ala Lys Lys Arg Lys
1               5                   10

<210> SEQ ID NO 63
<211> LENGTH: 6
<212> TYPE: PRT
<213> ORGANISM: Artificial Sequence
<220> FEATURE:
<223> OTHER INFORMATION: Synthetic construct

<400> SEQUENCE: 63

Arg Arg Lys Arg Glu His
1               5

<210> SEQ ID NO 64
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(3)
<223> OTHER INFORMATION: X can be any amino acid residue
<220> FEATURE:
<221> NAME/KEY: MISC_FEATURE
<222> LOCATION: (4)..(4)
<223> OTHER INFORMATION: X represents a hydrophobic residue such as Leu,
      Ile, Val, Phe, Trp, Tyr, Val, Met, and Pro

<400> SEQUENCE: 64

Pro Xaa Xaa Xaa
1

<210> SEQ ID NO 65
<211> LENGTH: 5
<212> TYPE: PRT
<213> ORGANISM: Artificial Sequence
<220> FEATURE:
<223> OTHER INFORMATION: Synthetic construct
```

```
<220> FEATURE:
<221> NAME/KEY: MISC_FEATURE
<222> LOCATION: (2)..(3)
<223> OTHER INFORMATION: X can be any amino acid residue
<220> FEATURE:
<221> NAME/KEY: MISC_FEATURE
<222> LOCATION: (4)..(4)
<223> OTHER INFORMATION: X represents a hydrophobic residue such as Leu,
      Ile, Val, Phe, Trp, Tyr, Val, Met, and Pro
<220> FEATURE:
<221> NAME/KEY: MISC_FEATURE
<222> LOCATION: (5)..(5)
<223> OTHER INFORMATION: X is either Ser or Thr

<400> SEQUENCE: 65

Pro Xaa Xaa Xaa Xaa
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X is either Leu or Gln

<400> SEQUENCE: 66

Pro Xaa Gly Met Thr Ser
1               5

<210> SEQ ID NO 67
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X is either Leu or Gln

<400> SEQUENCE: 67

Pro Xaa Gly Met Thr
1               5

<210> SEQ ID NO 68
<211> LENGTH: 3
<212> TYPE: PRT
<213> ORGANISM: Artificial Sequence
<220> FEATURE:
<223> OTHER INFORMATION: Synthetic construct

<400> SEQUENCE: 68

Val Gly Arg
1

<210> SEQ ID NO 69
<211> LENGTH: 7
<212> TYPE: PRT
<213> ORGANISM: Artificial Sequence
<220> FEATURE:
<223> OTHER INFORMATION: Synthetic construct

<400> SEQUENCE: 69

Glu Asn Leu Tyr Thr Gln Ser
1               5
```

<210> SEQ ID NO 70
<211> LENGTH: 5
<212> TYPE: PRT
<213> ORGANISM: Artificial Sequence
<220> FEATURE:
<223> OTHER INFORMATION: Synthetic construct

<400> SEQUENCE: 70

Asp Asp Asp Asp Lys
1               5

<210> SEQ ID NO 71
<211> LENGTH: 4
<212> TYPE: PRT
<213> ORGANISM: Artificial Sequence
<220> FEATURE:
<223> OTHER INFORMATION: Synthetic construct

<400> SEQUENCE: 71

Leu Val Pro Arg
1

<210> SEQ ID NO 72
<211> LENGTH: 277
<212> TYPE: PRT
<213> ORGANISM: Artificial sequence
<220> FEATURE:
<223> OTHER INFORMATION: Synthetic construct

<400> SEQUENCE: 72

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
                20                  25                  30

Ile Gln Met Thr Gln Ser Pro Ser Ser Leu Ser Ala Ser Val Gly Asp
            35                  40                  45

Arg Val Thr Ile Thr Cys Arg Ala Ser Gln Asp Val Asn Thr Ala Val
        50                  55                  60

Ala Trp Tyr Gln Gln Lys Pro Gly Lys Ala Pro Lys Leu Leu Ile Tyr
65                  70                  75                  80

Ser Ala Ser Phe Leu Glu Ser Gly Val Pro Ser Arg Phe Ser Gly Ser
                85                  90                  95

Arg Ser Gly Thr Asp Phe Thr Leu Thr Ile Ser Ser Leu Gln Pro Glu
            100                 105                 110

Asp Phe Ala Thr Tyr Tyr Cys Gln Gln His Tyr Thr Thr Pro Pro Thr
        115                 120                 125

Phe Gly Gln Gly Thr Lys Val Glu Ile Lys Arg Thr Gly Ser Thr Ser
    130                 135                 140

Gly Ser Gly Lys Pro Gly Ser Gly Glu Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Phe Asn Ile Lys Asp Thr Tyr Ile His Trp Val
            180                 185                 190

Arg Gln Ala Pro Gly Lys Gly Leu Glu Trp Val Ala Arg Ile Tyr Pro
        195                 200                 205

Thr Asn Gly Tyr Thr Arg Tyr Ala Asp Ser Val Lys Gly Arg Phe Thr
    210                 215                 220

```
Ile Ser Ala Asp Thr Ser Lys Asn Thr Ala Tyr Leu Gln Met Asn Ser
225                 230                 235                 240

Leu Arg Ala Glu Asp Thr Ala Val Tyr Tyr Cys Ser Arg Trp Gly Gly
            245                 250                 255

Asp Gly Phe Tyr Ala Met Asp Val Trp Gly Gln Gly Thr Leu Val Thr
            260                 265                 270

Val Ser Ser Gly Ser
            275

<210> SEQ ID NO 73
<211> LENGTH: 543
<212> TYPE: PRT
<213> ORGANISM: Artificial sequence
<220> FEATURE:
<223> OTHER INFORMATION: Synthetic construct

<400> SEQUENCE: 73

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
    130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300
```

Ile Val Val Cys Val Ser Phe Leu Val Phe Met Ile Ile Leu Gly Val
305                 310                 315                 320

Phe Arg Ile Arg Ala Ala His Arg Arg Thr Met Arg Met Lys Leu Leu
            325                 330                 335

Ser Ser Ile Glu Gln Ala Cys Asp Ile Cys Arg Leu Lys Lys Leu Lys
            340                 345                 350

Cys Ser Lys Glu Lys Pro Lys Cys Ala Lys Cys Leu Lys Asn Asn Trp
            355                 360                 365

Glu Cys Arg Tyr Ser Pro Lys Thr Lys Arg Ser Pro Leu Thr Arg Ala
        370                 375                 380

His Leu Thr Glu Val Glu Ser Arg Leu Glu Arg Leu Glu Gln Leu Phe
385                 390                 395                 400

Leu Leu Ile Phe Pro Arg Glu Asp Leu Asp Met Ile Leu Lys Met Asp
                405                 410                 415

Ser Leu Gln Asp Ile Lys Ala Leu Leu Thr Gly Leu Phe Val Gln Asp
            420                 425                 430

Asn Val Asn Lys Asp Ala Val Thr Asp Arg Leu Ala Ser Val Glu Thr
            435                 440                 445

Asp Met Pro Leu Thr Leu Arg Gln His Arg Ile Ser Ala Thr Ser Ser
        450                 455                 460

Ser Glu Glu Ser Ser Asn Lys Gly Gln Arg Gln Leu Thr Val Ser Ala
465                 470                 475                 480

Ala Ala Gly Gly Ser Gly Ser Gly Ser Asp Ala Leu Asp Asp
                485                 490                 495

Phe Asp Leu Asp Met Leu Gly Ser Asp Ala Leu Asp Asp Phe Asp Leu
            500                 505                 510

Asp Met Leu Gly Ser Asp Ala Leu Asp Asp Phe Asp Leu Asp Met Leu
            515                 520                 525

Gly Ser Asp Ala Leu Asp Asp Phe Asp Leu Asp Met Leu Gly Ser
        530                 535                 540

<210> SEQ ID NO 74
<211> LENGTH: 541
<212> TYPE: PRT
<213> ORGANISM: Artificial sequence
<220> FEATURE:
<223> OTHER INFORMATION: Synthetic construct

<400> SEQUENCE: 74

Met Ala Leu Pro Val Thr Ala Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

```
Phe Gly Gly Gly Thr Lys Leu Glu Ile Thr Gly Gly Gly Ser Gly
    130                 135                 140

Gly Gly Gly Ser Gly Gly Gly Ser Glu Val Lys Leu Gln Glu Ser
145             150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Gly Gly
                245                 250                 255

Ser Tyr Ala Met Asp Tyr Trp Gly Gln Gly Thr Ser Val Thr Val Ser
            260                 265                 270

Ser Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Ile Ala Thr Val
    290                 295                 300

Val Ile Ile Ile Ser Val Cys Met Leu Val Phe Val Val Ala Met Gly
305                 310                 315                 320

Val Tyr Arg Val Arg Ile Ala His Gln His Met Lys Leu Leu Ser Ser
                325                 330                 335

Ile Glu Gln Ala Cys Asp Ile Cys Arg Leu Lys Lys Leu Lys Cys Ser
            340                 345                 350

Lys Glu Lys Pro Lys Cys Ala Lys Cys Leu Lys Asn Asn Trp Glu Cys
        355                 360                 365

Arg Tyr Ser Pro Lys Thr Lys Arg Ser Pro Leu Thr Arg Ala His Leu
    370                 375                 380

Thr Glu Val Glu Ser Arg Leu Glu Arg Leu Glu Gln Leu Phe Leu Leu
385                 390                 395                 400

Ile Phe Pro Arg Glu Asp Leu Asp Met Ile Leu Lys Met Asp Ser Leu
                405                 410                 415

Gln Asp Ile Lys Ala Leu Leu Thr Gly Leu Phe Val Gln Asp Asn Val
            420                 425                 430

Asn Lys Asp Ala Val Thr Asp Arg Leu Ala Ser Val Glu Thr Asp Met
        435                 440                 445

Pro Leu Thr Leu Arg Gln His Arg Ile Ser Ala Thr Ser Ser Ser Glu
    450                 455                 460

Glu Ser Ser Asn Lys Gly Gln Arg Gln Leu Thr Val Ser Ala Ala Ala
465                 470                 475                 480

Gly Gly Ser Gly Gly Ser Gly Gly Ser Asp Ala Leu Asp Asp Phe Asp
                485                 490                 495

Leu Asp Met Leu Gly Ser Asp Ala Leu Asp Asp Phe Asp Leu Asp Met
            500                 505                 510

Leu Gly Ser Asp Ala Leu Asp Asp Phe Asp Leu Asp Met Leu Gly Ser
        515                 520                 525

Asp Ala Leu Asp Asp Phe Asp Leu Asp Met Leu Gly Ser
    530                 535                 540
```

-continued

```
<210> SEQ ID NO 75
<211> LENGTH: 537
<212> TYPE: PRT
<213> ORGANISM: Artificial sequence
<220> FEATURE:
<223> OTHER INFORMATION: Synthetic construct

<400> SEQUENCE: 75

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Ser Gly
    130                 135                 140

Gly Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Ala Thr Val Val
    290                 295                 300

Ile Val Val Cys Val Ser Phe Leu Val Phe Met Ile Ile Leu Gly Val
305                 310                 315                 320

Phe Arg Lys Arg Arg Arg Met Lys Leu Leu Ser Ser Ile Glu Gln Ala
                325                 330                 335

Cys Asp Ile Cys Arg Leu Lys Lys Leu Lys Cys Ser Lys Glu Lys Pro
            340                 345                 350

Lys Cys Ala Lys Cys Leu Lys Asn Asn Trp Glu Cys Arg Tyr Ser Pro
        355                 360                 365
```

```
Lys Thr Lys Arg Ser Pro Leu Thr Arg Ala His Leu Thr Glu Val Glu
370                 375                 380

Ser Arg Leu Glu Arg Leu Glu Gln Leu Phe Leu Leu Ile Phe Pro Arg
385                 390                 395                 400

Glu Asp Leu Asp Met Ile Leu Lys Met Asp Ser Leu Gln Asp Ile Lys
                405                 410                 415

Ala Leu Leu Thr Gly Leu Phe Val Gln Asp Asn Val Asn Lys Asp Ala
                420                 425                 430

Val Thr Asp Arg Leu Ala Ser Val Glu Thr Asp Met Pro Leu Thr Leu
                435                 440                 445

Arg Gln His Arg Ile Ser Ala Thr Ser Ser Ser Glu Glu Ser Ser Asn
450                 455                 460

Lys Gly Gln Arg Gln Leu Thr Val Ser Ala Ala Gly Gly Ser Gly
465                 470                 475                 480

Gly Ser Gly Gly Ser Asp Ala Leu Asp Asp Phe Asp Leu Asp Met Leu
                485                 490                 495

Gly Ser Asp Ala Leu Asp Asp Phe Asp Leu Asp Met Leu Gly Ser Asp
                500                 505                 510

Ala Leu Asp Asp Phe Asp Leu Asp Met Leu Gly Ser Asp Ala Leu Asp
                515                 520                 525

Asp Phe Asp Leu Asp Met Leu Gly Ser
                530                 535

<210> SEQ ID NO 76
<211> LENGTH: 538
<212> TYPE: PRT
<213> ORGANISM: Artificial sequence
<220> FEATURE:
<223> OTHER INFORMATION: Synthetic construct

<400> SEQUENCE: 76

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
                20                  25                  30

Ile Gln Met Thr Gln Thr Thr Ser Ser Leu Ser Ala Ser Leu Gly Asp
                35                  40                  45

Arg Val Thr Ile Ser Cys Arg Ala Ser Gln Asp Ile Ser Lys Tyr Leu
                50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
                100                 105                 110

Asp Ile Ala Thr Tyr Phe Cys Gln Gln Gly Asn Thr Leu Pro Tyr Thr
                115                 120                 125

Phe Gly Gly Gly Thr Lys Leu Glu Ile Thr Gly Gly Gly Gly Ser Gly
                130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
                180                 185                 190
```

Pro Pro Arg Lys Gly Leu Glu Trp Leu Gly Val Ile Trp Gly Ser Glu
            195                 200                 205

Thr Thr Tyr Tyr Asn Ser Ala Leu Lys Ser Arg Leu Thr Ile Ile Lys
        210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Ile Ala Thr Val
        290                 295                 300

Val Ile Ile Ile Ser Val Cys Met Leu Val Phe Val Val Ala Met Gly
305                 310                 315                 320

Val Tyr Arg Lys Arg Arg Arg Met Lys Leu Leu Ser Ser Ile Glu Gln
                325                 330                 335

Ala Cys Asp Ile Cys Arg Leu Lys Lys Leu Lys Cys Ser Lys Glu Lys
                340                 345                 350

Pro Lys Cys Ala Lys Cys Leu Lys Asn Asn Trp Glu Cys Arg Tyr Ser
            355                 360                 365

Pro Lys Thr Lys Arg Ser Pro Leu Thr Arg Ala His Leu Thr Glu Val
            370                 375                 380

Glu Ser Arg Leu Glu Arg Leu Glu Gln Leu Phe Leu Leu Ile Phe Pro
385                 390                 395                 400

Arg Glu Asp Leu Asp Met Ile Leu Lys Met Asp Ser Leu Gln Asp Ile
                405                 410                 415

Lys Ala Leu Leu Thr Gly Leu Phe Val Gln Asp Asn Val Asn Lys Asp
            420                 425                 430

Ala Val Thr Asp Arg Leu Ala Ser Val Glu Thr Asp Met Pro Leu Thr
            435                 440                 445

Leu Arg Gln His Arg Ile Ser Ala Thr Ser Ser Ser Glu Glu Ser Ser
450                 455                 460

Asn Lys Gly Gln Arg Gln Leu Thr Val Ser Ala Ala Ala Gly Gly Ser
465                 470                 475                 480

Gly Gly Ser Gly Gly Ser Asp Ala Leu Asp Asp Phe Asp Leu Asp Met
            485                 490                 495

Leu Gly Ser Asp Ala Leu Asp Asp Phe Asp Leu Asp Met Leu Gly Ser
            500                 505                 510

Asp Ala Leu Asp Asp Phe Asp Leu Asp Met Leu Gly Ser Asp Ala Leu
            515                 520                 525

Asp Asp Phe Asp Leu Asp Met Leu Gly Ser
            530                 535

<210> SEQ ID NO 77
<211> LENGTH: 21
<212> TYPE: PRT
<213> ORGANISM: Artificial sequence
<220> FEATURE:
<223> OTHER INFORMATION: Synthetic construct

<400> SEQUENCE: 77

Ala Thr Val Val Ile Val Cys Val Ser Phe Leu Val Phe Met Ile
1               5                   10                  15

```
Ile Leu Gly Val Phe
        20

<210> SEQ ID NO 78
<211> LENGTH: 22
<212> TYPE: PRT
<213> ORGANISM: Artificial sequence
<220> FEATURE:
<223> OTHER INFORMATION: Synthetic construct

<400> SEQUENCE: 78

Ile Ala Thr Val Val Ile Ile Ile Ser Val Cys Met Leu Val Phe Val
1               5                   10                  15

Val Ala Met Gly Val Tyr
        20

<210> SEQ ID NO 79
<211> LENGTH: 11
<212> TYPE: PRT
<213> ORGANISM: Artificial sequence
<220> FEATURE:
<223> OTHER INFORMATION: Synthetic construct

<400> SEQUENCE: 79

Arg Ile Arg Ala Ala His Arg Arg Thr Met Arg
1               5                   10

<210> SEQ ID NO 80
<211> LENGTH: 8
<212> TYPE: PRT
<213> ORGANISM: Artificial sequence
<220> FEATURE:
<223> OTHER INFORMATION: Synthetic construct

<400> SEQUENCE: 80

Arg Val Arg Ile Ala His Gln His
1               5
```

NOTCH RECEPTORS WITH HINGE DOMAIN

CROSS-REFERENCE TO RELATED APPLICATIONS

This application is a continuation application of U.S. patent application Ser. No. 17/217,618, filed on Mach 30, 2021, which is a continuation of International Patent Application No. PCT/US2020/052327 filed on Sep. 23, 2020, which claims the benefit of priority to U.S. Provisional Patent Application Nos. 62/905,251 and 62/905,263, both filed on Sep. 24, 2019, the disclosures of which are incorporated by reference herein in their entireties, including any drawings.

This invention was made with government support under grant no. OD025751 awarded by The National Institutes of Health. The government has certain rights in the invention.

INCORPORATION OF THE SEQUENCE LISTING

This application contains a Sequence Listing which is hereby incorporated by reference in its entirety. The accompanying Sequence Listing text file, named "Sequence Listing-048536-654C02US_ST25.txt," was created on Nov. 17, 2021 and is 141 KB.

FIELD

The present disclosure relates generally to new synthetic cellular receptors that bind cell-surface ligands and have selectable specificities and activities. The disclosure also provides compositions and methods useful for producing such receptors, nucleic acids encoding same, host cells genetically modified with the nucleic acids, as well as methods for modulating an activity of a cell and/or for the treatment of various health conditions or diseases, such as cancers.

BACKGROUND

An important problem limiting the development of engineered cell therapies in humans is the regulation of therapeutic gene expression to reduce or eliminate interactions causing significant side effects on administration of chimeric antigen receptor T cells (CAR-T) such as, for example, off-target activity, on-target, off-tumor activity (i.e., wherein the CAR-T target is also found on normal cells outside the tumor), and inability to modulate or turn off CAR-T activity when needed. A possible solution to these problems is to use a synthetic receptor that is capable of modifying gene expression and/or cellular behavior.

Notch receptors are transmembrane proteins that mediate cell-cell contact signaling and play a central role in development and other aspects of cell-to-cell communication, e.g. communication between two contacting cells, in which one contacting cell is a "receiver" cell and the other contacting cell is a "sender" cell. Notch receptors expressed in a receiver cell recognize their ligands (e.g., the delta/serrate/lag, or "DSL" family of proteins), expressed on a sending cell. The engagement of notch and delta on these contacting cells leads to two-step proteolysis of the notch receptor that ultimately causes the release of the intracellular portion of the receptor from the membrane into the cytoplasm. Notch has a metalloprotease cleavage site (denoted "S2"), which is normally protected from cleavage by the Notch negative regulatory region (NRR), a domain consisting of three LIN-12-Notch repeat (LNR) modules and a heterodimerization domain (HD) of the Notch extracellular subunit (NEC). It is believed that this proteolysis is regulated by the force exerted by the sending cell: the DSL ligand pulls on the Notch receptor and changes the conformation of the negative regulatory region, exposing the metalloprotease site. That site is then cleaved by a constitutively active protease, releasing the extracellular binding portion and negative regulatory region (NRR) of the receptor. Release of the extracellular binding portion of the receptor in turn exposes another intramembrane cleavage site(s) (denoted "S3"), which is/are cleaved by gamma secretase within the cell membrane to release the nuclear homing intracellular domain from the cell membrane. W. R. Gordon et al., *Dev Cell* (2015) 33:729-36. This released domain alters receiver cell behavior by functioning as a transcriptional regulator. Notch receptors are involved in and are required for a variety of cellular functions during development and are important for the function of a vast number of cell-types across species.

Examples of existing first-generation synthetic derivatives of Notch receptors, which are often referred to as "SynNotch receptors", exploit this straightforward signaling behavior by replacing the extracellular ligand-binding domain, which in wild-type Notch contains multiple EGF-like repeats, with an antibody derivative, and replacing the cytoplasmic domain with a transcription activator of choice, while still relying on the functionality of the Notch NRR (L. Morsut et al., Cell (2016) 164:780-91). Generally, SynNotch signaling correlates with ligand binding, but it is difficult to adjust the sensitivity and response of the receptor. Additionally, the NRR spans approximately 160 amino acids, making this domain alone the size of some mature proteins, such as insulin or epidermal growth factor (EGF). This makes expression of the chimeric receptor less efficient and, due to vector capacity-related size constraints, the resulting chimeric receptors can exceed the capacity of some cloning and transfection vectors.

SUMMARY

The present disclosure relates generally to immuno-therapeutics, such as chimeric polypeptides for use in modulating cell activities or in treating various health conditions or diseases. Particularly, provided herein are oligomerizable chimeric receptors that, surprisingly, retain the ability to transduce signals in response to ligand binding despite the complete absence of the Notch extracellular subunit (NEC), including the negative regulatory region (NRR). More particularly, these receptors incorporate an extracellular oligomerization domain to promote formation of oligomeric form, e.g., dimeric or trimeric form of the chimeric receptors. Without being bound to any particular theory, this design facilitates oligomerization or clustering of extracellular domains (ECD) and subsequently brings together intracellular domains (ICD) to activate cell signaling, e.g., T-cell signaling. Further, these receptors provide a range of sensitivity. Additionally, by completely omitting the native Notch NEC, polynucleotides encoding the receptors of the disclosure can be made smaller than SynNotch-encoding polynucleotides, which enables the use of vectors having more limited capacity, or facilitates the inclusion of additional elements that would otherwise be excluded by vector capacity-related size constraints.

In one aspect, provided herein are chimeric polynucleotides including, from N-terminus to C-terminus: (a) an extracellular ligand-binding domain having a binding affinity for a selected ligand; (b) a hinge domain capable of promoting oligomer formation of the chimeric polypeptide via intermolecular disulfide bonding; (c) a transmembrane domain including one or more ligand-inducible proteolytic cleavage sites; and (d) an intracellular domain including a transcriptional regulator, wherein binding of the selected ligand to the extracellular ligand-binding domain induces cleavage at a ligand-inducible proteolytic cleavage site disposed between the transcriptional regulator and the hinge domain, and wherein the chimeric polypeptide does not include a LIN-12-Notch repeat (LNR) and/or a heterodimerization domain (HD) of a Notch receptor.

Non-limiting exemplary embodiments of the chimeric polypeptides according to the present disclosure include one or more of the following features. In some embodiments, the transmembrane domain further includes a stop transfer sequence. In some embodiments, the extracellular domain includes an antigen-binding moiety capable of binding to a ligand on the surface of a cell. In some embodiments, the cell is a pathogen. In some embodiments, the cell is a human cell. In some embodiments, the human cell is a tumor cell. In some embodiments, the human cell is a terminally differentiated cell. In some embodiments, the ligand includes a protein or a carbohydrate. In some embodiments, the ligand is a cluster of differentiation (CD) marker. In some embodiments, the CD marker is selected from the group consisting of CD1, CD1a, CD1b, CD1c, CD1d, CD1e, CD2, CD3d, CD3e, CD3g, CD4, CD5, CD7, CD8a, CD8b, CD19, CD20, CD21, CD22, CD23, CD25, CD27, CD28, CD33, CD34, CD40, CD45, CD48, CD52, CD59, CD66, CD70, CD71, CD72, CD73, CD79A, CD79B, CD80 (B7.1), CD86 (B7.2), CD94, CD95, CD134, CD140 (PDGFR4), CD152, CD154, CD158, CD178, CD181 (CXCR1), CD182 (CXCR2), CD183 (CXCR3), CD210, CD246, CD252, CD253, CD261, CD262, CD273 (PD-L2), CD274 (PD-L1), CD276 (B7H3), CD279, CD295, CD339 (JAG1), CD340 (HER2), EGFR, FGFR2, CEA, AFP, CA125, MUC-1, MAGE, alkaline phosphatase, placental-like 2 (ALPPL2), B-cell maturation antigen (BCMA), green fluorescent protein (GFP), enhanced green fluorescent protein (EGFP), and signal regulatory protein α (SIRPα).

In another aspect, provided herein are nucleic acids including a nucleotide sequence that encodes a chimeric polypeptide as disclosed herein. In some embodiments, the nucleotide sequence is incorporated into an expression cassette or an expression vector.

In some embodiments, provided herein are recombinant cells including: (a) a chimeric polypeptide as disclosed herein; and/or (b) a recombinant nucleic acid as disclosed herein. Also provided, in a related aspect, are cell cultures including at least one recombinant cell as disclosed herein and a culture medium.

In another aspect, provided herein are pharmaceutical compositions including a pharmaceutically acceptable carrier and one or more of the following: (a) a recombinant nucleic acid as disclosed herein; and (b) a recombinant cell as disclosed herein. In some embodiments, the disclosed pharmaceutical composition includes a recombinant nucleic acid as disclosed herein and a pharmaceutically acceptable carrier. In some embodiments, the recombinant nucleic acid is encapsulated in a viral capsid or a lipid nanoparticle.

In another aspect, provided herein are methods for modulating an activity of a cell, including: (a) providing a recombinant cell of the disclosure, and (b) contacting it with a selected ligand, wherein binding of the selected ligand to the extracellular ligand-binding domain of the chimeric polypeptide induces cleavage of a ligand-inducible proteolytic cleavage site and releases the transcriptional regulator, wherein the released transcriptional regulator modulates an activity of the recombinant cell. Another aspect relates to methods for modulating an activity of a target cell in an individual, including administering to the individual an effective number of the recombinant cells of the disclosure, wherein the recombinant cells inhibit an activity of the target cell in the individual.

Another aspect relates to methods for treating a health condition (e.g., disease) in an individual, including administering to the individual an effective number of the recombinant cells of the disclosure, wherein the recombinant cells treat the health condition in the individual.

In another aspect, some embodiments of the disclosure relate to systems for modulating an activity of a cell, inhibiting a target cancer cell, or treating a health condition (e.g., disease) in an individual in need thereof, wherein the system includes one or more of: a chimeric polypeptide of the disclosure; a polynucleotide of the disclosure; a recombinant cell of the disclosure; or a pharmaceutical composition of the disclosure.

Another aspect of the disclosure relates to methods for making a recombinant cell of the disclosure, including (a) providing a cell capable of protein expression and (b) contacting the provided cell with a recombinant nucleic acid of the disclosure. In some embodiments, the cell is obtained by leukapheresis performed on a sample obtained from a subject, and the cell is contacted ex vivo. In some embodiments, the recombinant nucleic acid is encapsulated in a viral capsid or a lipid nanoparticle.

Yet another aspect of the disclosure is the use of one or more of: a chimeric polypeptide of the disclosure; a polynucleotide of the disclosure; a recombinant cell of the disclosure; or a pharmaceutical composition of the disclosure; for the treatment of a health condition. In some embodiments, the health condition is a disease, such as cancer. In some embodiments, the cancer is a solid tumor, a soft tissue tumor, or a metastatic lesion.

Another aspect of the disclosure is the use of one or more of: a chimeric polypeptide of the disclosure; a polynucleotide of the disclosure; a recombinant cell of the disclosure; or a pharmaceutical composition of the disclosure; for the manufacture of a medicament for the treatment of a health condition, e.g., disease.

The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

BRIEF DESCRIPTION OF THE DRAWINGS

FIG. 1A depicts the schematic structure of an existing synthetic Notch receptor (SynNotch), having a ligand recognition domain (for example, anti-CD19 scFv), a juxtamembrane domain (JMD) including a Notch negative regulatory region (NRR), a single-pass transmembrane domain (TMD), a stop transfer sequence (STS), and a transcriptional regulator (for example, Gal4VP64). FIG. 1B depicts the schematic structure of an exemplary second-generation synthetic Notch receptor as disclosed herein (Hinge-Notch receptor), in which the entire NEC of the wild-type Notch polypeptide, including the NRR, has been deleted. A hinge polypeptide sequence derived from CD8 hinge domain is inserted N-terminally to the TMD. The CD8 hinge sequence contains polypeptide motifs that promote dimer formation of the chimeric polypeptide via intermolecular disulfide bonding.

In FIG. 2A schematically shows an exemplary SynNotch1 receptor (Left panel) which was designed based upon human Notch1 proteins. The Middle panel schematically shows an exemplary CD8 Hinge-Notch1 receptor. Compared to SynNotch1 receptor in Left panel, CD8 Hinge-Notch1 receptor replaces the entire JMD with a CD8A hinge domain, which contains cysteine residues known to form disulfide bonds. The Right panel schematically an exemplary truncated CD8 Hinge-Notch1 receptor (truncCD8 Hinge-Notch1). Compared to CD8 Hinge-Notch1 receptors, truncCD8 Hinge-Notch1 receptors contain a C-terminal deletion of the CD8A hinge sequence, leaving a single cysteine residue and a shorter extracellular region. FIG. 2B is a summary of flow cytometry data of receptor expression. In these experiments, primary human T-cells were transduced with two lentiviral constructs expressing either a receptor or a transcriptional reporter plasmid and activated with anti-CD3/anti-CD28 Dynabeads (Gibco). Receptor signaling was measured using an AlexaFluor647-tagged anti-myc antibody (Cell Signaling). Reporter expression was measured through a constitutive mCitrine gene found on the reporter plasmid. Double positive cells were sorted for on Day 5 post initial T-cell stimulation and expanded further for activation testing. FIG. 2C summarizes the results of receptor activation testing, where transcriptional activation of an inducible BFP reporter gene was measured using a Fortessa X-50 (BD Biosciences).

FIG. 4A schematically illustrates various CD8 Hinge-Notch truncation variants including one or more hinge components denoted as "a", "b", "c", and "d". Component "a" represents the region N-terminal of the first cysteine residue. Component "b" represents the first cysteine residue. Component "c" represents the region between the first and second cysteine residues. Component "d" represents the second cysteine residue and the region from the second cysteine residue to the receptor transmembrane domain. The hinge components of the four variants tested are listed.

FIG. 4B summarizes the results of receptor activation testing in Jurkat T-cells. Transcriptional activation of an inducible BFP reporter gene was subsequently measured using a Fortessa X-50 (BD Biosciences). FIG. 4C shows the quantification of % BFP positive cells from data in FIG. 4B. FIG. 4D is a plot of Signal:Noise ratio from data in FIG. 4B.

FIGS. 6A-6B schematically summarizes the results from Hinge-Notch receptors containing alternative hinge domains derived from other sources. As demonstrated in FIG. 6A, in addition to CD8A, CD28, OX40, and IgG4 were found to possess usable hinge domains. In these experiments, four exemplary Hinge-Notch receptors: pIZ343 (truncated CD8Hinge-Notch), pIZ358 (CD28Hinge-Notch), pIZ360 (OX40Hinge-Notch), pIZ359 (IgG4Hinge-Notch). A brief description for each of the Hinge-Notch receptors is provided in Table 2. FIG. 6B depicts the quantification of % BFP positive cells from testing in FIG. 6A.

As shown in FIG. 7B, a previously generated reporter positive Jurkat T-cell line was transduced with a receptor construct. Receptor expression was measured using an AlexaFluor647-tagged anti-myc antibody (Cell Signaling). For receptor activation testing, $1 \times 10^3$ Jurkat T-cells expressing anti-CD19 receptors were co-cultured with: no additions (upper trace), $1 \times 10^5$ K562 cells (middle trace), or $1 \times 10^5$ ALPPL2+ K562 cells/$1 \times 10^5$K562 cells expressing an anti-GFP nanobody on the cell surface (lower trace) for 24 hours. Transcriptional activation of an inducible BFP reporter gene was subsequently measured using a Fortessa X-50 (BD Biosciences).

As illustrated in FIG. 8A, in addition to the Notch1 STS, another STS (e.g., Notch2 STS, Notch4 STS, DAG1 STS, PTPRF STS, and KL STS) can be used to affect receptor behavior. In these experiments, primary human T-cells were activated with anti-CD3/anti-CD28 Dynabeads (Gibco) and transduced with two lentiviral constructs expressing either a receptor or a transcriptional reporter construct. Receptor/reporter positive cells were sorted for on Day 5 post initial T-cell stimulation and expanded further for activation testing. For testing, $1 \times 10^5$ double positive T-cells expressing anti-CD19 receptors were co-cultured with: no additions (upper trace), $1 \times 10^5$ K562 cells (middle trace), or $1 \times 10^5$ CD19+ K562 cells (lower trace) for 24 hours. Transcriptional activation of an inducible BFP reporter gene was subsequently measured using a Fortessa X-50 (BD Biosciences). FIG. 8B depicts the quantification of activation data in FIG. 8A.

FIG. 9A illustrates the construct design for variants including either the full-length or a truncated form of the N-JMD domain of the construct pIZ341. Black bars indicate the amino acids composing each variant. "Full" refers to a full-length variant, including SEQ ID NO: 12. "Trunc 1" refers to a truncation variant No. 1, including SEQ ID NO: 39. "Trunc 2" refers to a truncation variant No. 2, including SEQ ID NO: 13. "Trunc 3" refers to a truncation variant No. 3, including SEQ ID NO: 40. "Trunc" 4 refers to a truncation variant No. 4, including SEQ ID NO: NO: 41. A comparison of expression of these CD8 hinge variants is shown in FIG. 9B. Specifically, primary human CD4+ T-cells were activated with anti-CD3/anti-CD28 Dynabeads and transduced with two lentiviral constructs, one expressing a hinge truncation variant receptor, and the other a BFP transcriptional reporter plus anti-Alkaline phosphatase, placental-like 2 (ALPPL2) CAR. Cells containing both constructs are sorted on Day 5 post initial T-cell stimulation and expanded further for activation testing. The left five panels of FIG. 9B show relative expression levels of each receptor, measured by anti-myc-tag staining (y-axis), versus the reporter construct expression levels, measured by GFP (x-axis). The rightmost panel of FIG. 9B shows MFI quantitation of receptor expression of CD8 hinge variants in double-positive cells. FIG. 9C shows 5 panels, representing the Full variant and the truncation variants 1 to 4, from left to right. For each variant, T-cells expressing anti-CD19 receptors were co-cultured with, from top to bottom, no additions (top trace), ALPPL2+ K562 cells (second trace from top), CD19+ K562 cells (third trace from top), or ALPPL2+ CD19+ (bottom trace). Transcriptional activation of an inducible BFP reporter gene was subsequently measured using a Fortessa X-50 (BD Biosciences).

In FIG. 11A. the left panel refers to a construct with an anti-BCMA scFv binding head, the middle panel refers to a construct with an anti-BCMA fully humanized VH binding head, and the right panel refers to a construct with an anti-BCMA fully humanized VH binding head with hinge domain optimized for the binding domain (Hinge5). A SIRPα binding head was similarly tested. $1\times10^5$ double positive T-cells expressing receptors were co-cultured with no addition (upper trace), or $1\times10^5$ K562 cells (lower trace) for two days (FIG. 11B). In FIG. 11C, different scFvs against the HER2 antigen were tested and compared using similar methods. $1\times10^5$ double positive T-cells expressing receptors were co-cultured with no addition (top trace), adherent HEK 293T cells (second trace from top), adherent MBMDA-468 cells (third trace from top), adherent MCF7 cells (fourth trace from top), or adherent SKBR3 cells (bottom trace) for two days (FIG. 11C). The left panel represents the anti-HER2 4D5-7 scFv binding head, while the right panel represents the anti-HER2 4D5-8 scFv binding head. For FIGS. 11A-11C, transcriptional activation of an inducible BFP reporter gene was subsequently measured using a Fortessa X-50 (BD Biosciences).

In FIG. 13A, the left panel shows relative expression of different receptors, measured by anti-myc-tag staining (y-axis), versus reporter construct marker expression (x-axis), while the right panel represents MFI quantitation of receptor expression of TMD mutant variants in double-positive cells. In FIG. 13B, T-cells expressing anti-CD19 receptors were co-cultured at a ratio of 1:1 with control CD19(-) or CD19(+) K562 cells. Transcriptional activation of an inducible BFP reporter gene was subsequently measured using a Fortessa X-50 (BD Biosciences). The left panel shows flow panels of activation profiles. The right panel represents BFP % plotted as a line graph.

Cells containing both constructs were sorted for on Day 5 post initial T-cell stimulation and expanded further for activation testing. For testing, $1 \times 10^5$ double positive T-cells expressing receptors were co-cultured with: $1 \times 10^5$ K562 cells ("−CAR" panels, blue), or $1 \times 10^5$ CD19+ K562 cells ("−CAR" panels, red). Similarly, $1 \times 10^5$ double positive T-cells expressing receptors were tested in the presence of CAR activity by co-culture with $1 \times 10^5$ ALPPL2+ K562 cells ("+CAR" panels, blue), or $1 \times 10^5$ ALPPL2+ CD19+ K562 cells ("+CAR" panels, red). Transcriptional activation of an inducible BFP reporter gene was subsequently measured using a Fortessa X-50 (BD Biosciences).

Figure 15A:
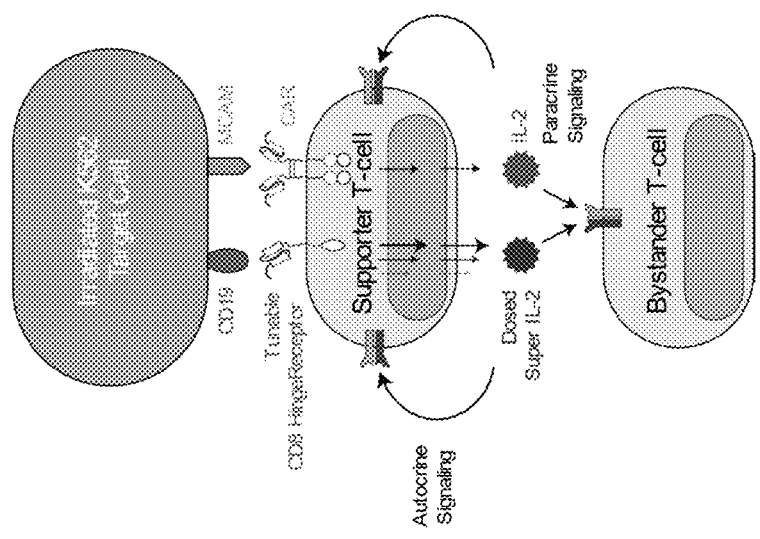
Figure 15B:
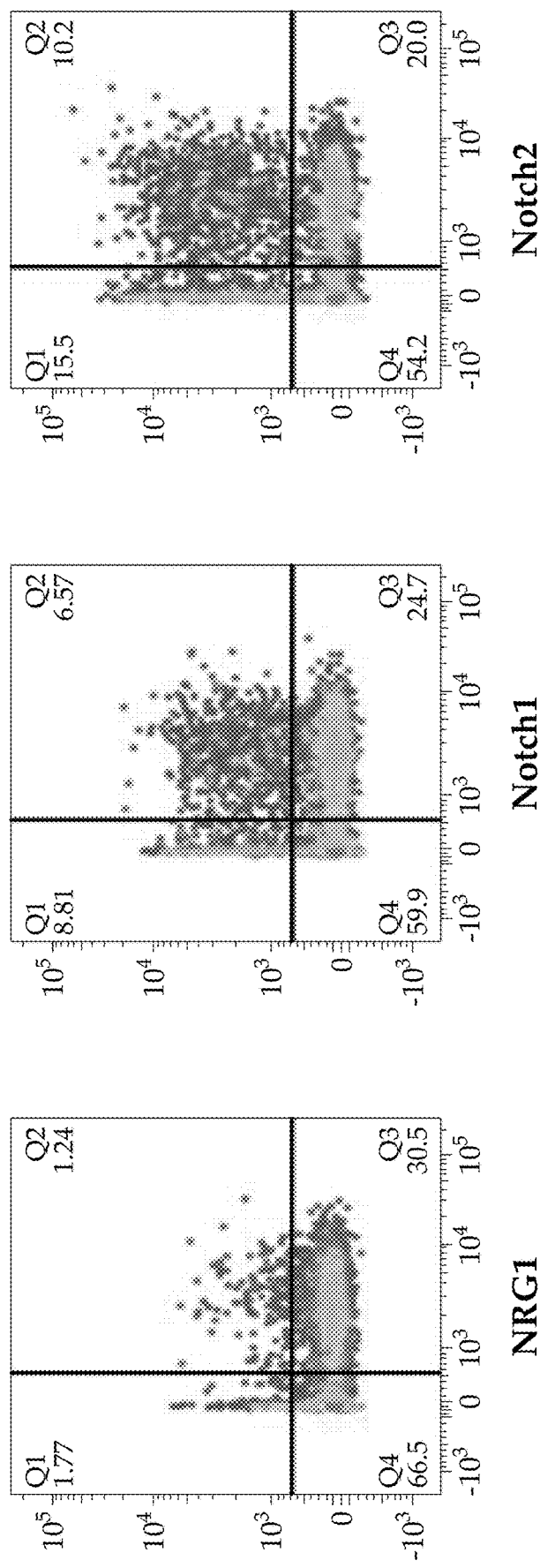

FIGS. 15A-15B schematically summarize the results from experiments for tunable, ligand-dependent expansion of T cells using Hinge-Notch-controlled expression of an engineered cytokine. FIG. 15A shows a diagram of T cells engineered with Hinge-Notch STS variants to provide ligand-triggered secretion of an engineered cytokine for autocrine and paracrine expansion of T cells. Expression profile of anti-CD19 Hinge-Notch receptors with the indicated STS modifications are shown in FIG. 15B. Primary human T-cells were activated with anti-CD3/anti-CD28 Dynabeads and transduced with two lentiviral constructs, one expressing a CAR against the MCAM antigen, and one expressing a Hinge-Notch receptor with inducible super-IL2 under Gal4-UAS control. Cells containing both constructs were sorted on Day 5 post initial T-cell stimulation and expanded further for activation testing. Receptor expression was determined by anti-myc-tag staining (γ-axis).

Figure 16:
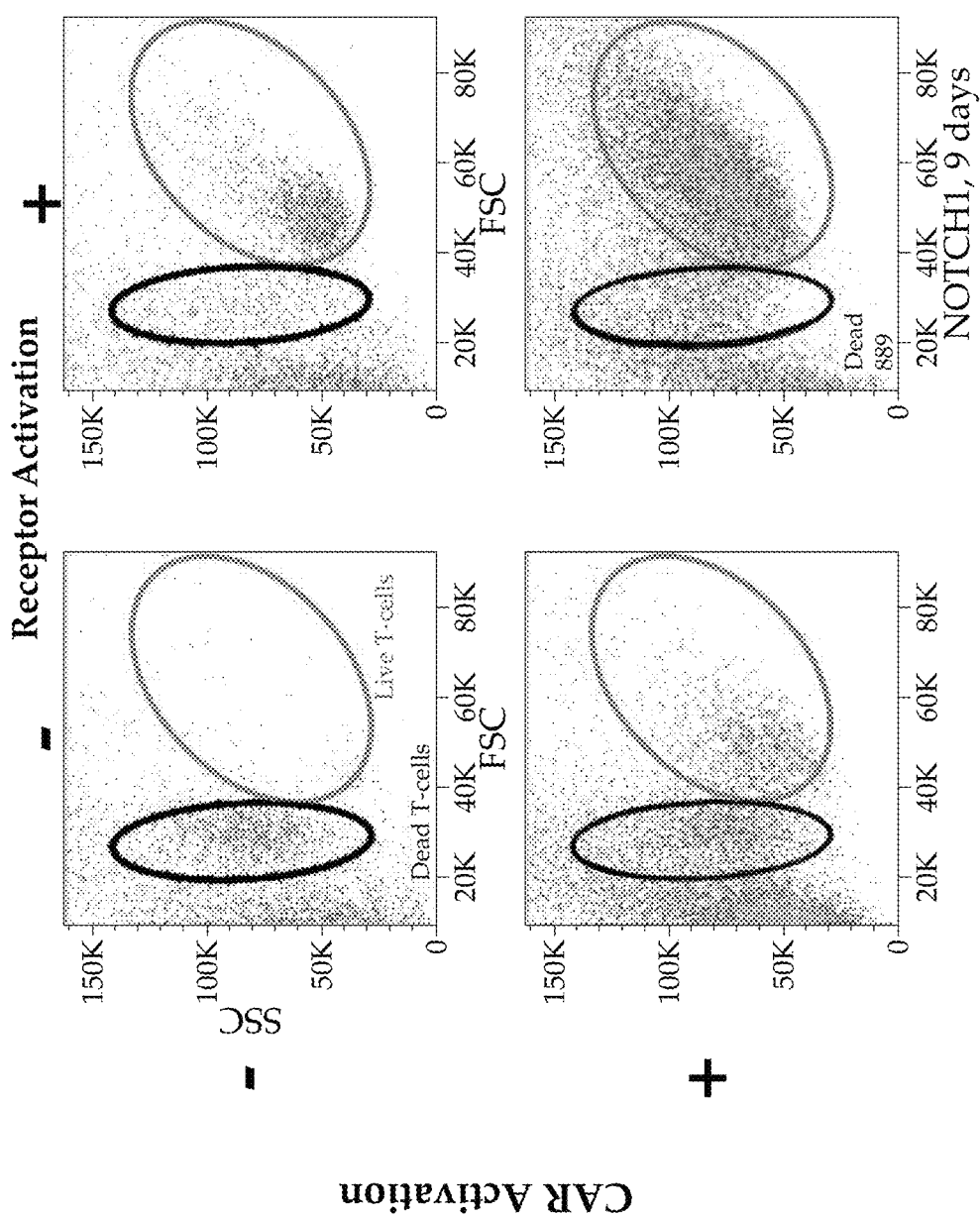

FIG. 16 schematically summarizes the results from experiments performed to demonstrate that ligand-triggered expression of super-IL2 improves cell viability of CAR-T cells. $1 \times 10^5$ double positive T-cells expressing anti-CD19 HingeNotch Notch1 STS receptors were co-cultured in media without IL-2, with no K562 cells (top left), with CD19+ K562 cells to trigger Hinge-Notch (top right), with MCAM+ K562 cells to trigger CAR activation (bottom left) or with MCAM+ and CD19+ K562 cells to trigger activation of both receptors (bottom right). After 9 days the proportion of live T cells by forward and side-scatter measurements using a Fortessa X-50 was assessed.

Figure 17:
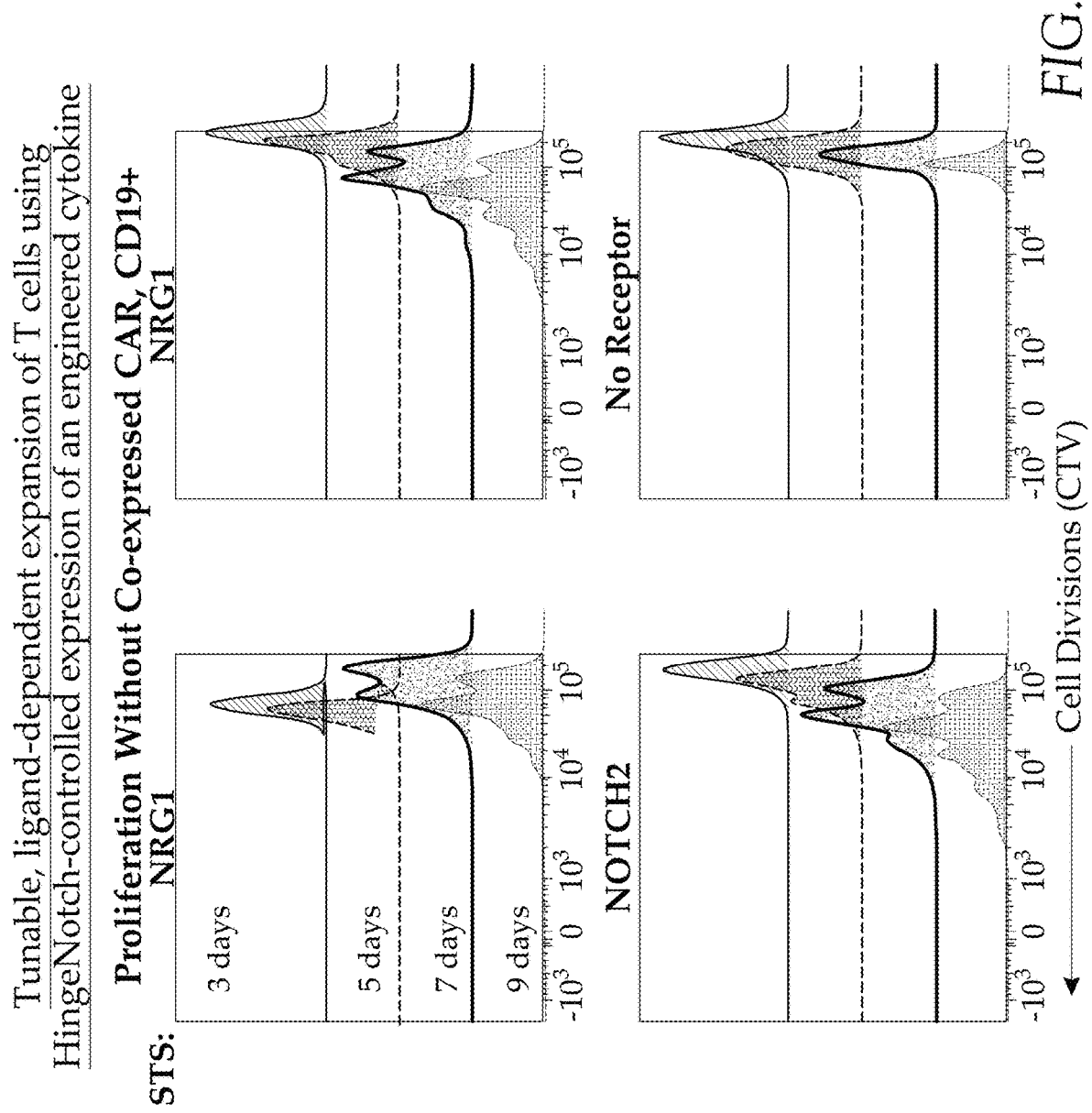
Figure 17:
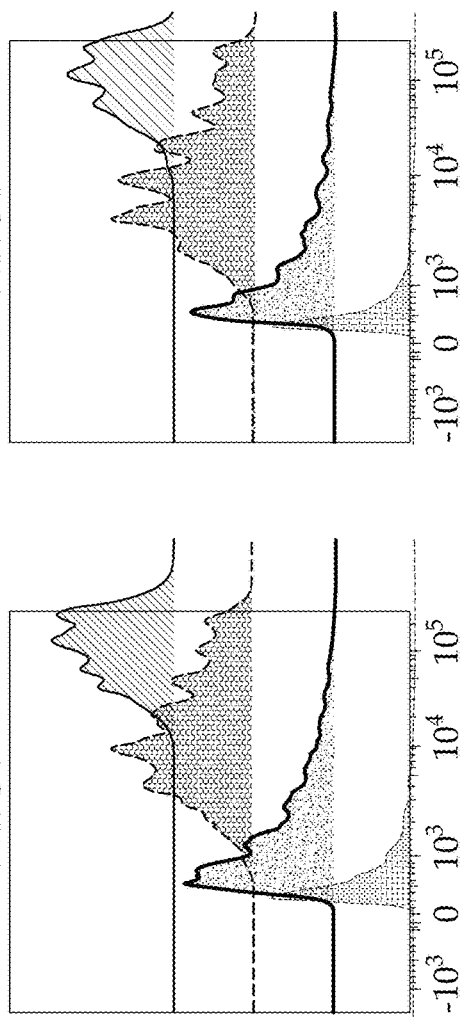
Figure 17:
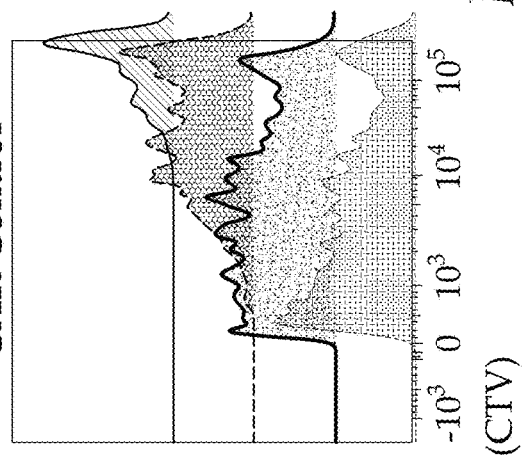
Figure 17:
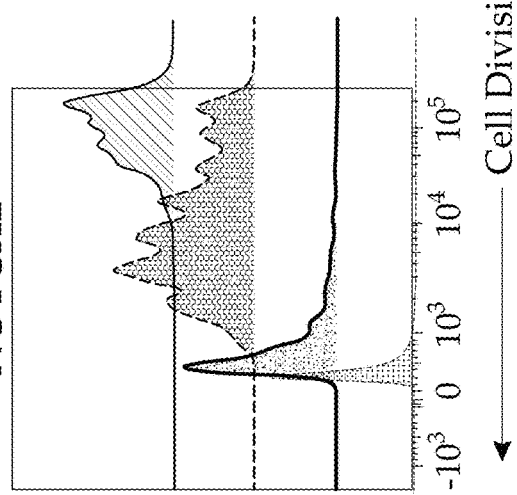

FIG. 17 schematically summarizes the results from experiments performed to demonstrate tunable proliferation of T cells with STS-variants of Hinge-Notch. Primary human T-cells were activated with anti-CD3/anti-CD28 Dynabeads and transduced with two lentiviral constructs, one expressing a CAR against the MCAM antigen, and one expressing a Hinge-Notch receptor with inducible super-IL2 under Gal4-UAS control (the right four panels). Hinge-Notch receptors containing 3 different STS variants (NRG1, Notch1, Notch2) were tested against a no Hinge-Notch control. Similarly, primary human T-cells were generated without CAR expression (left panels). T cells were stained with CellTrace Violet according to manufacturer's protocols, co-incubated with CD19+ K562 target cells in media without IL-2 and measured using a Fortessa X-50 at the indicated timepoints to assess proliferation by CTV signal decay.

Figure 18A:
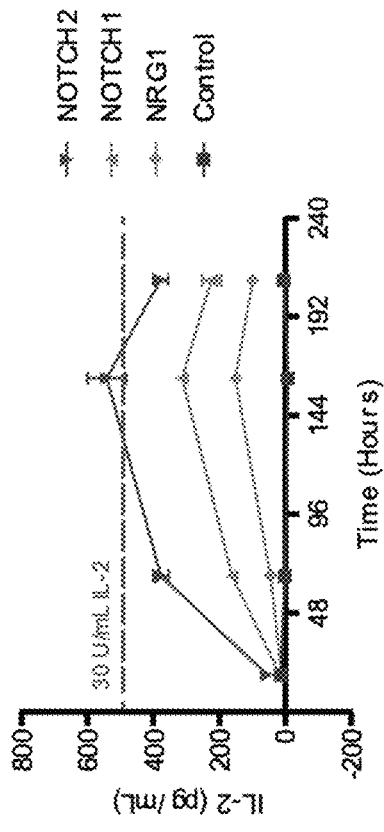
Figure 18B:
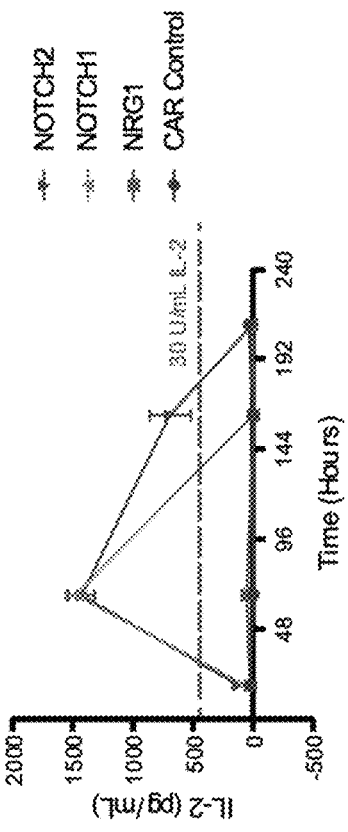

FIGS. 18A-18B schematically summarize the results from experiments performed to demonstrate tunable secretion of super-IL2 with STS-variants of Hinge-Notch. Primary human T-cells were activated with anti-CD3/anti-CD28 Dynabeads and transduced with a lentiviral construct Hinge-Notch receptor with inducible super-IL2 under Gal4-UAS control (FIG. 18A). Hinge-Notch receptors containing 3 different STS variants (NRG1, Notch1, Notch2) were tested against a no HingeNotch control. T cells were co-incubated with MCAM+ CD19+ K562 cells in media lacking IL-2, and at the indicated timepoints, supernatant IL-2 was measured using the Instant ELISA Kit according to manufacturer's protocols with a microplate reader. Red dotted line indicates a standard concentration of IL-2 used for culturing T cells. Graded secretion of super-IL2 was achieved by activation of STS-tuned Hinge-Notch receptors. For FIG. 18B, primary human T-cells were generated with an additional lentiviral vector expressing a CAR against MCAM.

Figure 19:
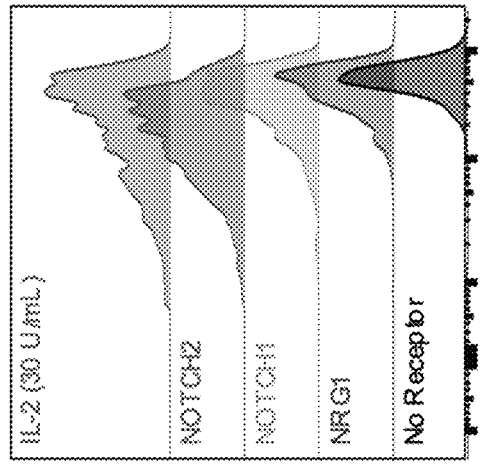
Figure 19:
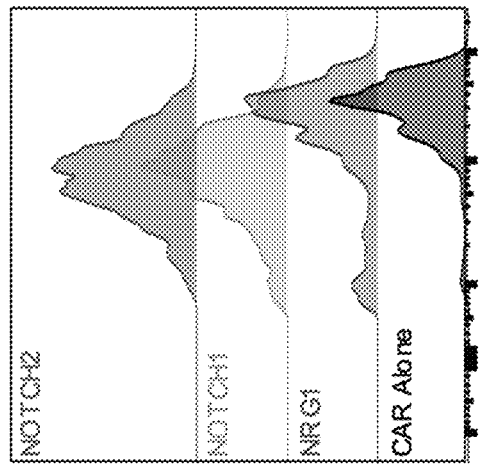

FIG. 19 schematically summarizes the results from experiments performed to demonstrate tunable secretion of super-IL2 with STS-variants of Hinge-Notch enhances proliferation of bystander T cells. Primary human T-cells were activated with anti-CD3/anti-CD28 Dynabeads and transduced with a lentiviral construct including a Hinge-Notch receptor with inducible super-IL2 under Gal4-UAS control (right panels). HingeNotch receptors containing 3 different STS variants (NRG1, Notch1, Notch2) were tested against a no HingeNotch control. HingeNotch T cells were co-incubated with "bystander" T cells stained with CellTrace Far Red expressing a CAR against MCAM (left panel) or with no CAR (right panel). T cells were co-incubated with MCAM+ CD19+ K562 cells in media lacking IL-2, and proliferation of the bystander T cells were assessed by measuring signal decay on a Fortessa X-50.

Figure 20:
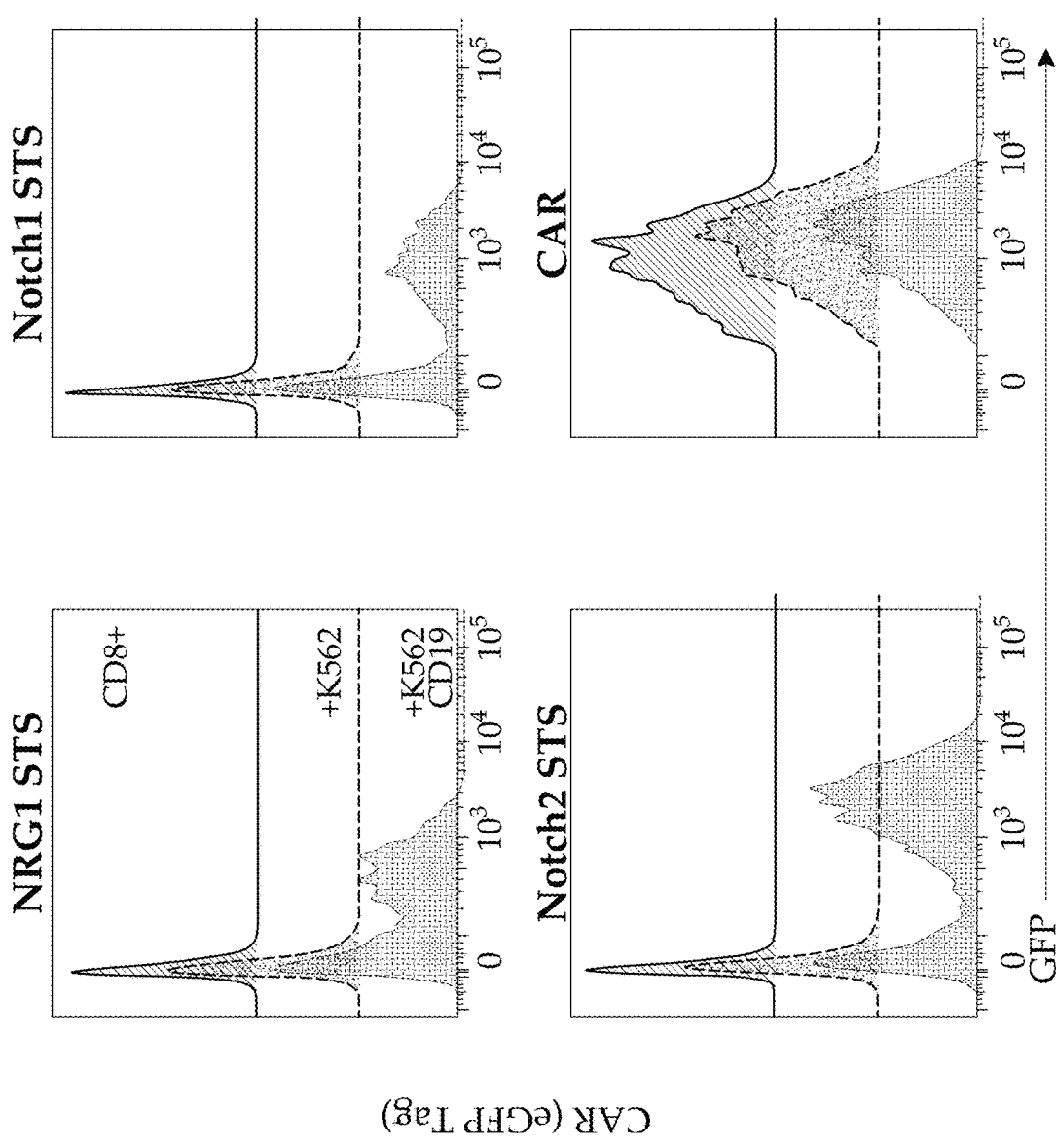

FIG. 20 schematically summarizes the results from experiments performed to test single lentiviral vector constructs containing Hinge-Notch receptors CAR circuits. Primary human T-cells were activated with anti-CD3/anti-CD28 Dynabeads and transduced with a single lentiviral construct containing constitutively expressed Hinge-Notch receptors with an inducible anti-MCAM CAR cassette under Gal4-UAS control. Cells were sorted for Hinge-Notch receptor expression via myc-tag on Day 5 post initial T-cell stimulation and expanded further for activation testing. Three STS-variants were tested as indicated, with constitutively expressed CAR used as a control. For testing, $1 \times 10^5$ T cells expressing anti-CD19 receptors were co-cultured with: no additions (upper trace), $5 \times 10^5$ K562 cells (middle trace), or $5 \times 10^4$ CD19+ K562 cells (lower trace). Transcriptional activation of the inducible CAR was subsequently measured by a GFP tag using a Fortessa X-50.

Figure 21:
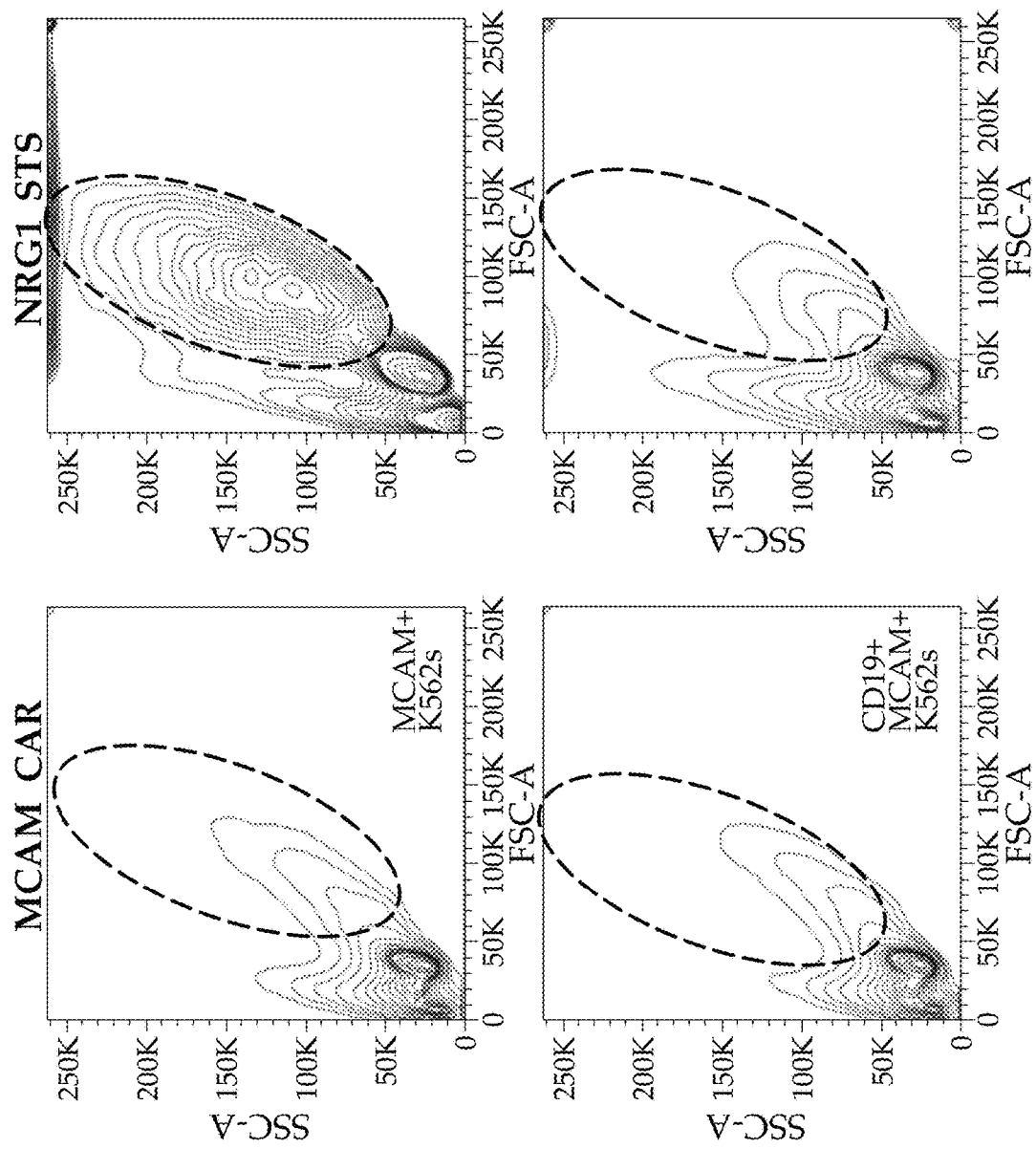
Figure 21:
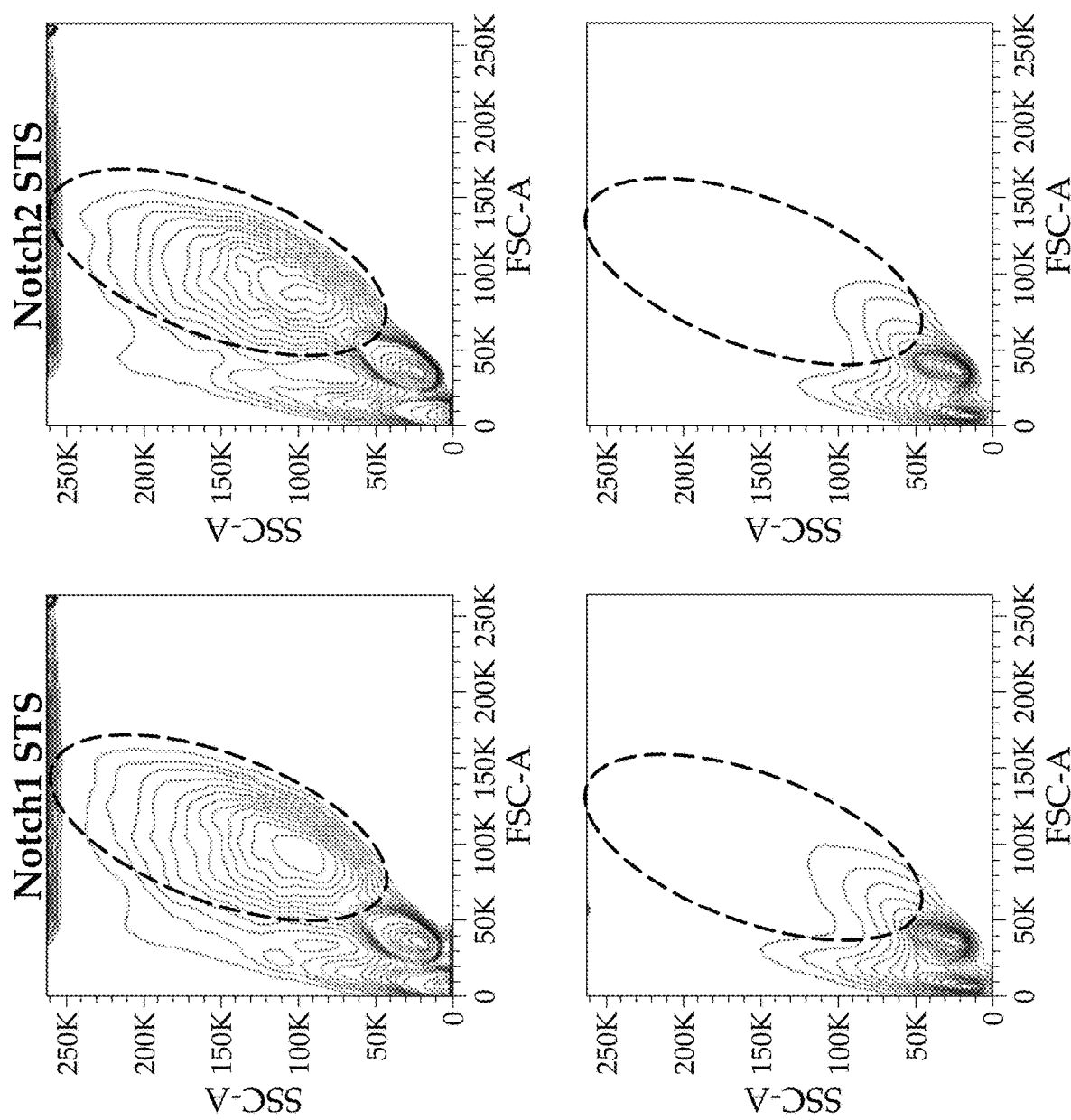

FIG. 21 schematically summarizes the results from experiments performed to demonstrate specific dual antigen target cell killing by T cells engineered with a single lentivector containing a HingeNotch CAR circuit. Primary human T-cells were activated with anti-CD3/anti-CD28 Dynabeads and transduced with a single lentiviral construct containing constitutively expressed HingeNotch-receptors with an inducible anti-MCAM CAR cassette under Gal4-UAS control. Cells were sorted for Hinge-Notch receptor expression via myc-tag on Day 5 post initial T-cell stimulation and expanded further for activation testing. Three STS-variants were tested as indicated, with constitutively expressed CAR used as a control. For testing, $1 \times 10^5$ T-cells expressing anti-CD19 receptors were co-cultured with $5 \times 10^5$ MCAM+ K562 cells or $5 \times 10^4$ MCAM+ CD19+ K562 cells. Target cell killing was assessed by forward/side-scatter of the K562 population using a Fortessa X-50.

Figure 22:
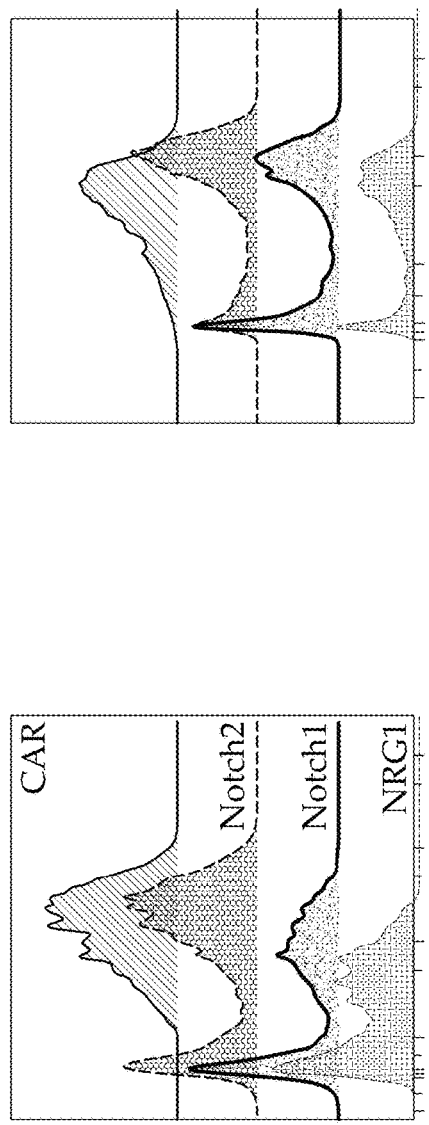
Figure 22:
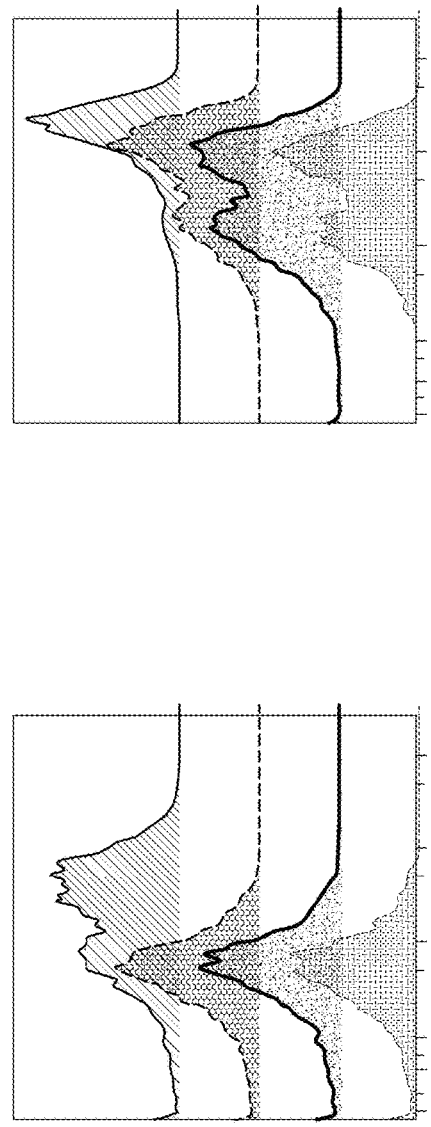

FIG. 22 schematically summarizes the results from experiments performed for testing single lentiviral vector constructs containing Hinge-Notch receptors for control of T cell activation and exhaustion. Primary human T-cells were activated with anti-CD3/anti-CD28 Dynabeads and transduced with a single lentiviral construct containing constitutively expressed Hinge-Notch receptors with an inducible anti-MCAM CAR cassette under Gal4-UAS control. Cells were sorted for Hinge-Notch receptor expression via myc-tag on Day 5 post initial T-cell stimulation and expanded further for activation testing. Three STS-variants were tested as indicated, with constitutively expressed CAR used as a control. For testing, $1\times10^5$ T-cells expressing anti-CD19 receptors were co-cultured with $5\times10^4$ CD19+ K562 cells. Transcriptional activation of the inducible CAR was subsequently measured by a GFP tag using a Fortessa X-50 (the left most panel). T cell activation and exhaustion were measure by expression of CD25 (the second panel from the left side) and CD39 (the third and fourth panels from the left side), respectively.

Figure 23:
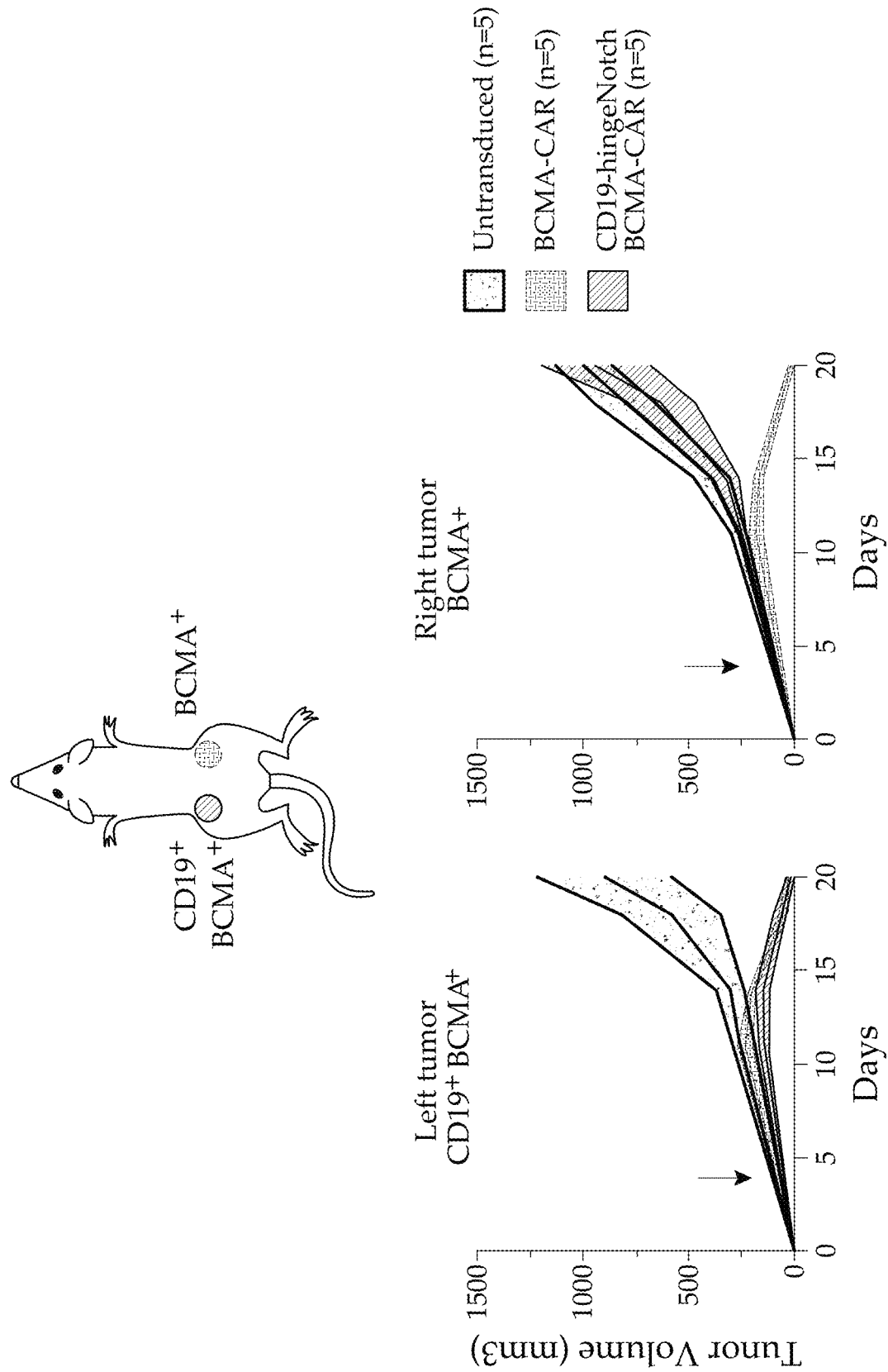
Figure 23:
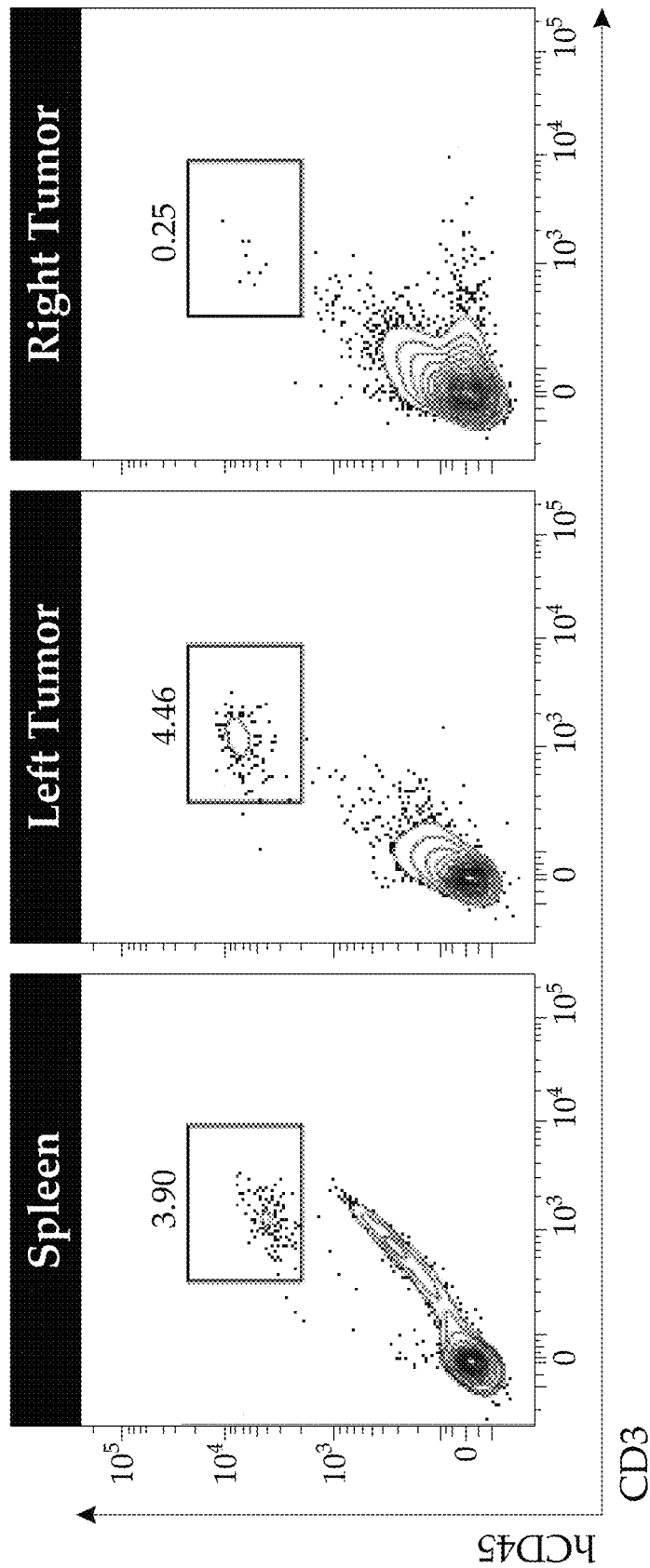
Figure 23:
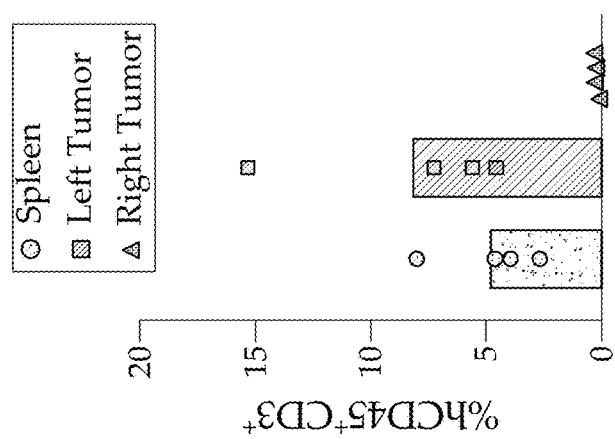
Figure 23:
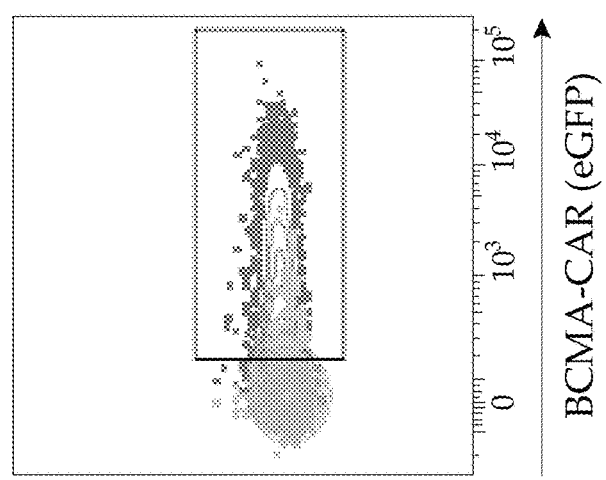
Figure 23:
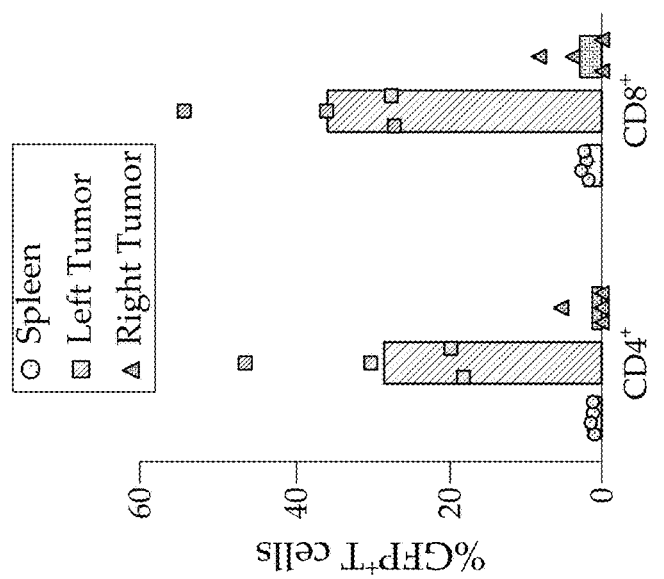

FIG. 23 schematically summarizes the results from experiments performed for in vivo testing of Hinge-Notch-to-CAR circuits. For unilateral tumors, NOD.Cg-Prkdc$^{scid}$ Il2rg$^{tm1Wjl}$/SzJ (NSG) mice were implanted with $1\times10^6$ K562-BCMA/CD19 tumor cells subcutaneously on the left flank. For contralateral tumors, NSG mice were implanted with $1\times10^6$ K562-BCMA/CD19 tumor cells on the left flank and with $1\times10^6$ K562-CD19 tumor cells on the right flank. Four days after tumor implantation, $2.5\times10^6$ engineered primary human CD4+ and CD8+ T cells (total of $5\times10^6$ T cells) were infused i.v. through tail vein injection. Tumor size was monitored via caliper 2-3 per week and mice were determined to have reached endpoint when tumors measured $\geq20$ mm. For immunophenotypic analysis, tumors and spleens were harvested 10 days post T cell implantation. Tumors were manually minced and digested in RPMI-1640 with 4 mg/ml Collagenase IV and 0.1 mg/ml DNase I at 37° C. for 30 min and spleens were manually dissociated and subjected to red blood cell lysis. The following antibodies were used: anti-CD45, anti-CD3, anti-CD4, and anti-CD8. Dead cells were excluded with Draq7. Samples were analyzed using FACSymphony X50 SORP and data was analyzed using FlowJo software.

DETAILED DESCRIPTION OF THE DISCLOSURE

The present disclosure generally relates to, among other things, a new class of oligomerizable chimeric polypeptide receptors engineered to modulate transcriptional regulation in a ligand-dependent manner. Particularly, the new receptors (termed "Hinge-Notch"), even though derived from Notch, do not require the Notch NEC subunit, particularly the NRR previously believed to be essential for the functioning of the receptors. This new class of receptors is synthetic and recombinant, and does not occur in nature. As described below, the chimeric polypeptides disclosed herein can be synthetic polypeptides, or can be engineered, designed, or modified so as to provide desired and/or improved properties, e.g., modulating transcription. The demonstration that the new Hinge-Notch receptors as disclosed herein are not only functional but demonstrate enhanced biologic activity is surprising and is completely contrary to the teachings in the field. In addition, the new chimeric receptors described herein incorporate an extracellular oligomerization domain to promote formation of oligomeric forms, e.g., dimeric or trimeric form of the chimeric receptors. It is believed that this design facilitates oligomerization/clustering of extracellular domains (ECD) and subsequently brings together intracellular domains (ICD) to activate cell signaling, e.g. T-cell signaling. In some embodiments, the receptors disclosed herein bind a target cell-surface ligand, which triggers proteolytic cleavage of the chimeric receptor and release of a transcriptional regulator that modulates a custom transcriptional program in the cell.

The disclosure also provides compositions and methods useful for producing such receptors, nucleic acids encoding same, host cells genetically modified with the nucleic acids, as well as methods for modulating an activity of a cell and/or for the treatment of various health condition, such as diseases (e.g., cancers).

In the following detailed description, reference is made to the accompanying drawings, which form a part hereof. In the drawings, similar symbols generally identify similar components, unless context dictates otherwise. The illustrative alternatives described in the detailed description, drawings, and claims are not meant to be limiting. Other alternatives may be used and other changes may be made without departing from the spirit or scope of the subject matter presented here. It will be readily understood that the aspects, as generally described herein, and illustrated in the Figures, can be arranged, substituted, combined, and designed in a wide variety of different configurations, all of which are explicitly contemplated and make part of this application.

Definitions

The singular form "a", "an", and "the" include plural references unless the context clearly dictates otherwise. For example, the term "a cell" includes one or more cells, including mixtures thereof. "A and/or B" is used herein to include all of the following alternatives: "A", "B", "A or B", and "A and B."

The terms "administration" and "administering", as used herein, refer to the delivery of a composition or formulation as disclosed herein by an administration route including, but not limited to, intravenous, intra-arterial, intracranial, intramuscular, intraperitoneal, subcutaneous, intramuscular, or combinations thereof. The term includes, but is not limited to, administration by a medical professional and self-administration.

"Cancer" refers to the presence of cells possessing characteristics typical of cancer-causing cells, such as uncontrolled proliferation, immortality, metastatic potential, rapid growth and proliferation rate, and certain characteristic morphological features. Some types of cancer cells can aggregate into a mass, such as a tumor, but some cancer cells can exist alone within a subject. A tumor can be a solid tumor, a soft tissue tumor, or a metastatic lesion. As used herein, the term "cancer" also encompass other types of non-tumor cancers. Non-limiting examples include blood cancers or hematological malignancies, such as leukemia, lymphoma, and myeloma. Cancers can include premalignant, as well as malignant cancers.

The terms "host cell" and "recombinant cell" are used interchangeably herein. It is understood that such terms, as well as "cell", "cell culture", "cell line", refer not only to the particular subject cell or cell line but also to the progeny or potential progeny of such a cell or cell line, without regard to the number of transfers or passages in culture. It should be understood that not all progeny are exactly identical to the parental cell. This is because certain modifications may occur in succeeding generations due to either mutation (e.g., deliberate or inadvertent mutations) or environmental influences (e.g., methylation or other epigenetic modifications), such that progeny may not, in fact, be identical to the parent cell, but are still included within the scope of the term as used herein, so long as the progeny retain the same functionality as that of the originally cell or cell line.

The term "operably linked"," as used herein, denotes a physical or functional linkage between two or more elements, e.g., polypeptide sequences or polynucleotide sequences, which permits them to operate in their intended fashion.

The term "percent identity," as used herein in the context of two or more nucleic acids or proteins, refers to two or more sequences or subsequences that are the same or have a specified percentage of nucleotides or amino acids that are the same (e.g., about 60% sequence identity, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the complement of a sequence. This definition also includes sequences that have deletions and/or additions, as well as those that have substitutions. Sequence identity can be calculated over a region that is at least about 20 amino acids or nucleotides in length, or over a region that is 10-100 amino acids or nucleotides in length, or over the entire length of a given sequence. Sequence identity can be calculated using published techniques and widely available computer programs, such as the GCS program package (Devereux et al, Nucleic Acids Res. 12:387, 1984), BLASTP, BLASTN, FASTA (Atschul et al., *J Mol Biol* 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof As used herein, and unless otherwise specified, a "therapeutically effective amount" of an agent is an amount sufficient to provide a therapeutic benefit in the treatment or management of a health condition, such as a disease (e.g., a cancer), or to delay or minimize one or more symptoms associated with the disease. A therapeutically effective amount of a compound means an amount of therapeutic agent, alone or in combination with other therapeutic agents, which provides a therapeutic benefit in the treatment or management of the disease. The term "therapeutically effective amount" can encompass an amount that improves overall therapy of the disease, reduces or avoids symptoms or causes of the disease, or enhances the therapeutic efficacy of another therapeutic agent. An example of an "effective amount" is an amount sufficient to contribute to the treatment, prevention, or reduction of a symptom or symptoms of a disease, which could also be referred to as a "therapeutically effective amount." A "reduction" of a symptom means decreasing of the severity or frequency of the symptom(s), or elimination of the symptom(s). The exact amount of a composition including a "therapeutically effective amount" will depend on the purpose of the treatment, and will be ascertainable by one skilled in the art using known techniques (see, e.g., Lieberman, *Pharmaceutical Dosage Forms* (vols. 1-3, 2010); Lloyd, *The Art, Science and Technology of Pharmaceutical Compounding* (2016); Pickar, *Dosage Calculations* (2012); and *Remington: The Science and Practice of Pharmacy*, 22nd Edition, 2012, Gennaro, Ed., Lippincott, Williams & Wilkins).

As used herein, a "subject" or an "individual" includes animals, such as human (e.g., human individuals) and non-human animals. In some embodiments, a "subject" or "individual" is a patient under the care of a physician. Thus, the subject can be a human patient or an individual who has, is at risk of having, or is suspected of having a disease of interest (e.g., cancer) and/or one or more symptoms of the disease. The subject can also be an individual who is diagnosed with a risk of the condition of interest at the time of diagnosis or later. The term "non-human animals" includes all vertebrates, e.g., mammals, e.g., rodents, e.g., mice, and non-mammals, such as non-human primates, e.g., sheep, dogs, cows, chickens, amphibians, reptiles, etc.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

All ranges disclosed herein also encompass any and all possible sub-ranges and combinations of sub-ranges thereof. Any listed range can be recognized as sufficiently describing and enabling the same range being broken down into at least equal halves, thirds, quarters, fifths, tenths, etc. As a non-limiting example, each range discussed herein can be readily broken down into a lower third, middle third and upper third, and so forth. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

Notch Receptors

Notch receptors are transmembrane proteins that normally transduce signals upon binding to surface-bound ligands expressed on adjacent cells. Notch signals rely on cell-cell contact. Evolutionary divergence of vertebrates and invertebrates has been accompanied by at least two rounds of gene duplication involving the Notch receptors: flies possess a single Notch gene, worms two (GLP-1 and LIN-12), and mammals four (NOTCH1-4). Transduction of Notch signals relies on three key events: (i) ligand recognition, (ii) conformational exposure of the ligand-dependent cleavage site, and (iii) assembly of nuclear transcriptional activation complexes.

Canonical Notch signals are transduced by a process called regulated intramembrane proteolysis. Notch receptors are normally maintained in a resting, proteolytically resistant conformation on the cell surface, but ligand binding initiates a proteolytic cascade that releases the intracellular portion of the receptor (also known as intracellular notch (ICN) or Notch intracellular domain (NICD)) from the membrane. The critical, regulated cleavage step is effected by ADAM metalloproteases and occurs at a site called S2 immediately external to the plasma membrane. This truncated receptor, dubbed NEXT (for Notch extracellular truncation), remains membrane tethered until it is processed at site S3 by gamma secretase, a multiprotein enzyme complex.

After gamma secretase-mediated cleavage, the ICN ultimately enters the nucleus, where it assembles a transcriptional activation complex that contains a DNA-binding transcription factor termed CSL (C-promoter-binding factor in mammals; also known as RBP-J)/Suppressor of hairless in *Drosophila melanogaster* or Lag1 in *Caenorhabditis elegans*), and a transcriptional coactivator of the Mastermind/Lag-3 family. This complex then engages additional coactivator proteins such as p300 to recruit the basal transcription machinery and activate the expression of downstream target genes.

Notch receptors have a modular domain organization. The Notch extracellular subunit (NEC) of Notch receptors consist of a series of N-terminal epidermal growth factor receptor (EGFR)-like repeats that are responsible for ligand binding. O-linked glycosylation of these EGFR repeats, including modification by O-fucose, Fringe, and Rumi glycosyltransferases, also modulates the activity of Notch receptors in response to different ligand subtypes in flies and mammals.

The EGFR repeats are followed by three LIN-12/Notch repeat (LNR) modules, which are unique to Notch receptors, and are widely reported to participate in preventing premature receptor activation. The heterodimerization (HD) domain of Notch1 is divided by furin cleavage, so that its N-terminal part terminates the Notch extracellular subunit (NEC), and its C-terminal half constitutes the beginning of the Notch transmembrane (N™) subunit. Following the extracellular HD-C region of the NEC is a transmembrane segment and an intracellular region (ICN), which includes a transcriptional activator. Additional information regarding Notch receptors and Notch-mediated cell signaling can be found in, for example, W. R. Gordon et al., *Dev Cell* (2015) 33:729-36 and W. R. Gordon et al., *J. Cell Sci.* (2008) 121:3109-19, both of which are hereby incorporated by reference.

Compositions of the Disclosure

As described in greater detail below, the present disclosure provides a new class of oligomerizable chimeric polypeptide receptors engineered to modulate transcriptional regulation in a ligand-dependent manner with various advantages over existing synthetic Notch receptors. For example, since natural Notch receptors are large with the NEC subunit containing several dozen tandem EGFR-like repeats, by omitting the Notch regulatory regions, or even the entire NEC subunit, polynucleotides encoding the receptors of the disclosure can be made smaller than natural Notch receptors and existing SynNotch-encoding polynucleotides, which enables the use of vectors having more limited capacity, or the inclusion of additional elements that would otherwise be excluded by vector capacity-related size constraints.

One skilled in the art will understand that the chimeric polypeptide receptors disclosed herein facilitate amplified activation under certain cellular and environmental contexts. This type of feedback on the receptor activity is a new feature that can be exploited to enhance and tune the production of therapeutic payloads by engineered cells. Furthermore, as described in further detail below, a number of the receptor variants disclosed herein are easier to express than existing SynNotch receptors, as they can be transduced at higher efficiencies and are expressed at higher levels on the cell surface of human primary T cells.

In addition, as described in greater detail below, certain chimeric polypeptide receptors disclosed herein have better activity than existing SynNotch receptors as determined by, e.g., ligand-induced signal levels of a desired transcriptional output. For example, Hinge-Notch and truncHinge-Notch provide higher rates of ligand-induced signal than the corresponding SynNotch, and provide lower rates of signal when not ligand-induced. In addition, certain chimeric polypeptide receptors disclosed herein provide a more modular platform for engineering additional Notch receptors. This modular platform facilitates domains with distinct functions being easily swapped with corresponding domains from, e.g., other species, enabling customization of receptors activation profile. As described in greater detail in the Examples, certain Hinge-Notch and truncated Hinge-Notch receptors as provided herein, in addition to being smaller than existing synNotch receptors and well-expressed, can be customized to a vast degree, with all elements of the receptor extracellular, transmembrane, and intracellular domains available for customization. For example, testing of various CD8 HingeNotch receptors as described herein demonstrated that a variety of extracellular domains are possible. In sharp contrast, a similar process performed on the existing SynNotch1 regulatory domain leads to either loss of expression or loss of switch-like function.

Without being bound to any particular theory, it is believed that the HingeNotch receptors described herein can provide higher levels of ligand-induced signal when compared to either murine or human versions of SynNotch1. It is also believed that HingeNotch receptors described herein can provide lower levels of signal in the absence of ligand when compared to murine versions of SynNotch1 (e.g., lower noise signal signal). For example, existing SynNotch receptors can be engineered with ligand-binding domains such as scFvs and nanobodies, but it has been difficult to use natural extracellular domains from receptors/ligands on SynNotch receptors. In contrast, the second-generation Notch receptors provided herein are amenable to the use of other types of ligand binding domains, e.g., binding domains other than scFv, thus expanding the landscape of targetable diseases and tissues. For example, experiments presented in the Examples section below demonstrated the ability to use eGFP as ligand-binding domain, which can bind the anti-GFP nanobody LaG17 expressed on the surface of a target cell. In contrast, existing synthetic Notch receptor such as murine and human SynNotch1 were not compatible with eGFP as a ligand-binding domain.

As described in the Examples, certain chimeric polypeptide receptors have been tested and validated in primary human T cells. These new receptors are expected to show similar performance in mouse models. The receptors disclosed herein may be engineered into various immune cell types for enhanced discrimination and elimination of tumors, or in engineered cells for control of autoimmunity and tissue regeneration. Accordingly, engineered cells, such as immune cells engineered to express one of more of the chimeric receptors disclosed herein, are also within the scope of the disclosure.

Chimeric Polypeptides

As outlined above, some embodiments of the present disclosure relate to novel, non-naturally occurring chimeric polypeptides engineered to modulate transcriptional regulation in a ligand-dependent manner. In particular, the new receptors, even though derived from Notch, do not require the Notch regulatory regions (NRRs) previously believed to be essential for the functioning of the receptors. Furthermore, the new engineered receptors described herein incorporate an extracellular oligomerization domain (e.g., hinge domain) to promote oligomerization to form higher order oligomeric, e.g., dimeric or trimeric, forms of the chimeric receptors. In some embodiments, the hinge domain includes polypeptide motifs capable of promoting oligomer formation of the chimeric polypeptide via intermolecular disulfide bonding. The extracellular oligomerization domain can replace part or all of the Notch extracellular domain. In some embodiments, the receptors disclosed herein bind a target cell-surface ligand, which triggers proteolytic cleavage of the receptors and release of a transcriptional regulator that modulates a custom transcriptional program in the cell.

In some embodiments, provided herein is a chimeric polypeptide including, from N-terminus to C-terminus: (a) an extracellular ligand-binding domain (ECD) having a binding affinity for a selected ligand; (b) a hinge domain capable of promoting oligomer formation of the chimeric polypeptide via intermolecular disulfide bonding; (c) a transmembrane domain (TMD) including one or more ligand-inducible proteolytic cleavage sites; and (d) an intracellular domain (ICD) including a transcriptional regulator, wherein binding of the selected ligand to the ECD induces cleavage at a ligand-inducible proteolytic cleavage site(s) between the transcriptional regulator and the hinge domain, and wherein the chimeric polypeptide does not include a LIN-12-Notch repeat (LNR) and/or a heterodimerization domain (HD) of a Notch receptor.

Extracellular Domains (ECD)

In some embodiments, the ECD of the chimeric polypeptide receptors (e.g., Hinge-Notch receptors) disclosed herein has a binding affinity for one or more target ligands. The target ligand is expressed on a cell surface, or is otherwise anchored, immobilized, or restrained so that it can exert a mechanical force on the chimeric receptor. As such, without being bound to any particular theory, binding of the ECD of a chimeric receptor provided herein to a cell-surface ligand does not necessarily remove the target ligand from the target cell surface, but instead enacts a mechanical pulling force on the chimeric receptor. For example, an otherwise soluble ligand may be targeted if it is bound to a surface, or to a molecule in the extracellular matrix. In some embodiments, the target ligand is a cell-surface ligand. Non-limiting examples of suitable ligand types include cell surface receptors; adhesion proteins; carbohydrates, lipids, glycolipids, lipoproteins, and lipopolysaccharides that are surface-bound; integrins; mucins; and lectins. In some embodiments, the ligand is a protein. In some embodiments, the ligand is a carbohydrate.

In some embodiments, the ligand is a cluster of differentiation (CD) marker. In some embodiments, the CD marker is selected from the group consisting of CD1, CD1a, CD1b, CD1c, CD1d, CD1e, CD2, CD3d, CD3e, CD3g, CD4, CD5, CD7, CD8a, CD8b, CD19, CD20, CD21, CD22, CD23, CD25, CD27, CD28, CD33, CD34, CD40, CD45, CD48, CD52, CD59, CD66, CD70, CD71, CD72, CD73, CD79A, CD79B, CD80 (B7.1), CD86 (B7.2), CD94, CD95, CD134, CD140 (PDGFR4), CD152, CD154, CD158, CD178, CD181 (CXCR1), CD182 (CXCR2), CD183 (CXCR3), CD210, CD246, CD252, CD253, CD261, CD262, CD273 (PD-L2), CD274 (PD-L1), CD276 (B7H3), CD279, CD295, CD339 (JAG1), CD340 (HER2), EGFR, FGFR2, CEA, AFP, CA125, MUC-1, and MAGE.

In some embodiments, the extracellular domain includes the ligand-binding portion of a receptor. In some embodiments, the extracellular domain includes an antigen-binding moiety that binds to one or more target antigens. In some embodiments, the antigen-binding moiety includes one or more antigen-binding determinants of an antibody or a functional antigen-binding fragment thereof. One skilled in the art upon reading the present disclosure will readily understand that the term "functional fragment thereof" or "functional variant thereof" refers to a molecule having quantitative and/or qualitative biological activity in common with the wild-type molecule from which the fragment or variant was derived. For example, a functional fragment or a functional variant of an antibody is one which retains essentially the same ability to bind to the same epitope as the antibody from which the functional fragment or functional variant was derived. For instance, an antibody capable of binding to an epitope of a cell surface receptor may be truncated at the N-terminus and/or C-terminus, and the retention of its epitope binding activity assessed using assays known to those of skill in the art. In some embodiments, the antigen-binding moiety is selected from the group consisting of an antibody, a nanobody, a diabody, a triabody, or a minibody, an F(ab')$_2$ fragment, an F(ab) fragment, a single chain variable fragment (scFv), and a single domain antibody (sdAb), or a functional fragment thereof. In some embodiments, the antigen-binding moiety includes an scFv.

The antigen-binding moiety can include naturally-occurring amino acid sequences or can be engineered, designed, or modified to provide desired and/or improved properties such as, e.g., binding affinity. Generally, the binding affinity of an antigen-binding moiety, e.g., an antibody, for a target antigen (e.g., CD19 antigen) can be calculated by the Scatchard method described by Frankel et al., *Mol. Immunol,* 16:101-06, 1979. In some embodiments, binding affinity is measured by an antigen/antibody dissociation rate. In some embodiments, binding affinity is measured by a competition radioimmunoassay. In some embodiments, binding affinity is measured by ELISA. In some embodiments, antibody affinity is measured by flow cytometry. An antibody that "selectively binds" an antigen (such as CD19) is an antigen-binding moiety that does not significantly bind other antigens but binds the antigen with high affinity, e.g., with an equilibrium constant (KD) of 100 nM or less, such as 60 nM or less, for example, 30 nM or less, such as, 15 nM or less, or 10 nM or less, or 5 nM or less, or 1 nM or less, or 500 pM or less, or 400 pM or less, or 300 pM or less, or 200 μM or less, or 100 μM or less.

A skilled artisan can select an ECD based on the desired localization or function of a cell that is genetically modified to express a chimeric polypeptide or Hinge-Notch receptor of the present disclosure. For example, a chimeric polypeptide or miniNotch receptor with an ECD including an antibody specific for a HER2 antigen can target cells to HER2-expressing breast cancer cells. In some embodiments, the ECD of the disclosed polypeptide Hinge-Notch receptors is capable of binding a tumor-associated antigen (TAA) or a tumor-specific antigen (TSA). A skill artisan will understand that TAAs include a molecule, such as e.g., protein, present on tumor cells and on normal cells, or on many normal cells, but at much lower concentration than on tumor cells. In contrast, TSAs generally include a molecule, such as e.g., protein which is present on tumor cells but absent from normal cells.

In some cases, the antigen-binding moiety is specific for an epitope present in an antigen that is expressed by a tumor cell, i.e., a tumor-associated antigen. The tumor-associated antigen can be an antigen associated with, e.g., a breast cancer cell, a B cell lymphoma, a pancreatic cancer, a Hodgkin lymphoma cell, an ovarian cancer cell, a prostate cancer cell, a mesothelioma, a lung cancer cell, a non-Hodgkin B-cell lymphoma (B-NHL) cell, an ovarian cancer cell, a prostate cancer cell, a mesothelioma cell, a melanoma cell, a chronic lymphocytic leukemia cell, an acute lymphocytic leukemia cell, a neuroblastoma cell, a glioma, a glioblastoma, a colorectal cancer cell, etc. It will also be understood that a tumor-associated antigen may also be expressed by a non-cancerous cell. In some embodiments, the antigen-binding domain is specific for an epitope present in a tissue-specific antigen. In some embodiments, the antigen-binding domain is specific for an epitope present in a disease-associated antigen.

Non-limiting examples of suitable target antigens include CD19, B7H3 (CD276), BCMA (CD269), alkaline phosphatase, placental-like 2 (ALPPL2), green fluorescent protein (GFP), enhanced green fluorescent protein (EGFP), signal regulatory protein α (SIRPα), CD123, CD171, CD179a, CD20, CD213A2, CD22, CD24, CD246, CD272, CD30, CD33, CD38, CD44v6, CD46, CD71, CD97, CEA, CLDN6, CLECL1, CS-1, EGFR, EGFRvIII, ELF2M, EpCAM, EphA2, Ephrin B2, FAP, FLT3, GD2, GD3, GM3, GPRC5D, HER2 (ERBB2/neu), IGLL1, IL-11Rα, KIT (CD 117), MUC1, NCAM, PAP, PDGFR-β, PRSS21, PSCA, PSMA, ROR1, SSEA-4, TAG72, TEM1/CD248, TEM7R, TSHR, VEGFR2, ALPI, citrullinated vimentin, cMet, and Axl.

In some embodiments, the target antigen is selected from CD19, B7H3 (CD276), BCMA (CD269), ALPPL2, CD123, CD171, CD179a, CD20, CD213A2, CD22, CD24, CD246, CD272, CD30, CD33, CD38, CD44v6, CD46, CD71, CD97, CEA, CLDN6, CLECL1, CS-1, EGFR, EGFRvIII, ELF2M, EpCAM, EphA2, Ephrin B2, FAP, FLT3, GD2, GD3, GM3, GPRC5D, HER2 (ERBB2/neu), IGLL1, IL-11Rα, KIT (CD117), MUC1, NCAM, PAP, PDGFR-β, PRSS21, PSCA, PSMA, ROR1, SSEA-4, TAG72, TEM1/CD248, TEM7R, TSHR, VEGFR2, ALPI, citrullinated vimentin, cMet, Axl, GPC2, human epidermal growth factor receptor 2 (Her2/neu), CD276 (B7H3), IL-13Rα1, IL-13Rα2, α-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD123, CD93, CD99, CD117, chromogranin, cytokeratin, desmin, glial fibrillary acidic protein (GFAP), gross cystic disease fluid protein (GCDFP-15), ALK, DLK1, FAP, NY-ESO, WT1, HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysin, thyroglobulin, thyroid transcription factor-1, AOC3 (VAP-1), CAM-3001, CCL11 (eotaxin-1), CD125, CD147 (basigin), CD154 (CD40L), CD2, CD20, CD23 (IgE receptor), CD25 (a subunit of the heterodimeric IL-2 receptor), CD3, CD4, CD5, IFN-α, IFN-γ, IgE, IgE Fc region, IL-1, IL-12, IL-23, IL-13, IL-17, IL-17A, IL-22, IL-4, IL-5, IL-5, IL-6, IL-6 receptor, integrin α4, integrin α4β7, LFA-1 (CD11α), myostatin, OX-40, scleroscin, SOST, TGFβ1, TNF-α, VEGF-A, pyruvate kinase isoenzyme type M2 (tumor M2-PK), CD20, CD5, CD7, CD3, TRBC1, TRBC2, BCMA, CD38, CD123, CD93, CD34, CD1α, SLAMF7/CS1, FLT3, CD33, CD123, TALLA-1, CSPG4, DLL3, Kappa light chain, Lamba light chain, CD16/FcγRIII, CD64, FITC, CD22, CD27, CD30, CD70, GD2 (ganglioside G2), GD3, EGFRvIII (epidermal growth factor variant III), EGFR and isovariants thereof, TEM-8, sperm protein 17 (Sp17), mesothelin.

Further non-limiting examples of suitable antigens include PAP (prostatic acid phosphatase), prostate stem cell antigen (PSCA), prostein, NKG2D, TARP (T cell receptor gamma alternate reading frame protein), Trp-p8, STEAP1 (six-transmembrane epithelial antigen of the prostate 1), an abnormal ras protein, an abnormal p53 protein, integrin p3 (CD61), galactin, K-Ras (V-Ki-ras2 Kirsten rat sarcoma viral oncogene), Ral-B, GPC2, CD276 (B7H3), or IL-13Rα. In some embodiments, the antigen is Her2. In some embodiments, the antigen is ALPPL2. In some embodiments, the antigen is BCMA. In some embodiments, the antigen-binding moiety of the ECD is specific for a reporter protein, such as GFP and eGFP. Non-limiting examples of such antigen binding moiety include a LaG17 anti-GFP nanobody. In some embodiments, the antigen-binding moiety of the ECD includes an anti-BCMA fully-humanized VH domain (FHVH). In some embodiments, the antigen is signal regulatory protein α (SIRPα).

Additional antigens suitable for targeting by the chimeric polypeptide receptors disclosed herein include, but are not limited to GPC2, human epidermal growth factor receptor 2 (Her2/neu), CD276 (B7H3), IL-13Rα1, IL-13Rα2, α-fetoprotein (AFP), carcinoembryonic antigen (CEA), cancer antigen-125 (CA-125), CA19-9, calretinin, MUC-1, epithelial membrane protein (EMA), epithelial tumor antigen (ETA). Other suitable target antigens include, but are not limited to, tyrosinase, melanoma-associated antigen (MAGE), CD34, CD45, CD123, CD93, CD99, CD117, chromogranin, cytokeratin, desmin, glial fibrillary acidic protein (GFAP), gross cystic disease fluid protein (GCDFP-15), ALK, DLK1, FAP, NY-ESO, WT1, HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysin, thyroglobulin, thyroid transcription factor-1.

Additional antigens suitable for targeting by the chimeric receptors disclosed herein include, but are not limited to, those associated with an inflammatory disease such as, AOC3 (VAP-1), CAM-3001, CCL11 (eotaxin-1), CD125, CD147 (basigin), CD154 (CD40L), CD2, CD20, CD23 (IgE receptor), CD25 (a subunit of the heteromeric of IL-2 receptor), CD3, CD4, CD5, IFN-α, IFN-γ, IgE, IgE Fc region, IL-1, IL-12, IL-23, IL-13, IL-17, IL-17A, IL-22, IL-4, IL-5, IL-5, IL-6, IL-6 receptor, integrin α4, integrin α4β7, LFA-1 (CD11α), myostatin, OX-40, scleroscin, SOST, TGFβ1, TNF-α, and VEGF-A.

Further antigens suitable for targeting by the chimeric polypeptides and Hinge-Notch receptors disclosed herein include, but are not limited to the pyruvate kinase isoenzyme type M2 (tumor M2-PK), CD20, CD5, CD7, CD3, TRBC1, TRBC2, BCMA, CD38, CD123, CD93, CD34, CD1α, SLAMF7/CS1, FLT3, CD33, CD123, TALLA-1, CSPG4, DLL3, Kappa light chain, Lamba light chain, CD16/FcγRIII, CD64, FITC, CD22, CD27, CD30, CD70, GD2 (ganglioside G2), GD3, EGFRvIII (epidermal growth factor variant III), EGFR and isovariants thereof, TEM-8, sperm protein 17 (Sp17), mesothelin. Further non-limiting examples of suitable antigens include PAP (prostatic acid phosphatase), prostate stem cell antigen (PSCA), prostein, NKG2D, TARP (T cell receptor gamma alternate reading frame protein), Trp-p8, STEAP1 (six-transmembrane epithelial antigen of the prostate 1), an abnormal ras protein, an abnormal p53 protein, integrin β3 (CD61), galactin, K-Ras (V-Ki-ras2 Kirsten rat sarcoma viral oncogene), and Ral-B. In some embodiments, the antigen is GPC2, CD19, Her2/neu, CD276 (B7H3), IL-13Rα1, or IL-13Rα2. In some embodiments, the antigen is Her2. In some embodiments, the antigen is ALPPL2. In some embodiments, the antigen is BCMA. In some embodiments, the antigen-binding moiety of the ECD is specific for a reporter protein, such as GFP and eGFP. Non-limiting examples of such antigen binding moiety include a LaG17 anti-GFP nanobody. In some embodiments, the antigen-binding moiety of the ECD includes an anti-BCMA fully-humanized VH domain (FHVH).

In some embodiments, antigens suitable for targeting by the chimeric polypeptides and Hinge-Notch receptors disclosed herein include ligands derived from a pathogen. For example, the antigen can be HER2 produced by HER2-positive breast cancer cells. In some embodiments, the antigen can be CD19 that is expressed on B-cell leukemia. In some embodiments, the antigen can be EGFR that is expressed on glioblastoma multiform (GBM) but much less expressed so on healthy CNS tissue. In some embodiments, the antigen can be CEA that is associated with cancer in adults, for example colon cancer.

In some embodiments, the antigen-binding moiety of the ECD is specific for a cell surface target, where non-limiting examples of cell surface targets include CD19, CD30, Her2, CD22, ENPP3, EGFR, CD20, CD52, CD11α, and α-integrin. In some embodiments, the chimeric polypeptides and Hinge-Notch receptors disclosed herein include an extracellular domain having an antigen-binding moiety that binds CD19, CEA, HER2, MUC1, CD20, ALPPL2, BCMA, or EGFR. In some embodiments, the chimeric polypeptides provided herein (e.g., Hinge-Notch receptors) include an extracellular domain including an antigen-binding moiety that binds CD19. In some embodiments, the chimeric polypeptides provided herein (e.g., Hinge-Notch receptors) include an extracellular domain including an antigen-binding moiety that binds ALPPL2. In some embodiments, the chimeric polypeptides provided herein (e.g., Hinge-Notch receptors) include an extracellular domain including an antigen-binding moiety that binds BCMA. In some embodiments, the chimeric polypeptides provided herein (e.g., Hinge-Notch receptors) include an extracellular domain including an antigen-binding moiety that binds Her2.

In some embodiments, the chimeric polypeptides and Hinge-Notch receptors disclosed herein include an extracellular domain including an antigen-binding moiety that binds CD19, ALPPL2, BCMA, or Her2. In some embodiments, the antigen-binding moiety includes an amino acid sequence having at least 70%, at least 75%, at least 80%, at least 85%, at least 90%, at least 95%, at least 96%, at least 97%, at least 98%, at least 99% sequence identity to one or more of SEQ ID NOS: 9-11, 36-38, and 72 in the Sequence Listing. In some embodiments, the antigen-binding moiety includes an amino acid sequence having at least 90% sequence identity to a sequence selected from the group consisting of SEQ ID NOS: 9-11, 36-38, and 72. In some embodiments, the antigen-binding moiety includes an amino acid sequence having at least 95% sequence identity to a sequence selected from the group consisting of SEQ ID NOS: 9-11, 36-38, and 72. In some embodiments, the antigen-binding moiety includes an amino acid sequence having 100% sequence identity to one or more of SEQ ID NOS: 9-11, 36-38, and 72. In some embodiments, the antigen-binding moiety includes an amino acid sequence having a sequence selected from the group consisting of SEQ ID NOS: 9-11, 36-38, and 72, wherein one, two, three, four, or five of the amino acid residues in any one of the SEQ ID NOS: 9-11, 36-38, and 72 is/are substituted by a different amino acid residue.

Hinge Domain

As outlined above, the Notch extracellular domains located N-terminally to the TMD of the chimeric polypeptide of the disclosure include an oligomerization domain (e.g., hinge domain) containing one or more polypeptide motifs that promote oligomer formation of the chimeric polypeptides via intermolecular disulfide bonding. In these instances, within the chimeric Notch receptors disclosed herein, the hinge domain generally includes a flexible oligo- or polypeptide connector region disposed between the ECD and the TMD. Thus, the hinge domain provides flexibility between the ECD and TMD and also provides sites for intermolecular disulfide bonding between two or more chimeric polypeptide monomers to form an oligomeric complex. In some embodiments, the hinge domain includes motifs that promote dimer formation of the chimeric polypeptides disclosed herein. In some embodiments, the hinge domain includes motifs that promote trimer formation of the chimeric polypeptides disclosed herein (e.g., a hinge domain derived from OX40).

Hinge polypeptide sequences suitable for the compositions and methods of the disclosure can be naturally-occurring hinge polypeptide sequences (e.g., those from naturally-occurring immunoglobulins). Alternatively, a hinge polypeptide sequence can be a synthetic sequence that corresponds to a naturally-occurring hinge polypeptide sequence, or can be an entirely synthetic hinge sequence, or can be engineered, designed, or modified to provide desired and/or improved properties, e.g., modulating transcription. Suitable hinge polypeptide sequences include, but are not limited to, those derived from IgA, IgD, and IgG subclasses, such as IgG1 hinge domain, IgG2 hinge domain, IgG3 hinge domain, and IgG4 hinge domain, or a functional variant thereof. In some embodiments, the hinge polypeptide sequence contains one or more CXXC motifs. In some embodiments, the hinge polypeptide sequence contains one or more CPPC motifs. Additional information in this regard can be found in, for example, a recent review by Vidarsson G. et al., *Frontiers Immunol*. Oct. 20, 2014, which is hereby incorporated by reference in its entirety.

Accordingly, in some embodiments, the hinge domain includes a hinge polypeptide sequence derived from an IgG1 hinge domain or a functional variant thereof. In some embodiments, the hinge domain includes a hinge polypeptide sequence derived from an IgG2 hinge domain or a functional variant thereof. In some embodiments, the hinge domain includes a hinge polypeptide sequence derived from an IgG3 hinge domain or a functional variant thereof. In some embodiments, the hinge domain includes a hinge polypeptide sequence derived from an IgG4 hinge domain or a functional variant thereof. In some embodiments, the hinge domain includes a hinge polypeptide sequence derived from an IgA hinge domain or a functional variant thereof. In some embodiments, the hinge domain includes a hinge polypeptide sequence derived from an IgD hinge domain or a functional variant thereof.

Additional hinge polypeptide sequences suitable for the compositions and methods disclosed herein include, but are not limited to, hinge polypeptide sequences derived from a CD8α hinge domain, a CD28 hinge domain, a CD152 hinge domain, a PD-1 hinge domain, a CTLA4 hinge domain, an OX40 hinge domain, an FcγRIIIα hinge domain, and functional variants thereof. In some embodiments, the hinge domain includes a hinge polypeptide sequence derived from a CD8α hinge domain or a functional variant thereof. In some embodiments, the hinge domain includes a hinge polypeptide sequence derived from a CD28 hinge domain or a functional variant thereof. In some embodiments, the hinge domain includes a hinge polypeptide sequence derived from an OX40 hinge domain or a functional variant thereof. In some embodiments, the hinge domain includes a hinge polypeptide sequence derived from an IgG4 hinge domain or a functional variant thereof.

In principle, there are no particular limitations to the length and/or amino acid composition of the hinge domain other than it confers flexibility and the capacity for oligomerization. However, one skilled in the art will readily appreciate that the length and amino acid composition of the hinge polypeptide sequence can be optimized to vary the orientation and/or proximity of the ECD and the TMD relative to one another, as well as of the chimeric polypeptide monomers to one another, to achieve a desired activity of the chimeric polypeptide of the disclosure. In some embodiments, any arbitrary single-chain peptide including about one to 100 amino acid residues (e.g., 2, 3, 4, 5, 6, 7, 8, 9, 10, 11, 12, 13, 14, 15, 16, 17, 18, 19, 20, etc. amino acid residues) can be used as a hinge domain. In some embodiments, the hinge domain includes about 5 to 50, about 10 to 60, about 20 to 70, about 30 to 80, about 40 to 90, about 50 to 100, about 60 to 80, about 70 to 100, about 30 to 60, about 20 to 80, about 30 to 90 amino acid residues. In some embodiments, the hinge domain includes about 1 to 10, about 5 to 15, about 10 to 20, about 15 to 25, about 20 to 40, about 30 to 50, about 40 to 60, about 50 to 70 amino acid residues. In some embodiments, the hinge domain includes about 40 to 70, about 50 to 80, about 60 to 80, about 70 to 90, or about 80 to 100 amino acid residues. In some embodiments, the hinge domain includes about 1 to 10, about 5 to 15, about 10 to 20, about 15 to 25 amino acid residues. In some embodiments, the hinge domain includes a sequence having at least 80% sequence identity, such as, at least 80%, at least 85%, at least 90%, at least 95%, at least 96%, at least 97%, at least 98%, or 99% sequence identity to a sequence selected from the group consisting of SEQ ID NOS: 12-16 and 39-42 in the Sequence Listing. In some embodiments, the hinge domain includes an amino acid sequence having at least 90% sequence identity to a sequence selected from the group consisting of SEQ ID NOS: 12-16 and 39-42. In some embodiments, the hinge domain includes an amino acid sequence having at least 95% sequence identity to a sequence selected from the group consisting of SEQ ID NOS: 12-16 and 39-42. In some embodiments, the hinge domain includes an amino acid sequence having about 100% sequence identity to a sequence selected from the group consisting of SEQ ID NOS: 12-16 and 39-42. In some embodiments, the hinge domain includes an amino acid sequence having a sequence selected from the group consisting of SEQ ID NOS: 12-16 and 39-42, wherein one, two, three, four, or five of the amino acid residues in any one of the SEQ ID NOS: 12-16 and 39-42 is/are substituted by a different amino acid residue.

Transmembrane Domain (TMD)

As outlined above, the chimeric polypeptides of the disclosure include a transmembrane domain including one or more ligand-inducible proteolytic cleavage sites.

Examples of proteolytic cleavage sites in a Notch receptor (e.g., S2 or S3) are as described above. Additional proteolytic cleavage sites suitable for the compositions and methods disclosed herein include, but are not limited to, a metalloproteinase cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). For example, the cleavage sequence of MMP-9 is Pro-X-X-Hy (wherein, X represents an arbitrary residue; Hy, a hydrophobic residue such as Leu, Ile, Val, Phe, Trp, Tyr, Val, Met, and Pro) (SEQ ID NO: 64), e.g., Pro-X-X-Hy-(Ser/Thr) (SEQ ID NO: 65), e.g., Pro-Leu/Gln-Gly-Met-Thr-Ser (SEQ ID NO: 66) or Pro-Leu/Gln-Gly-Met-Thr (SEQ ID NO: 67). Another example of a suitable protease cleavage site is a plasminogen activator cleavage site, e.g., a urokinase-type plasminogen activator (uPA) or a tissue plasminogen activator (tPA) cleavage site. Another example of a suitable protease cleavage site is a prolactin cleavage site. Specific examples of cleavage sequences of uPA and tPA include sequences comprising Val-Gly-Arg (SEQ ID NO: 68). Another exemplary protease cleavage site that can be included in a proteolytically cleavable linker is a tobacco etch virus (TEV) protease cleavage site, e.g., Glu-Asn-Leu-Tyr-Thr-Gln-Ser (SEQ ID NO: 69), where the protease cleaves between the glutamine and the serine. Another example of a protease cleavage site that can be included in a proteolytically cleavable linker is an enterokinase cleavage site, e.g., Asp-Asp-Asp-Asp-Lys (SEQ ID NO: 70), where cleavage occurs after the lysine residue. Another example of a protease cleavage site that can be included in a proteolytically cleavable linker is a thrombin cleavage site, e.g., Leu-Val-Pro-Arg (SEQ ID NO: 71). Additional suitable linkers including protease cleavage sites include sequences cleavable by the following proteases: a PreScission™ protease (a fusion protein including human rhinovirus 3C protease and glutathione-S-transferase), a thrombin, cathepsin B, Epstein-Barr virus protease, MMP-3 (stromelysin), MMP-7 (matrilysin), MMP-9; thermolysin-like MMP, matrix metalloproteinase 2 (MMP-2), cathepsin L; cathepsin D, matrix metalloproteinase 1 (MMP-1), urokinase-type plasminogen activator (uPA), membrane type 1 matrixmetalloproteinase (MT-MMP), stromelysin 3 (or MMP-11), thermolysin, fibroblast collagenase and stromelysin-1, matrix metalloproteinase 13 (collagenase-3), tissue-type plasminogen activator (tPA), human prostate-specific antigen, kallikrein (hK3), neutrophil elastase, and calpain (calcium activated neutral protease). Proteases that are not native to the host cell in which the receptor is expressed (for example, TEV) can be used as a further regulatory mechanism, in which activation of the Hinge-Notch is not possible until the protease is expressed or otherwise provided. Additionally, a protease may be tumor-associated or disease-associated (expressed to a significantly higher degree than in normal tissue), and serve as an independent regulatory mechanism. For example, some matrix metalloproteases are highly expressed in certain cancer types.

Generally, the TMD suitable for the chimeric polypeptides and Hinge-Notch receptors disclosed herein can be any transmembrane domain of a Type 1 transmembrane receptor including at least one 7-secretase cleavage site. Detailed description of the structure and function of the 7-secretase complex as well as its substrate proteins, including amyloid precursor protein (APP) and Notch, can, for example, be found in a recent review by Zhang et al., *Frontiers Cell Neurosci* (2014). Non-limiting suitable TMDs from Type 1 transmembrane receptors include those from CLSTN1, CLSTN2, APLP1, APLP2, LRP8, APP, BTC, TGBR3, SPN, CD44, CSF1R, CXCL16, CX3CL1, DCC, DLL1, DSG2, DAG1, CDH1, EPCAM, EPHA4, EPHB2, EFNB1, EFNB2, ErbB4, GHR, HLA-A, and IFNAR2, wherein the TMD includes at least one 7-secretase cleavage site. Additional TMDs suitable for the compositions and methods described herein include, but are not limited to, transmembrane domains from Type 1 transmembrane receptors IL1R1, IL1R2, IL6R, INSR, ERN1, ERN2, JAG2, KCNE1, KCNE2, KCNE3, KCNE4, KL, CHL1, PTPRF, SCN1B, SCN3B, NPR3, NGFR, PLXDC2, PAM, AGER, ROBO1, SORCS3, SORCS1, SORL1, SDC1, SDC2, SPN, TYR, TYRP1, DCT, VASN, FLT1, CDH5, PKHD1, NECTIN1, PCDHGC3, NRG1, LRP1B, CDH2, NRG2, PTPRK, SCN2B, Nradd, and PTPRM. In some embodiments, the TMD of the chimeric polypeptides or Notch receptors of the disclosure is a TMD derived from the TMD of a member of the calsyntenin family, such as, alcadein alpha and alcadein gamma. In some embodiments, the TMD of the chimeric polypeptides or Notch receptors of the disclosure is a TMD known for Notch receptors. In some embodiments, the TMD of the chimeric polypeptides or Notch receptors of the disclosure is a TMD derived from a different Notch receptor. For example, in a Hinge-Notch receptor based on human Notch1, the Notch1 TMD can be substituted with a Notch2 TMD, Notch3 TMD, Notch4 TMD, or a Notch TMD from a non-human animal such as *Danio rerio, Drosophila melanogaster, Xenopus laevis*, or *Gallus gallus*.

In some embodiments, the transmembrane domain includes an amino acid sequence exhibiting at least 70%, at least 75%, at least 80%, at least 85%, at least 90%, at least 95%, at least 96%, at least 97%, at least 98%, at least 99% sequence identity to one or more of SEQ ID NOS: 17, 77, and 78 in the Sequence Listing. In some embodiments, the transmembrane domain includes an amino acid sequence having at least 90% sequence identity to a sequence selected from the group consisting of NOS: 17, 77, and 78. In some embodiments, the transmembrane domain includes an amino acid sequence having at least 95% sequence identity to a sequence selected from the group consisting of NOS: 17, 77, and 78. In some embodiments, the transmembrane domain includes an amino acid sequence having about 100% sequence identity to one or more of NOS: 17, 77, and 78. In some embodiments, the transmembrane domain includes an amino acid sequence having a sequence selected from the group consisting of NOS: 17, 77, and 78, wherein one, two, three, four, or five of the amino acid residues in any one of the NOS: 17, 77, and 78 is/are substituted by a different amino acid residue. In some embodiments, the amino acid substitution(s) within the TMD includes one or more substitutions within a "GV" motif of the TMD. In some embodiments, at least one of such substitution(s) is a substitution to alanine. For example, one, two, three, four, five, or more of the amino acid residues of the sequence FMYVAAAAFVLLFFVGCGVLLS (SEQ ID NO: 17), as well as the sequence as set forth in SEQ ID NO: 77 or 78, may be substituted by a different amino acid residue. In some embodiments, the amino acid residue at position 18 and/or 19 of the "GV" motif within SEQ ID NO: 17 is substituted by a different amino acid residue. In some embodiments, the glycine residue at position 18 of SEQ ID NO: 17 is substituted by a different amino acid residue. In some embodiments, the valine residue at position 19 of SEQ ID NO: 17 is substituted by a different amino acid residue. In some embodiments, the transmembrane domain includes an amino acid sequence having a sequence corresponding to SEQ ID NO: 17 with a mutation at the position corresponding to position 18 of SEQ ID NO: 17, such as G18A mutations. In some embodiments, the transmembrane domain includes an amino acid sequence having a sequence corresponding to SEQ ID NO: 17 with a mutation at the position corresponding to position 19 of SEQ ID NO: 17, such as V19A mutations.

Stop-Transfer-Sequence

In some embodiments, the chimeric polypeptides and Hinge-Notch receptors of the disclosure include a stop-transfer-sequence (STS) which constitutes a highly-charged domain located C-terminally to the TMD. Without being bound to any particular theory, such a highly-charged domain disposed between the TMD and the ICD prevents the ICD from entering the membrane. The STS is linked to the TMD and the ICD in the following order, from N-terminus to C-terminus, TMD-STS-ICD. In principle, there are no particular limitations to the length and/or amino acid composition of the STS. In some embodiments, any arbitrary single-chain peptide comprising about 4 to about 40 amino acid residues (e.g., 4, 5, 6, 7, 8, 9, 10, 11, 12, 13, 14, 15, 16, 17, 18, 19, or 20, etc. amino acid residues) can be used as a STS. In some embodiments, the STS includes about 4 to 15, about 6 to 20, about 8 to 25, about 10 to 30, about 12 to 35, about 14 to 40, about 5 to 40, about 10 to 35, about 15 to 30, about 20 to 25, about 20 to 40, about 10 to 30, about 4 to 20, or about 5 to 25 amino acid residues. In some embodiments, the STS includes about 4 to 10, about 5 to 12, about 6 to 14, about 7 to 18, about 8 to 20, about 9 to 22, about 10 to 24, or about 11 to 26 amino acid residues. In some embodiments, the STS includes about 4 to 10 residues, such as, 4, 5, 6, 7, 8, 9, or 10 amino acid residues.

In some embodiments, the STS includes a sequence having at least 70% sequence identity, such as, at least 70%, at least 75%, at least 80%, at least 85%, at least 90%, at least 95%, at least 96%, at least 97%, at least 98%, or 99% sequence identity to a STS sequence from Notch1, Notch2, Notch3, Notch4, CLSTN1, CLSTN2, CSF1R, CXCL16, DAG1, GHR, PTPRF, AGER, KL, NRG1, LRP1B, Jag2, EPCAM, KCNE3, CDH2, NRG2, PTPRK, BTC, EPHA3, IL1R2, or PTPRM. In some embodiments, the STS includes a sequence comprising only Lys (K) or Arg® in the first 4 residues. In some embodiments, the STS includes one, two, three, four, five, or more basic residues. In some embodiments, the STS includes five, four, three, two, one, or zero aromatic residues or residues with hydrophobic and/or bulky side chains.

In some embodiments, the STS includes a sequence having at least 80% sequence identity, such as, at least 80%, at least 85%, at least 90%, at least 95%, at least 96%, at least 97%, at least 98%, or 99% sequence identity to a sequence selected from the group consisting of SEQ ID NOS: 18-19, 43-63, 79, and 80 in the Sequence Listing. In some embodiments, the STS includes an amino acid sequence having at least 90% sequence identity to a sequence selected from the group consisting of SEQ ID NOS: 18-19, 43-63, 79, and 80. In some embodiments, the STS includes an amino acid sequence having at least 95% sequence identity to a sequence selected from the group consisting of SEQ ID NOS: 18-19, 43-63, 79, and 80. In some embodiments, the STS includes an amino acid sequence having about 100% sequence identity to a sequence selected from the group consisting of SEQ ID NOS: 18-19, 43-63, 79, and 80. In some embodiments, the STS includes an amino acid sequence having a sequence selected from the group consisting of SEQ ID NOS: 18-19, 43-63, 79, and 80, wherein one, two, three, four, or five of the amino acid residues in any one of the SEQ ID NOS: 18-19, 43-63, 79, and 80 is/are substituted by a different amino acid residue. In some embodiments, the STS includes a sequence having at least 70% sequence identity, such as, at least 70%, at least 75%, at least 80%, at least 85%, at least 90%, at least 95%, at least 96%, at least 97%, at least 98%, or 99% sequence identity to a STS sequence from Notch1, Notch2, Notch3, Notch4, CLSTN1, CLSTN2, JAG2, PTPRF, LRP1B, NRG2, KCNE2, KCNE3, KCNE4, AGER, PKHD1, GHR, PTPRM, DAG1, NRG1, EPCAM, KL, PTPRK, CXCL16, or any one listed in Tables 3 and 4. In some embodiments, the STS includes a sequence comprising only Lys (K) or Arg® in the first 4 residues. In some embodiments, the STS includes one, two, three, four, five, or more basic residues. In some embodiments, the STS comprises five, four, three, two, one, or zero aromatic residues or residues with hydrophobic and/or bulky side chains.

Intracellular Domain

The chimeric polypeptides and Hinge-Notch receptors of the disclosure include a transcriptional regulator. The transcriptional regulator of the disclosure is a polypeptide element that acts to activate or inhibit the transcription of a promoter-driven DNA sequence. Transcriptional regulators suitable for the compositions and methods of the disclosure can be naturally-occurring transcriptional regulators or can be engineered, designed, or modified so as to provide desired and/or improved properties, e.g., modulating transcription. As discussed above, the engineered receptors of the present disclosure are advantageous in that they can provide the ability to trigger a custom transcriptional program in engineered cells. In some embodiments, transcriptional regulator of the disclosure is a custom transcriptional regulator that drives transcription off a specific sequence that only appears once in the engineered cell.

In some embodiments, the transcriptional regulator directly regulates differentiation of the cell. In some embodiments, the transcriptional regulator indirectly modulates (e.g., regulates) differentiation of the cell by modulating the expression of a second transcription factor. It will be understood by one having ordinary skill in the art that a transcriptional regulator can be a transcriptional activator or a transcriptional repressor. In some embodiments, the transcriptional regulator is a transcriptional repressor. In some embodiments, the transcriptional regulator is a transcriptional activator. In some embodiments, the transcriptional regulator can further include a nuclear localization signal. In some embodiments, the transcriptional regulator is selected from Gal4-VP16, Gal4-VP64, tetR-VP64, ZFHD1-VP64, Gal4-KRAB, and HAP1-VP16. In some embodiments, the transcriptional regulator is Gal4-VP64.

Chimeric polypeptides and Hinge-Notch receptors of the present disclosure can be chimeric polypeptides of any length, including chimeric polypeptides that are generally between about 100 amino acids (aa) to about 1000 aa, e.g., from about 100 aa to about 200 aa, from about 150 aa to about 250 aa, from about 200 aa to about 300 aa, from about 250 aa to about 350 aa, from about 300 aa to about 400 aa, from about 350 aa to about 450 aa, from about 400 aa to about 500 aa in length. In some embodiments, the disclosed chimeric polypeptides are generally between about 400 aa to about 450 aa, from about 450 aa to about 500 aa, from about 500 aa to about 550 aa, from about 550 aa to about 600 aa, from about 600 aa to about 650 aa, from about 650 aa to about 700 aa, from about 700 aa to about 750 aa, from about 750 aa to about 800 aa, from about 800 aa to about 850 aa, from about 850 aa to about 900 aa, from about 900 aa to about 950 aa, or from about 950 aa to about 1000 aa in length. In some cases, the chimeric polypeptides of the present disclosure have a length of about 300 aa to about 400 aa. In some cases, the chimeric polypeptides of the present disclosure have a length of about 300 aa to about 350 aa. In some cases, the chimeric polypeptides of the present disclosure have a length of about 300 aa to about 325 aa. In some cases, the chimeric polypeptides of the present disclosure have a length of about 350 aa to about 400 aa. In some cases, the chimeric polypeptides of the present disclosure have a length of 750 aa to 850 aa. In some embodiments, the chimeric polypeptides of the present disclosure have a length of about 525 aa, about 538 aa, about 539 aa, about 542 aa, about 550 aa, about 556 aa, or about 697 aa.

Additional Domains

In some embodiments, the Notch extracellular domains located N-terminally to the TMD can further include an additional domain, for example a membrane localization signal such as a CD8A signal, a detectable marker such as a myc tag or his tag, and the like. Without being bound to any particular theory, it may be beneficial to incorporate additional domains N-terminally to the hinge domain. This is because, incorporating bulky features (such as an NRR) adjacent to the TMD would affect receptor activity, unless it is spaced far enough away. It is also contemplated that the chimeric polypeptides and HingeNotch receptors as described herein can be further engineered to include one or more additional features such as, a signal sequence, a detectable label, a tumor-specific cleavage site, a disease-specific cleavage site, or combinations thereof. For example, several proteases (such as matrix metalloproteases) are upregulated in cancers, allowing tumor-specific cleavage specificity not via a specific cleavage site but via higher levels of specific proteases. Additional information in this regard can be found in, for example, J. S. Dudani et al., Annu. Rev. Cancer Biol. (2018), 2:353-76, which is herein incorporated by reference.

In some embodiments, the chimeric polypeptide or Hinge-Notch receptor of the disclosure includes: (a) a hinge domain including an amino acid sequence having at least 80% sequence identity to any one of SEQ ID NO: 12-16 and 39-42; (b) a transmembrane domain including an amino acid sequence having at least 80% sequence identity to any one of SEQ ID NOS: 17, 77, and 78; and (c) a stop-transfer-sequence domain including an amino acid sequence having at least 80% sequence identity to any one of SEQ ID NOS: 18-19, 43-63, 79, and 80. In some embodiments, the chimeric polypeptide or Hinge-Notch receptor of the disclosure includes: (a) a hinge domain including an amino acid sequence having at least 90/a sequence identity to any one of SEQ ID NO: 12-16 and 39-42; (b) a transmembrane domain including an amino acid sequence having at least 90% sequence identity to any one of SEQ ID NOS: 17, 77, and 78; and (c) a stop-transfer-sequence domain including an amino acid sequence having at least 90% sequence identity to any one of SEQ ID NOS: 18-19, 43-63, 79, and 80. In some embodiments, the chimeric polypeptide or Hinge-Notch receptor of the disclosure includes: (a) a hinge domain including an amino acid sequence having at least 95% sequence identity to any one of SEQ ID NO: 12-16 and 39-42; (b) a transmembrane domain including an amino acid sequence having at least 95% sequence identity to any one of SEQ ID NOS: 17, 77, and 78; and (c) a stop-transfer-sequence domain including an amino acid sequence having at least 95% sequence identity to any one of SEQ ID NOS: 18-19, 43-63, 79, and 80.

In some embodiments, the chimeric polypeptide of the disclosure includes an amino acid sequence having at least about 80%, 90%, 95%, 96%, 97, 98%, 99%, or 100% sequence identity to a chimeric receptor disclosed herein. In some embodiments, provided herein are chimeric polypeptides including an amino acid sequence having at least about 80%, 90%, 95%, 96%, 97, 98%, 99%, or 100% sequence identity to any one of SEQ ID NOS: 1-8, 24-35, and 73-76 identified in the Sequence Listing. In some embodiments, the chimeric polypeptides include an amino acid sequence having at least about 80%, 90%, 95%, 96%, 97, 98%, 99%, or 100% sequence identity to SEQ ID NO: 1. In some embodiments, the chimeric polypeptides include an amino acid sequence having at least about 80%, 90%, 95%, 96%, 97, 98%, 99%, or 100% sequence identity to SEQ ID NO: 2. In some embodiments, the chimeric polypeptides include an amino acid sequence having at least about 80%, 90%, 95%, 96%, 97, 98%, 99%, or 100% sequence identity to SEQ ID NO: 3. In some embodiments, the chimeric polypeptides include an amino acid sequence having at least about 80%, 90%, 95%, 96%, 97, 98%, 99%, or 100% sequence identity to SEQ ID NO: 4. In some embodiments, the chimeric polypeptides include an amino acid sequence having at least about 80%, 90%, 95%, 96%, 97, 98%, 99%, or 100% sequence identity to SEQ ID NO: 5. In some embodiments, the chimeric polypeptides include an amino acid sequence having at least about 80%, 90%, 95%, 96%, 97, 98%, 99%, or 100% sequence identity to SEQ ID NO: 6. In some embodiments, the chimeric polypeptides include an amino acid sequence having at least about 80%, 90%, 95%, 96%, 97, 98%, 99%, or 100% sequence identity to SEQ ID NO: 7. In some embodiments, the chimeric polypeptides include an amino acid sequence having at least about 80%, 90%, 95%, 96%, 97, 98%, 99%, or 100% sequence identity to SEQ ID NO: 8. In some embodiments, the chimeric polypeptides include an amino acid sequence having at least about 80%, 90%, 95%, 96%, 97, 98%, 99%, or 100% sequence identity to SEQ ID NO: 24. In some embodiments, the chimeric polypeptides include an amino acid sequence having at least about 80%, 90%, 95%, 96%, 97, 98%, 99%, or 100% sequence identity to SEQ ID NO: 25. In some embodiments, the chimeric polypeptides include an amino acid sequence having at least about 80%, 90%, 95%, 96%, 97, 98%, 99%, or 100% sequence identity to SEQ ID NO: 26. In some embodiments, the chimeric polypeptides include an amino acid sequence having at least about 80%, 90%, 95%, 96%, 97, 98%, 99%, or 100% sequence identity to SEQ ID NO: 27. In some embodiments, the chimeric polypeptides include an amino acid sequence having at least about 80%, 90%, 95%, 96%, 97, 98%, 99%, or 100% sequence identity to SEQ ID NO: 28. In some embodiments, the chimeric polypeptides include an amino acid sequence having at least about 80%, 90%, 95%, 96%, 97, 98%, 99%, or 100% sequence identity to SEQ ID NO: 29. In some embodiments, the chimeric polypeptides include an amino acid sequence having at least about 80%, 90%, 95%, 96%, 97, 98%, 99%, or 100% sequence identity to SEQ ID NO: 30. In some embodiments, the chimeric polypeptides include an amino acid sequence having at least about 80%, 90%, 95%, 96%, 97, 98%, 99%, or 100% sequence identity to SEQ ID NO: 31. In some embodiments, the chimeric polypeptides include an amino acid sequence having at least about 80%, 90%, 95%, 96%, 97, 98%, 99%, or 100% sequence identity to SEQ ID NO: 32. In some embodiments, the chimeric polypeptides include an amino acid sequence having at least about 80%, 90%, 95%, 96%, 97, 98%, 99%, or 100% sequence identity to SEQ ID NO: 33. In some embodiments, the chimeric polypeptides include an amino acid sequence having at least about 80%, 90%, 95%, 96%, 97, 98%, 99%, or 100% sequence identity to SEQ ID NO: 34. In some embodiments, the chimeric polypeptides include an amino acid sequence having at least about 80%, 90%, 95%, 96%, 97, 98%, 99%, or 100% sequence identity to SEQ ID NO: 35. In some embodiments, the chimeric polypeptides include an amino acid sequence having at least about 80%, 90%, 95%, 96%, 97, 98%, 99%, or 100% sequence identity to SEQ ID NO: 73. In some embodiments, the chimeric polypeptides include an amino acid sequence having at least about 80%, 90%, 95%, 96%, 97, 98%, 99%, or 100% sequence identity to SEQ ID NO: 74. In some embodiments, the chimeric polypeptides include an amino acid sequence having at least about 80%, 90%, 95%, 96%, 97, 98%, 99%, or 100% sequence identity to SEQ ID NO: 75. In some embodiments, the chimeric polypeptides include an amino acid sequence having at least about 80%, 90%, 95%, 96%, 97, 98%, 99%, or 100% sequence identity to SEQ ID NO: 76.

Nucleic Acid Molecules

In another aspect, provided herein are various nucleic acid molecules including nucleotide sequences encoding the chimeric polypeptides and Hinge-Notch receptors of the disclosure, including expression cassettes, and expression vectors containing these nucleic acid molecules operably linked to heterologous nucleic acid sequences such as, for example, regulatory sequences which allow in vivo expression of the receptor in a host cell.

Nucleic acid molecules of the present disclosure can be of any length, including for example, between about 1.5 Kb and about 50 Kb, between about 5 Kb and about 40 Kb, between about 5 Kb and about 30 Kb, between about 5 Kb and about 20 Kb, or between about 10 Kb and about 50 Kb, for example between about 15 Kb to 30 Kb, between about 20 Kb and about 50 Kb, between about 20 Kb and about 40 Kb, about 5 Kb and about 25 Kb, or about 30 Kb and about 50 Kb.

In some embodiments, provided herein is a nucleic acid molecule including a nucleotide sequence encoding a chimeric polypeptide or Hinge-Notch receptor including, from N-terminus to C-terminus: (a) an extracellular ligand-binding domain having a binding affinity for a selected ligand; (b) a hinge domain capable of promoting oligomer formation of the chimeric polypeptide via intermolecular disulfide bonding; (c) a transmembrane domain including one or more ligand-inducible proteolytic cleavage sites; and (d) an intracellular domain including a transcriptional regulator, wherein binding of the selected ligand to the extracellular ligand-binding domain induces cleavage at a ligand-inducible proteolytic cleavage site disposed between the transcriptional regulator and the hinge domain, and wherein the chimeric polypeptide does not include a LIN-12-Notch repeat (LNR) and/or a heterodimerization domain (HD) of a Notch receptor.

In some embodiments, the nucleotide sequence is incorporated into an expression cassette or an expression vector. It will be understood that an expression cassette generally includes a construct of genetic material that contains coding sequences and enough regulatory information to direct proper transcription and/or translation of the coding sequences in a recipient cell, in vivo and/or ex vivo. Generally, the expression cassette may be inserted into a vector for targeting to a desired host cell and/or into an individual. As such, in some embodiments, an expression cassette of the disclosure include a coding sequence for the chimeric polypeptide as disclosed herein, which is operably linked to expression control elements, such as a promoter, and optionally, any or a combination of other nucleic acid sequences that affect the transcription or translation of the coding sequence.

In some embodiments, the nucleotide sequence is incorporated into an expression vector. It will be understood by one skilled in the art that the term "vector" generally refers to a recombinant polynucleotide construct designed for transfer between host cells, and that may be used for the purpose of transformation, e.g., the introduction of heterologous DNA into a host cell. As such, in some embodiments, the vector can be a replicon, such as a plasmid, phage, or cosmid, into which another DNA segment may be inserted so as to bring about the replication of the inserted segment. In some embodiments, the expression vector can be an integrating vector.

In some embodiments, the expression vector can be a viral vector. As will be appreciated by one of skill in the art, the term "viral vector" is widely used to refer either to a nucleic acid molecule (e.g., a transfer plasmid) that includes virus-derived nucleic acid elements that generally facilitate transfer of the nucleic acid molecule or integration into the genome of a cell or to a viral particle that mediates nucleic acid transfer. Viral particles will generally include various viral components and sometimes also host cell components in addition to nucleic acid(s). The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, including LTRs that are primarily derived from a lentivirus, which is a genus of retrovirus.

In some embodiments, provided herein are nucleic acid molecules encoding a polypeptide with an amino acid sequence having at least about 80%, 90%, 95%, 96%, 97, 98%, 99%, or 100% sequence identity to a chimeric receptor disclosed herein. In some embodiments, provided herein are nucleic acid molecules encoding a polypeptide with an amino acid sequence having at least about 80%, 90%, 95%, 96%, 97, 98%, 99%, or 100% sequence identity to any one of SEQ ID NOS: 1-8, 24-35, and 73-76 identified in the Sequence Listing. In some embodiments, the nucleic acid molecules encode a polypeptide with an amino acid sequence having at least about 80%, 90%, 95%, 96%, 97, 98%, 99%, or 100% sequence identity to SEQ ID NO: 1. In some embodiments, the nucleic acid molecules encode a polypeptide with an amino acid sequence having at least about 80%, 90%, 95%, 96%, 97, 98%, 99%, or 100% sequence identity to SEQ ID NO: 2. In some embodiments, the nucleic acid molecules encode a polypeptide with an amino acid sequence having at least about 80%, 90%, 95%, 96%, 97, 98%, 99%, or 100% sequence identity to SEQ ID NO: 3. In some embodiments, the nucleic acid molecules encode a polypeptide with an amino acid sequence having at least about 80%, 90%, 95%, 96%, 97, 98%, 99%, or 100% sequence identity to SEQ ID NO: 4. In some embodiments, the nucleic acid molecules encode a polypeptide with an amino acid sequence having at least about 80%, 90%, 95%, 96%, 97, 98%, 99%, or 100% sequence identity to SEQ ID NO: 5. In some embodiments, the nucleic acid molecules encode a polypeptide with an amino acid sequence having at least about 80%, 90%, 95%, 96%, 97, 98%, 99%, or 100% sequence identity to SEQ ID NO: 6. In some embodiments, the nucleic acid molecules encode a polypeptide with an amino acid sequence having at least about 80%, 90%, 95%, 96%, 97, 98%, 99%, or 100% sequence identity to SEQ ID NO: 7. In some embodiments, the nucleic acid molecules encode a polypeptide with an amino acid sequence having at least about 80%, 90%, 95%, 96%, 97, 98%, 99%, or 100% sequence identity to SEQ ID NO: 8. In some embodiments, the nucleic acid molecules encode a polypeptide with an amino acid sequence having at least about 80%, 90%, 95%, 96%, 97, 98%, 99%, or 100% sequence identity to SEQ ID NO: 24. In some embodiments, the nucleic acid molecules encode a polypeptide with an amino acid sequence having at least about 80%, 90%, 95%, 96%, 97, 98%, 99%, or 100% sequence identity to SEQ ID NO: 25. In some embodiments, the nucleic acid molecules encode a polypeptide with an amino acid sequence having at least about 80%, 90%, 95%, 96%, 97, 98%, 99%, or 100% sequence identity to SEQ ID NO: 26. In some embodiments, the nucleic acid molecules encode a polypeptide with an amino acid sequence having at least about 80%, 90%, 95%, 96%, 97, 98%, 99%, or 100% sequence identity to SEQ ID NO: 27. In some embodiments, the nucleic acid molecules encode a polypeptide with an amino acid sequence having at least about 80%, 90%, 95%, 96%, 97, 98%, 99%, or 100% sequence identity to SEQ ID NO: 28. In some embodiments, the nucleic acid molecules encode a polypeptide with an amino acid sequence having at least about 80%, 90%, 95%, 96%, 97, 98%, 99%, or 100% sequence identity to SEQ ID NO: 29. In some embodiments, the nucleic acid molecules encode a polypeptide with an amino acid sequence having at least about 80%, 90%, 95%, 96%, 97, 98%, 99%, or 100% sequence identity to SEQ ID NO: 30. In some embodiments, the nucleic acid molecules encode a polypeptide with an amino acid sequence having at least about 80%, 90%, 95%, 96%, 97, 98%, 99%, or 100% sequence identity to SEQ ID NO: 31. In some embodiments, the nucleic acid molecules encode a polypeptide with an amino acid sequence having at least about 80%, 90%, 95%, 96%, 97, 98%, 99%, or 100% sequence identity to SEQ ID NO: 32. In some embodiments, the nucleic acid molecules encode a polypeptide with an amino acid sequence having at least about 80%, 90%, 95%, 96%, 97, 98%, 99%, or 100% sequence identity to SEQ ID NO: 33. In some embodiments, the nucleic acid molecules encode a polypeptide with an amino acid sequence having at least about 80%, 90%, 95%, 96%, 97, 98%, 99%, or 100% sequence identity to SEQ ID NO: 34. In some embodiments, the nucleic acid molecules encode a polypeptide with an amino acid sequence having at least about 80%, 90%, 95%, 96%, 97, 98%, 99%, or 100% sequence identity to SEQ ID NO: 35. In some embodiments, the nucleic acid molecules encode a polypeptide with an amino acid sequence having at least about 80%, 90%, 95%, 96%, 97, 98%, 99%, or 100% sequence identity to SEQ ID NO: 73. In some embodiments, the nucleic acid molecules encode a polypeptide with an amino acid sequence having at least about 80%, 90%, 95%, 96%, 97, 98%, 99%, or 100% sequence identity to SEQ ID NO: 74. In some embodiments, the nucleic acid molecules encode a polypeptide with an amino acid sequence having at least about 80%, 90%, 95%, 96%, 97, 98%, 99%, or 100% sequence identity to SEQ ID NO: 75. In some embodiments, the nucleic acid molecules encode a polypeptide with an amino acid sequence having at least about 80%, 90%, 95%, 96%, 97, 98%, 99%, or 100% sequence identity to SEQ ID NO: 76.

The nucleic acid sequences encoding the chimeric receptors can be optimized for expression in the host cell of interest. For example, the G-C content of the sequence can be adjusted to average levels for a given cellular host, as calculated by reference to known genes expressed in the host cell. Methods for codon usage optimization are known in the art. Codon usages within the coding sequence of the chimeric receptor disclosed herein can be optimized to enhance expression in the host cell, such that about 1%, about 5%, about 10%, about 25%, about 50%, about 75%, or up to 100% of the codons within the coding sequence have been optimized for expression in a particular host cell.

Some embodiments disclosed herein relate to vectors or expression cassettes including a recombinant nucleic acid molecule encoding the chimeric receptors disclosed herein. The expression cassette generally contains coding sequences and sufficient regulatory information to direct proper transcription and/or translation of the coding sequences in a recipient cell, in vivo and/or ex vivo. The expression cassette may be inserted into a vector for targeting to a desired host cell and/or into an individual. An expression cassette can be inserted into a plasmid, cosmid, virus, autonomously replicating polynucleotide molecule, phage, as a linear or circular, single-stranded or double-stranded, DNA or RNA polynucleotide molecule, derived from any source, capable of genomic integration or autonomous replication, including a nucleic acid molecule where one or more nucleic acid sequences has been linked in a functionally operative manner, i.e., operably linked.

Also provided herein are vectors, plasmids, or viruses containing one or more of the nucleic acid molecules encoding any chimeric receptor or Hinge-Notch receptor disclosed herein. The nucleic acid molecules can be contained within a vector that is capable of directing their expression in, for example, a cell that has been transformed/transduced with the vector. Suitable vectors for use in eukaryotic and prokaryotic cells are known in the art and are commercially available, or readily prepared by a skilled artisan. See for example, Sambrook, J., & Russell, D. W. (2012). *Molecular Cloning. A Laboratory Manual* (4th ed.). Cold Spring Harbor, N.Y.: Cold Spring Harbor Laboratory and Sambrook, J., & Russel, D. W. (2001). *Molecular Cloning. A Laboratory Manual* (3rd ed.). Cold Spring Harbor, N.Y.: Cold Spring Harbor Laboratory (jointly referred to herein as "Sambrook"); Ausubel, F. M. (1987). *Current Protocols in Molecular Biology*. New York, N.Y.: Wiley (including supplements through 2014); Bollag, D. M. et al. (1996). *Protein Methods*. New York, N.Y.: Wiley-Liss; Huang, L. et al. (2005). *Nonviral Vectors for Gene Therapy*. San Diego: Academic Press; Kaplitt, M. G. et al. (1995). *Viral Vectors: Gene Therapy and Neuroscience Applications*. San Diego, Calif.: Academic Press; Lefkovits, I. (1997). *The Immunology Methods Manual. The Comprehensive Sourcebook of Techniques*. San Diego, Calif.: Academic Press; Doyle, A. et al. (1998). *Cell and Tissue Culture: Laboratory Procedures in Biotechnology*. New York, N.Y.: Wiley; Mullis, K. B., Ferré, F. & Gibbs, R. (1994). *PCR: The Polymerase Chain Reaction*. Boston: Birkhauser Publisher; Greenfield, E. A. (2014). *Antibodies: A Laboratory Manual* (2nd ed.). New York, N.Y.: Cold Spring Harbor Laboratory Press; Beaucage, S. L. et al. (2000). *Current Protocols in Nucleic Acid Chemistry*. New York, N.Y.: Wiley, (including supplements through 2014); and Makrides, S. C. (2003). *Gene Transfer and Expression in Mammalian Cells*. Amsterdam, NL: Elsevier Sciences B.V., the disclosures of which are incorporated herein by reference).

DNA vectors can be introduced into eukaryotic cells via conventional transformation or transfection techniques. Suitable methods for transforming or transfecting host cells can be found in Sambrook et al. (2012, supra) and other standard molecular biology laboratory manuals, such as, calcium phosphate transfection, DEAE-dextran mediated transfection, transfection, microinjection, cationic lipid-mediated transfection, electroporation, transduction, scrape loading, ballistic introduction, nucleoporation, hydrodynamic shock, and infection.

Viral vectors that can be used in the disclosure include, for example, retrovirus vectors, adenovirus vectors, and adeno-associated virus vectors, lentivirus vectors, herpes virus, simian virus 40 (SV40), and bovine papilloma virus vectors (see, for example, Gluzman (Ed.), *Eukaryotic Viral Vectors*, CSH Laboratory Press, Cold Spring Harbor, N.Y.). For example, a chimeric receptor as disclosed herein can be produced in a eukaryotic host, such as a mammalian cells (e.g., COS cells, NIH 3T3 cells, or HeLa cells). These cells are available from many sources, including the American Type Culture Collection (Manassas, Va.). In selecting an expression system, care should be taken to ensure that the components are compatible with one another. Artisans or ordinary skill are able to make such a determination. Furthermore, if guidance is required in selecting an expression system, skilled artisans may consult P. Jones, "Vectors: Cloning Applications", John Wiley and Sons, New York, N.Y., 2009).

The nucleic acid molecules provided can contain naturally occurring sequences, or sequences that differ from those that occur naturally, but, due to the degeneracy of the genetic code, encode the same polypeptide, e.g., antibody. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (e.g., either a sense or an antisense strand).

The nucleic acid molecules are not limited to sequences that encode polypeptides (e.g., antibodies); some or all of the non-coding sequences that lie upstream or downstream from a coding sequence (e.g., the coding sequence of a chimeric receptor) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

Recombinant Cells and Cell Cultures

The nucleic acid of the present disclosure can be introduced into a host cell, such as, for example, a human T lymphocyte, to produce a recombinant cell containing the nucleic acid molecule. Accordingly, some embodiments of the disclosure relate to methods for making a recombinant cell, including (a) providing a cell capable of protein expression and (b) contacting the provided cell with a recombinant nucleic acid of the disclosure.

Introduction of the nucleic acid molecules of the disclosure into cells can be achieved by methods known to those skilled in the art such as, for example, viral infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

Accordingly, in some embodiments, the nucleic acid molecules can be delivered by viral or non-viral delivery vehicles known in the art. For example, the nucleic acid molecule can be stably integrated in the host genome, or can be episomally replicating, or present in the recombinant host cell as a mini-circle expression vector for transient expression. Accordingly, in some embodiments, the nucleic acid molecule is maintained and replicated in the recombinant host cell as an episomal unit. In some embodiments, the nucleic acid molecule is stably integrated into the genome of the recombinant cell. Stable integration can be achieved using classical random genomic recombination techniques or with more precise techniques such as guide RNA-directed CRISPR/Cas9 genome editing, or DNA-guided endonuclease genome editing with NgAgo (*Natronobacterium gregoryi* Argonaute), or TALENs genome editing (transcription activator-like effector nucleases). In some embodiments, the nucleic acid molecule is present in the recombinant host cell as a mini-circle expression vector for transient expression.

The nucleic acid molecules can be encapsulated in a viral capsid or a lipid nanoparticle, or can be delivered by viral or non-viral delivery means and methods known in the art, such as electroporation. For example, introduction of nucleic acids into cells may be achieved by viral transduction. In a non-limiting example, adeno-associated virus (AAV) is engineered to deliver nucleic acids to target cells via viral transduction. Several AAV serotypes have been described, and all of the known serotypes can infect cells from multiple diverse tissue types. AAV is capable of transducing a wide range of species and tissues in vivo with no evidence of toxicity, and it generates relatively mild innate and adaptive immune responses.

Lentiviral-derived vector systems are also useful for nucleic acid delivery and gene therapy via viral transduction. Lentiviral vectors offer several attractive properties as gene-delivery vehicles, including: (i) sustained gene delivery through stable vector integration into host genome; (ii) the capability of infecting both dividing and non-dividing cells; (iii) broad tissue tropisms, including important gene- and cell-therapy-target cell types; (iv) no expression of viral proteins after vector transduction; (v) the ability to deliver complex genetic elements, such as polycistronic or intron-containing sequences; (vi) a potentially safer integration site profile; and (vii) a relatively easy system for vector manipulation and production.

In some embodiments, host cells can be genetically engineered (e.g., transduced or transformed or transfected) with, for example, a vector construct of the present application that can be, for example, a viral vector or a vector for homologous recombination that includes nucleic acid sequences homologous to a portion of the genome of the host cell, or can be an expression vector for the expression of the polypeptides of interest. Host cells can be either untransformed cells or cells that have already been transfected with at least one nucleic acid molecule.

In some embodiments, the recombinant cell is a prokaryotic cell or a eukaryotic cell. In some embodiments, the cell is in vivo. In some embodiments, the cell is ex vivo. In some embodiments, the cell is in vitro. In some embodiments, the recombinant cell is a eukaryotic cell. In some embodiments, the recombinant cell is an animal cell. In some embodiments, the animal cell is a mammalian cell. In some embodiments, the animal cell is a human cell. In some embodiments, the cell is a non-human primate cell. In some embodiments, the mammalian cell is an immune cell, a neuron, an epithelial cell, and endothelial cell, or a stem cell.

In some embodiments, the recombinant cell is an immune system cell, e.g., a lymphocyte (e.g., a T cell or NK cell), or a dendritic cell. In some embodiments, the immune cell is a B cell, a monocyte, a natural killer (NK) cell, a basophil, an eosinophil, a neutrophil, a dendritic cell, a macrophage, a regulatory T cell, a helper T cell ($T_H$), a cytotoxic T cell ($T_{CTL}$), or other T cell. In some embodiments, the immune system cell is a T lymphocyte.

In some embodiments, the cell is a stem cell. In some embodiments, the cell is a hematopoietic stem cell. In some embodiments of the cell, the cell is a lymphocyte. In some embodiments, the cell is a precursor T cell or a T regulatory (Treg) cell. In some embodiments, the cell is a CD34+, CD8+, or a CD4+ cell. In some embodiments, the cell is a CD8+ T cytotoxic lymphocyte cell selected from the group consisting of naïve CD8+ T cells, central memory CD8+ T cells, effector memory CD8+ T cells, and bulk CD8+ T cells. In some embodiments of the cell, the cell is a CD4+ T helper lymphocyte cell selected from the group consisting of naïve CD4+ T cells, central memory CD4+ T cells, effector memory CD4+ T cells, and bulk CD4+ T cells. In some embodiments, the cell can be obtained by leukapheresis performed on a sample obtained from a subject. In some embodiments, the subject is a human patient.

In some embodiments, the recombinant cell further includes a first and a second nucleic acid molecule as disclosed herein, wherein the first nucleic acid molecule and the second nucleic acid molecule do not have the same sequence. In some embodiments, the recombinant cell further includes a first and a second chimeric polypeptide or Hinge-Notch receptor as disclosed herein, wherein the first chimeric polypeptide or Hinge-Notch receptor and the second chimeric polypeptide or Hinge-Notch receptor do not have the same sequence. In some embodiments, the first chimeric polypeptide or Hinge-Notch receptor modulates the expression and/or activity of the second chimeric polypeptide or Hinge-Notch receptor.

In some embodiments, the recombinant cell further includes an expression cassette encoding a protein of interest operably linked to a promoter, wherein expression of the protein of interest is modulated by the chimeric receptor transcriptional regulator. In some embodiments, the protein of interest is heterologous to the recombinant cell. A heterologous protein is one that is not normally found in the cell, e.g., not normally produced by the cell. In principle, there are no particular limitations with regard to suitable proteins whose expression can be modulated by the chimeric receptor transcriptional regulator. Exemplary types of proteins suitable for use with the compositions and methods disclosed herein include cytokines, cytotoxins, chemokines, immunomodulators, pro-apoptotic factors, anti-apoptotic factors, hormones, differentiation factors, dedifferentiation factors, immune cell receptors, or reporters. In some embodiments, the immune cell receptor is a T-cell receptor (TCR). In some embodiments, the immune cell receptor is a chimeric antigen receptor (CAR). In some embodiments, the expression cassette encoding the protein of interest is incorporated into the same nucleic acid molecule that encodes the chimeric receptor of the disclosure. In some embodiments, the expression cassette encoding the protein of interest is incorporated into a second expression vector that is separate from the nucleic acid molecule encoding the chimeric receptor of the disclosure. In another aspect, provided herein are cell cultures including at least one recombinant cell as disclosed herein, and a culture medium. Generally, the culture medium can be any suitable culture medium for culturing the cells described herein. Techniques for transforming a wide variety of the above-mentioned host cells and species are known in the art and described in the technical and scientific literature. Accordingly, cell cultures including at least one recombinant cell as disclosed herein are also within the scope of this application. Methods and systems suitable for generating and maintaining cell cultures are known in the art.

Pharmaceutical Compositions

In some embodiments, the nucleic acids, and recombinant cells of the disclosure can be incorporated into compositions, including pharmaceutical compositions. Such compositions generally include the nucleic acids, and/or recombinant cells, and a pharmaceutically acceptable excipient, e.g., carrier.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™. (BASF, Parsippany, N.J.), or phosphate buffered saline (PBS). In all cases, the composition should be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. Prevention of the action of microorganisms can be achieved by various antibacterial and antifungal agents, for example, parabens, chlorobutanol, phenol, ascorbic acid, thimerosal, and the like. In many cases, it will be generally to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above.

In some embodiments, the chimeric polypeptides and Notch receptors of the disclosure can also be administered by transfection or infection using methods known in the art, including but not limited to the methods described in McCaffrey et al. (*Nature* 418:6893, 2002), Xia et al. (*Nature Biotechnol.* 20:1006-10, 2002), or Putnam (*Am. J. Health Syst. Pharm.* 53:151-60, 1996, erratum at *Am. J. Health Syst. Pharm.* 53:325, 1996).

Methods of the Disclosure

Administration of any one of the therapeutic compositions described herein, e.g., nucleic acids, recombinant cells, and pharmaceutical compositions, can be used to treat patients for relevant health conditions or diseases, such as cancers and chronic infections. In some embodiments, the nucleic acids, recombinant cells, and pharmaceutical compositions described herein can be incorporated into therapeutic agents for use in methods of treating an individual who has, who is suspected of having, or who may be at high risk for developing one or more autoimmune disorders or diseases associated with checkpoint inhibition. Exemplary autoimmune disorders and diseases can include, without limitation, celiac disease, type 1 diabetes, Graves' disease, inflammatory bowel disease, multiple sclerosis, psoriasis, rheumatoid arthritis, and systemic lupus erythematosus.

Accordingly, in one aspect, some embodiments of the disclosure relate to methods for inhibiting an activity of a target cell in an individual, the methods include administering to the individual a first therapy including one or more of nucleic acids, recombinant cells, and pharmaceutical compositions as disclosed herein, wherein the first therapy inhibits the target cell. For example, the target cell may be inhibited if its proliferation is reduced, if its pathologic or pathogenic behavior is reduced, if it is destroyed or killed, etc. Inhibition includes a reduction of the measured pathologic or pathogenic behavior of at least about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the methods include administering to the individual an effective number of the recombinant cells disclosed herein, wherein the recombinant cells inhibit an activity of the target cells in the individual. Generally, the target cells of the disclosed methods can be any cell type in an individual and can be, for example an acute myeloma leukemia cell, an anaplastic lymphoma cell, an astrocytoma cell, a B-cell cancer cell, a breast cancer cell, a colon cancer cell, an ependymoma cell, an esophageal cancer cell, a glioblastoma cell, a glioma cell, a leiomyosarcoma cell, a liposarcoma cell, a liver cancer cell, a lung cancer cell, a mantle cell lymphoma cell, a melanoma cell, a neuroblastoma cell, a non-small cell lung cancer cell, an oligodendroglioma cell, an ovarian cancer cell, a pancreatic cancer cell, a peripheral T-cell lymphoma cell, a renal cancer cell, a sarcoma cell, a stomach cancer cell, a carcinoma cell, a mesothelioma cell, or a sarcoma cell. In some embodiments, the target cell is a pathogenic cell.

In another aspect, some embodiments of the disclosure relate to methods for the treatment of a health condition (e.g., disease) in an individual in need thereof, the methods include administering to the individual a first therapy including one or more of the recombinant cells including a chimeric polypeptide or Hinge Notch receptor as disclosed herein, and/or pharmaceutical compositions as disclosed herein, wherein the first therapy treats the health condition in the individual. In some embodiments, the methods include administering to the individual a first therapy including an effective number of the recombinant cells as disclosed herein, wherein the recombinant cells treat the health condition.

In another aspect, some embodiments of the disclosure relate to methods for assisting in the treatment of a health condition (e.g., disease) in an individual in need thereof, the methods including administering to the individual a first therapy including one or more of chimeric polypeptides, Hinge-Notch receptors, nucleic acids, recombinant cells, and pharmaceutical compositions as disclosed herein, and a second therapy, wherein the first and second therapies together treat the disease in the individual. In some embodiments, the methods include administering to the individual a first therapy including an effective number of the recombinant cells as disclosed herein, wherein the recombinant cells treat the health condition.

Administration of Recombinant Cells to an Individual

In some embodiments, the methods of the disclosure involve administering an effective amount of the recombinants cells of the disclosure to an individual in need of such treatment. This administering step can be accomplished using any method of implantation delivery in the art. For example, the recombinant cells of the disclosure can be infused directly in the individual's bloodstream or otherwise administered to the individual.

In some embodiments, the methods disclosed herein include administering, which term is used interchangeably with the terms "introducing," implanting," and "transplanting," recombinant cells into an individual, by a method or route that results in at least partial localization of the introduced cells at a desired site such that a desired effect(s) is/are produced. The recombinant cells or their differentiated progeny can be administered by any appropriate route that results in delivery to a desired location in the individual where at least a portion of the administered cells or components of the cells remain viable. The period of viability of the cells after administration to an individual can be as short as a few hours, e.g., twenty-four hours, to a few days, to as long as several years, or even the lifetime of the individual, i.e., long-term engraftment.

When provided prophylactically, the recombinant cells described herein can be administered to an individual in advance of any symptom of a disease or condition to be treated. Accordingly, in some embodiments the prophylactic administration of a recombinant cell population prevents the occurrence of symptoms of the disease or condition.

When provided therapeutically in some embodiments, recombinant cells are provided at (or after) the onset of a symptom or indication of a disease or condition, e.g., upon the onset of disease or condition.

For use in the various embodiments described herein, an effective amount of recombinant cells as disclosed herein, can be at least $10^2$ cells, at least $5\times10^2$ cells, at least $10^3$ cells, at least $5\times10^3$ cells, at least $10^4$ cells, at least $5\times10^4$ cells, at least $10^3$ cells, at least $2\times10^3$ cells, at least $3\times10^3$ cells, at least $4\times10^5$ cells, at least $5\times10^5$ cells, at least $6\times10^5$ cells, at least $7\times10^3$ cells, at least $8\times10$ cells, at least $9\times10$ cells, at least $1\times10^6$ cells, at least $2\times10^6$ cells, at least $3\times10^6$ cells, at least $4\times10^6$ cells, at least $5\times10^6$ cells, at least $6\times10^6$ cells, at least $7\times10^6$ cells, at least $8\times10^6$ cells, at least $9\times10^6$ cells, or multiples thereof. The recombinant cells can be derived from one or more donors or can be obtained from an autologous source. In some embodiments, the recombinant cells are expanded in culture prior to administration to an individual in need thereof.

In some embodiments, the delivery of a recombinant cell composition (e.g., a composition including a plurality of recombinant cells according to any of the cells described herein) into an individual by a method or route results in at least partial localization of the cell composition at a desired site. A composition including recombinant cells can be administered by any appropriate route that results in effective treatment in the individual, e.g., administration results in delivery to a desired location in the individual where at least a portion of the composition delivered, e.g., at least $1\times10^4$ cells, is delivered to the desired site for a period of time. Modes of administration include injection, infusion, instillation. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion. In some embodiments, the route is intravenous. For the delivery of cells, delivery by injection or infusion is a preferred mode of administration.

In some embodiments, the recombinant cells are administered systemically, e.g., via infusion or injection. For example, a population of recombinant cells are administered other than directly into a target site, tissue, or organ, such that it enters, the individual's circulatory system and, thus, is subject to metabolism and other similar biological processes.

The efficacy of a treatment including any of the compositions provided herein for the treatment of a disease or condition can be determined by a skilled clinician. However, one skilled in the art will appreciate that a treatment is considered effective if any one or all of the signs or symptoms or markers of disease are improved or ameliorated. Efficacy can also be measured by failure of an individual to worsen as assessed by decreased hospitalization or need for medical interventions (e.g., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

As discussed above, a therapeutically effective amount includes an amount of a therapeutic composition that is sufficient to promote a particular beneficial effect when administered to an individual, such as one who has, is suspected of having, or is at risk for a disease. In some embodiments, an effective amount includes an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate effective amount can be determined by one of ordinary skill in the art using routine experimentation.

In some embodiments of the disclosed methods, the individual is a mammal. In some embodiments, the mammal is a human. In some embodiments, the individual has or is suspected of having a disease associated with inhibition of cell signaling mediated by a cell surface ligand or antigen. The diseases suitable for being treated by the compositions and methods of the disclosure include, but are not limited to, cancers, autoimmune diseases, inflammatory diseases, and infectious diseases. In some embodiments, the disease is a cancer or a chronic infection.

Additional Therapies

As discussed above, the recombinant cells, and pharmaceutical compositions described herein can be administered in combination with one or more additional therapeutic agents such as, for example, chemotherapeutics or anti-cancer agents or anti-cancer therapies. Administration "in combination with" one or more additional therapeutic agents includes simultaneous (concurrent) and consecutive administration in any order. In some embodiments, the one or more additional therapeutic agents, chemotherapeutics, anti-cancer agents, or anti-cancer therapies is selected from the group consisting of chemotherapy, radiotherapy, immunotherapy, hormonal therapy, toxin therapy, and surgery. "Chemotherapy" and "anti-cancer agent" are used interchangeably herein. Various classes of anti-cancer agents can be used. Non-limiting examples include: alkylating agents, antimetabolites, anthracyclines, plant alkaloids, topoisomerase inhibitors, podophyllotoxin, antibodies (e.g., monoclonal or polyclonal), tyrosine kinase inhibitors (e.g., imatinib mesylate (Gleevec® or Glivec®)), hormone treatments, soluble receptors and other antineoplastics.

Methods for Modulating an Activity of a Cell

In another aspect, provided herein are various methods for modulating an activity of a cell. The methods include the steps of: (a) providing an effective amount of any of the recombinant cells provided herein, and (b) contacting it with a selected ligand, wherein binding of the selected ligand to the extracellular ligand-binding domain induces cleavage of a ligand-inducible proteolytic cleavage site and releases the transcriptional regulator, wherein the released transcriptional regulator modulates an activity of the recombinant cell. One skilled in the art upon reading the present disclosure will appreciate that the disclosed methods can be carried out in vivo, ex vivo, or in vitro.

Non-limiting exemplary cellular activities that can be modulated using the methods provide herein include, but are not limited to, gene expression, proliferation, apoptosis, non-apoptotic death, differentiation, dedifferentiation, migration, secretion of a gene product, cellular adhesion, and cytolytic activity.

In some embodiments, the released transcriptional regulator modulates expression of a gene product of the cell. In some embodiments, the released transcriptional regulator modulates expression of a heterologous gene product in the cell. A heterologous gene product is one that is not normally found in the native cell, e.g., not normally produced by the cell. For example, the cell can be genetically modified with a nucleic acid including a nucleotide sequence encoding the heterologous gene product.

In some embodiments, the heterologous gene product is a secreted gene product. In some embodiments, the heterologous gene product is a cell surface gene product. In some cases, the heterologous gene product is an intracellular gene product. In some embodiments, the released transcriptional regulator simultaneously modulates expression of two or more heterologous gene products in the cell.

In some embodiments, the heterologous gene product in the cell is selected from the group consisting of a chemokine, a chemokine receptor, a chimeric antigen receptor, a cytokine, a cytokine receptor, a differentiation factor, a growth factor, a growth factor receptor, a hormone, a metabolic enzyme, a pathogen-derived protein, a proliferation inducer, a receptor, an RNA guided nuclease, a site-specific nuclease, a T-cell receptor (TCR), a chimeric antigen receptor (CAR), a toxin, a toxin-derived protein, a transcriptional regulator, a transcriptional activator, a transcriptional repressor, a translation regulator, a translational activator, a translational repressor, an activating immuno-receptor, an antibody, an apoptosis inhibitor, an apoptosis inducer, an engineered T cell receptor, an immuno-activator, an immuno-inhibitor, and an inhibiting immuno-receptor.

In some embodiments, the released transcriptional regulator modulates differentiation of the cell, and wherein the cell is an immune cell, a stem cell, a progenitor cell, or a precursor cell.

The chimeric receptors of the disclosure provide a higher degree of expression than a standard SynNotch receptor, when using identical binding domains and ICDs. Depending on the ligand/binding domain pair and their affinity, the chimeric polypeptides or Hinge-Notch receptors of the disclosure can provide expression enhancement of about 10%, about 15%, about 20%, about 25%, about 30%, about 35%, about 40%, about 45%, or about 50% higher than a corresponding SynNotch receptor.

Additionally, the chimeric receptors of the disclosure can provide transcriptional regulation that responds to the degree of T cell activation, independent of ligand binding. For example, when expressed in a T cell, some receptors of the disclosure provide a stronger ligand-induced signal when the T-cell is activated as compared to the ligand-induced signal when the T-cell is not activated. This permits additional flexibility in use, for example in cases where it is desired to enhance or suppress a T cell response when activated despite the absence of the chimeric receptor ligand.

Systems and Kits

Also provided herein are systems and kits including the chimeric polypeptides, Hinge-Notch receptors, recombinant nucleic acids, recombinant cells, or pharmaceutical compositions provided and described herein as well as written instructions for making and using the same. For example, provided herein, in some embodiments, are systems and/or kits that include one or more of: an chimeric polypeptide as described herein, a Hinge-Notch receptor as described herein, a recombinant nucleic acids as described herein, a recombinant cell as described herein, or a pharmaceutical composition as described herein. In some embodiments, the systems and/or kits of the disclosure further include one or more syringes (including pre-filled syringes) and/or catheters (including pre-filled syringes) used to administer one any of the provided chimeric polypeptides, Hinge-Notch receptors, recombinant nucleic acids, recombinant cells, or pharmaceutical compositions to an individual. In some embodiments, a kit can have one or more additional therapeutic agents that can be administered simultaneously or sequentially with the other kit components for a desired purpose, e.g., for modulating an activity of a cell, inhibiting a target cancer cell, or treating a health condition (e.g., disease) in an individual in need thereof.

Any of the above-described systems and kits can further include one or more additional reagents, where such additional reagents can be selected from: dilution buffers; reconstitution solutions, wash buffers, control reagents, control expression vectors, negative control polypeptides, positive control polypeptides, reagents for in vitro production of the chimeric receptor polypeptides.

In some embodiments, the components of a system or kit can be in separate containers. In some other embodiments, the components of a system or kit can be combined in a single container.

In some embodiments, a system or kit can further include instructions for using the components of the kit to practice the methods. The instructions for practicing the methods are generally recorded on a suitable recording medium. For example, the instructions can be printed on a substrate, such as paper or plastic, etc. The instructions can be present in the kits as a package insert, in the labeling of the container of the kit or components thereof (i.e., associated with the packaging or sub-packaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g., via the internet), can be provided. An example of this embodiment is a kit that includes a web address where the instructions can be viewed and/or from which the instructions can be downloaded. As with the instructions, this means for obtaining the instructions can be recorded on a suitable substrate.

All publications and patent applications mentioned in this disclosure are herein incorporated by reference to the same extent as if each individual publication or patent application was specifically and individually indicated to be incorporated by reference.

No admission is made that any reference cited herein constitutes prior art. The discussion of the references states what their authors assert, and the inventors reserve the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purpose.

No admission is made that any reference cited herein constitutes prior art. The discussion of the references states what their authors assert, and the inventors reserve the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

EXAMPLES

The practice of the present disclosure will employ, unless otherwise indicated, conventional techniques of molecular biology, microbiology, cell biology, biochemistry, nucleic acid chemistry, and immunology, which are well known to those skilled in the art. Such techniques are explained fully in the literature cited above.

Additional embodiments are disclosed in further detail in the following examples, which are provided by way of illustration and are not in any way intended to limit the scope of this disclosure or the claims.

Example 1

Design and Construction of Chimeric Receptor and Response Element Constructs

This Example describes the design and construction of a family of chimeric Notch receptors. Detailed information for various exemplary receptors of the disclosure can be found in Tables 1 and 2 below.

TABLE 1

This table provides a brief description for each of the chimeric Notch receptors, their corresponding components, as well as corresponding sequence identifiers as set forth in the Sequence Listing.

| Construct ID | Receptor Description | ECD | N-JMD | TMD | STS | TF | Full sequence |
|---|---|---|---|---|---|---|---|
| pIZ341 | anti-CD19scFv-CD8Hinge-Notch1TMD-Gal4VP64 | SEQ ID NO: 9 | SEQ ID NO: 12 | SEQ ID NO: 17 | SEQ ID NO: 18 | SEQ ID NO: 20 | SEQ ID NO: 1 |
| pIZ343 | anti-CD19scFv-CD8Hinge2-Notch1TMD-Gal4VP64 | SEQ ID NO: 9 | SEQ ID NO: 13 | SEQ ID NO: 17 | SEQ ID NO: 18 | SEQ ID NO: 20 | SEQ ID NO: 2 |
| pIZ358 | anti-CD19scFv-CD28Hinge-Notch1TMD-Gal4VP64 | SEQ ID NO: 9 | SEQ ID NO: 14 | SEQ ID NO: 17 | SEQ ID NO: 18 | SEQ ID NO: 20 | SEQ ID NO: 3 |
| pIZ359 | anti-CD19scFv-IgG4Hinge-Notch1TMD-Gal4VP64 | SEQ ID NO: 9 | SEQ ID NO: 15 | SEQ ID NO: 17 | SEQ ID NO: 18 | SEQ ID NO: 20 | SEQ ID NO: 4 |
| pIZ360 | anti-CD19scFv-OX40-Notch1TMD-Gal4VP64 | SEQ ID NO: 9 | SEQ ID NO: 16 | SEQ ID NO: 17 | SEQ ID NO: 18 | SEQ ID NO: 20 | SEQ ID NO: 5 |
| pIZ361 | anti-CD19scFv-CD8Hinge2-Notch1TMD-Notch2STS-Gal4VP64 | SEQ ID NO: 9 | SEQ ID NO: 13 | SEQ ID NO: 17 | SEQ ID NO: 19 | SEQ ID NO: 20 | SEQ ID NO: 6 |
| pIZ343FYIA | anti-ALPPL2scFv-CD8Hinge2-Notch1TMD-Gal4VP64 | SEQ ID NO: 10 | SEQ ID NO: 13 | SEQ ID NO: 17 | SEQ ID NO: 18 | SEQ ID NO: 20 | SEQ ID NO: 7 |
| pIZ343eGFP | eGFP-CD8Hinge2-Notch1TMD-Gal4VP64 | SEQ ID NO: 11 | SEQ ID NO: 13 | SEQ ID NO: 17 | SEQ ID NO: 18 | SEQ ID NO: 20 | SEQ ID NO: 8 |
| pIZ342 | anti-CD19scFv-CD8Hinge1-Notch1TMD-Gal4VP64 | SEQ ID NO: 9 | SEQ ID NO: 39 | SEQ ID NO: 17 | SEQ ID NO: 18 | SEQ ID NO: 20 | SEQ ID NO: 24 |

TABLE 1-continued

This table provides a brief description for each of the chimeric Notch receptors, their corresponding components, as well as corresponding sequence identifiers as set forth in the Sequence Listing.

| Construct ID | Receptor Description | ECD | N-JMD | TMD | STS | TF | Full sequence |
|---|---|---|---|---|---|---|---|
| pIZ362 | anti-CD19scFV-CD8Hinge3-Notch1TMD-Notch1STS-Gal4VP64 | SEQ ID NO: 9 | SEQ ID NO: 40 | SEQ ID NO: 17 | SEQ ID NO: 18 | SEQ ID NO: 20 | SEQ ID NO: 25 |
| pIZ363 | anti-CD19scFV-CD8Hinge4-Notch1TMD-Notch1STS-Gal4VP64 | SEQ ID NO: 9 | SEQ ID NO: 41 | SEQ ID NO: 17 | SEQ ID NO: 18 | SEQ ID NO: 20 | SEQ ID NO: 26 |
| pIZ361FYIA | anti-ALPPL2scFv-CD8Hinge2-Notch1TMD-Notch2STS-Gal4VP64 | SEQ ID NO: 10 | SEQ ID NO: 13 | SEQ ID NO: 17 | SEQ ID NO: 19 | SEQ ID NO: 20 | SEQ ID NO: 27 |
| pIZ343BCMA | anti-BCMAscFV-CD8Hinge2-Notch1TMD-Gal4VP64 | SEQ ID NO: 36 | SEQ ID NO: 13 | SEQ ID NO: 17 | SEQ ID NO: 18 | SEQ ID NO: 20 | SEQ ID NO: 28 |
| pIZ361BCMA | anti-BCMAscFV-CD8Hinge2-Notch1TMD-Notch2STS-Gal4VP64 | SEQ ID NO: 36 | SEQ ID NO: 13 | SEQ ID NO: 17 | SEQ ID NO: 19 | SEQ ID NO: 20 | SEQ ID NO: 29 |
| pIZ343(4D5-8) | anti-Her2scFV_4D5-8-CD8Hinge2-Notch1TMD-Gal4VP64 | SEQ ID NO: 37 | SEQ ID NO: 13 | SEQ ID NO: 17 | SEQ ID NO: 18 | SEQ ID NO: 20 | SEQ ID NO: 30 |
| pIZ361(4D5-8) | anti-Her2scFV_4D5-8-CD8Hinge2-Notch1TMD-Notch2STS-Gal4VP64 | SEQ ID NO: 37 | SEQ ID NO: 13 | SEQ ID NO: 17 | SEQ ID NO: 19 | SEQ ID NO: 20 | SEQ ID NO: 31 |
| pIZ343(4D5-7) | anti-Her2scFV_4D5-7-CD8Hinge2-Notch1TMD-Gal4VP64 | SEQ ID NO: 72 | SEQ ID NO: 13 | SEQ ID NO: 17 | SEQ ID NO: 18 | SEQ ID NO: 20 | SEQ ID NO: 32 |
| pIZ361(4D5-7) | anti-Her2scFV_4D5-7-CD8Hinge2-Notch1TMD-Notch2STS-Gal4VP64 | SEQ ID NO: 72 | SEQ ID NO: 13 | SEQ ID NO: 17 | SEQ ID NO: 19 | SEQ ID NO: 20 | SEQ ID NO: 33 |
| pRay068A | anti-BCMA_FHVH33-CD8Hinge2-Notch1TMD-Notch2STS-Gal4VP64 | SEQ ID NO: 38 | SEQ ID NO: 13 | SEQ ID NO: 17 | SEQ ID NO: 19 | SEQ ID NO: 20 | SEQ ID NO: 34 |
| pRay068B | anti-BCMA_FHVH33-CD8Hinge5-Notch1TMD-Notch2STS-Gal4VP64 | SEQ ID NO: 38 | SEQ ID NO: 42 | SEQ ID NO: 17 | SEQ ID NO: 19 | SEQ ID NO: 20 | SEQ ID NO: 35 |
| pIZ370 | anti-CD19scFv-CD8Hinge2-CLSTN1TMD-CLSTN1STS-Gal4VP64 | SEQ ID NO: 9 | SEQ ID NO: 13 | SEQ ID NO: 77 | SEQ ID NO: 79 | SEQ ID NO: 20 | SEQ ID NO: 73 |
| pIZ371 | antiCD19scFv-CD8Hinge2-CLSTN2TMD-CLSTN2STS-Gal4VP64 | SEQ ID NO: 9 | SEQ ID NO: 13 | SEQ ID NO: 78 | SEQ ID NO: 80 | SEQ ID NO: 20 | SEQ ID NO: 74 |
| pTMD201 | antiCD19scFv-CD8Hinge2-CLSTN1TMD-Notch1STS-Gal4VP64 | SEQ ID NO: 9 | SEQ ID NO: 13 | SEQ ID NO: 77 | SEQ ID NO: 18 | SEQ ID NO: 20 | SEQ ID NO: 75 |

TABLE 1-continued

This table provides a brief description for each of the chimeric Notch receptors, their corresponding components, as well as corresponding sequence identifiers as set forth in the Sequence Listing.

| Construct ID | Receptor Description | ECD | N-JMD | TMD | STS | TF | Full sequence |
|---|---|---|---|---|---|---|---|
| pTMD202 | antiCD19scFv-CD8Hinge2-CLSTN2TMD-Notch1STS-Gal4VP64 | SEQ ID NO: 9 | SEQ ID NO: 13 | SEQ ID NO: 78 | SEQ ID NO: 18 | SEQ ID NO: 20 | SEQ ID NO: 76 |

ECD: extracellular domain; N-JMD: N-terminal juxtamembrane domain (i.e., hinge domain); TMD: transmembrane domain; STS: stop-transfer-sequence; TF: transcriptional factor.

TABLE 2

This table provides a brief description for each of the chimeric Notch receptors and the respective components (with components separated by commas). Unless otherwise noted, the entry refers to a protein of human origin. For example, "Notch1, Notch1" indicates that two sequence from Notch1 were fused to generate this protein module.

| Construct ID | Receptor Description | ECD | N-JMD | TMD | STS | TF |
|---|---|---|---|---|---|---|
| pIZ341 | anti-CD19 scFv connected to hsNotch1TMD_Gal4VP64 with full CD8 hinge | CD8a signal peptide, myc-tag, anti-CD19 scFv | CD8 hinge | Notch1 | Notch1 | Gal4, VP64 |
| pIZ343 | anti-CD19 scFv connected to hsNotch1TMD_Gal4VP64 with truncated CD8 hinge, one cysteine | CD8a signal peptide, myc-tag, anti-CD19 scFv | truncated CD8 hinge | Notch1 | Notch1 | Gal4, VP64 |
| pIZ358 | anti-CD19 scFv connected to hsNotch1TMD_Gal4VP64 with CD28 Hinge | CD8a signal peptide, myc-tag, anti-CD19 scFv | CD28 hinge | Notch1 | Notch1 | Gal4, VP64 |
| pIZ359 | anti-CD19 scFv connected to hsNotch1TMD_Gal4VP64 with IgG4 Hinge | CD8a signal peptide, myc-tag, anti-CD19 scFv | (GGGGS)3 hinge | Notch1 | Notch1 | Gal4, VP64 |
| pIZ360 | anti-CD19 scFv connected to hsNotch1TMD_Gal4VP64 with OX40 trimeric hinge | CD8a signal peptide, myc-tag, anti-CD19 scFv | OX40 hinge | Notch1 | Notch1 | Gal4, VP64 |
| pIZ361 | pIZ343 with human Notch1 STS replaced by Notch2 STS | CD8a signal peptide, myc-tag, anti-CD19 scFv | truncated CD8 hinge | Notch1 | Notch2 | Gal4, VP64 |
| pIZ343FYIA | anti-ALPPL2 connected to hsNotch1TMD_Gal4VP64 with truncated CD8 hinge, one cysteine | scFv(FYIA) peptide, myc-tag, anti-ALPPL2 scFv | CD8a signal truncated CD8 hinge | Notch1 | Notch1 | Gal4, VP64 |
| pIZ343eGFP | pIZ343 with GFP extracellular domain | Mouse IgKVIII signal peptide, eGFP | truncated CD8 hinge | Notch1 | Notch1 | Gal4, VP64 |
| pIZ342 | anti-CD19 scFv connected to hsNotch1TMD_Gal4VP64 with truncated CD8 hinge, no cysteines | CD8a signal peptide, myc-tag, anti-CD19 scFv | truncated CD8 hinge | Notch1 | Notch1 | Gal4, VP64 |
| pIZ362 | anti-CD19 scFv connected to hsNotch1TMD_Gal4VP64 with N-truncated CD8 hinge, one cysteine | CD8a signal peptide, myc-tag, anti-CD19 scFv | N-truncated CD8Hinge | Notch1 | Notch1 | Gal4, VP64 |
| pIZ363 | anti-CD19 scFv connected to hsNotch1TMD_Gal4VP64 with N-truncated CD8 hinge, two cysteines | CD8a signal peptide, myc-tag, anti-CD19 scFv | N-truncated CD8Hinge | Notch1 | Notch1 | Gal4, VP64 |
| pIZ361FYIA | anti-ALPPL2 scFv(FYIA) connected to hsNotch1TMD_Gal4VP64 with truncated CD8 hinge, one cysteine, Notch2 STS | CD8a signal peptide, myc-tag, anti-ALPPL2 scFv | truncated CD8 hinge | Notch1 | Notch2 | Gal4, VP64 |

TABLE 2-continued

This table provides a brief description for each of the chimeric Notch receptors and the respective components (with components separated by commas). Unless otherwise noted, the entry refers to a protein of human origin. For example, "Notch1, Notch1" indicates that two sequence from Notch1 were fused to generate this protein module.

| Construct ID | Receptor Description | ECD | N-JMD | TMD | STS | TF |
|---|---|---|---|---|---|---|
| pIZ343BCMA | anti-BCMA scFV connected to hsNotch1TMD_Gal4VP64 with truncated CD8 hinge, one cysteine | CD8a signal peptide, myc-tag, anti-B CMA scFv | truncated CD8 hinge | Notch1 | Notch1 | Gal4, VP64 |
| pIZ361BCMA | anti-BCMA scFV connected to hsNotch1TMD_Gal4VP64 with truncated CD8 hinge, one cysteine, Notch2 STS | CD8a signal peptide, myc-tag, anti-B CMA scFv | truncated CD8 hinge | Notch1 | Notch2 | Gal4, VP64 |
| pIZ343(4D5-8) | anti-Her2 scFV (4D5-8) connected to hsNotch1TMD_Gal4VP64 with truncated CD8 hinge, one cysteine | CD8a signal peptide, myc-tag, anti-HER2 scFv | truncated CD8 hinge | Notch1 | Notch1 | Gal4, VP64 |
| pIZ361(4D5-8) | anti-Her2 scFV (4D5-8) connected to hsNotch1TMD_Gal4VP64 with truncated CD8 hinge, one cysteine, Notch2 STS | CD8a signal peptide, myc-tag, anti-HER2 scFv | truncated CD8 hinge | Notch1 | Notch2 | Gal4, VP64 |
| pIZ343(4D5-7) | anti-Her2 scFV (4D5-7) connected to hsNotch1TMD_Gal4VP64 with truncated CD8 hinge, one cysteine | CD8a signal peptide, myc-tag, anti-HER2 scFv | truncated CD8 hinge | Notch1 | Notch1 | Gal4, VP64 |
| pIZ361(4D5-7) | anti-Her2 scFV (4D5-7) connected to hsNotch1TMD_Gal4VP64 with truncated CD8 hinge, one cysteine, Notch2 STS | CD8a signal peptide, myc-tag, anti-HER2 scFv | truncated CD8 hinge | Notch1 | Notch2 | Gal4, VP64 |
| pRay068A | anti-BCMA fully humanized VH domain connected to hsNotch1TMD_Gal4VP64 with truncated CD8 hinge, one cysteine, Notch2 STS | CD8a signal peptide, anti-BCMA VH domain | truncated CD8 hinge | Notch1 | Notch2 | Gal4, VP64 |
| pRay068B | anti-BCMA fully humanized VH domain connected to hsNotch1TMD_Gal4VP64 with truncated CD8 hinge, one cysteine, Notch2 STS | CD8a signal peptide, anti-BCMA VH domain | truncated CD8 hinge | Notch1 | Notch2 | Gal4, VP64 |
| pIZ370 | antiCD19scFv-CD8Hinge2-CLSTN1TMD-CLSTN1STS-Gal4VP64 | CD8a signal peptide, myc-tag, anti-CD19 scFv | truncated CD8 hinge | CLSTN1 | CLSTN1 | Gal4, VP64 |
| pIZ371 | antiCD19scFv-CD8Hinge2-CLSTN2TMD-CLSTN2STS-Gal4VP64 | CD8a signal peptide, myc-tag, anti-CD19 scFv | truncated CD8 hinge | CLSTN2 | CLSTN2 | Gal4, VP64 |
| pTMD201 | antiCD19scFv-CD8Hinge2-CLSTN1TMD-Notch1STS-Gal4VP64 | CD8a signal peptide, myc-tag, anti-CD19 scFv | truncated CD8 hinge | CLSTN1 | Notch1 | Gal4, VP64 |
| pTMD202 | antiCD19scFv-CD8Hinge2-CLSTN2TMD-Notch1STS-Gal4VP64 | CD8a signal peptide, myc-tag, anti-CD19 scFv | truncated CD8 hinge | CLSTN2 | Notch1 | Gal4, VP64 |

The chimeric receptors described in Tables 1-2 above were built by fusing a single-chain antigen-binding fragment (scFv) recognizing CD19 (Porter D L et al., 2011), ALPPL2 (FYIA), BCMA, Her2, or an anti-BCMA fully humanized $V_H$ domain, to the corresponding receptor scaffold and a synthetic transcriptional regulator GAL4-VP64. For the construction of these receptors, DNA fragments coding for the amino acid sequences provided in Table 1 and Sequence Listing were PCR amplified from synthesized gene fragments or plasmids containing DNA sequence for the indicated protein, and assembled using standard cloning techniques (e.g., overhang PCR, fusion PCR, and In-fusion cloning) with flanking translation start and stop sequences, into a BamHI cloning site of the lentiviral expression vector pHR-SIN-pGK (L. Morsut et al., Cell (2016) 164:780-91; Addgene plasmid #76120).

The transcriptional regulator GAL4-VP64 used in these experiments contained a DNA domain from yeast GAL4 transcription factor fused to an activation domain VP64, which consists of a tetrameric repeat of the minimal activation domain (amino acids 437-447) of the herpes simplex protein VP16. As illustrated in Table 2, most exemplary receptors contained an N-terminal CD8α signal peptide (MALPVTALLLPLALLLHAARP) (SEQ ID NO: 21) for membrane targeting, while one exemplary receptor (pIZ343eGFP) contained a Mouse IgKVIII signal peptide. In addition, most exemplary receptors contained a myc-tag (EQKLISEEDL) (SEQ ID NO: 22) for suitable determination of surface expression with an antibody conjugated to a fluorescent dye (α-myc A647®, Cell Signaling Technology, Cat #2233). The receptors were each cloned into a modified lentiviral pHR'SIN:CSW vector (KT Roybal et al., Cell 2016 Oct. 6; 167(2):419-32) containing a phosphoglycerate kinase (PGK) promoter for all primary T cell experiments described in Examples 3-4 below.

The pHR'SIN:CSW vector was also modified to produce the response element plasmids. For this purpose, five copies of a target sequence for binding of GAL4 DBD domain (GGAGCACTGTCCTCCGAACG) (SEQ ID NO: 23) were cloned 5' to a minimal pybTATA promoter. Also included in the response element plasmids is a PGK promoter that constitutively drives expression of a yellow fluorescent reporter protein (mCitrine) to suitably identify successfully transduced T cells.

For the construction of all inducible BFP vectors, the coding sequence for a blue fluorescent reporter protein (BFP) was cloned via a BamHI site in the multiple cloning site located 3' to the GAL4 response elements. For the construction of all inducible CAR vectors, the CARs were tagged C-terminally with a green fluorescent reporter protein (GFP) and were cloned via a BamHI site in the multiple cloning site located 3' to the GAL4 response elements. All constructs were cloned via cloning kit (In-Fusion® cloning, Clontech #ST0345) according to the manufacturer's instructions.

Example 2

Primary Human T-Cell Isolation and Culture

This Example describes the isolation and culture of primary human T cells that were subsequently used in various cell transduction experiments described in Example 3 below.

In these experiments, primary CD4$^+$ and CD8$^+$ T cells were isolated from blood after apheresis and enriched by negative selection using human T-cell isolation kits (human CD4$^+$ or CD8$^+$ enrichment cocktail; STEMCELL Technologies Cat #15062 and 15063). Blood was obtained from Blood Centers of the Pacific (San Francisco, Calif.) as approved by the University Institutional Review Board. T cells were cryopreserved in growth medium (RPMI-1640, UCSF cell culture core) with 20% human AB serum (Valley Biomedical Inc., #HP1022) and 10% DMSO. After thawing, T cells were cultured in human T cell medium containing X-VIVO™ 15 (Lonza #04-418Ω), 5% Human AB serum and 10 mM neutralized N-acetyl L-Cysteine (Sigma-Aldrich #A9165) supplemented with 30 units/mL IL-2 (NCI BRB Preclinical Repository) for all experiments.

Example 3

Human T Cells were Stably Transduced with Lentiviral Vectors

The Example describes a general protocol used for lentiviral transduction of human T cells, unless specified otherwise in this specification.

Generally, lentiviral vectors pseudo-typed with vesicular stomatitis virus envelope G protein (VSV-G) (pantropic vectors) were produced via transfection of Lenti-X™ 293T cells (Clontech #11131D) with a pHR'SIN:CSW transgene expression vector and the viral packaging plasmids pCMVdR8.91 and pMD2.G using Mirus TransIT®-Lenti (Mirus, #MIR 6606). Generally, primary T cells were thawed the same day and, after 24 hours in culture, were stimulated with beads having anti-CD3 and anti-CD28 antibodies bound to the surface (Human T-Activator CD3/CD28 Dynabeads®, Life Technologies #11131D) at a 1:3 cell:bead ratio. At 48 hours, viral supernatant was harvested and the primary T cells were exposed to the virus for 24 hours. At Day 5 post T-cell stimulation, the beads were removed, and the T cells expanded until Day 14 when they were rested and could be used in assays. T cells were sorted for assays with a Beckton Dickinson (BD Biosciences) FACSAriam™ flow cytometer. AND-gate T cells exhibiting basal CAR expression were gated out during sorting.

Example 4

Stimulation of Primary T Cells In Vitro

This Example describes experiments performed to demonstrate the stimulation of primary T cells in vitro by the chimeric Hinge-Notch polypeptides described herein, unless specified otherwise in this specification.

For all in vitro T-cell stimulations, 1×10 T cells were co-cultured with sender cells at a 1:1 ratio in flat bottom 96-well tissue culture plates. The cultures were analyzed at 24 hours for reporter activation with a BD Fortessa™ X-50. All flow cytometry analysis was performed in FlowJo™ software (TreeStar, Inc.).

Example 5

Figures 1A, 1B:
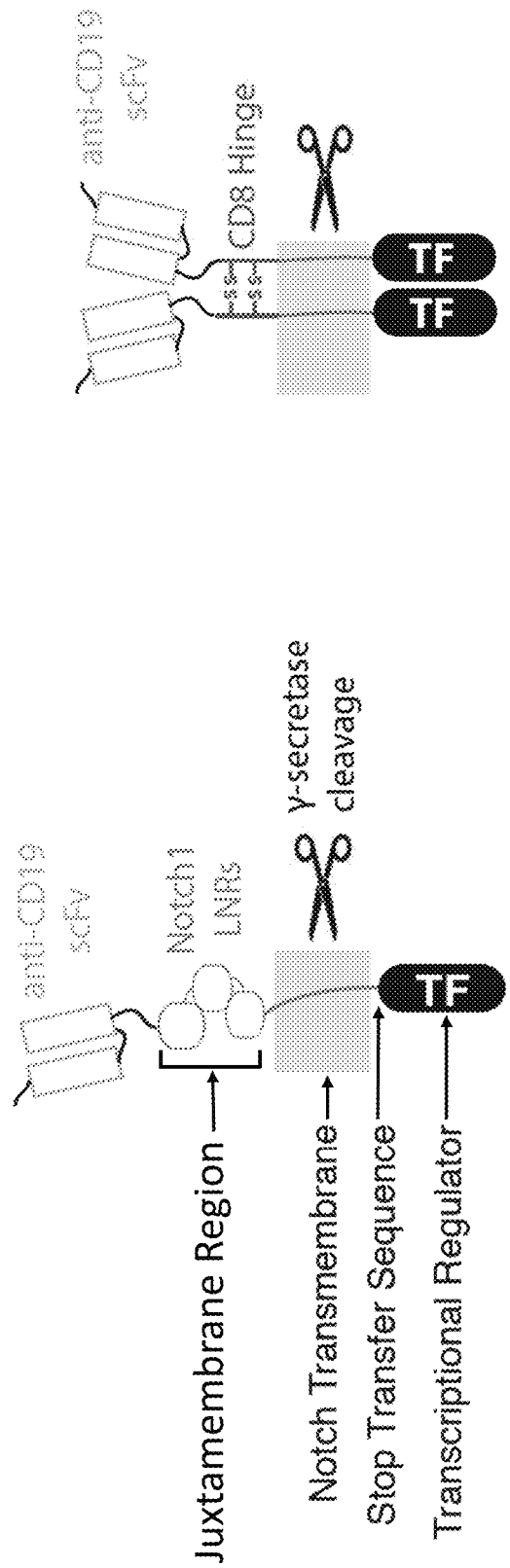
FIGS. 1A-1B schematically illustrate differences between a SynNotch receptor and a chimeric polypeptide of the disclosure.
Figure 2A:
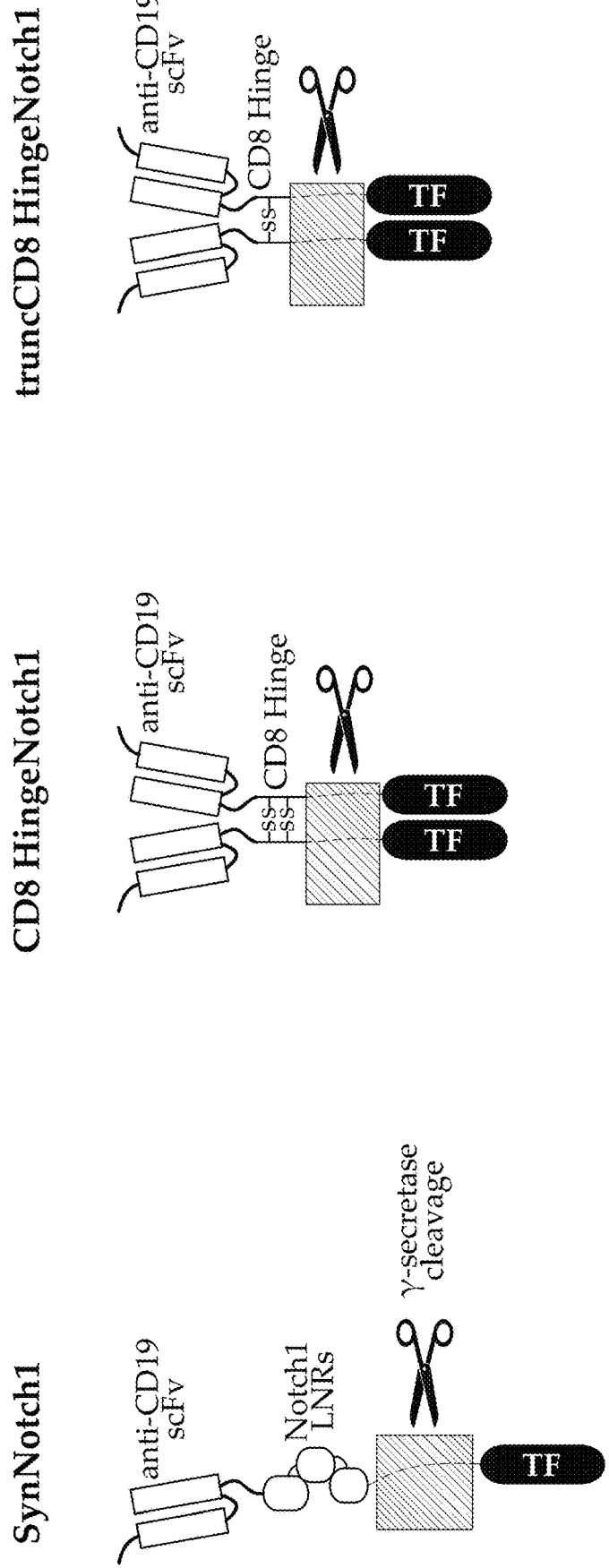
FIGS. 2A-2C schematically summarize the design of Hinge-Notch receptors, their expression, and activation in primary T CD4+ T cells.
Figure 2B:
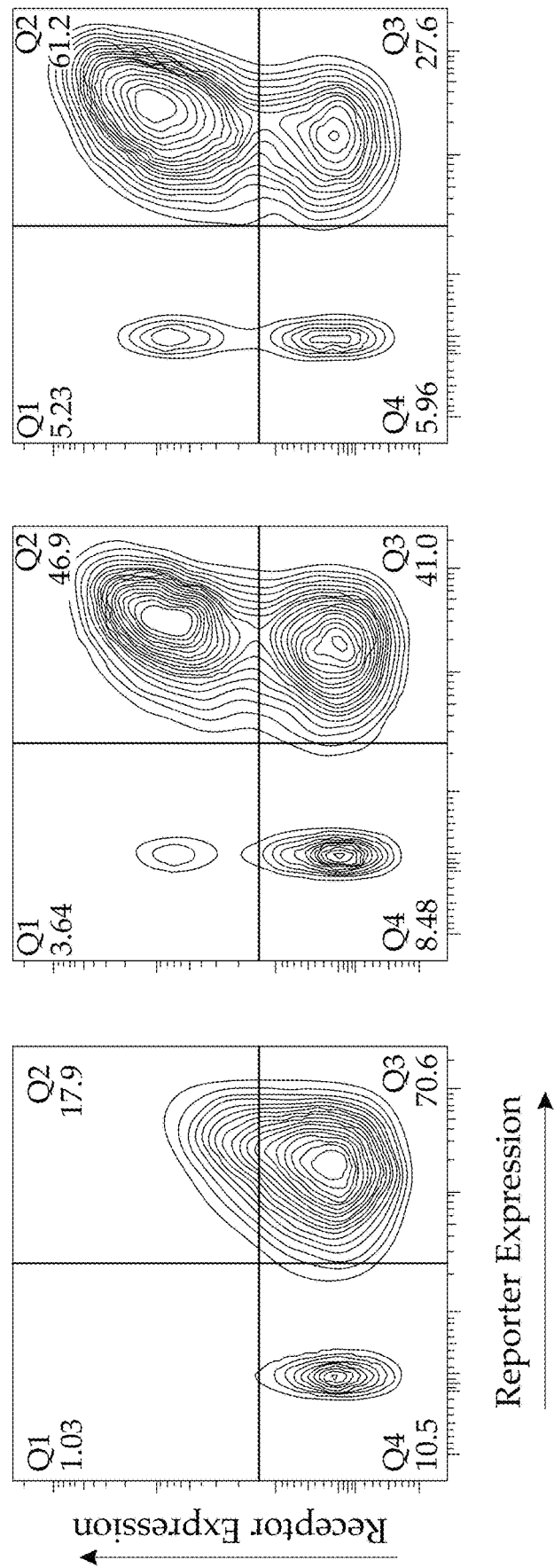
Figure 2C:
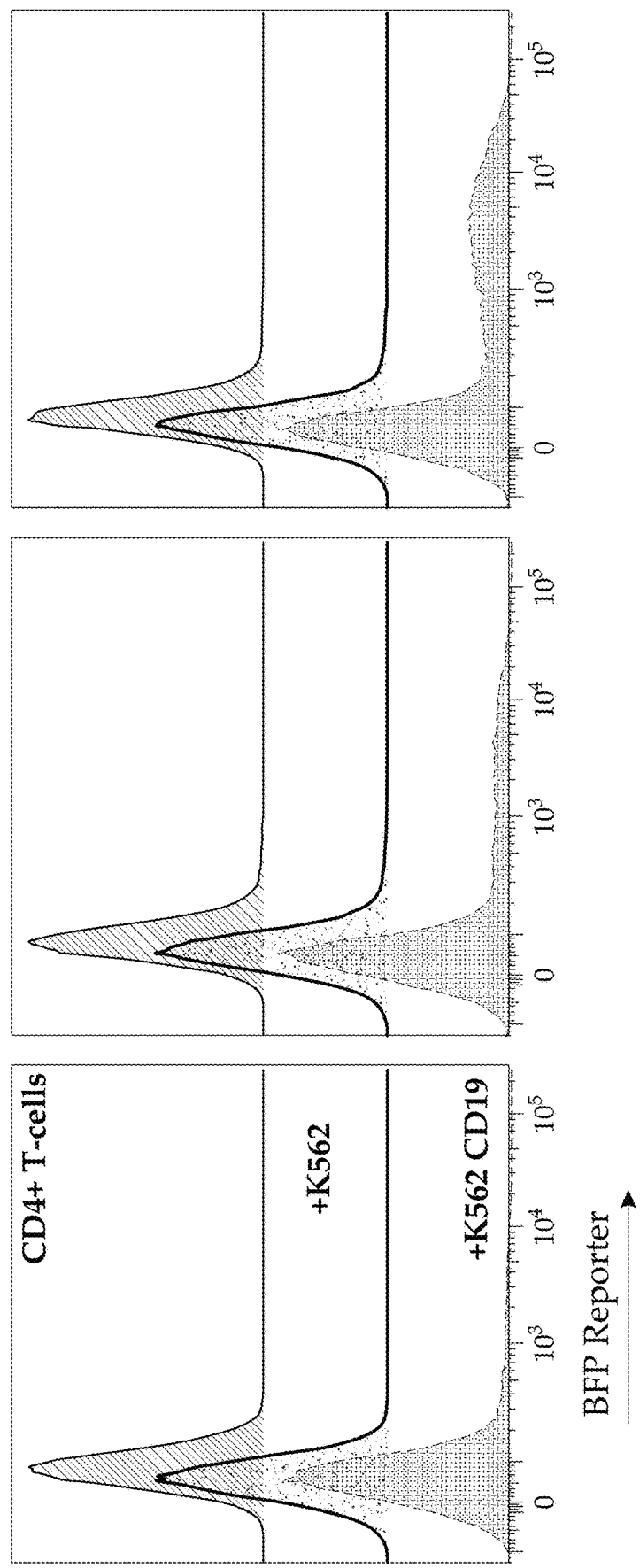

CD8Hinge-Notch Receptor Design. Expression, and Activation in Primary T CD4$^+$ Cells This Example describes the design of CD8Hinge-Notch receptors, and the results of experiments performed to evaluate their expression and activation in primary T CD4$^+$ T cells. Two variants of CD8Hinge-Notch receptors were constructed. As shown in FIG. 2A, an exemplary SynNotch1 receptor is shown on the Left panel, which was designed based upon human Notch1 proteins. The Middle panel schematically shows an exemplary CD8 Hinge-Notch1 receptor. Compared to the SynNotch1 receptor in left panel, CD8 Hinge-Notch1 receptors replace the NRR with a CD8 hinge domain, which contains cysteine residues known to form disulfide bonds. The Right panel schematically shows an exemplary truncated CD8 Hinge-Notch1 receptors (truncCD8 Hinge-Notch1). Compared to CD8 Hinge-Notch1 receptors, truncCD8 Hinge-Notch1 receptors contain a C-terminal deletion of the CD8 hinge sequence, leaving a single cysteine residue and a shorter extracellular region. FIG. 2B is a summary of flow cytometry data of receptor expression. In these experiments, primary human T-cells were activated with anti-CD3/anti-CD28 Dynabeads (Gibco) and transduced with two lentiviral constructs expressing either a receptor or a transcriptional reporter construct. Receptor expression was measured using an AlexaFluor647-tagged anti-myc antibody (Cell Signaling). Reporter expression was measured through a constitutive mCitrine gene found on the reporter plasmid. Double positive cells were sorted for on Day 5 post initial T-cell stimulation and expanded further for activation testing. FIG. 2C summarizes the results of receptor activation testing. In these experiments, 1×10$^5$ double positive T-cells expressing anti-CD19 receptors were co-cultured with: no additions (upper trace), 1×10$^5$ K562 cells (middle trace), or 1×10$^5$ CD19+ K562 cells (lower trace) for 24 hours. Transcriptional activation of an inducible BFP reporter gene was subsequently measured using a Fortessa X-50 (BD Biosciences). The results described in this Example demonstrate that both CD8Hinge-Notch receptor and truncCD8 Hinge-Notch1 were expressed in primary T CD4+ T cells.

Example 6

CD8Hinge Receptor Activation with T-Cell Stimulation

Figure 3:
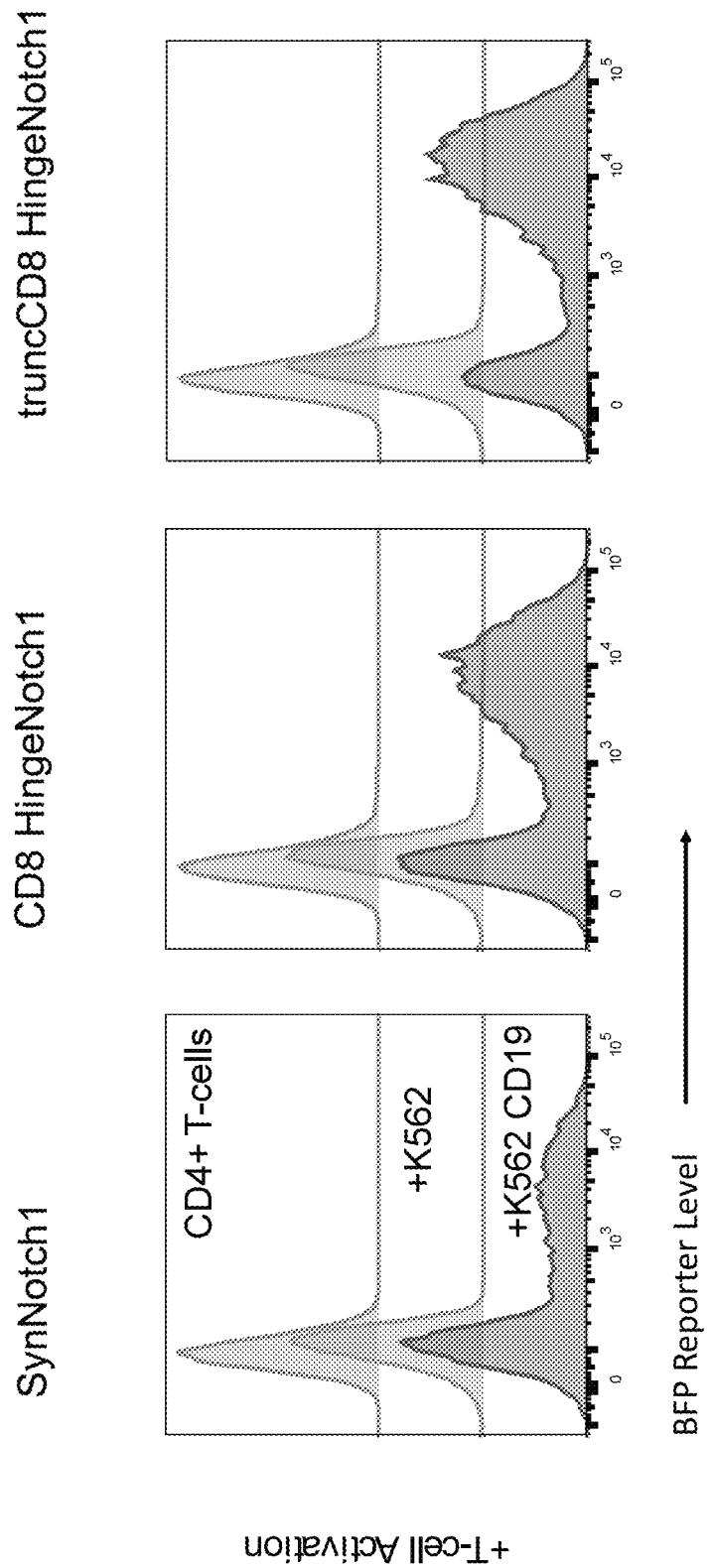
FIG. 3 schematically summarizes the results of experiments performed to demonstrate receptor activation with concurrent T-cell activation. In these experiments, to simulate T-cell activation, anti-MCAM, anti-CD3 Bi-specific T-cell Engagers (MCAM BiTE®s) were used, which activate the T-cell receptor in the presence of K562 cells. $1 \times 10^5$ double positive T-cells expressing anti-CD19 receptors were co-cultured with: MCAM BiTE®s (upper trace), $1 \times 10^5$ K562 cells+MCAM BiTE®s (middle trace), or $1 \times 10^5$ CD19+ K562 cells+MCAM BiTE®s (lower trace) for 24 hours. Transcriptional activation of an inducible BFP reporter gene was subsequently measured using a Fortessa X-50 (BD Biosciences), and demonstrated increased reporter signal as compared to the signal obtained from non-activated T-cells in FIG. 2.

This Example describes the results of experiments performed to demonstrate gene activation medicated by CD8Hinge-Notch receptors described herein with concurrent T-cell activation. These experiments were conducted using the same CD8Hinge-Notch receptor variants described above in Example 5. The results of receptor activation testing with concurrent T-cell activation is shown in FIG. 3B. In these experiments, to simulate T-cell activation, anti-MCAM, anti-CD3 Bi-specific T-cell Engagers (MCAM BiTEs) were used, which activate the T-cell receptor in the presence of K562 cells. $1 \times 10^5$ double positive T-cells expressing anti-CD19 receptors were co-cultured with: MCAM BiTEs (upper trace), $1 \times 10^5$ K562 cells+ MCAM BiTEs (middle trace), or $1 \times 10^5$ CD19+ K562 cells+ MCAM BiTEs (lower trace) for 24 hours. Transcriptional activation of an inducible BFP reporter gene was subsequently measured using a Fortessa X-50 (BD Biosciences). The results described in this Example demonstrate that both CD8Hinge-Notch receptor and truncCD8 Hinge-Notch1 can activate transcription with or without concurrent T-cell activation.

Example 7

CD8Hinge Optimization

Figure 4A:
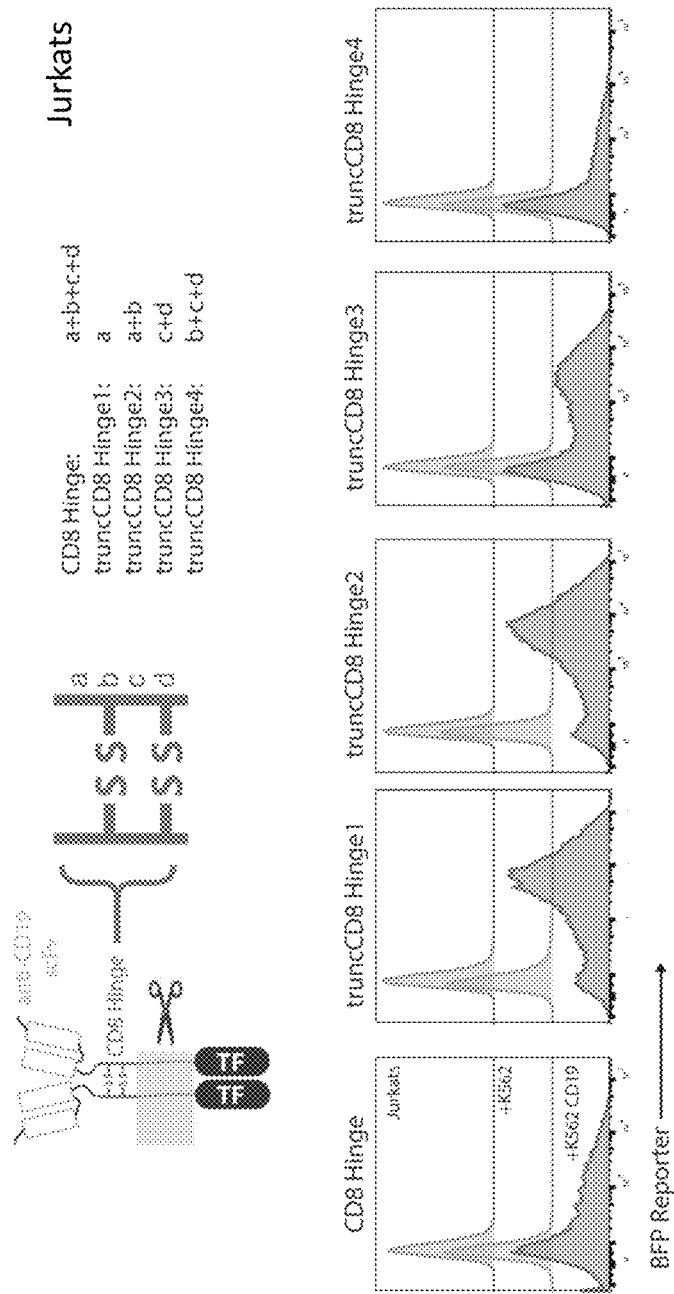
FIGS. 4A-4D summarize the results of experiments performed to optimize the hinge domain in the context of chimeric Notch receptors.
Figure 4B:
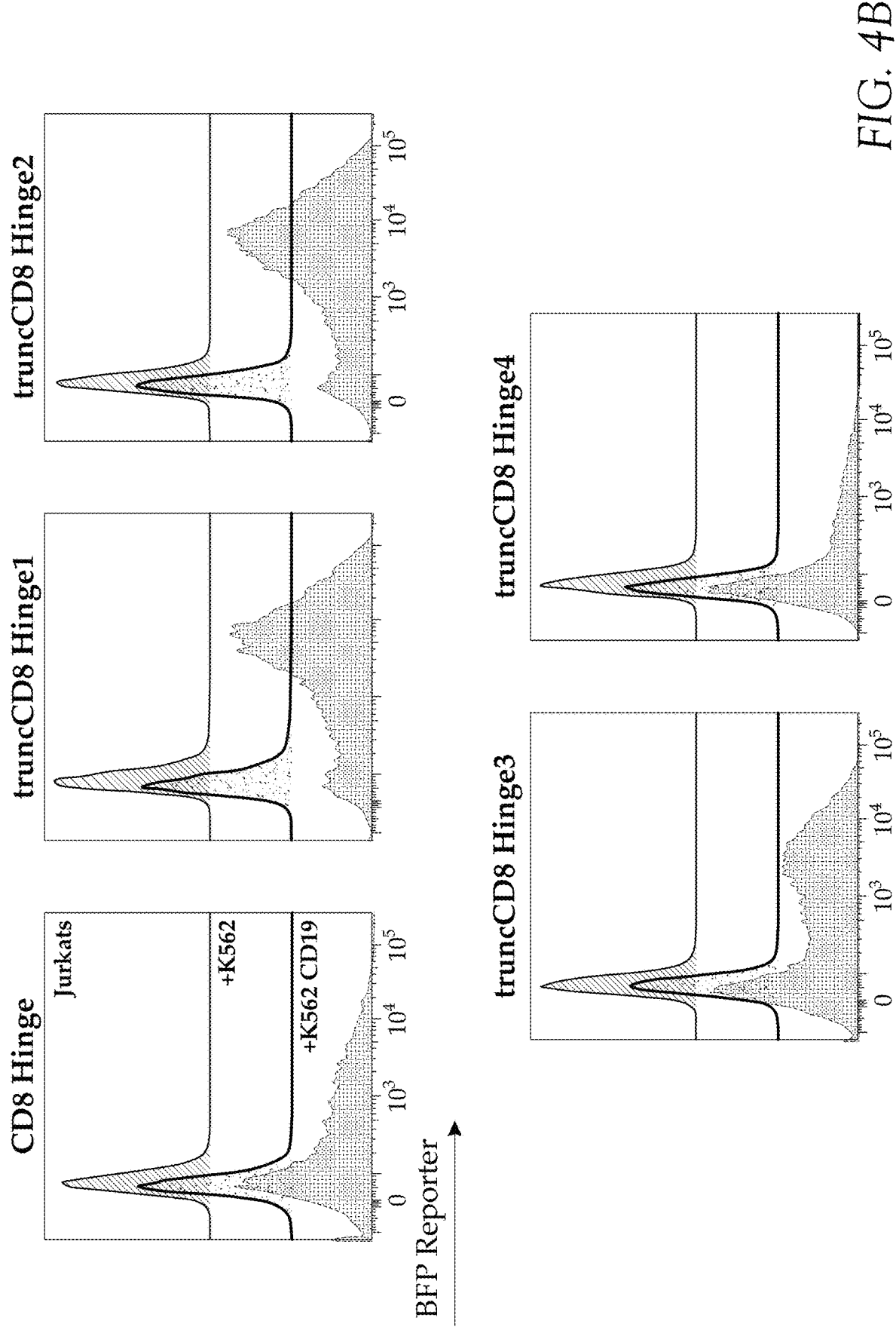
Figures 4C, 4D:
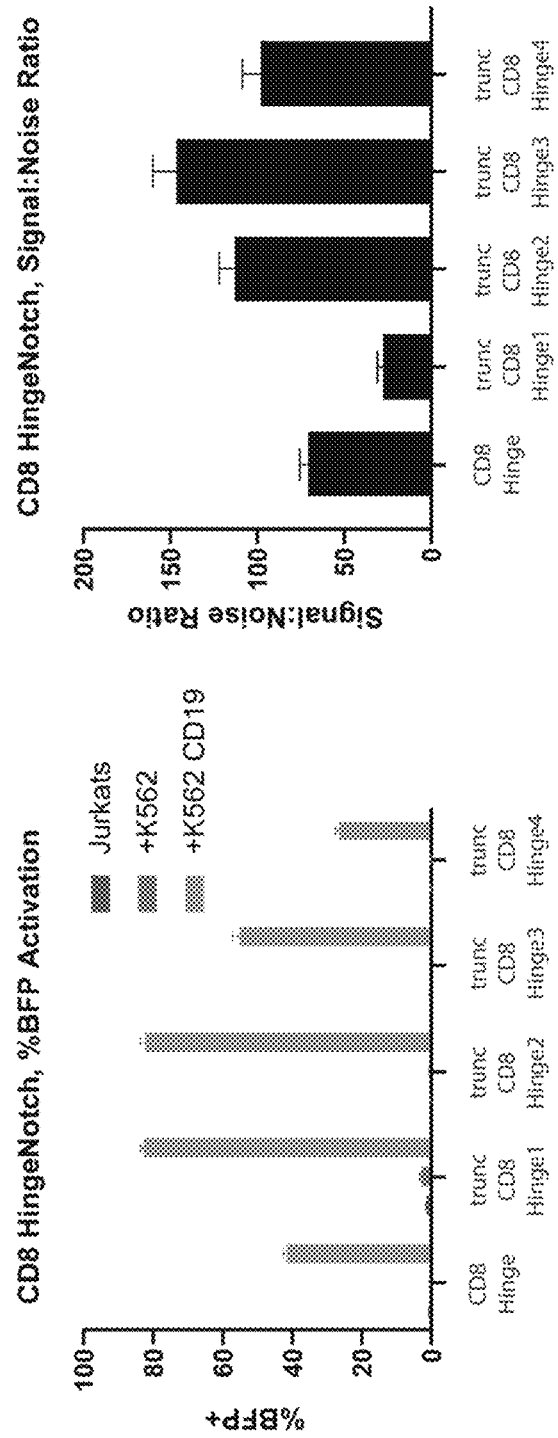

This Example describes the results of experiments performed to optimize the CD8 hinge domain in the context of chimeric Notch receptors. Four variants of the CD8 hinge domain were tested: truncCD8 Hinge1, truncCD8 Hinge2, truncCD8 Hinge3, and truncCD8 Hinge4. The structural differences among these CD8 hinge domain variants are shown in FIG. 4A, where the hinge components are denoted as "a", "b", "c", and "d". Component "a" represents the region N-terminal of the first cysteine residue. Component "b" represents the first cysteine residue. Component "c" represents the region in between the first and second cysteine residues. Component "d" represents the second cysteine residue and the region from the second cysteine residue to the receptor transmembrane domain. FIG. 4B summarizes the results of receptor activation testing in Jurkat T-cells. Transcriptional activation of an inducible BFP reporter gene was subsequently measured using a Fortessa X-50 (BD Biosciences). FIG. 4C shows the quantification of % BFP positive cells from data in FIG. 4B. The results described in this Example demonstrate that all four variants of the CD8 hinge domain could activate transcription, as measured by BFP expression levels. However, truncCD8 hinge1 and 2-Notch1 receptors are optimal in that they activate transcription to high levels with ligand and exhibit minimal ligand-independent transcriptional regulation (FIG. 4B).

Example 8

TruncCD8Hinge2 Receptor Activation Testing with Concurrent PKC Signaling

Figure 5:
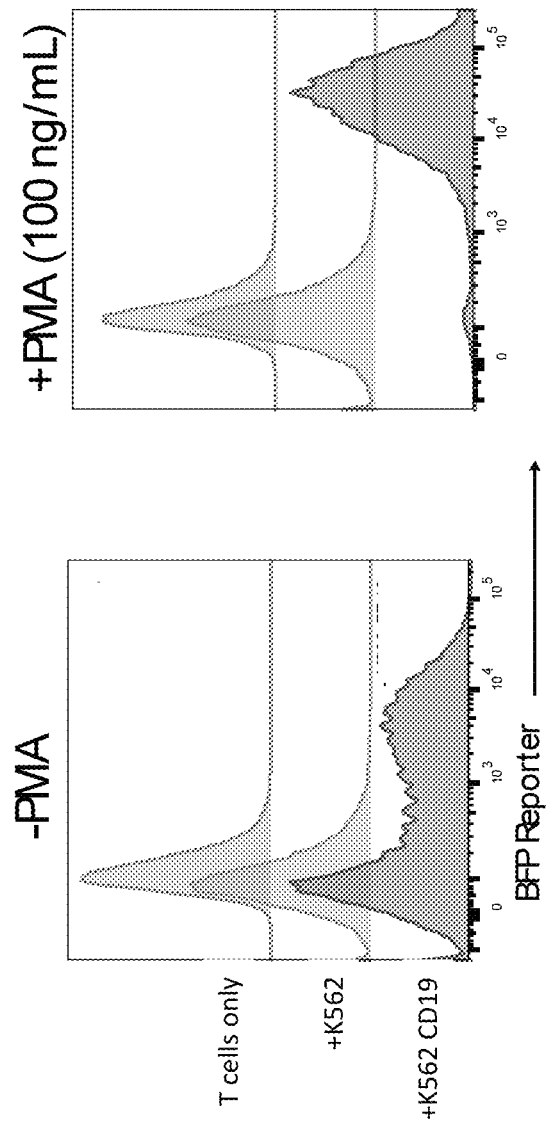
FIG. 5 schematically summarizes the results from experiments performed to test truncCD8Hinge2 receptor activation with concurrent PKC (protein kinase C) signaling. In these experiments, to simulate PKC signaling, phorbol 12-myristate 13-acetate (PMA) was added. $1 \times 10^5$ double positive T-cells expressing anti-CD19 receptors were co-cultured with: no additional cells (upper trace), $1 \times 10^5$ K562 cells (middle trace), or $1 \times 10$ CD19+ K562 cells (lower trace) for 24 hours, with and without PMA. Transcriptional activation of an inducible BFP reporter gene was subsequently measured using a Fortessa X-50 (BD Biosciences).

This Example describes the results from experiments performed to test gene activation mediated by the truncCD8Hinge2 receptor described in Example 7 above with concurrent PKC signaling. In these experiments, to simulate PKC signaling, phorbol 12-myristate 13-acetate (PMA), a DAG analog, was added. As shown in FIG. 5, $1 \times 10^5$ double positive T-cells expressing anti-CD19 receptors were co-cultured with: no additional cells (upper trace), $1 \times 10^5$ K562 cells (middle trace), or $1 \times 10^5$ CD19+ K562 cells (lower trace) for 24 hours, with and without PMA. Transcriptional activation of an inducible BFP reporter gene was subsequently measured using a Fortessa X-50 (BD Biosciences). The results described in this Example demonstrate that truncCD8 Hinge2-Notch1 can activate transcription with or without concurrent PKC signaling.

Example 9

Testing of Hinge Domains from Alternative Sources

This Example describes the results from experiments performed with Hinge-Notch receptors containing alternative hinge domains derived from other sources. In these experiments, Hinge-Notch receptors were constructed with hinge domain derived from CD28, OX40, and IgG4 (see, e.g., FIG. 6A). Four exemplary Hinge-Notch receptors: pIZ343 (truncated CD8Hinge2-Notch), pIZ358 (CD28Hinge-Notch), pIZ360 (OX40Hinge-Notch), pIZ359 (IgG4Hinge-Notch) were tested. A brief description for each of the Hinge-Notch receptors is also provided in Table 2. As shown in FIG. 6B, each of the Hinge-Notch constructs pIZ343 (truncated CD8Hinge-Notch), pIZ358 (CD28Hinge-Notch), pIZ360 (OX40Hinge-Notch), pIZ359 (IgG4Hinge-Notch) were able to stimulate primary T cells as determined by expression of BFP reporter gene. A previously generated reporter positive Jurkat T-cell line is transduced with a receptor construct. Receptor expression was measured using an AlexaFluor647-tagged anti-myc antibody (Cell Signaling). For receptor activation testing. $1 \times 10^5$ Jurkat T-cells expressing anti-CD19 receptors are co-cultured with: no additions (upper trace), $1 \times 10^5$ K562 cells (middle trace), or $1 \times 10^5$ CD19+ K562 cells (lower trace) for 24 hours. Transcriptional activation of an inducible BFP reporter gene was subsequently measured using a Fortessa X-50 (BD Biosciences). FIG. 6B depicts the quantification of % BFP positive cells from testing results in FIG. 6A. The experiments described in this Example demonstrate that in addition to CD8A, other usable hinge domains can be derived from alternative sources such as, CD28, OX40, and IgG4.

Example 10

Testing of Hinge-Notch Receptors Containing Alternative Ligand Recognition Domains This Example describes the results from experiments performed to test Hinge-Notch receptors containing alternative ligand recognition domains.

Figures 7A, 7B:
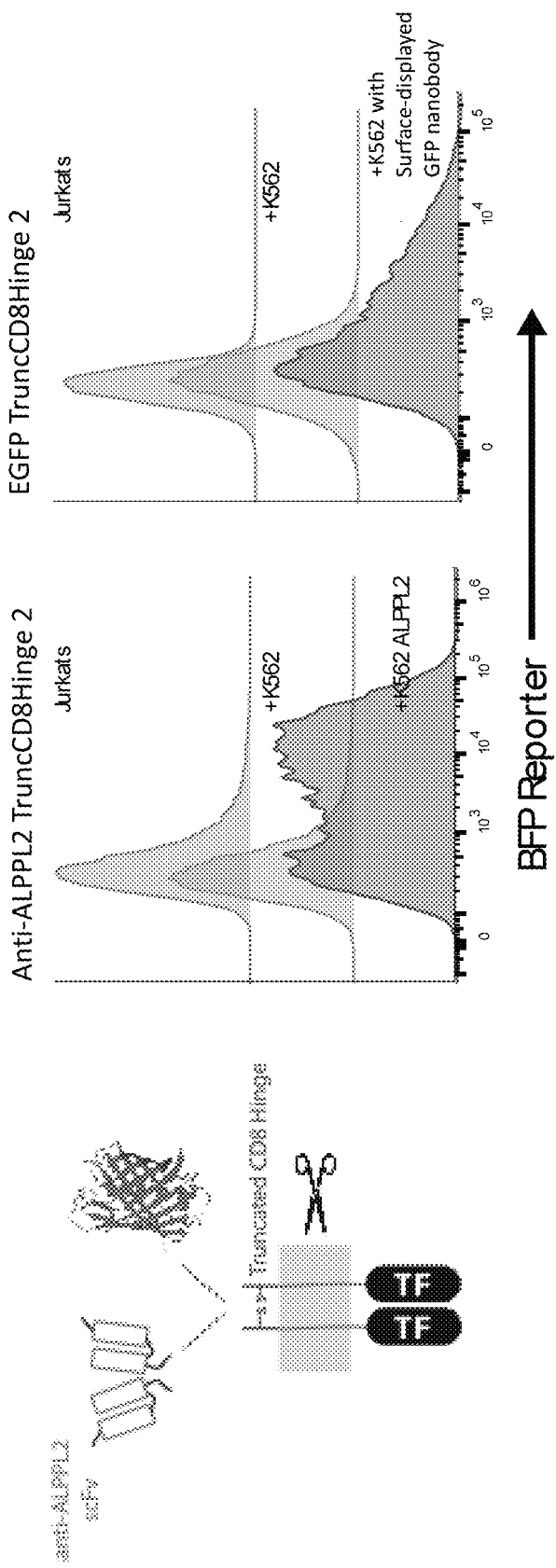
FIGS. 7A-7B schematically summarize the results from experiments performed to test Hinge-Notch receptors containing other ligand recognition domains. As demonstrated in FIG. 7A, in addition to the anti-CD19 scFv, the anti-ALPPL2 scFv and eGFP can be used as ligand recognition domains.

As demonstrated in FIG. 7A, in addition to the anti-CD19 scFV, the anti-ALPPL2 scFV and eGFP were also used as ligand recognition domains. As shown in FIG. 7B, a previously generated reporter positive Jurkat T-cell line was transduced with a receptor construct. Receptor expression was measured using an AlexaFluor647-tagged anti-myc antibody (Cell Signaling). For receptor activation testing. $1 \times 10^5$ Jurkat T-cells expressing anti-CD19 receptors were co-cultured with: no additions (upper trace), $1 \times 10^5$ K562 cells (middle trace), or $1 \times 10^5$ ALPPL2+ K562 cells/$1 \times 10^5$ K562 cells expressing an anti-GFP nanobody on the cell surface (lower trace) for 24 hours. Transcriptional activation of an inducible BFP reporter gene was subsequently measured using a Fortessa X-50 (BD Biosciences). The experiments described in this Example demonstrate that in addition to CD19, other usable ligand recognition domains can be derived from alternative sources.

Example 11

Testing of Hinge-Notch Receptors Containing Alternative Stop-Transfer-Sequences (STS)

This Example describes the results from experiments performed to test Hinge-Notch receptors containing alternative STS.

Figure 8A:
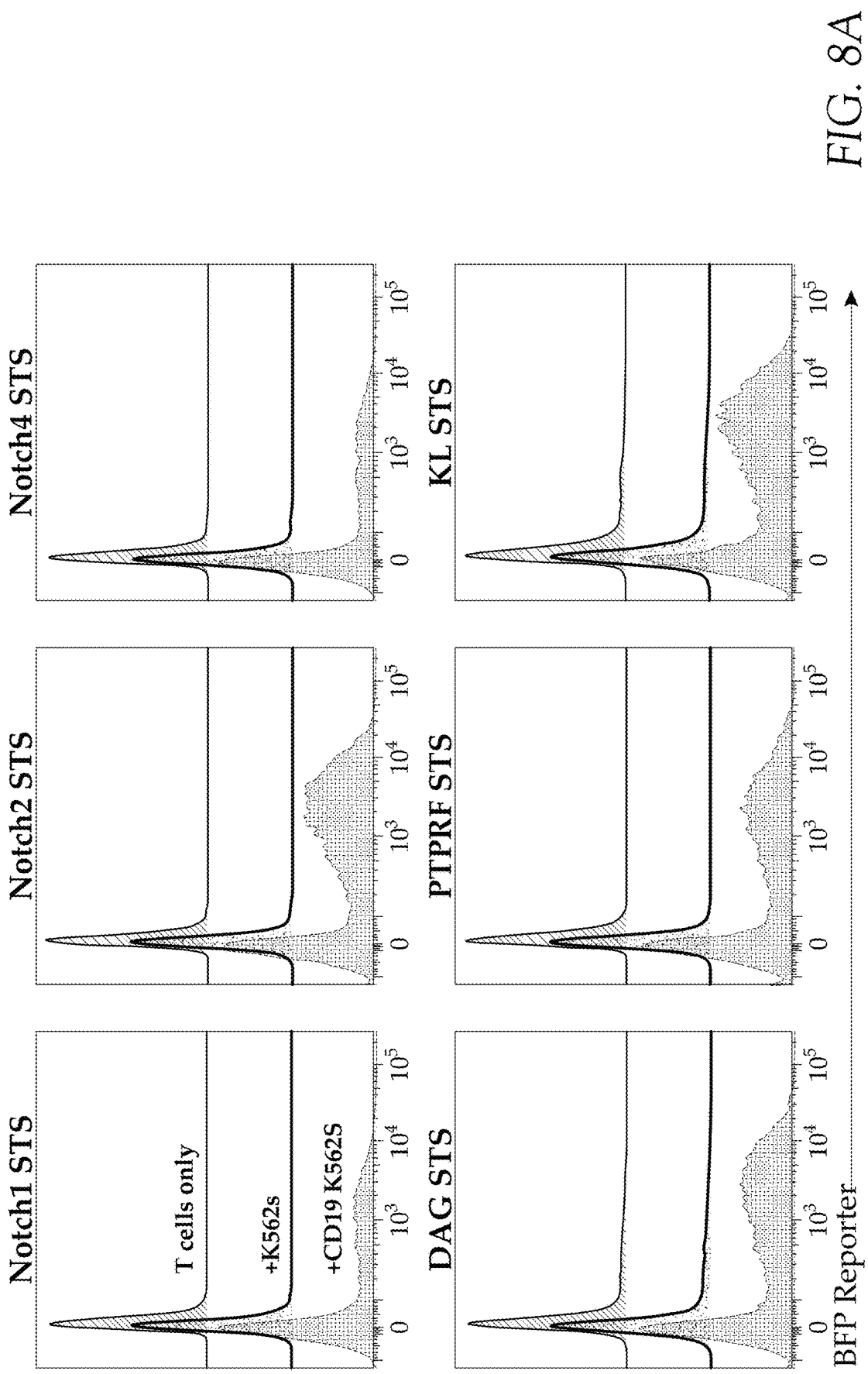
FIGS. 8A-8B schematically summarize the results from experiments performed to test Hinge-Notch receptors with other stop-transfer-sequences (STS).
Figure 8B:
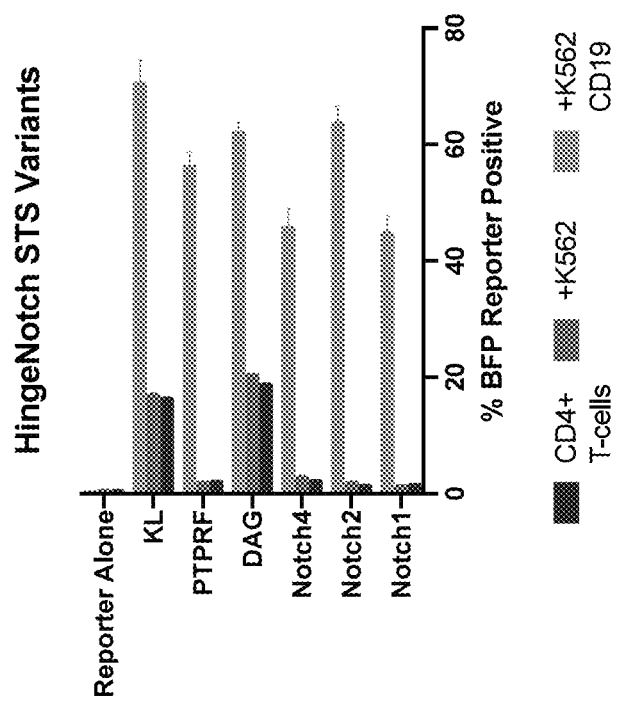

As illustrated in FIG. 8A, in addition to the Notch1 STS, another STS (e.g., Notch2 STS, Notch4 STS, DAG STS, PTPRF STS, and KL STS) can be used to affect receptor behavior. In these experiments, primary human T-cells were activated with anti-CD3/anti-CD28 Dynabeads (Gibco) and transduced with two lentiviral constructs expressing either a receptor or a transcriptional reporter construct. Receptor/reporter positive cells were sorted for on Day 5 post initial T-cell stimulation and expanded further for activation testing. For testing, $1\times10^5$ double positive T-cells expressing anti-CD19 receptors were co-cultured with: no additions (upper trace), $1\times10^5$ K562 cells (middle trace), or $1\times10^5$ CD19+ K562 cells (lower trace) for 24 hours. Transcriptional activation of an inducible BFP reporter gene was subsequently measured using a Fortessa X-50 (BD Biosciences). FIG. 8B depicts the quantification of activation data in FIG. 8A. The experiments described in this Example demonstrate that in addition to Notch1 STS, other usable stop-transfer-sequences can be derived from alternative sources.

Example 12

Generation of Reporter Jurkat T Cells

This Example describes the generation of reporter Jurkat T cells that were subsequent used for the testing of various Hinge-Notch receptors described herein.

In these experiments, E6-1 Jurkat T cells (ATCC# TIB-152) were lentivirally transduced with a reporter plasmid carrying an inducible BFP reporter gene and a constitutive mCitrine reporter gene, as described previously (K. T. Roybal et al., Cell, 164:1-10, 2016). Reporter-positive Jurkat cells were sorted for mCitrine expression using a Beckton Dickinson (BD Biosciences) FACSAria™ II flow cytometer and expanded.

Lentiviral particles were produced with the receptor transgene expression vector as described previously (L. Morsut et al., Cell (2016) 164:780-91). Reporter-positive Jurkat cells were transduced with individual receptors and expanded for experimentation in 96 well plates.

Example 13

This Example describes experiments performed to demonstrate the stimulation of Jurkat T cells in vitro by the chimeric Hinge-Notch polypeptides described herein.

Four CD8 Hinge-Notch variants are tested. FIG. 4A schematically illustrates four CD8 Hinge-Notch truncation variants including one or more hinge components. FIG. 4B summarizes the results of experiments performed to test receptor activation in Jurkat T-cells. In these experiments, a previously generated reporter positive Jurkat T-cell line was transduced with each of the CD8 Hinge-Notch variants. Receptor expression was measured using an AlexaFluor647-tagged anti-myc antibody (Cell Signaling). For receptor activation testing, $1\times10^5$ Jurkat T-cells expressing anti-CD19 receptors were co-cultured with: no additions (upper trace), $1\times10^5$ K562 cells (middle trace), or $1\times10^5$ CD19+ K562 cells (lower trace) for 24 hours. Transcriptional activation of an inducible BFP reporter gene was subsequently measured using a Fortessa X-50 (BD Biosciences). From this testing, truncCD8 Hinge2 was determined to be the optimal configuration and was used in subsequent studies. FIG. 4C shows the quantification of % BFP positive cells from data in FIG. 4B (No additions, with K562, with CD19+ K562 cells). FIG. 4D is a plot of Signal:Noise ratio from data in FIG. 4B. Values from Jurkat T-cells stimulated with CD19+ K562 were divided by values from Jurkat T-cells stimulated with K562 cells.

Example 14

This Example describes experiments performed for optimizing the chimeric CD8 Hinge-Notch polypeptides described herein.

Figure 9A:
FIGS. 9A-9C schematically summarize the results from experiments performed to evaluate the functionality of various Hinge-Notch truncation variants, as exemplified by Hinge-Notch1 constructs, in order to optimize Hinge-Notch receptors.
Figure 9B:
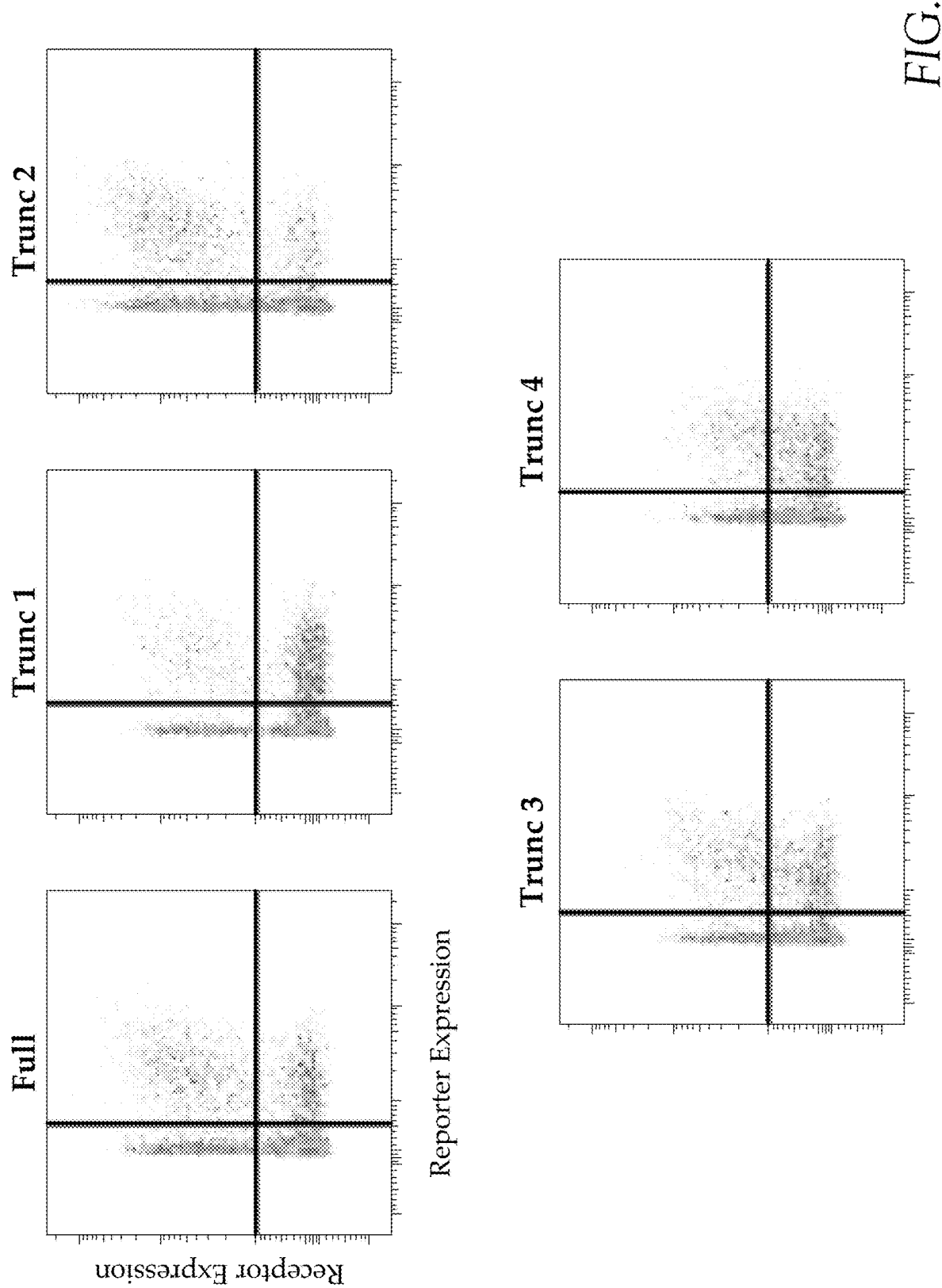
Figure 9B:
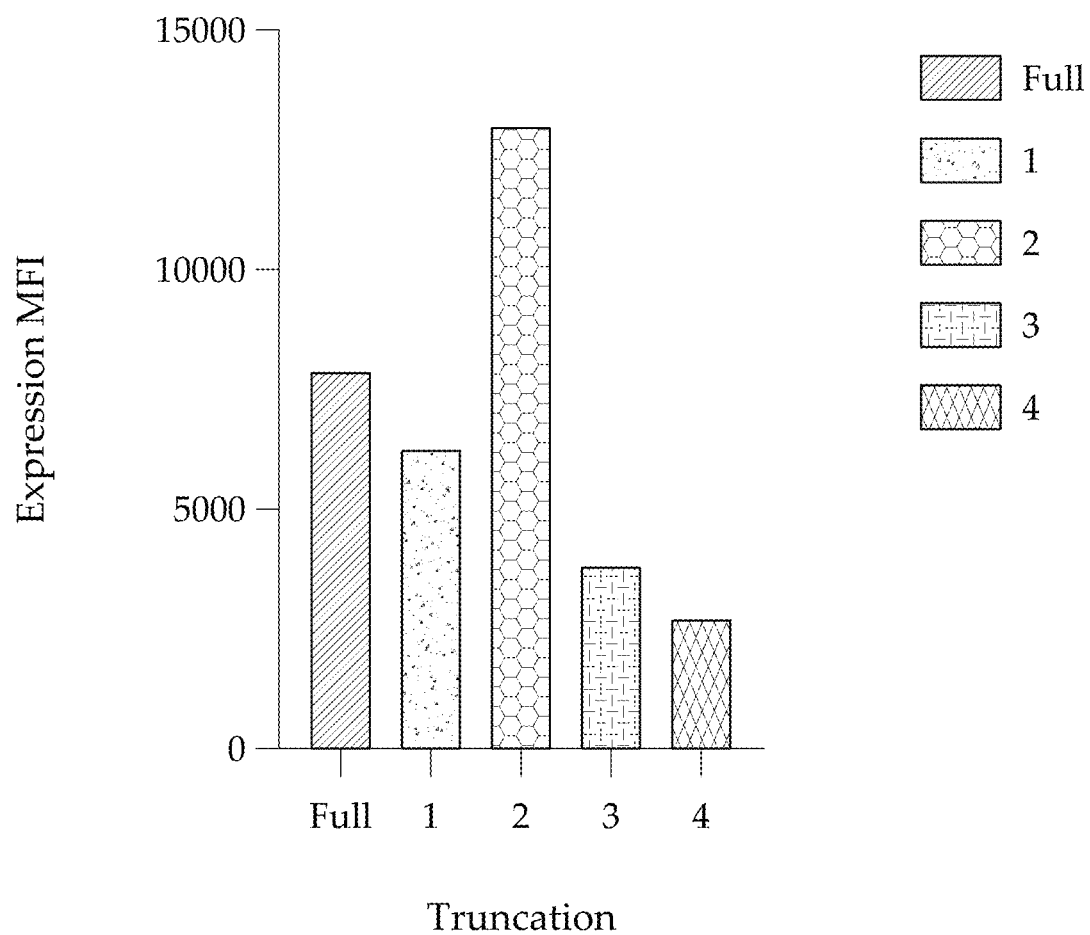
Figure 9C:
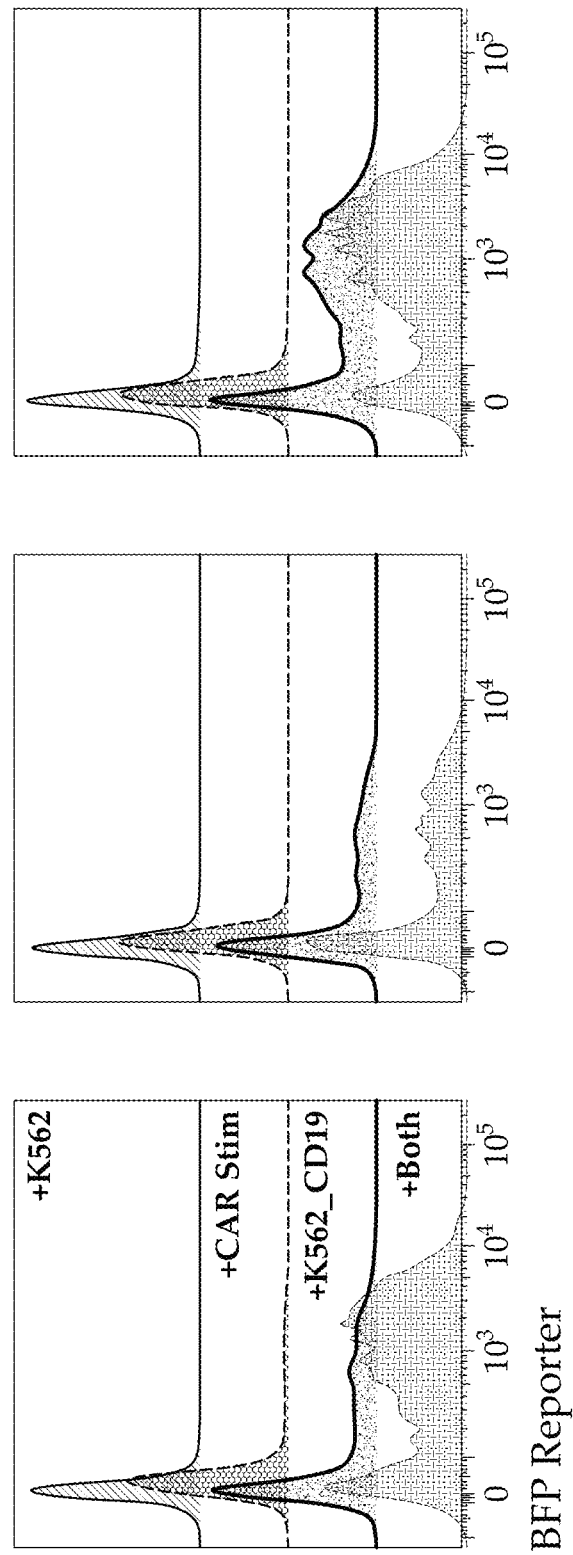
Figure 9C:
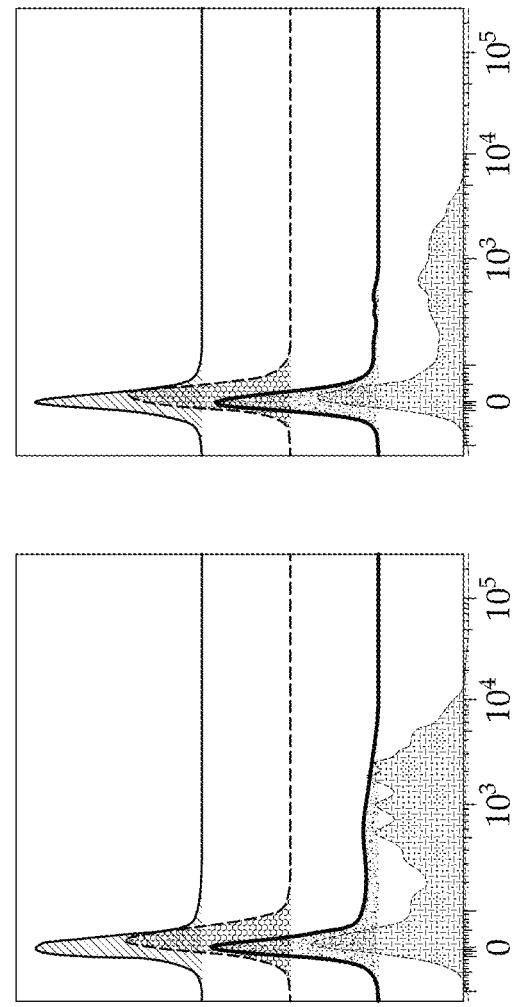

Multiple exemplary CD8 Hing truncation variants were prepared. As shown in FIG. 9A, exemplary variants including either the full-length or a truncated form of TTTPA-PRPPTPAPTIASQPLSLRPEACRPAAGGAVHTRGLD-FACD (SEQ ID NO: 12), corresponding to the N-JMD domain of the construct pIZ341. Black bars indicate the amino acids composing each variant. As the result, variants for comparison in FIGS. 9A-9C are: the "Full" variant, which includes SEQ ID NO: 12; the "Trunc 1" variant, which includes SEQ ID NO: 39; the "Trunc 2" variant, which includes SEQ ID NO: 13; the "Trunc 3" variant, which includes SEQ ID NO: 40; and the "Trunc" 4 variant, which includes SEQ ID NO: 41. A comparison of expression of these CD8 hinge variants is shown in FIG. 9B. Specifically, primary human CD4+ T-cells were activated with anti-CD3/anti-CD28 Dynabeads (Gibco) and transduced with two lentiviral constructs, one expressing a hinge truncation variant receptor, and the other a BFP transcriptional reporter plus anti-ALPPL2 CAR. Cells containing both constructs were sorted on Day 5 post initial T-cell stimulation and expanded further for activation testing. The left five panels of FIG. 9B show relative expression levels of each receptor, measured by anti-myc-tag staining (y-axis), versus the reporter construct expression levels, measured by GFP (x-axis). The right most panel of FIG. 9B shows MFI quantitation of receptor expression of CD8 hinge variants in double-positive cells. As shown from top to bottom in each panel of FIG. 9C, T-cells expressing anti-CD19 receptors were co-cultured with: no additions (top trace), ALPPL2+ K562 cells (second trace from top), CD19+ K562 cells (third trace from top), or ALPPL2+ CD19+ (bottom trace). Transcriptional activation of an inducible BFP reporter gene is subsequently measured using a Fortessa X-50 (BD Biosciences).

Example 15

This Example describes experiments performed to demonstrate activation of Hinge-Notch constructs with different ligand-binding domains and their dependence on proteolytic activity of ADAM proteases and gamma-secretase.

Figure 10:
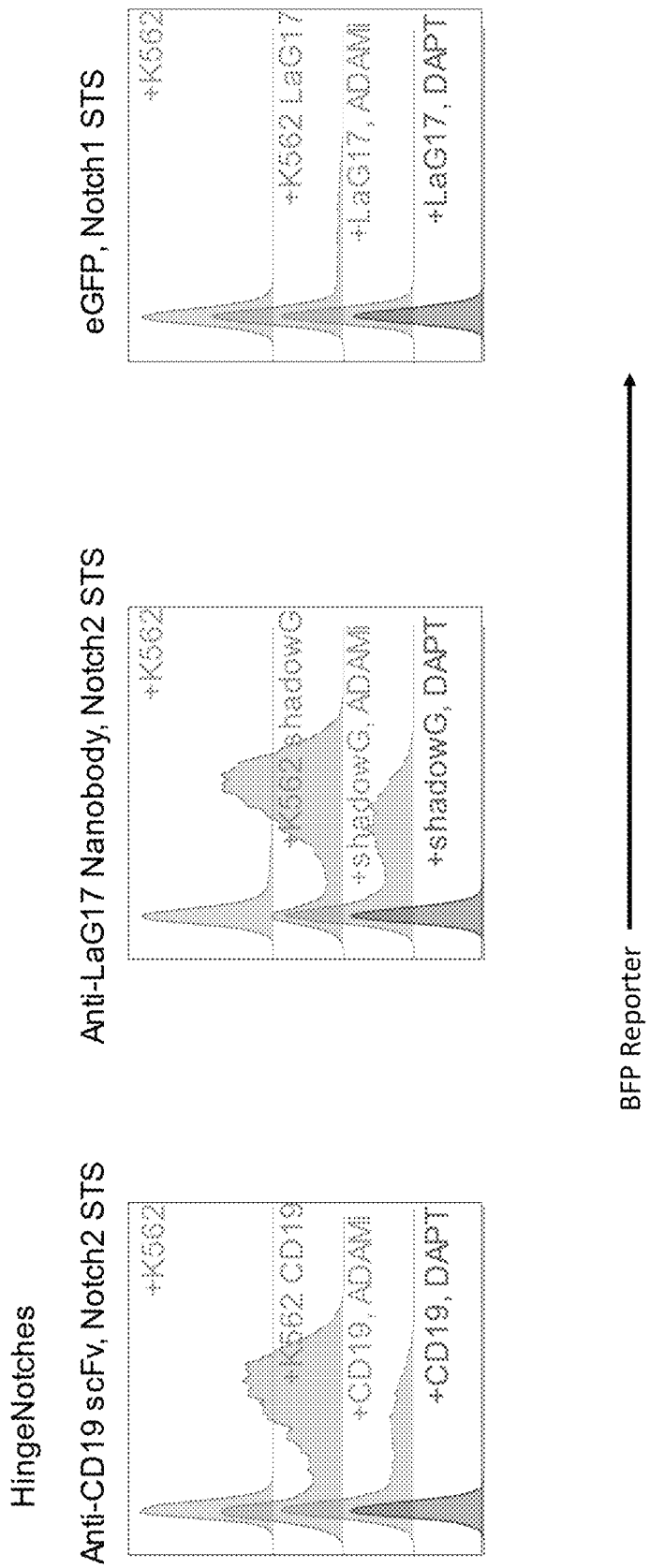
FIG. 10 schematically summarizes the results from experiments performed to test Hinge-Notch variants with different binding domains and their dependence on proteolytic activity. Primary human CD4+ T-cells were activated with anti-CD3/anti-CD28 Dynabeads and transduced with two lentiviral constructs, one expressing a hinge receptor with indicated binding head truncation variant receptor, and the other a transcriptional reporter. Cells containing both constructs were sorted on Day 5 post initial T-cell stimulation and expanded further for activation testing. For testing, $1\times10^5$ double positive T-cells expressing receptors were co-cultured with $1\times10^5$ K562 cells (top trace), $1\times10^5$ Ligand+K562 cells (second trace from top), $1\times10^5$ Ligand+K562 cells with an ADAM10 inhibitor (third trace from top), or $1\times10^5$ Ligand+K562 cells with a gamma-secretase inhibitor, DAPT (bottom trace). Transcriptional activation of an inducible BFP reporter gene was subsequently measured using a Fortessa X-50 (BD Biosciences).

Three exemplary Hinge-Notch constructs were prepared, including one construct having an anti-CD19 scFv as the ligand recognition domain and a Notch2 STS domain, another construct having an anti-LaG17 nanobody as the ligand recognition domain and a Notch2 STS domain, and a third construct having an eGFP extracellular domain and a Notch1 STS domain. Primary human CD4+ T-cells were activated with anti-CD3/anti-CD28 Dynabeads (Gibco) and transduced with two lentiviral constructs, one expressing a hinge receptor with indicated binding head truncation variant receptor, and the other a transcriptional reporter (FIG. 10). Cells containing both constructs were sorted on Day 5 post initial T-cell stimulation and expanded further for activation testing. For testing, $1 \times 10^5$ double positive T-cells expressing receptors were co-cultured with $1 \times 10^5$ K562 cells (top trace), $1 \times 10^5$ Ligand+K562 cells (second trace from top), $1 \times 10^5$ Ligand+K562 cells with an ADAM10 inhibitor (third trace from top), or $1 \times 10^5$ Ligand+K562 cells with a gamma-secretase inhibitor, DAPT (bottom trace). Transcriptional activation of an inducible BFP reporter gene was subsequently measured using a Fortessa X-50 (BD Biosciences).

Example 16

This Example describes experiments performed to demonstrate activation characteristics of exemplary Notch2 STS Hinge-Notch constructs with an expanded set of ligand-binding domains.

Figure 11A:
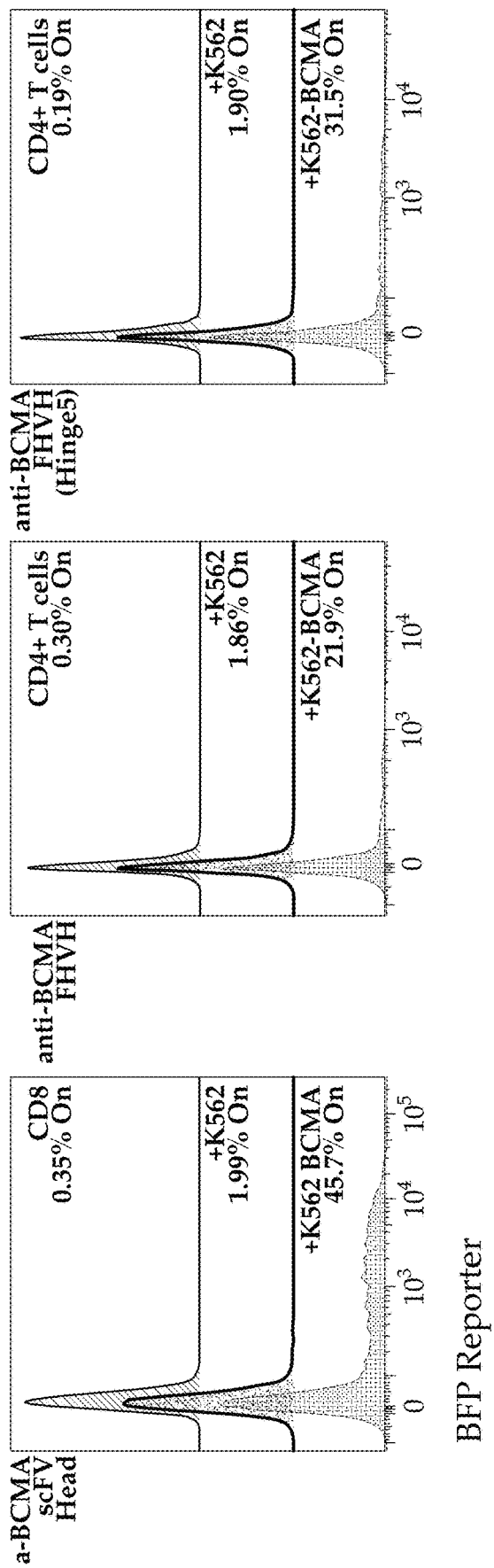
FIGS. 11A-11C schematically summarize the results from experiments performed to test Hinge-Notch variants with different binding domains and a Notch2 STS domain. Primary CD4+ human T-cells were activated with anti-CD3/anti-CD28 Dynabeads and transduced with two lentiviral constructs, one expressing a hinge receptor with indicated binding head hingeNotch receptor, and the other a transcriptional reporter. Cells containing both constructs were sorted on Day 5 post initial T-cell stimulation and expanded further for activation testing. For testing, $1\times10^5$ double positive T-cells expressing receptors were co-cultured with no addition (upper trace), $1\times10^5$ K562 cells (middle trace), or $1\times10^5$ BCMA+ K562 cells (lower trace) for two days (FIG. 11A).

Testing were performed with different binding heads against the BCMA antigen. Primary CD4+ human T-cells were activated with anti-CD3/anti-CD28 Dynabeads (Gibco) and transduced with two lentiviral constructs, one expressing a hinge receptor with indicated binding head hingeNotch receptor, and the other a transcriptional reporter. Cells containing both constructs were sorted on Day 5 post initial T-cell stimulation and expanded further for activation testing. For testing, $1 \times 10^5$ double positive T-cells expressing receptors were co-cultured with no addition (upper trace), $1 \times 10^5$ K562 cells (middle trace), or $1 \times 10^5$ BCMA+ K562 cells (lower trace) for two days (FIG. 11A). Transcriptional activation of an inducible BFP reporter gene was subsequently measured using a Fortessa X-50 (BD Biosciences). In FIG. 11A, the left panel refers to a construct with an anti-BCMA scFv binding head, the middle panel refers to a construct with an anti-BCMA fully humanized VH binding head, and the right panel refers to a construct with an anti-BCMA fully humanized VH binding head with hinge domain optimized for the binding domain (Hinge5).

Figures 11B, 11C:
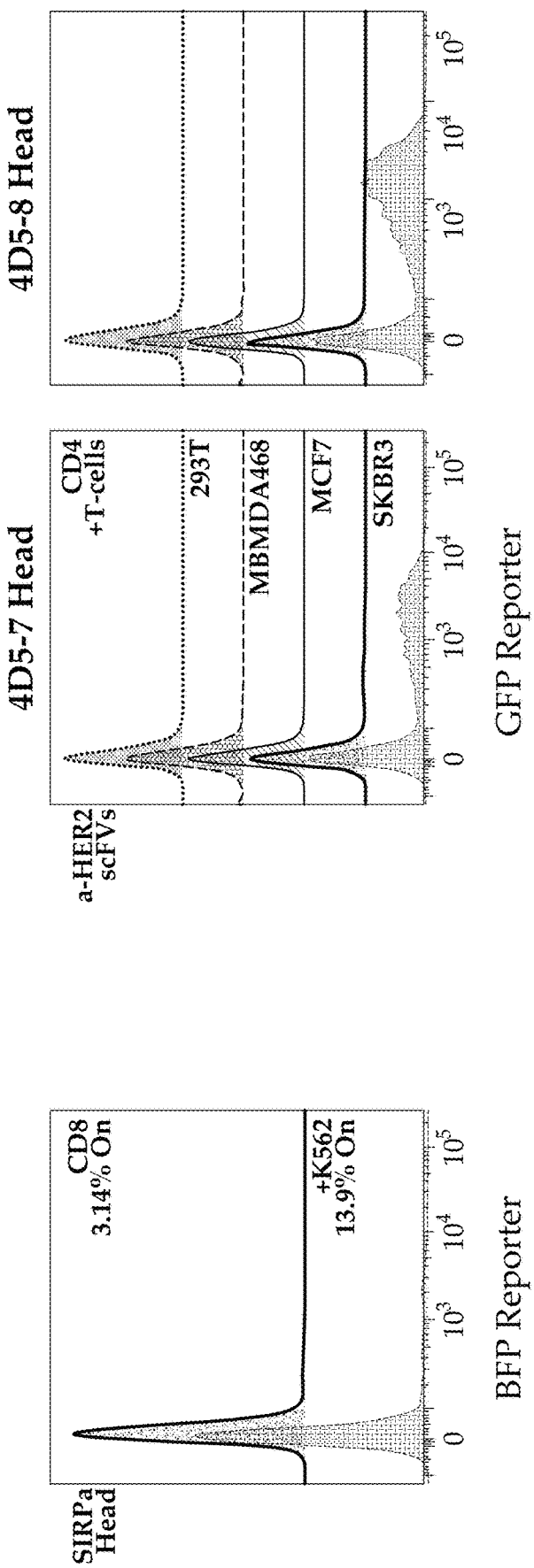

A SIRPα binding head was similarly tested. Primary CD8+ human T-cells were activated with anti-CD3/anti-CD28 Dynabeads (Gibco) and transduced with two lentiviral constructs, one expressing a hinge receptor with indicated binding head hingeNotch receptor, and the other a transcriptional reporter. Cells containing both constructs were sorted on Day 5 post initial T-cell stimulation and expanded further for activation testing. For testing, $1 \times 10^5$ double positive T-cells expressing receptors were co-cultured with no addition (blue), or $1 \times 10^5$ K562 cells as indicated (red) for two days (FIG. 11B). Transcriptional activation of an inducible BFP reporter gene was subsequently measured using a Fortessa X-50 (BD Biosciences).

Different scFvs against the HER2 antigen were tested and compared. Primary CD4+ human T-cells were activated with anti-CD3/anti-CD28 Dynabeads (Gibco) and transduced with two lentiviral constructs, one expressing a hinge receptor with indicated binding head hingeNotch receptor, and the other a transcriptional reporter. Cells containing both constructs were sorted on Day 5 post initial T-cell stimulation and expanded further for activation testing. For testing, $1 \times 10^5$ double positive T-cells expressing receptors were co-cultured with no addition (top trace), adherent HEK 293T cells (second trace from top), adherent MBMDA-468 cells (third trace from top), adherent MCF7 cells (fourth trace from top), or adherent SKBR3 cells (bottom trace) for two days (FIG. 11C). Transcriptional activation of an inducible BFP reporter gene was subsequently measured using a Fortessa X-50 (BD Biosciences). In FIG. 11C, the left panel represents the anti-HER2 4D5-7 scFv binding head, while the right panel represents the anti-HER2 4D5-8 scFv binding head.

Example 17

Figure 12:
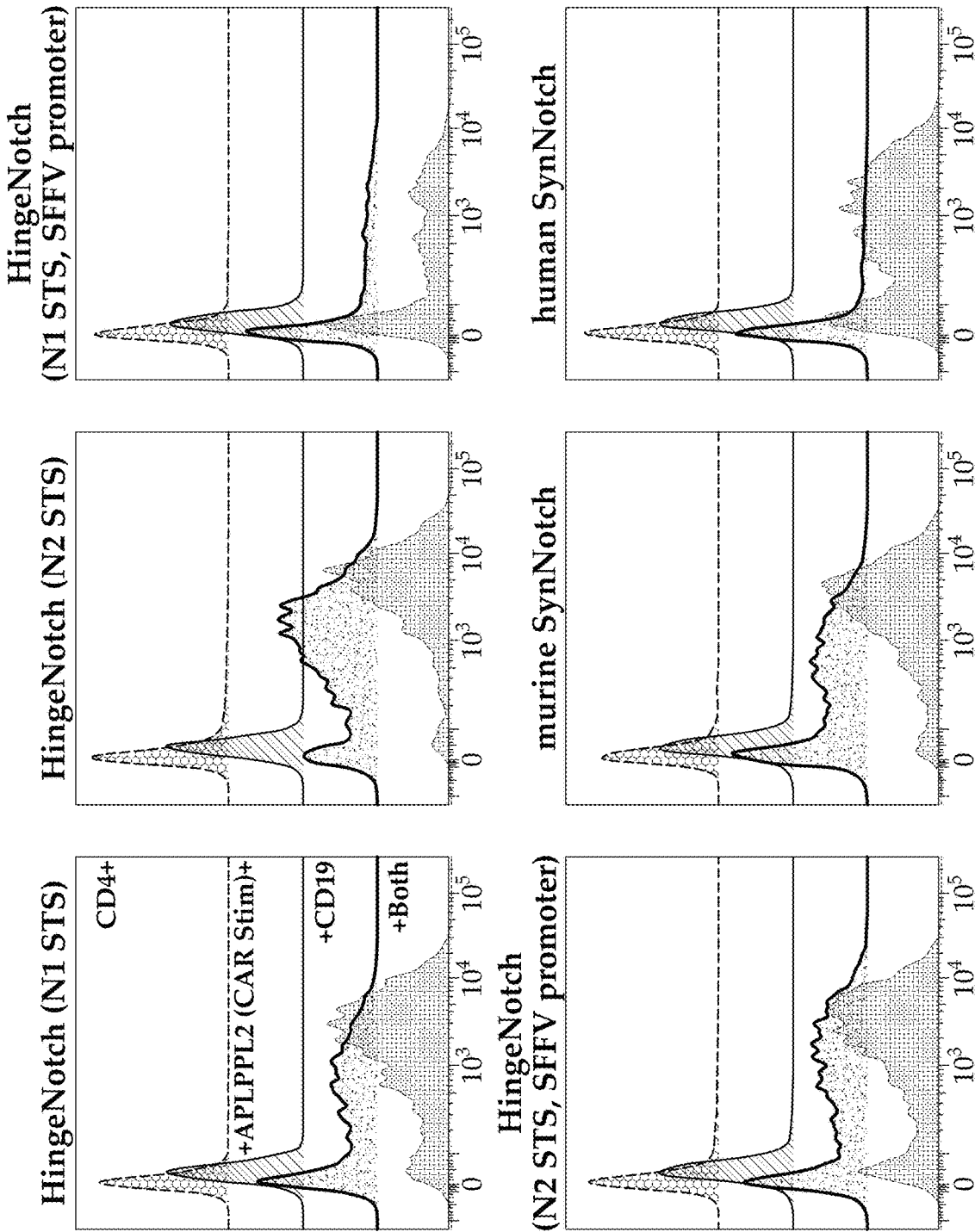
FIG. 12 schematically summarizes the results from experiments performed to compare activation of Hinge-Notch variants with different promoters and STS domains. For testing, $1\times10$ double positive T-cells expressing anti-CD19 receptors were co-cultured with no additions (top trace), $1\times10^5$ ALPPL2+ K562 cells (second trace from top), $1\times10^5$ CD19+ K562 cells (third trace from top), or $1\times10$ ALPPL2+ CD19+ K562 cells (bottom trace). Transcriptional activation of an inducible BFP reporter gene was subsequently measured using a Fortessa X-50 (BD Biosciences). Activation using murine and human original synNotch constructs were included for comparison.

This Example describes experiments performed to compare activation of Hinge-Notch variants with different promoters and STS domains. For testing, $1 \times 10^5$ double positive T-cells expressing anti-CD19 receptors were co-cultured with no additions (top trace), $1 \times 10^5$ ALPPL2+ K562 cells (second trace from top), $1 \times 10^5$ CD19+ K562 cells (third trace from top), or $1 \times 10^5$ ALPPL2+ CD19+ K562 cells (bottom trace) (FIG. 12). Transcriptional activation of an inducible BFP reporter gene was subsequently measured using a Fortessa X-50 (BD Biosciences). Activation using murine and human original synNotch constructs were included for comparison.

Example 18

This Example describes mutational analysis of the Notch1 transmembrane domain (TMD) in Hinge-Notch constructs.

Figure 13A:
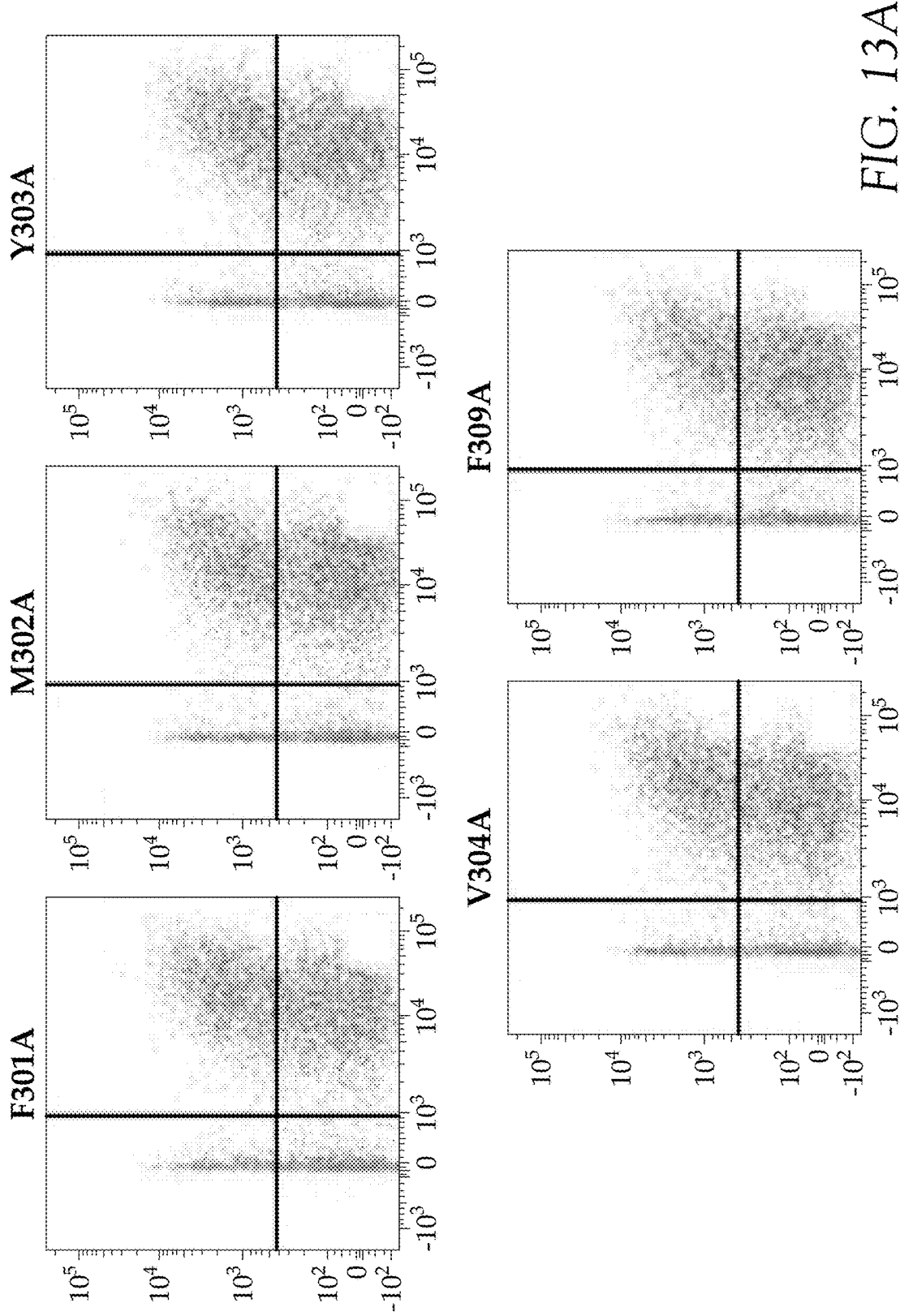
FIGS. 13A-13B schematically summarize the results from experiments for mutational analysis of the Notch1 transmembrane domain (TMD) in Hinge-Notch constructs. Variants with different alanine mutations in the TMD domain of the Hinge-Notch construct were prepared. Each amino acid residue from position 301 (F) through position 322 (S) in the TMD of Hinge-Notch were individually mutated to alanine. Primary human CD4+ T-cells were activated with anti-CD3/anti-CD28 Dynabeads and transduced with two lentiviral constructs, one expressing a TMD mutant variant, and the other containing a BFP transcriptional reporter. Cells containing both constructs were sorted for on Day 5 post initial T-cell stimulation and expanded further for activation testing.
Figure 13A:
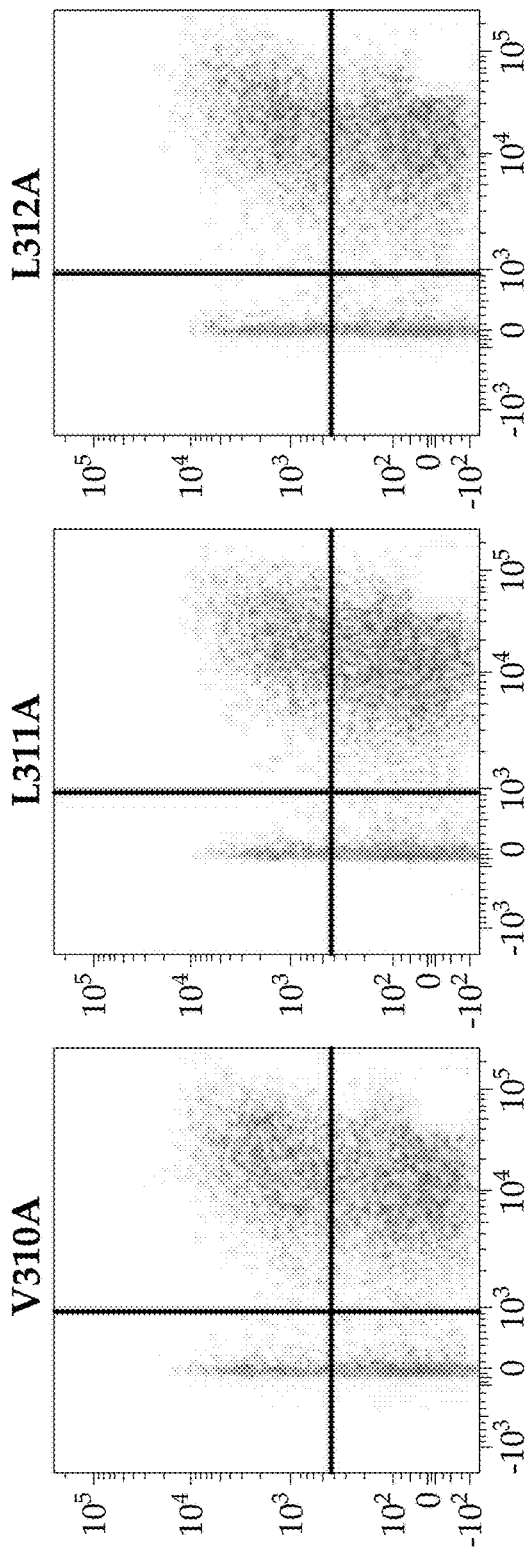
Figure 13A:
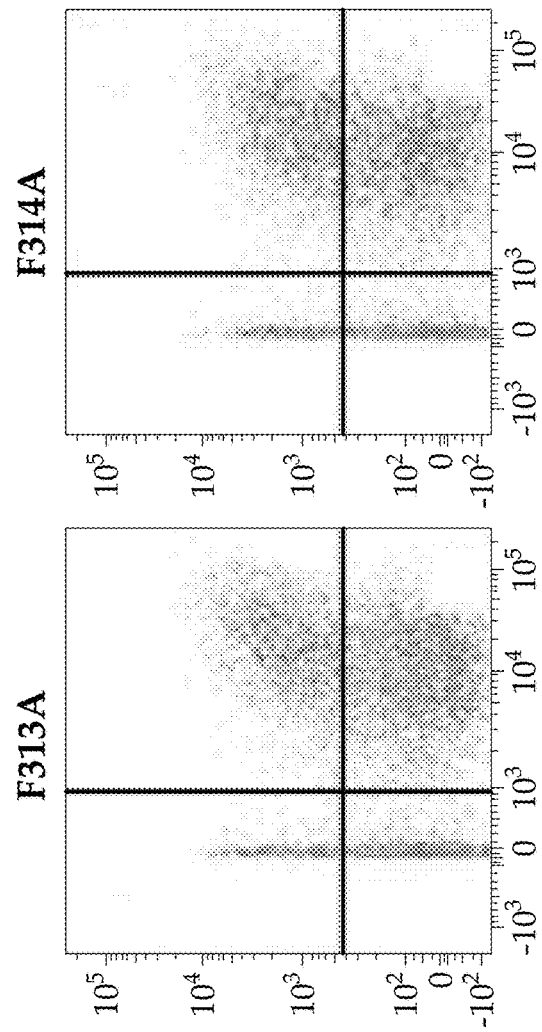
Figure 13A:
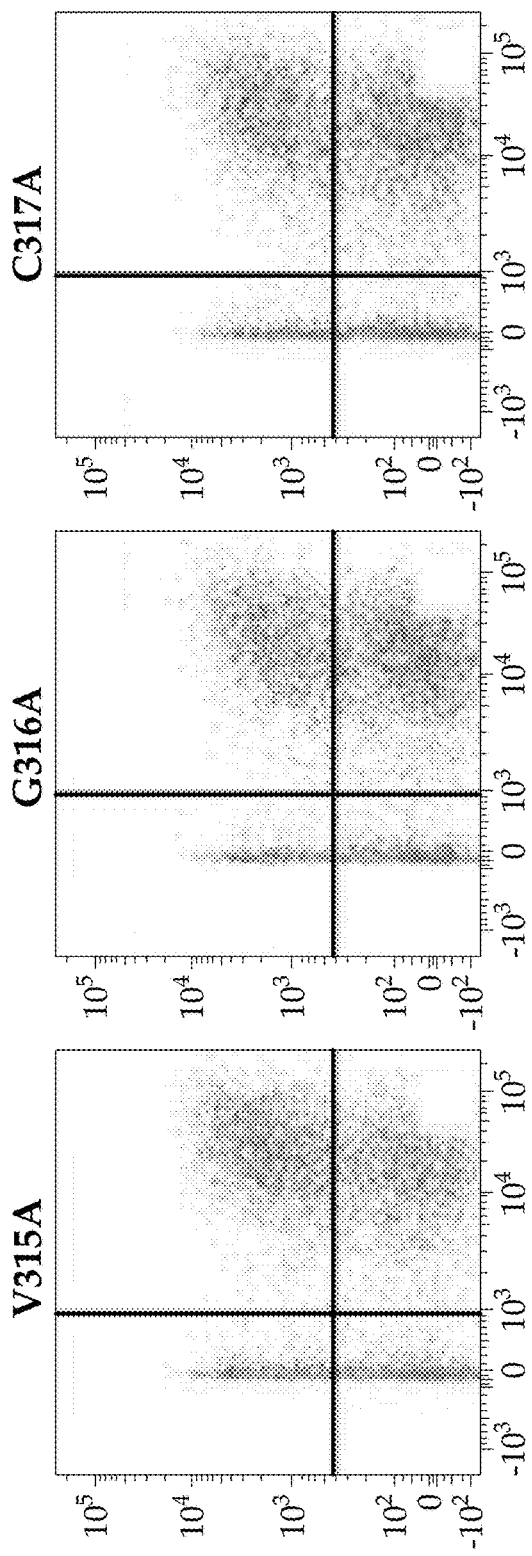
Figure 13A:
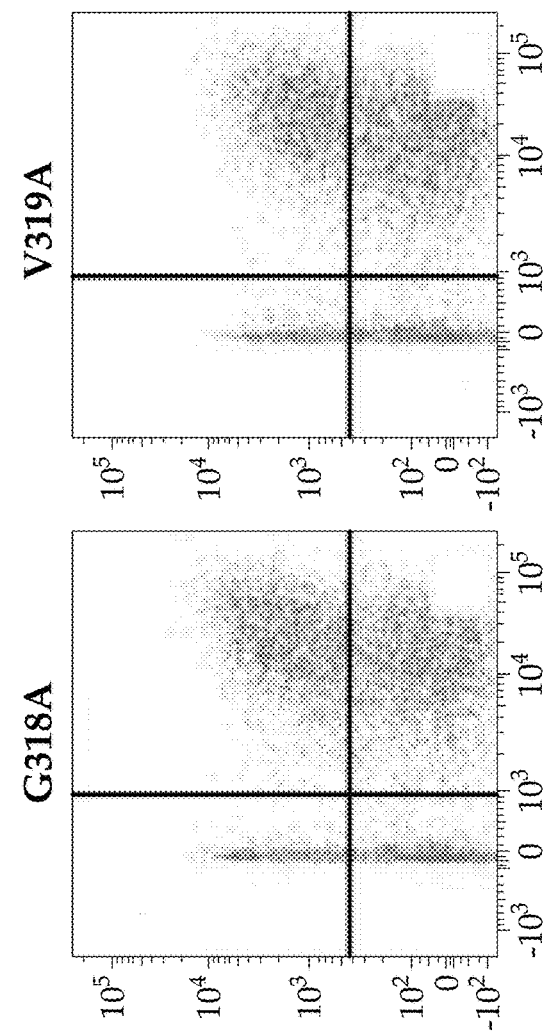
Figure 13A:
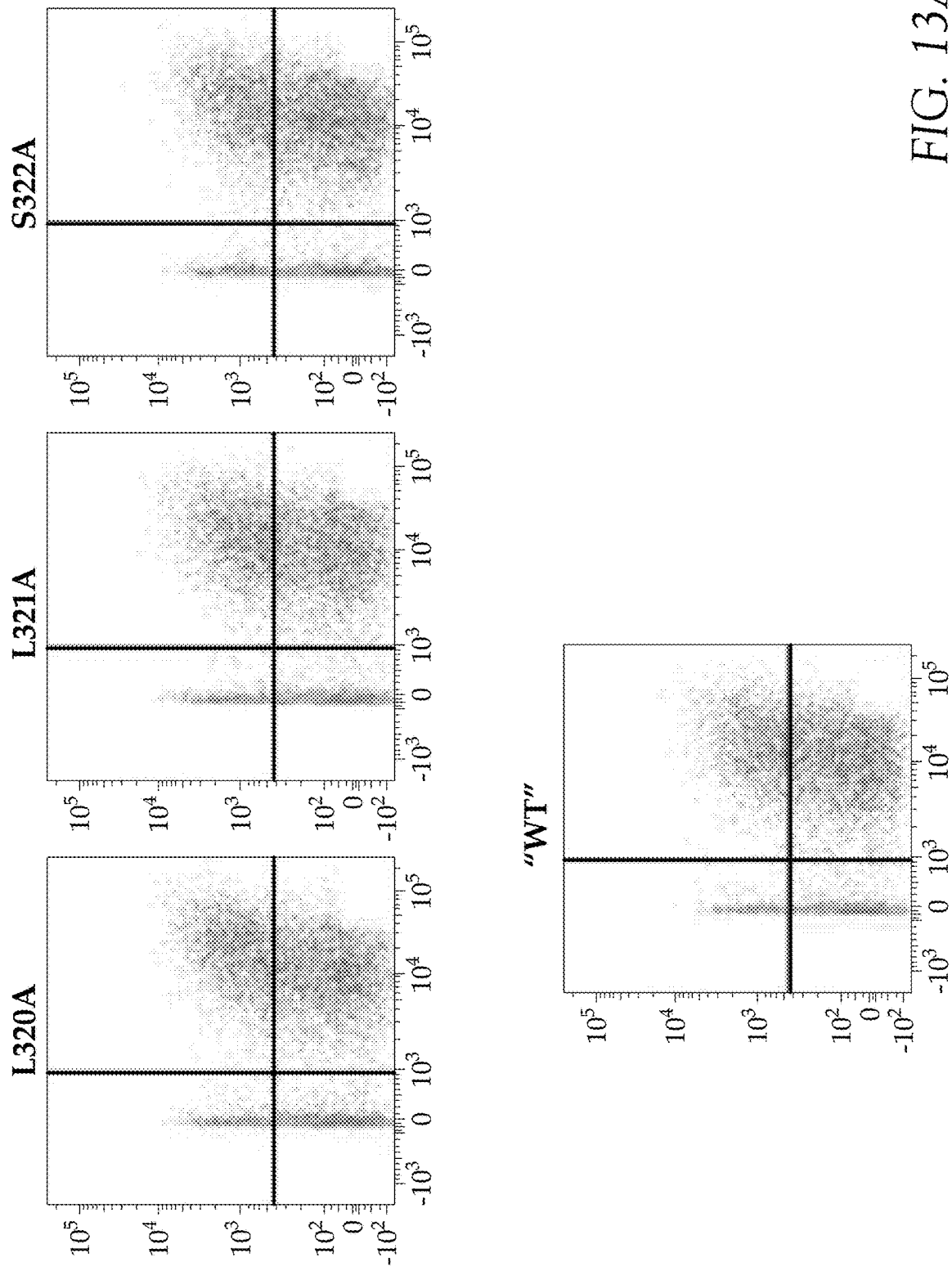
Figure 13A:
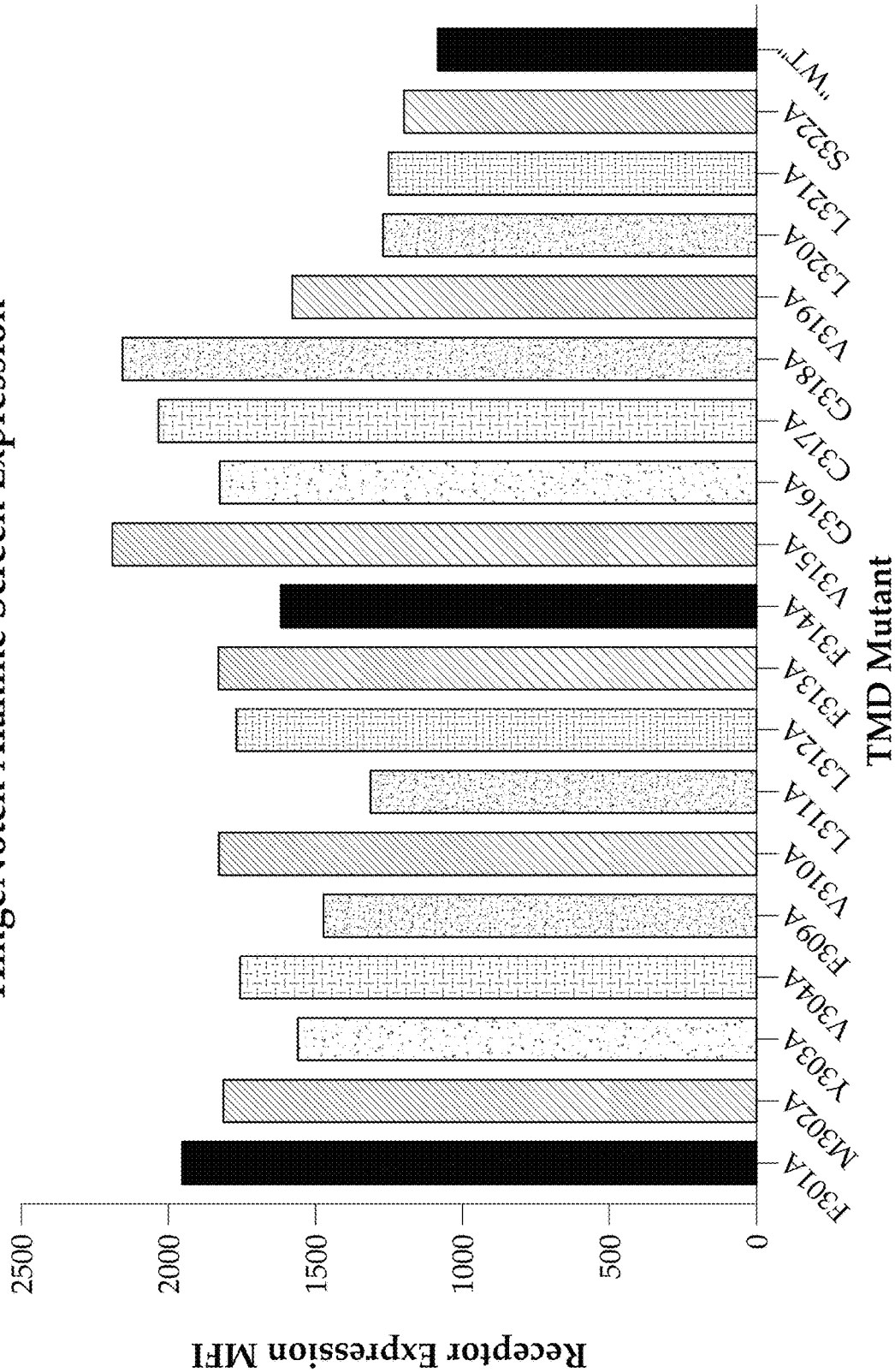

Variants with different alanine mutations in the TMD domain of the Hinge-Notch construct were prepared. Each amino acid residue from position 301 (F) through position 322 (S) in the TMD of Hinge-Notch were individually mutated to alanine. Primary human CD4+ T-cells were activated with anti-CD3/anti-CD28 Dynabeads (Gibco) and transduced with two lentiviral constructs, one expressing a TMD mutant variant, and the other containing a BFP transcriptional reporter. Cells containing both constructs were sorted for on Day 5 post initial T-cell stimulation and expanded further for activation testing. In FIG. 13A, the left panel shows relative expression of different receptors, measured by anti-myc-tag staining (y-axis), versus reporter construct marker expression (x-axis), while the right panel represents MFI quantitation of receptor expression of TMD mutant variants in double-positive cells.

Figure 13B:
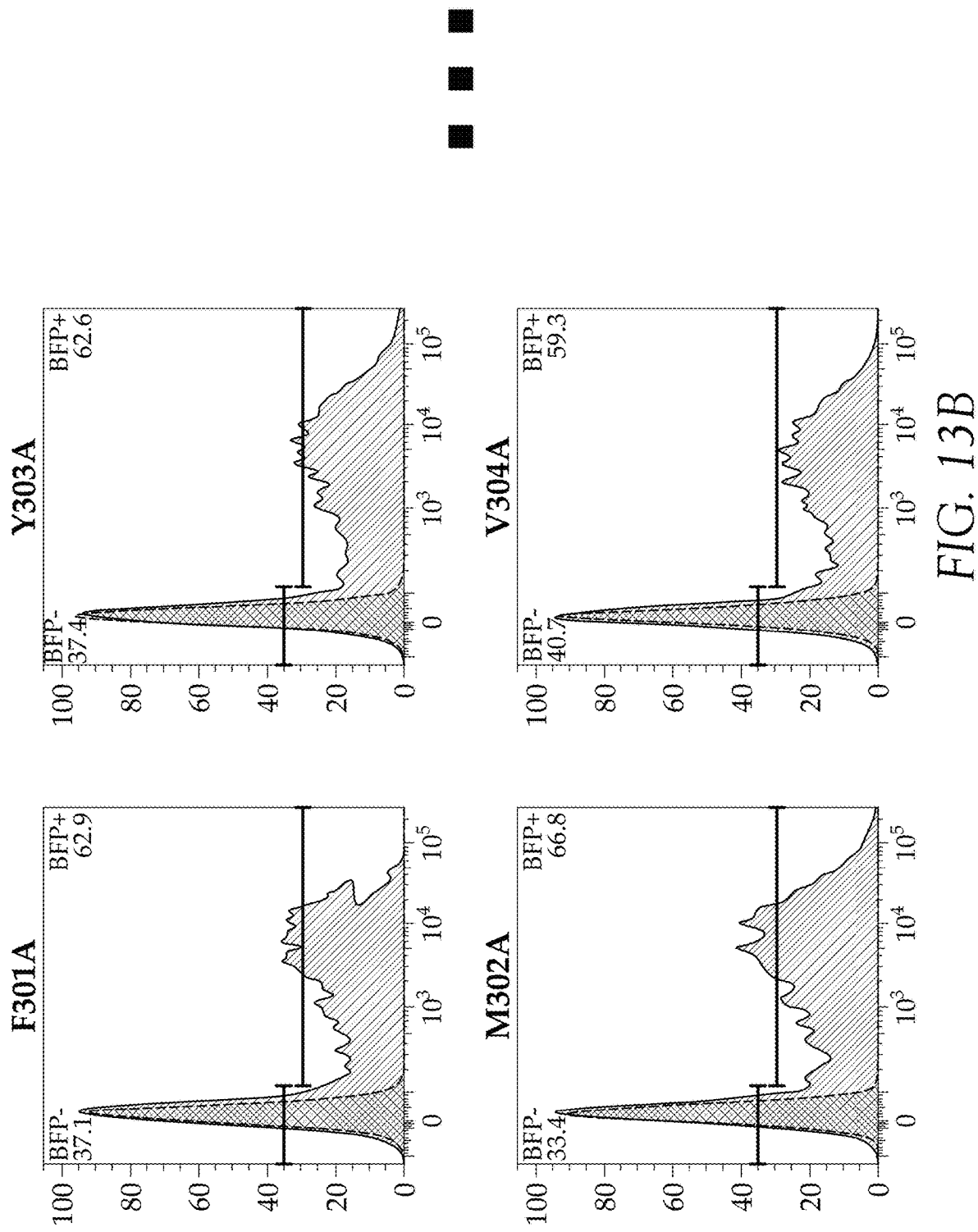
Figure 13B:
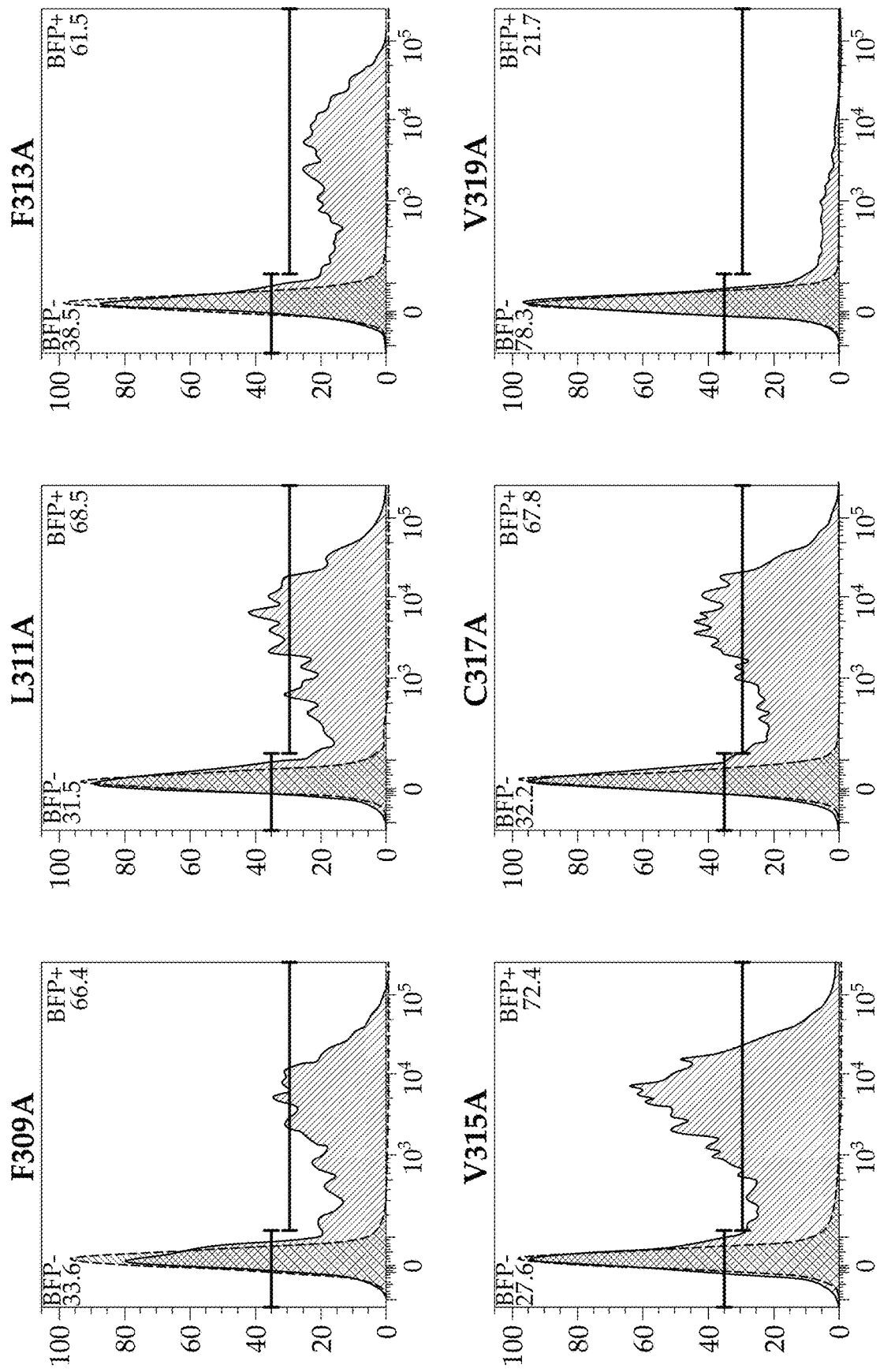
Figure 13B:
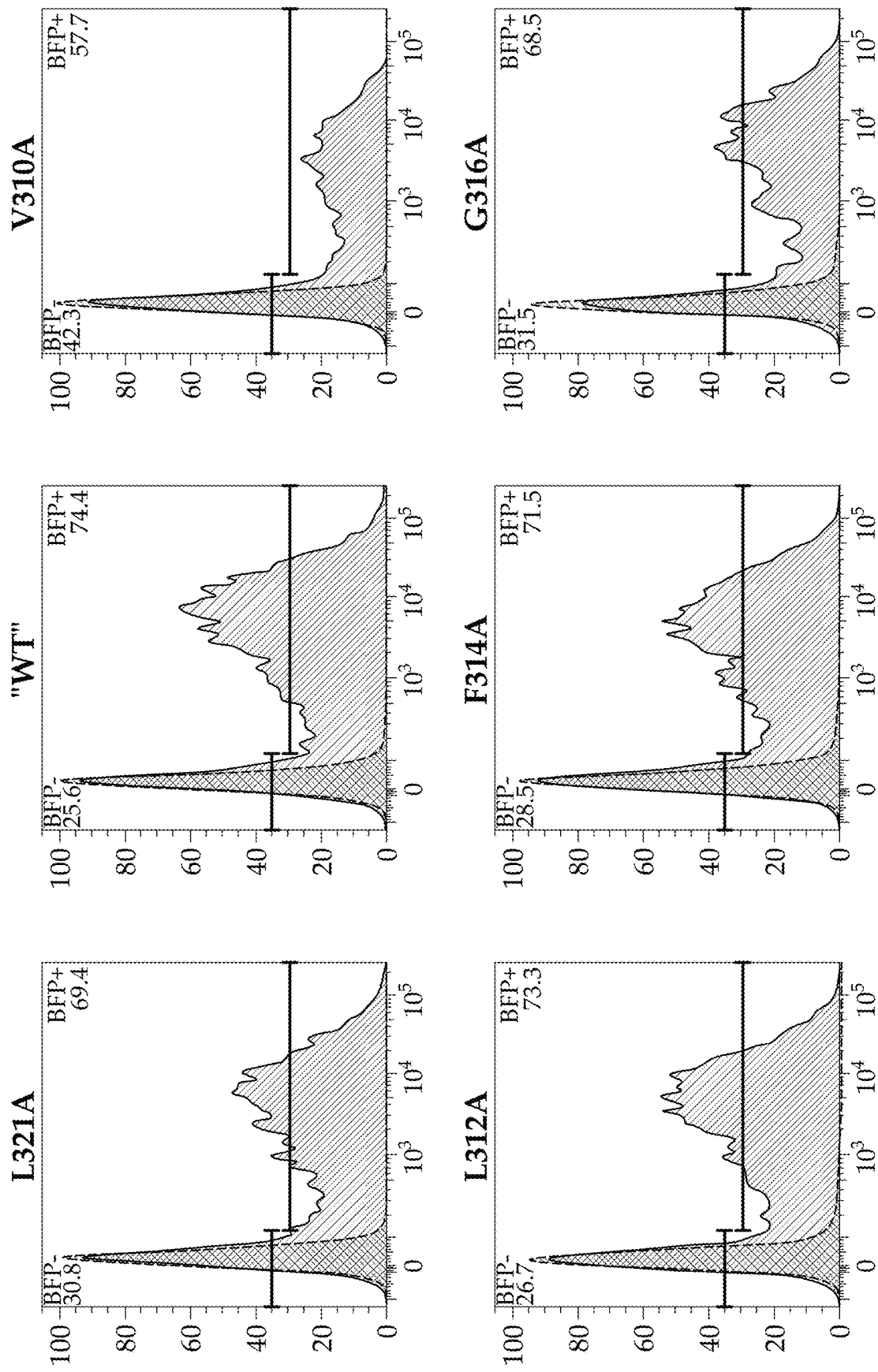
Figure 13B:
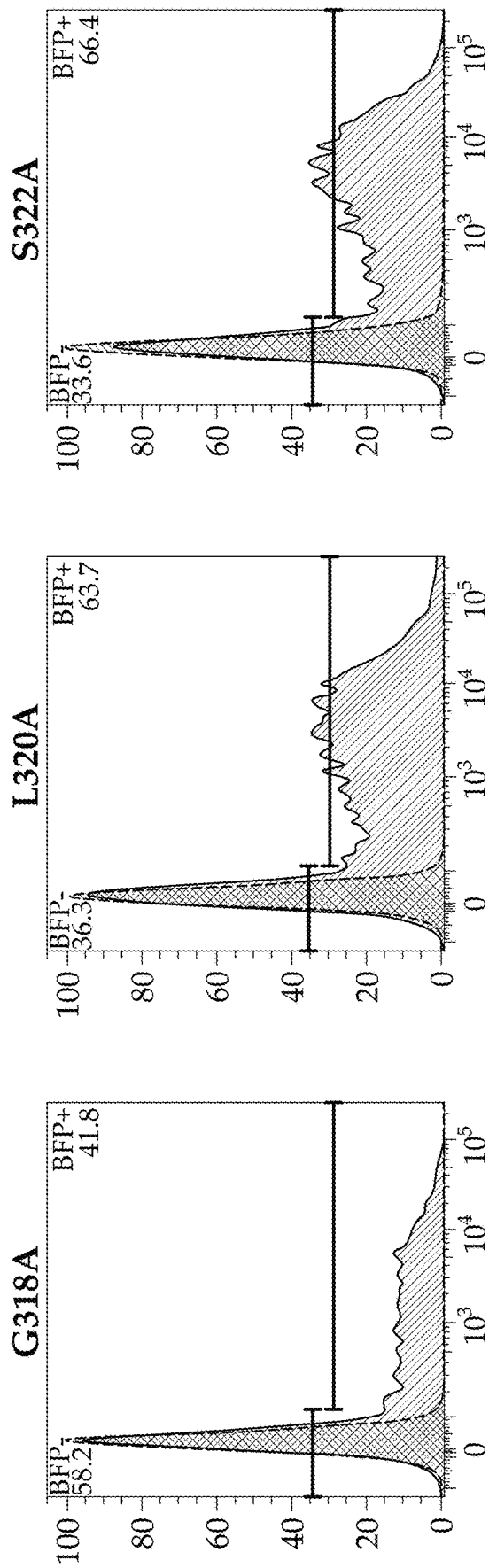
Figure 13B:
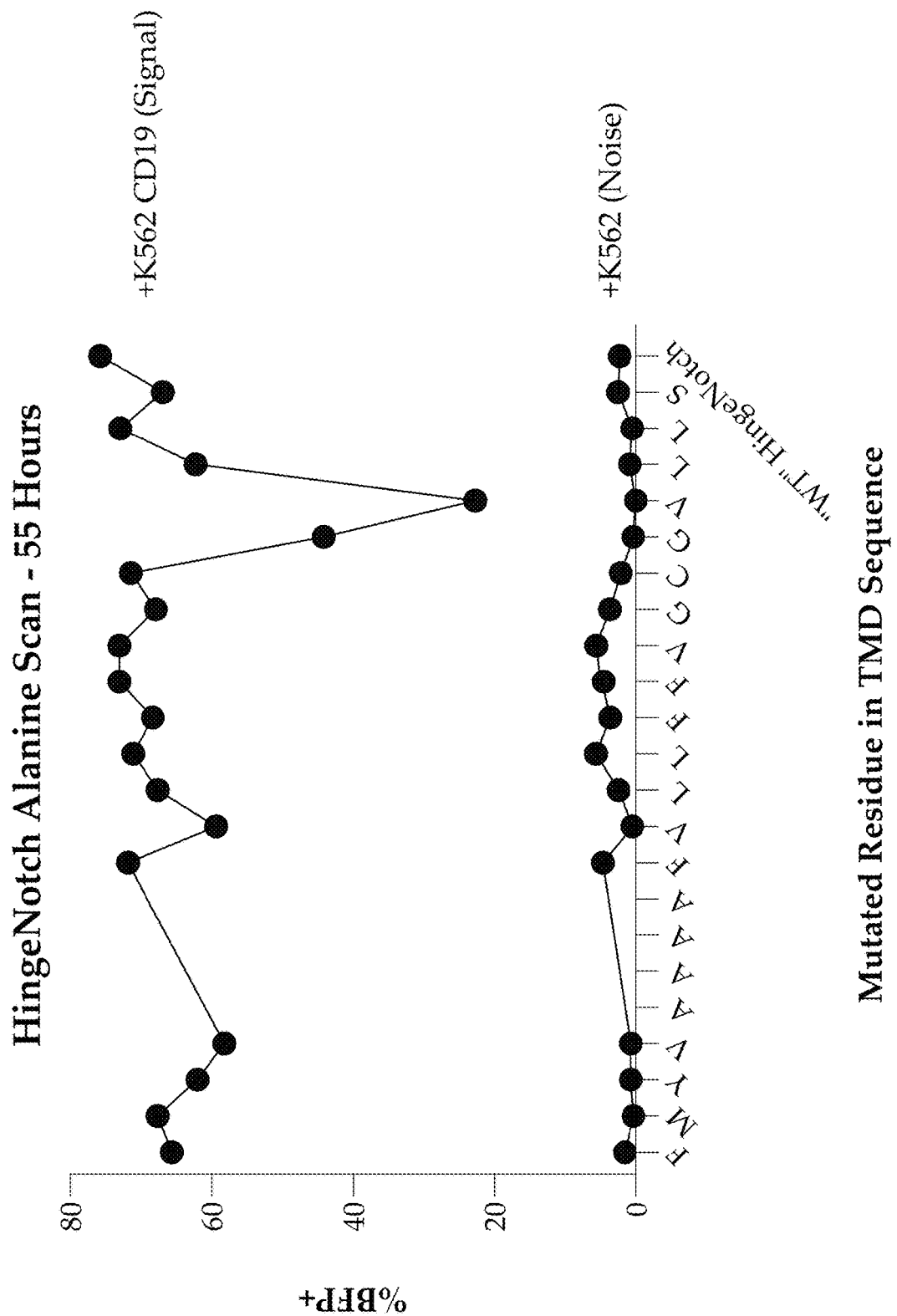

As shown in FIG. 13B, T-cells expressing anti-CD19 receptors were co-cultured at a ratio of 1:1 with control CD19(−) or CD19(+) K562 cells. Transcriptional activation of an inducible BFP reporter gene was subsequently measured using a Fortessa X-50 (BD Biosciences). The left panel shows flow panels of activation profiles. The right panel represents BFP % plotted as a line graph. Results indicate the importance of the glycine (G) and valine (V) residues in the C-terminal end of the TMD.

Example 19

This Example describes mutational analysis for the transmembrane domain (TMD) and the STS domain in Hinge-Notch constructs.

Figure 14:
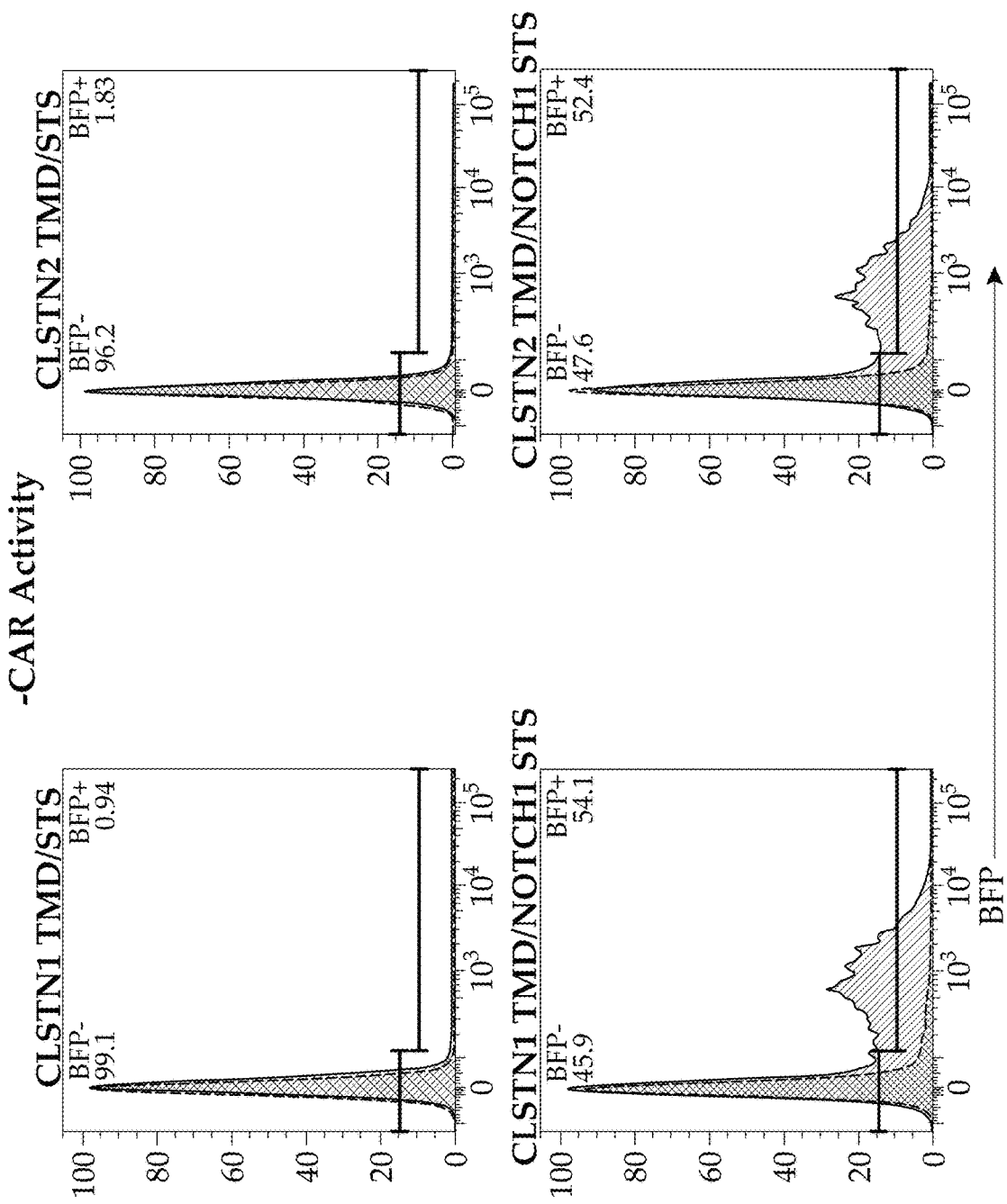
FIG. 14 schematically summarizes the results from experiments for mutational analysis for the transmembrane domain (TMD) and the STS domain in Hinge-Notch constructs. Four types of exemplary Hinge Notch receptors were using in this Example, all of which including an anti-CD19 scFv domain, a truncated CD8 Hinge domain, and a Gal4VP64 domain, plus different TMD domains (CLSTN1 TMD or CLSTN2 TMD) and different STS domains (CLSTN1 STS, CLSTN2 STS, or Notch1 STS). Primary human CD4+ T-cells were activated with anti-CD3/anti-CD28 Dynabeads (Gibco) and transduced with two lentiviral constructs, one expressing a hinge receptor with TMD/STS combination as indicated, and the other a transcriptional reporter with constitutively expressed anti-ALPPL2 CAR.
Figure 14:
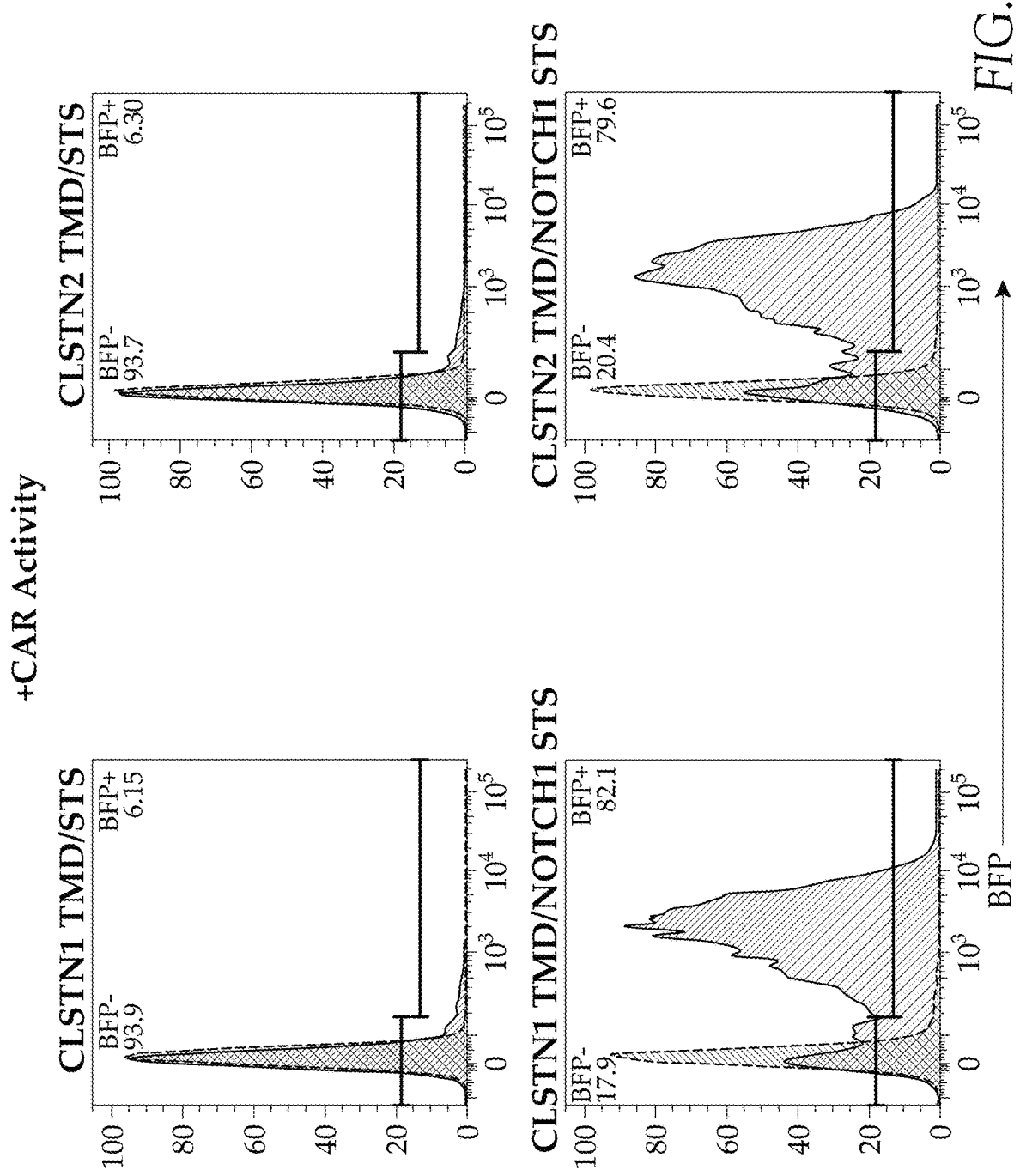

Four types of exemplary Hinge Notch receptors (SEQ ID NOS: 73-76) were using in this Example, all of which including an anti-CD19 scFv domain, a truncated CD8 Hinge domain, and a Gal4VP64 domain. For choices of STS and TMD domains, the four constructs comprise: CLSTN1 TMD and CLSTN1 STS (SEQ ID NO: 73), CLSTN2 TMD and CLSTN2 STS (SEQ ID NO: 74), CLSTN1 TMD and Notch1 STS (SEQ ID NO: 75), CLSTN2 TMD and Notch1 STS (SEQ ID NO: 76). Primary human CD4+ T-cells were activated with anti-CD3/anti-CD28 Dynabeads (Gibco) and transduced with two lentiviral constructs, one expressing a hinge receptor with TMD/STS combination as indicated, and the other a transcriptional reporter with constitutively expressed anti-ALPPL2 CAR. Cells containing both constructs were sorted for on Day 5 post initial T-cell stimulation and expanded further for activation testing. As shown in FIG. 14, $1 \times 10^5$ double positive T-cells expressing receptors were co-cultured with: $1 \times 10^5$ K562 cells ("−CAR" panels, blue), or $1 \times 10^5$ CD19+K562 cells ("−CAR" panels, red). Similarly, $1 \times 10^5$ double positive T-cells expressing receptors were tested in the presence of CAR activity by co-culture with $1 \times 10^5$ ALPPL2+K562 cells ("+CAR" panels, blue), or $1 \times 10^5$ ALPPL2+ CD19+ K562 cells ("+CAR" panels, red). Transcriptional activation of an inducible BFP reporter gene was subsequently measured using a Fortessa X-50 (BD Biosciences).

Example 20

This Example describes Table 3 of activation characteristics of hingeNotch STS variants without additional T cell stimulation.

Primary human CD4+ T-cells were activated with anti-CD3/anti-CD28 Dynabeads (Gibco) and transduced with two lentiviral constructs, one expressing a hinge receptor, and the other a transcriptional reporter with constitutive eGFP-tagged anti-ALPPL2 CAR expression. Cells containing both constructs were sorted for on Day 5 post initial T-cell stimulation and expanded further for activation testing. For testing, T-cells expressing receptors were co-cultured with K562 cells or CD19+ K562 cells. BFP reporter gene was subsequently measured using a Fortessa X-50 (BD Biosciences). Signal to noise ratios from the MFIs of BFP+ cells under CD19+ K562 versus K562 conditions are plotted against the delta change in MFI in the two conditions, as in Table 3 below.

TABLE 3

This table provides data without stimulation of co-expressed anti-ALPPL2 CAR with ALPPL2+ K562. "Reporter alone" represents a reporter plasmid and was expressed in all samples.

| Recptor from which STS is derived | STS Sequence | Average Signal To Noise | Average MFI Difference (MFI of ON − MFI of OFF) |
|---|---|---|---|
| Notch 1 | RKRRR (SEQ ID NO: 18) | 20.55472264 | 889.5 |
| Notch 2 | KRKRKH (SEQ ID NO: 19) | 5.236923077 | 1259 |
| Notch 4 | RRRREH (SEQ ID NO: 43) | 10.30799476 | 1020 |
| CSF1R | KYKQKPK (SEQ ID NO: 44) | 3.093253968 | 801 |
| CXCL16 | KRRR (SEQ ID NO: 45) | 14.3580786 | 1286.5 |
| DAG1 | RKKRKGK (SEQ ID NO: 46) | 2.823255814 | 2519 |
| GHR | KQQRIK (SEQ ID NO: 47) | 2.216494845 | 141 |
| PTPRF | KRKRTH (SEQ ID NO: 48) | 10.48407643 | 1178 |
| AGER | RRQRR (SEQ ID NO: 49) | 11.92390524 | 1132.5 |
| KL | KKGRRSYK (SEQ ID NO: 50) | 3.723350254 | 880 |
| NRG1 | KTKKQRKKLHDRLR (SEQ ID NO: 51) | 9.416666667 | 806.5 |
| LRP1B | KRKRRTKTIRR (SEQ ID NO: 52) | 2.315500686 | 1014 |
| Jag2 | RKRRKERERSRLPR (SEQ ID NO: 53) | 5.090909091 | 1323 |
| EPCAM | RKKRMAKYEK (SEQ ID NO: 54) | 1.640226629 | 864 |
| KCNE3 | RSRKVDKR (SEQ ID NO: 55) | 9.779546846 | 976 |
| CDH2 | KRRDKERQAK (SEQ ID NO: 56) | 2.262402089 | 1134 |
| NRG2 | KTKKQRKQMHNHLR (SEQ ID NO: 57) | 8.322951605 | 1259 |
| PTPRK | KKSKLAKKRK (SEQ ID NO: 58) | 2.375 | 1248 |
| BTC | HPLRKRRKRKKK (SEQ ID NO: 59) | 1.232854864 | 480 |
| EPHA3 | RRRSKYSKAK (SEQ ID NO: 60) | 2.969369369 | 1289.5 |

TABLE 3-continued

This table provides data without stimulation of co-expressed anti-ALPPL2 CAR with ALPPL2+ K562. "Reporter alone" represents a reporter plasmid and was expressed in all samples.

| Recptor from which STS is derived | STS Sequence | Average Signal To Noise | Average MFI Difference (MFI of ON - MFI of OFF) |
|---|---|---|---|
| IL1R2 | HRRCKHRTGK (SEQ ID NO: 61) | 2.413043478 | 980 |
| PTPRM | KKRKLAKKRK (SEQ ID NO: 62) | 2.305630027 | 1317 |
| Notch3 | RRKREH (SEQ ID NO: 63) | 12.84705882 | 1191 |
| Reporter Alone | N/A | 0.408 | 114 |

Example 21

This Example describes Table 4 of activation characteristics of hingeNotch STS variants with T cell stimulation.

Primary human CD4+ T-cells were activated with anti-CD3/anti-CD28 Dynabeads (Gibco) and transduced with two lentiviral constructs, one expressing a hinge receptor, and the other a transcriptional reporter with constitutive eGFP+ anti-ALPPL2 CAR expression. Cells containing both constructs were sorted for on Day 5 post initial T-cell stimulation and expanded further for activation testing. For testing, T-cells expressing receptors were co-cultured with K562 cells or CD19+ K562 cells. BFP reporter gene was subsequently measured using a Fortessa X-50 (BD Biosciences). Signal to noise ratios from the MFIs of BFP+ cells under CD19+ K562 versus K562 conditions are plotted against the delta change in MFI in the two conditions. Activation was examined as in Example 19 but with additional ALPPL2+ K562 co-incubation for CAR activation. PGP-24DNA

TABLE 4

This table provides data with stimulation of co-expressed anti-ALPPL2 CAR with ALPPL2+ K562. "Reporter alone" represents a reporter plasmid and was expressed in all samples.

| Recptor from which STS is derived | STS Sequence | Average Signal To Noise | Average MFI Difference (MFI of ON - MFI of OFF) |
|---|---|---|---|
| Notch 1 | RKRRR (SEQ ID NO: 18) | 115.1879699 | 1639.5 |
| Notch 2 | KRKRKH (SEQ ID NO: 19) | 15.51369863 | 4189 |
| Notch 4 | RRRREH (SEQ ID NO: 43) | 24.14523449 | 1483 |
| CSF1R | KYKQKPK (SEQ ID NO: 44) | 5.44982699 | 1512 |
| CXCL16 | KRRR (SEQ ID NO: 45) | 27.93162393 | 1687.5 |
| DAG1 | RKKRKGK (SEQ ID NO: 46) | 7.403225806 | 4639 |
| GHR | KQQRIK (SEQ ID NO: 47) | 2.673553719 | -51.5 |
| PTPRF | KRKRTH (SEQ ID NO: 48) | 50.78034682 | 2574.5 |
| AGER | RRQRR (SEQ ID NO: 49) | 105.6603774 | 1792 |
| KL | KKGRRSYK (SEQ ID NO: 50) | 6.534357661 | 1567.5 |
| NRG1 | KTKKQRKKLHDRLR (SEQ ID NO: 51) | 24.99036609 | 637 |
| LRP1B | KRKRRTKTIRR (SEQ ID NO: 52) | 10.30285381 | 2558 |
| Jag2 | RKRRKERERSRLPR (SEQ ID NO: 53) | 21.38095238 | 3320.5 |
| EPCAM | RKKRMAKYEK (SEQ ID NO: 54) | 2.48189415 | 2372.5 |
| KCNE3 | RSRKVDKR (SEQ ID NO: 55) | 62.54752852 | 1900.5 |
| CDH2 | KRRDKERQAK (SEQ ID NO: 56) | 4.24047619 | 2834 |

TABLE 4-continued

This table provides data with stimulation of co-expressed anti-ALPPL2 CAR with ALPPL2+ K562. "Reporter alone" represents a reporter plasmid and was expressed in all samples.

| Receptor from which STS is derived | STS Sequence | Average Signal To Noise | Average MFI Difference (MFI of ON – MFI of OFF) |
|---|---|---|---|
| NRG2 | KTKKQRKQMHNHLR (SEQ ID NO: 57) | 15.82959641 | 2201 |
| PTPRK | KKSKLAKKRK (SEQ ID NO: 58) | 6.761506276 | 2514.5 |
| BTC | HPLRKRRKRKKK (SEQ ID NO: 59) | 1.713168188 | 423 |
| EPHA3 | RRRSKYSKAK (SEQ ID NO: 60) | 6.307971014 | 2274 |
| IL1R2 | HRRCKHRTGK (SEQ ID NO: 61) | 4.775 | 2027 |
| PTPRM | KKRKLAKKRK (SEQ ID NO: 62) | 9.289501591 | 2517.5 |
| Notch3 | RRKREH (SEQ ID NO: 63) | 29.22939068 | 1987.5 |
| Reporter Alone | N/A | 1.719298246 | 422.5 |

Example 22

This Example describes experiments performed to demonstrate controlled EL-2 production by T cells engineered Hinge-Notch STS variants.

FIG. 15A shows a diagram of T cells engineered with Hinge-Notch STS variants to provide ligand-triggered secretion of an engineered cytokine for autocrine and paracrine expansion of T cells. Expression profile of anti-CD19 Hinge-Notch receptors with the indicated STS modifications are shown in FIG. 15B. Primary human T-cells were activated with anti-CD3/anti-CD28 Dynabeads (Gibco) and transduced with two lentiviral constructs, one expressing a CAR against the MCAM antigen, and one expressing a Hinge-Notch receptor with inducible super-IL2 under Gal4-UAS control. Cells containing both constructs were sorted on Day 5 post initial T-cell stimulation and expanded further for activation testing. Receptor expression was determined by anti-myc-tag staining (y-axis).

Example 23

This Example describes experiments performed to demonstrate that ligand-triggered expression of super-IL2 improves cell viability of CAR-T cells.

1×10⁵ double positive T-cells expressing anti-CD19 Hinge-Notch Notch1 STS receptors were co-cultured in media without IL-2, with no K562 cells (top left), with CD19+ K562 cells to trigger Hinge-Notch (top right), with MCAM+ K562 cells to trigger CAR activation (bottom left) or with MCAM+ and CD19+ K562 cells to trigger activation of both receptors (bottom right) (FIG. 16). After 9 days the proportion of live T cells by forward and side-scatter measurements using a Fortessa X-50 (BD Biosciences) was assessed. Co-activation of both receptors resulted in the most viable cells, followed by Hinge-Notch activation (and subsequent super-IL2 induction), CAR activation alone, and no activation of either receptor.

Example 24

This Example describes experiments performed to demonstrate tunable proliferation of T cells with STS-variants of Hinge-Notch.

Primary human T-cells were activated with anti-CD3/anti-CD28 Dynabeads (Gibco) and transduced with two lentiviral constructs, one expressing a CAR against the MCAM antigen, and one expressing a Hinge-Notch receptor with inducible super-IL2 under Gal4-UAS control (the right four panels of FIG. 17). Hinge-Notch receptors containing 3 different STS variants (NRG1, Notch1, Notch2) were tested against a no Hinge-Notch control. Similarly, primary human T-cells were generated without CAR expression (left panels of FIG. 17). T cells were stained with CellTrace Violet (Invitrogen) according to manufacturer's protocols, co-incubated with CD19+ K562 target cells in media without IL-2 and measured using a Fortessa X-50 (BD Biosciences) at the indicated timepoints to assess proliferation by CTV signal decay.

Example 25

This Example describes experiments performed to demonstrate tunable secretion of super-IL2 with STS-variants of Hinge-Notch.

Primary human T-cells were activated with anti-CD3/anti-CD28 Dynabeads (Gibco) and transduced with a lentiviral construct Hinge-Notch receptor with inducible super-IL2 under Gal4-UAS control (FIG. 18A). Hinge-Notch receptors containing 3 different STS variants (NRG1, Notch1, Notch2) were tested against a no HingeNotch control. T cells were co-incubated with MCAM+ CD19+ K562 cells in media lacking IL-2, and at the indicated timepoints, supernatant IL-2 was measured using the Instant ELISA Kit (Invitrogen) according to manufacturer's protocols with a microplate reader (Tecan). Red dotted line indicates a standard concentration of IL-2 used for culturing T cells. Graded secretion of super-IL2 was achieved by activation of STS-tuned HingeNotch receptors.

For FIG. 18B, primary human T-cells were generated with an additional lentiviral vector expressing a CAR against MCAM. Enhanced uptake of IL-2 by CAR-expressing cells resulted in loss of supernatant IL2 in CAR-only and NRG1-STS Hinge-Notch T cells. In contrast, greater induction of super-IL2 by Notch1 and Notch2-STS based receptors initially outpaces this uptake, before proliferation and K562 elimination reduces supernatant levels.

Example 26

This Example describes experiments performed to demonstrate tunable secretion of super-IL2 with STS-variants of Hinge-Notch enhances proliferation of bystander T cells.

Primary human T-cells were activated with anti-CD3/anti-CD28 Dynabeads (Gibco) and transduced with a lentiviral construct including a Hinge-Notch receptor with inducible super-IL2 under Gal4-UAS control (right panels of FIG. 19). HingeNotch receptors containing 3 different STS variants (NRG1, Notch1, Notch2) were tested against a no HingeNotch control. HingeNotch T cells were co-incubated with "bystander" T cells stained with CellTrace Far Red (Invitrogen) expressing a CAR against MCAM (left panel of FIG. 19) or with no CAR (right panel of FIG. 19). T cells were co-incubated with MCAM+ CD19+ K562 cells in media lacking IL-2, and proliferation of the bystander T cells were assessed by measuring signal decay on a Fortessa X-50 (BD Biosciences). For bystander T cells with and without CAR expression, proliferation was enhanced in graded fashion by STS variants of Hinge-Notch-activated T cells.

Example 27

This Example describes experiments performed to test single lentiviral vector constructs containing Hinge-Notch receptors CAR circuits.

Primary human T-cells were activated with anti-CD3/anti-CD28 Dynabeads (Gibco) and transduced with a single lentiviral construct containing constitutively expressed Hinge-Notch receptors with an inducible anti-MCAM CAR cassette under Gal4-UAS control. Cells were sorted for Hinge-Notch receptor expression via myc-tag on Day 5 post initial T-cell stimulation and expanded further for activation testing. Three STS-variants were tested as indicated, with constitutively expressed CAR used as a control (FIG. 20). For testing, $1\times10^5$ T cells expressing anti-CD19 receptors were co-cultured with: no additions (upper trace), $5\times10^5$ K562 cells (middle trace), or $5\times10^4$ CD19+ K562 cells (lower trace). Transcriptional activation of the inducible CAR was subsequently measured by a GFP tag using a Fortessa X-50 (BD Biosciences).

Example 28

This Example describes experiments performed to demonstrate specific dual antigen target cell killing by T cells engineered with a single lentivector containing a HingeNotch CAR circuit.

Primary human T-cells were activated with anti-CD3/anti-CD28 Dynabeads (Gibco) and transduced with a single lentiviral construct containing constitutively expressed HingeNotch-receptors with an inducible anti-MCAM CAR cassette under Gal4-UAS control. Cells were sorted for Hinge-Notch receptor expression via myc-tag on Day 5 post initial T-cell stimulation and expanded further for activation testing. Three STS-variants were tested as indicated, with constitutively expressed CAR used as a control. For testing, $1\times10^5$ T-cells expressing anti-CD19 receptors were co-cultured with $5\times10$ MCAM+ K562 cells or $5\times10^4$ MCAM+ CD19+ K562 cells. Target cell killing was assessed by forward/side-scatter of the K562 population using a Fortessa X-50 (BD Biosciences). As shown in FIG. 21, Hinge-Notch circuits effectively and specifically clear target cells containing both MCAM+ and CD19+ antigens.

Example 29

This Example describes experiments performed for testing single lentiviral vector constructs containing Hinge-Notch receptors for control of T cell activation and exhaustion.

Primary human T-cells were activated with anti-CD3/anti-CD28 Dynabeads (Gibco) and transduced with a single lentiviral construct containing constitutively expressed Hinge-Notch receptors with an inducible anti-MCAM CAR cassette under Gal4-UAS control. Cells were sorted for Hinge-Notch receptor expression via myc-tag on Day 5 post initial T-cell stimulation and expanded further for activation testing. Three STS-variants were tested as indicated, with constitutively expressed CAR used as a control. For testing, $1\times10$ T-cells expressing anti-CD19 receptors were co-cultured with $5\times10^4$ CD19+ K562 cells. Transcriptional activation of the inducible CAR was subsequently measured by a GFP tag using a Fortessa X-50 (BD Biosciences) (the left most panel of FIG. 22). T cell activation and exhaustion were measure by expression of CD25 and CD39, respectively (FIG. 22).

Example 30

This Example describes experiments performed for in vivo testing of Hinge-Notch-to-CAR circuits.

As shown in FIG. 23, for unilateral tumors, NOD.Cg-Prkdc$^{scid}$Il2rg$^{tm1Wjl}$/SzJ (NSG) mice were implanted with $1\times10^6$ K562-BCMA/CD19 tumor cells subcutaneously on the left flank. For contralateral tumors, NSG mice were implanted with $1\times10^6$ K562-BCMA/CD19 tumor cells on the left flank and with $1\times10^6$ K562-CD19 tumor cells on the right flank. Four days after tumor implantation, $2.5\times10^6$ engineered primary human CD4+ and CD8+ T cells (total of $5\times10^6$ T cells) were infused i.v. through tail vein injection. Tumor size was monitored via caliper 2-3 per week and mice were determined to have reached endpoint when tumors measured ≥20 mm. For immunophenotypic analysis, tumors and spleens were harvested 10 days post T cell implantation. Tumors were manually minced and digested in RPMI-1640 with 4 mg/ml Collagenase IV (Worthington Biochemical Corporation) and 0.1 mg/ml DNase I (MilliporeSigma) at 37° C. for 30 min and spleens were manually dissociated and subjected to red blood cell lysis (ACK; KD medical). The following antibodies were used: anti-CD45 (2D1, 368516, Biolegend), anti-CD3 (UCHT1, 300464, Biolegend), anti-CD4 (SK3, 563552, BD biosciences), and anti-CD8 (RPA-T8, 563823, BD Biosciences). Dead cells were excluded with Draq7 (Abcam). Samples were analyzed using FACSymphony X50 SORP (BD Biosciences) and data was analyzed using FlowJo software (BD Biosciences).

Example 31

This Example summarizes the results of experiments as provided and discussed herein for the Notch receptors described in Table 1.

TABLE 5

| Construct ID | Receptor Description | Experiment Result for Activity |
|---|---|---|
| pIZ341 | anti-CD19scFv-CD8Hinge-Notch1TMD-Gal4VP64 | Demonstrated that a full CD8 Hinge is sufficient as a ligand-sensitive domain |
| pIZ343 | anti-CD19scFv-CD8Hinge2-Notch1TMD-Gal4VP64 | Demonstrated that a truncated CD8 Hinge is sufficient as a ligand-sensitive domain, better controlled than pIZ341 or pIZ342. |
| pIZ358 | anti-CD19scFv-CD28Hinge-Notch1TMD-Gal4VP64 | Demonstrated that other hinge domains besides CD8 Hinge can be used as ligand-sensitive domains, activates about as well as a truncated CD8 Hinge. |
| pIZ359 | anti-CD19scFv-IgG4Hinge-Notch1TMD-Gal4VP64 | Demonstrated that other hinge domains besides CD8 Hinge can be used as ligand-sensitive domains. |
| pIZ360 | anti-CD19scFv-OX40-Notch1TMD-Gal4VP64 | Demonstrated that other hinge domains besides CD8 Hinge can be used as ligand-sensitive domains. |
| pIZ361 | anti-CD19scFv-CD8Hinge2-Notch1TMD-Notch2STS-Gal4VP64 | Demonstrates that Notch2 STS improves signal of receptors that do not contain Notch-based ECDs. |
| pIZ343FYIA | anti-ALPPL2scFv-CD8Hinge2-Notch1TMD-Gal4VP64 | Activated against M28, ALPPL2+ K562. |
| pIZ343eGFP | eGFP-CD8Hinge2-Notch1TMD-Gal4VP64 | Activated against LaG17+ K562. |
| pIZ342 | anti-CD19scFv-CD8Hinge1-Notch1TMD-Gal4VP64 | Demonstrated that a truncated CD8 Hinge is sufficient as a ligand-sensitive domain, better controlled than pIZ341. |
| pIZ362 | anti-CD19scFV-CD8Hinge3-Notch1TMD-Notch1STS-Gal4VP64 | Demonstrated that a truncated CD8 Hinge is sufficient as a ligand-sensitive domain, weaker than pIZ343. |
| pIZ363 | anti-CD19scFV-CD8Hinge4-Notch1TMD-Notch1STS-Gal4VP64 | Demonstrated that a truncated CD8 Hinge is sufficient as a ligand-sensitive domain, weaker than pIZ343. |
| pIZ361FYIA | anti-ALPPL2scFv-CD8Hinge2-Notch1TMD-Notch2STS-Gal4VP64 | Activated against M28, ALPPL2+ K562. |
| pIZ343BCMA | anti-BCMAscFV-CD8Hinge2-Notch1TMD-Gal4VP64 | Activated against BCMA+ K562. |
| pIZ361BCMA | anti-BCMAscFV-CD8Hinge2-Notch1TMD-Notch2STS-Gal4VP64 | Activated against BCMA+ K562. |
| pIZ343(4D5-8) | anti-Her2scFV_4D5-8-CD8Hinge2-Notch1TMD-Gal4VP64 | Activated against Her2+ SKBR3. |
| pIZ361(4D5-8) | anti-Her2scFV_4D5-8-CD8Hinge2-Notch1TMD-Notch2STS-Gal4VP64 | Activated against Her2+ SKBR3. |
| pIZ343(4D5-7) | anti-Her2scFV_4D5-7-CD8Hinge2-Notch1TMD-Gal4VP64 | Activated against Her2+ SKBR3. |
| pIZ361(4D5-7) | anti-Her2scFV_4D5-7-CD8Hinge2-Notch1TMD-Notch2STS-Gal4VP64 | Activated against Her2+ SKBR3. |
| pRay068A | anti-BCMA_FHVH33-CD8Hinge2-Notch1TMD-Notch2STS-Gal4VP64 | Activated against BCMA+ K562. |
| pRay068B | anti-BCMA_FHVH33-CD8Hinge5-Notch1TMD-Notch2STS-Gal4VP64 | Activated against BCMA+ K562. |
| pIZ370 | anti-CD19scFv-CD8Hinge2-CLSTN1TMD-CLSTN1STS-Gal4VP64 | Activated poorly against CD19+ K562. |
| pIZ371 | antiCD19scFv-CD8Hinge2-CLSTN2TMD-CLSTN2STS-Gal4VP64 | Activated poorly against CD19+ K562. |
| pTMD201 | antiCD19scFv-CD8Hinge2-CLSTN1TMD-Notch1STS-Gal4VP64 | Activated well against CD19+ K562. |
| pTMD202 | antiCD19scFv-CD8Hinge2-CLSTN2TMD-Notch1STS-Gal4VP64 | Activated well against CD19+ K562. |

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

REFERENCES

Dudani J. S., Warren A. D., and Bhatia S. N., Harnessing Protease Activity to Improve Cancer Care. Annu. Rev. Cancer Biol. 2018. 2:353-76.

David L. Porter, M. D., Bruce L. Levine, Ph.D., Michael Kalos, Ph.D., Adam Bagg, M. D., and Carl H. June, M. D. Chimeric Antigen Receptor-Modified T Cells in Chronic Lymphoid Leukemia. *N. Engl J Med.* 2011 Aug. 25; 365(8):725-33.

Gordon W R et al., The molecular logic of Notch signaling—a structural and biochemical perspective. *J. Cell Sci.* (2008) 121:3109-19.

Gordon W R et al., Mechanical Allostery: Evidence for a Force Requirement in the Proteolytic Activation of Notch. *Dev Cell* (2015) 33:729-36.

Morsut L, Roybal K T, Xiong X, Gordley R M, Coyle S M, Thomson M, and Lim W A. Engineering Customized Cell Sensing and Response Behaviors Using Synthetic Notch Receptors. *Cell.* 2016 Feb. 11; 164(4):780-91.

Naso M F, Tomkowicz B, Perry W L 3rd, Strohl W R. Adeno-Associated Virus (AAV) as a Vector for Gene Therapy. *BioDrugs.* 2017; 31(4):317-34.

Nasri M, Karimi A, Allahbakhshian Farsani M. Production, purification and titration of a lentivirus-based vector for gene delivery purposes. *Cytotechnology.* 2014; 66(6): 1031-38.

Roybal K T, Jasper Z. Williams, Leonardo Morsut, Levi J. Rupp, Isabel Kolinko, Joseph H. Choe, Whitney J. Walker, Krista A. McNally, and Wendell A. Lim. Engineering T cells with Customized Therapeutic Response Programs Using Synthetic Notch Receptors. *Cell.* 2016 Oct. 6; 167(2):419-32.

Samulski and Muzyczka (2014). AAV-Mediated Gene Therapy for Research and Therapeutic Purposes. *Annu. Rev. Virol.* 1:427.

Sakuma, et al. (2012). Lentiviral vectors: basic to translational. *Biochem. J.* 443:603. Watson D. J., Wolfe J. H. Viral vectors for gene therapy: methods and protocols. Totowa, N.J., USA: Humana Press; 2003. pp. 383-404.

Vidarsson G. et al., IgG subclasses and allotypes: from structure to effector functions. *Frontiers Immunol.* 2014, Oct. 20; 5:520.

---

What is claimed is:

1. A chimeric polypeptide comprising, from N-terminus to C-terminus:
   a) an extracellular ligand-binding domain having a binding affinity for a selected ligand;
   b) a hinge domain from CD8a, CD28, OX40, or IgG4;
   c) a transmembrane domain from a human Notch receptor comprising one or more ligand-inducible proteolytic cleavage sites; and
   d) an intracellular domain comprising a transcriptional regulator, wherein binding of the selected ligand to the extracellular ligand-binding domain induces cleavage at a ligand-inducible proteolytic cleavage site disposed between the transcriptional regulator and the hinge domain, and wherein the chimeric polypeptide does not comprise a LIN-12-Notch repeat (LNR) nor a heterodimerization domain (HD) of a Notch receptor.

2. The chimeric polypeptide of claim 1, wherein the transmembrane domain further comprises a stop-transfer-sequence.

3. The chimeric polypeptide of claim 1, wherein the extracellular domain comprises an antigen-binding moiety capable of binding to a ligand on the surface of a cell.

4. The chimeric polypeptide of claim 3, wherein the cell is a human cell.

5. The chimeric polypeptide of claim 3, wherein the cell is a tumor cell.

6. The chimeric polypeptide of claim 1, wherein the ligand comprises a protein or a carbohydrate.

7. The chimeric polypeptide of claim 6, wherein the ligand is selected from the group consisting of CD1, CD1a, CD1b, CD1c, CD1d, CD1e, CD2, CD3d, CD3e, CD3g, CD4, CD5, CD7, CD8a, CD8b, CD19, CD20, CD21, CD22, CD23, CD25, CD27, CD28, CD33, CD34, CD40, CD45, CD48, CD52, CD59, CD66, CD70, CD71, CD72, CD73, CD79A, CD79B, CD80 (B7.1), CD86 (B7.2), CD94, CD95, CD134, CD140 (PDGFR4), CD152, CD154, CD158, CD178, CD181 (CXCR1), CD182 (CXCR2), CD183 (CXCR3), CD210, CD246, CD252, CD253, CD261, CD262, CD273 (PD-L2), CD274 (PD-L1), CD276 (B7H3), CD279, CD295, CD339 (JAG1), CD340 (HER2), EGFR, FGFR2, CEA, AFP, CA125, MUC-1, MAGE, alkaline phosphatase, placental-like 2 (ALPPL2), B-cell maturation antigen (BCMA), green fluorescent protein (GFP), enhanced green fluorescent protein (EGFP), and signal regulatory protein a (SIRPa).

8. The chimeric polypeptide of claim 1, wherein the ligand is selected from cell surface receptors, adhesion proteins, integrins, mucins, lectins, tumor associated antigens, and tumor-specific antigens.

9. The chimeric polypeptide of claim 3, wherein the antigen-binding moiety is selected from the group consisting of an antibody, a nanobody, a diabody, a triabody, a minibody, an F(a1302 fragment, an F(ab)v fragment, a single chain variable fragment (scFv), a single domain antibody (sdAb), and a functional fragment thereof.

10. The chimeric polypeptide of claim 1, wherein the ligand is a tumor-associated antigen selected from the group consisting of CD19, B7H3 (CD276), BCMA (CD269), ALPPL2, CD123, CD171, CD179a, CD20, CD213A2, CD22, CD24, CD246, CD272, CD30, CD33, CD38, CD44v6, CD46, CD71, CD97, CEA, CLDN6, CLECL1, CS-1, EGFR, EGFRvIII, ELF2M, EpCAM, EphA2, Ephrin B2, FAP, FLT3, GD2, GD3, GM3, GPRC5D, HER2 (ERBB2/neu), IGLL1, IL-11Ra, KIT (CD117), MUC1, NCAM, PAP, PDGFR-β, PRSS21, PSCA, PSMA, ROR1, SIRPa, SSEA-4, TAG72, TEM1/CD248, TEM7R, TSHR, VEGFR2, ALPI, citrullinated vimentin, cMet, and Axl.

11. The chimeric polypeptide of claim 1, wherein the one or more ligand-inducible proteolytic cleavage sites comprises a gamma secretase cleavage site.

12. The chimeric polypeptide of claim 1, wherein the intracellular domain comprises a nuclear localization sequence and a transcriptional regulator sequence selected from the group consisting of Gal4-VP16, Gal4-VP64, tetR-VP64, ZFHD1-VP64, Gal4-KRAB, and HAP1-VP16.

13. The chimeric polypeptide of claim 1, further comprising an additional proteolytic cleavage site, a signal sequence, a detectable label, a tumor-specific cleavage site, a disease-specific cleavage site, and combinations thereof.

14. A recombinant nucleic acid comprising a nucleotide sequence encoding a chimeric polypeptide according to claim 1.

15. A recombinant cell comprising a chimeric polypeptide according to claim 1.

16. The recombinant cell of claim 15, wherein the chimeric polypeptide is expressed from a recombinant nucleic acid that has been transduced into the cell.

17. The recombinant cell of claim 15, wherein the recombinant cell is a mammalian cell.

18. The recombinant cell of claim 17, wherein the mammalian cell is an immune cell, a neuron, an epithelial cell, and endothelial cell, or a stem cell.

19. The recombinant cell of claim 18, wherein the recombinant cell is an immune cell selected from the group consisting of a B cell, a monocyte, a natural killer cell, a basophil, an eosinophil, a neutrophil, a dendritic cell, a macrophage, a regulatory T cell, a helper T cell, a cytotoxic T cell, and other T cells.

20. The recombinant cell of claim 19, wherein the T cell is a CD4+T cell or a CD8+T cell.

21. A method for the treatment of a health condition in an individual in need thereof, the method comprising administering to the individual a first therapy comprising an effective number of the recombinant cell according to claim 15, wherein the recombinant cell treats the health condition in the individual.

22. The chimeric polypeptide of claim 1, wherein the CD8α hinge domain has a sequence selected from the group consisting of SEQ ID NO: 12, SEQ ID NO: 13, SEQ ID NO: 39, SEQ ID NO: 40, and SEQ ID NO: 41.

23. The chimeric polypeptide of claim 1, wherein the CD28 hinge domain has the sequence of SEQ ID NO: 14.

24. The chimeric polypeptide of claim 1, wherein the IgG4 hinge domain has the sequence of SEQ ID NO: 15.

25. The chimeric polypeptide of claim 1, wherein OX40 hinge domain has the sequence of SEQ ID NO: 16.

26. The chimeric polypeptide of claim 1, wherein the transmembrane domain is from human Notch 1 receptor.

27. The chimeric polypeptide of claim 1, wherein the transmembrane domain is from human Notch 2 receptor.

28. The chimeric polypeptide of claim 1, wherein the transmembrane domain is from human Notch 3 receptor.

29. The chimeric polypeptide of claim 1, wherein the transmembrane domain is from human Notch 4 receptor.

* * * * *

UNITED STATES PATENT AND TRADEMARK OFFICE
CERTIFICATE OF CORRECTION

PATENT NO. : 11,617,766 B2
APPLICATION NO. : 17/529091
DATED : April 4, 2023
INVENTOR(S) : Kole T. Roybal et al.

It is certified that error appears in the above-identified patent and that said Letters Patent is hereby corrected as shown below:

In the Claims

In Column 167, Line 46, in Claim 1, delete "CD8a," and insert -- CD8α, --.

In Column 168, Line 67, in Claim 9, delete "F(a1302" and insert -- F(ab)$_2$ --.

In Column 170, Line 3, in Claim 18, delete "and" and insert -- an --.

Signed and Sealed this
Sixteenth Day of July, 2024

Katherine Kelly Vidal
*Director of the United States Patent and Trademark Office*